US011628218B2

(12) United States Patent
Getts et al.

(10) Patent No.: US 11,628,218 B2
(45) Date of Patent: Apr. 18, 2023

(54) ENGINEERED CHIMERIC FUSION PROTEIN COMPOSITIONS AND METHODS OF USE THEREOF

(71) Applicant: Myeloid Therapeutics, Inc., Cambridge, MA (US)

(72) Inventors: Daniel Getts, Stow, MA (US); Yuxiao Wang, Belmont, MA (US); Bruce McCreedy, Jr., Raleigh, NC (US)

(73) Assignee: MYELOID THERAPEUTICS, INC., Cambridge, MA (US)

( * ) Notice: Subject to any disclaimer, the term of this patent is extended or adjusted under 35 U.S.C. 154(b) by 0 days.

(21) Appl. No.: 17/590,504

(22) Filed: Feb. 1, 2022

(65) Prior Publication Data

US 2022/0152199 A1  May 19, 2022

Related U.S. Application Data

(63) Continuation of application No. PCT/US2021/058104, filed on Nov. 4, 2021.

(60) Provisional application No. 63/109,445, filed on Nov. 4, 2020, provisional application No. 63/162,205, filed on Mar. 17, 2021, provisional application No. 63/196,994, filed on Jun. 4, 2021, provisional application No. 63/251,400, filed on Oct. 1, 2021.

(51) Int. Cl.

| A61K 39/395 | (2006.01) |
| A61K 9/127 | (2006.01) |
| A61P 35/00 | (2006.01) |
| A61K 9/00 | (2006.01) |
| A61K 38/17 | (2006.01) |

(52) U.S. Cl.
CPC ........ *A61K 39/3955* (2013.01); *A61K 9/0019* (2013.01); *A61K 9/127* (2013.01); *A61K 38/1774* (2013.01); *A61P 35/00* (2018.01)

(58) Field of Classification Search
CPC .... A61K 9/00; A61K 38/1774; A61K 39/395; A61P 35/00
See application file for complete search history.

(56) References Cited

U.S. PATENT DOCUMENTS

| 4,470,461 A | 9/1984 | Stapp |
| 4,522,811 A | 6/1985 | Eppstein et al. |
| 5,122,464 A | 6/1992 | Wilson et al. |
| 5,391,377 A | 2/1995 | Barnwell |
| 5,633,234 A | 5/1997 | August et al. |
| 5,773,244 A | 6/1998 | Ares, Jr. et al. |
| 5,776,910 A | 7/1998 | Schreiber et al. |
| 6,210,963 B1 | 4/2001 | Haddada et al. |
| 6,468,798 B1 | 10/2002 | Debs et al. |
| 7,833,789 B2 | 11/2010 | Naldini et al. |
| 7,926,300 B2 | 4/2011 | Roberts et al. |
| 8,198,020 B2 | 6/2012 | Francois et al. |
| 8,574,575 B2 | 11/2013 | Govindan et al. |
| 8,709,412 B2 | 4/2014 | Jones et al. |
| 9,045,541 B2 | 6/2015 | Eckelman et al. |
| 9,149,519 B2 | 10/2015 | Landau et al. |
| 9,221,908 B2 | 12/2015 | Frazier et al. |
| 9,428,569 B2 | 8/2016 | Spencer et al. |
| 9,518,116 B2 | 12/2016 | Frazier et al. |
| 9,663,575 B2 | 5/2017 | Eckelman et al. |
| 9,745,368 B2 | 8/2017 | Milone et al. |
| 9,820,350 B2 | 11/2017 | Pyshos et al. |
| 9,845,345 B2 | 12/2017 | Ring et al. |
| 9,850,312 B2 * | 12/2017 | Agatsuma .......... A61K 47/6859 |
| 9,913,920 B2 | 3/2018 | Movahedi et al. |
| 10,034,900 B2 | 7/2018 | Senju |
| 10,081,680 B2 | 9/2018 | Weiskopf et al. |
| 10,106,609 B2 | 10/2018 | Yang et al. |
| 10,259,859 B2 | 4/2019 | Pons et al. |
| 10,259,873 B2 | 4/2019 | Frazier et al. |
| 10,299,335 B2 | 5/2019 | Pyshos et al. |
| 10,415,017 B2 | 9/2019 | O'Neill |
| 10,428,143 B2 | 10/2019 | Krummel et al. |
| 10,602,584 B2 | 3/2020 | Pyshos et al. |
| 10,774,125 B2 | 9/2020 | Ring et al. |
| 10,980,836 B1 | 4/2021 | Getts et al. |
| 11,013,764 B2 | 5/2021 | Getts et al. |
| 11,026,973 B2 | 6/2021 | Getts et al. |
| 11,034,749 B2 | 6/2021 | Gill et al. |
| 11,041,023 B2 | 6/2021 | Vale et al. |
| 2004/0053873 A1 | 3/2004 | Barman et al. |
| 2005/0031628 A1 | 2/2005 | George et al. |
| 2006/0018889 A1 | 1/2006 | Li et al. |
| 2006/0188891 A1 | 8/2006 | Bickmore, Jr. et al. |

(Continued)

FOREIGN PATENT DOCUMENTS

| CA | 2850380 C | 8/2015 |
| EP | 0338841 B1 | 3/1995 |

(Continued)

OTHER PUBLICATIONS

Ali, M. et al., "Induction of neoantigen-reactive T cells from healthy donors", Nature Protocols (2019).
Altschul et al., Basic local alignment search tool. J. Mol. Biol. 215:403-410, 1990.
Alvey C, Discher DE. 2017. Engineering macrophages to eat Cancer: from "marker of self" CD47 and phagocytosis to differentiation. Journal of Leukocyte Biology 102:31-40.
Alvey CM, Spinier KR, Irianto J, Pfeifer CR, Hayes B, Xia Y, Cho S, Dingal P, Hsu J, Smith L, Tewari M, Discher DE. 2017. SIRPA-Inhibited, Marrow-Derived macrophages engorge, accumulate, and differentiate in Antibody-Targeted regression of solid tumors. Current Biology 27:2065-2077.

(Continued)

*Primary Examiner* — Michael G. Hartley
*Assistant Examiner* — Jagadishwar R Samala
(74) *Attorney, Agent, or Firm* — Wilson Sonsini Goodrich & Rosati

(57) ABSTRACT

Compositions and methods for making and using engineered cells, such as, engineered myeloid cells that express a chimeric fusion protein that has a binding domain capable to binding surface molecules on target cells such as diseased cells.

22 Claims, 88 Drawing Sheets

Specification includes a Sequence Listing.

(56) References Cited

U.S. PATENT DOCUMENTS

| | | |
|---|---|---|
| 2008/0254027 A1 | 10/2008 | Bernett et al. |
| 2010/0111852 A1 | 5/2010 | Yoshida |
| 2011/0250203 A1 | 10/2011 | Klitgaard et al. |
| 2011/0287038 A1 | 11/2011 | Slawin et al. |
| 2011/0293603 A1 | 12/2011 | Saraiva et al. |
| 2014/0134142 A1 | 5/2014 | Smith et al. |
| 2014/0140989 A1 | 5/2014 | Eckelman et al. |
| 2014/0161805 A1 | 6/2014 | Jamieson et al. |
| 2014/0242701 A1 | 8/2014 | Shiku et al. |
| 2015/0057161 A1 | 2/2015 | Schultze et al. |
| 2015/0274826 A1 | 10/2015 | Frazier et al. |
| 2016/0137733 A1 | 5/2016 | Frazier et al. |
| 2016/0250258 A1 | 9/2016 | Delaney et al. |
| 2016/0251435 A1 | 9/2016 | Eckelman et al. |
| 2017/0087185 A1 | 3/2017 | Crane et al. |
| 2017/0151281 A1 | 6/2017 | Wagner et al. |
| 2017/0151282 A1 | 6/2017 | Discher et al. |
| 2017/0166657 A1 | 6/2017 | O'Neill et al. |
| 2017/0226183 A1 | 8/2017 | Schiffer-Mannioui |
| 2017/0233452 A1 | 8/2017 | McIvor et al. |
| 2017/0246278 A1 | 8/2017 | Vera Valdes et al. |
| 2017/0283498 A1 | 10/2017 | Frazier et al. |
| 2017/0292118 A1 | 10/2017 | Duchateau et al. |
| 2018/0000899 A1 | 1/2018 | Francois et al. |
| 2018/0030553 A1 | 2/2018 | Tang et al. |
| 2018/0057592 A1 | 3/2018 | Frazier et al. |
| 2018/0104308 A1 | 4/2018 | Mamonkin et al. |
| 2018/0105600 A1 | 4/2018 | Pons et al. |
| 2018/0133252 A9 | 5/2018 | Wilson et al. |
| 2018/0142019 A1 | 5/2018 | Manning et al. |
| 2018/0155405 A1 | 6/2018 | Ring et al. |
| 2018/0171021 A1 | 6/2018 | Karlsson et al. |
| 2018/0186878 A1 | 7/2018 | Rosenthal |
| 2018/0221503 A1 | 8/2018 | Kadiyala et al. |
| 2018/0244748 A1 | 8/2018 | Gill et al. |
| 2018/0250395 A1 | 9/2018 | Pietsch et al. |
| 2018/0319883 A1 | 11/2018 | Weiskopf et al. |
| 2018/0325953 A1 | 11/2018 | Poznansky et al. |
| 2018/0334653 A1 | 11/2018 | O'Neill |
| 2018/0355011 A1 | 12/2018 | Lim et al. |
| 2019/0010219 A1 | 1/2019 | Short |
| 2019/0023761 A1 | 1/2019 | Pule et al. |
| 2019/0038671 A1 | 2/2019 | Fan et al. |
| 2019/0062450 A1 | 2/2019 | De Palma et al. |
| 2019/0070277 A1 | 3/2019 | O'Neill et al. |
| 2019/0112373 A1 | 4/2019 | Manning et al. |
| 2019/0119379 A1 | 4/2019 | Gottschalk et al. |
| 2019/0119396 A1 | 4/2019 | Liu et al. |
| 2019/0144522 A1 | 5/2019 | Bari et al. |
| 2019/0169266 A1 | 6/2019 | Pons et al. |
| 2019/0233496 A1 | 8/2019 | Rosenthal |
| 2019/0240343 A1 | 8/2019 | Ahmed et al. |
| 2019/0248892 A1 | 8/2019 | Frazier et al. |
| 2019/0263928 A1 | 8/2019 | Watanabe et al. |
| 2019/0275150 A1 | 9/2019 | Pincetic et al. |
| 2019/0292257 A1 | 9/2019 | Bedoya et al. |
| 2019/0336615 A1 | 11/2019 | Thompson et al. |
| 2019/0345217 A1 | 11/2019 | Ma et al. |
| 2019/0381158 A1 | 12/2019 | Gunn |
| 2020/0239592 A1 | 7/2020 | Vale et al. |
| 2020/0247870 A1 | 8/2020 | Gill et al. |
| 2020/0255517 A1 | 8/2020 | Riddell et al. |
| 2020/0345773 A1 | 11/2020 | Getts et al. |
| 2020/0345774 A1 | 11/2020 | Getts et al. |
| 2021/0046110 A1 | 2/2021 | Gill et al. |
| 2021/0252053 A1 | 8/2021 | Wagner et al. |
| 2021/0277140 A1 | 9/2021 | Vale et al. |
| 2021/0299172 A1 | 9/2021 | Getts et al. |
| 2021/0361703 A1 | 11/2021 | Getts et al. |
| 2022/0001031 A1 | 1/2022 | Getts et al. |
| 2022/0002375 A1 | 1/2022 | Gill et al. |
| 2022/0002376 A1 | 1/2022 | Gill et al. |
| 2022/0002377 A1 | 1/2022 | Gill et al. |
| 2022/0033465 A1 | 2/2022 | Gill et al. |
| 2022/0033466 A1 | 2/2022 | Gill et al. |
| 2022/0033467 A1 | 2/2022 | Gill et al. |
| 2022/0041688 A1 | 2/2022 | Gill et al. |

FOREIGN PATENT DOCUMENTS

| | | |
|---|---|---|
| EP | 2626415 A2 | 8/2013 |
| EP | 2953643 A1 | 12/2015 |
| EP | 2242512 B1 | 4/2016 |
| EP | 3197495 A1 | 8/2017 |
| EP | 2956343 B1 | 12/2018 |
| EP | 3504244 A1 | 7/2019 |
| EP | 3519441 A1 | 8/2019 |
| EP | 3574018 A2 | 12/2019 |
| GB | 2572005 A | 9/2019 |
| WO | WO-9505835 A1 | 3/1995 |
| WO | WO-1995005835 A1 | 3/1995 |
| WO | WO-02077029 A2 | 10/2002 |
| WO | WO-02077029 A3 | 5/2003 |
| WO | WO-2004050855 A2 | 6/2004 |
| WO | WO-2004050855 A3 | 2/2005 |
| WO | WO-2007113572 A1 | 10/2007 |
| WO | WO-2008011599 A2 | 1/2008 |
| WO | WO-2008011599 A3 | 2/2009 |
| WO | WO-2012005763 A1 | 1/2012 |
| WO | WO-2012045389 A1 | 4/2012 |
| WO | WO 2012170930 * | 12/2012 |
| WO | WO-2013123088 A1 | 8/2013 |
| WO | WO-2014055668 A1 | 4/2014 |
| WO | WO-2014153114 A1 | 9/2014 |
| WO | WO-2016033331 A1 | 3/2016 |
| WO | WO-2016040441 A1 | 3/2016 |
| WO | WO-2016070136 A1 | 5/2016 |
| WO | WO-2016126608 A1 | 8/2016 |
| WO | WO-2016149254 A1 | 9/2016 |
| WO | WO-2016172606 A1 | 10/2016 |
| WO | WO-2017019848 A1 | 2/2017 |
| WO | WO-2017044487 A1 | 3/2017 |
| WO | WO-2017050884 A1 | 3/2017 |
| WO | WO-2017025944 A3 | 4/2017 |
| WO | WO-2017136633 A1 | 8/2017 |
| WO | WO-2017172981 A2 | 10/2017 |
| WO | WO-2018038684 A1 | 3/2018 |
| WO | WO 2018064076 * | 4/2018 |
| WO | WO-2018064076 A1 | 4/2018 |
| WO | WO-2018073394 A1 | 4/2018 |
| WO | WO-2018083126 A1 | 5/2018 |
| WO | WO-2018140831 A3 | 8/2018 |
| WO | WO-2018169948 A1 | 9/2018 |
| WO | WO-2018231871 A1 | 12/2018 |
| WO | WO-2019005641 A1 | 1/2019 |
| WO | WO-2019032624 A1 | 2/2019 |
| WO | WO-2019055946 A1 | 3/2019 |
| WO | WO-2019067328 A1 | 4/2019 |
| WO | WO-2019070704 A1 | 4/2019 |
| WO | WO-2019086512 A1 | 5/2019 |
| WO | WO-2019129146 A1 | 7/2019 |
| WO | WO-2019191332 A1 | 10/2019 |
| WO | WO-2019191334 A1 | 10/2019 |
| WO | WO-2019191340 A1 | 10/2019 |
| WO | WO 2019201995 * | 10/2019 |
| WO | WO-2020095044 A1 | 5/2020 |
| WO | WO-2020097193 A1 | 5/2020 |
| WO | WO-2020223550 A1 | 11/2020 |
| WO | WO-2020252208 A2 | 12/2020 |
| WO | WO-2021046243 A2 | 3/2021 |
| WO | WO-2021119538 A1 | 6/2021 |

OTHER PUBLICATIONS

Ancuta et al. (BMC Genomics 2009 10:403, pp. 1-19).

Andreesen R, Scheibenbogen C, Brugger W, Krause S, Meerpohl HG, Leser HG, Engler H, Lo hr GW. 1990. Adoptive transfer of tumor cytotoxic macrophages generated in vitro from circulating blood monocytes: a new approach to Cancer immunotherapy. Cancer Research 50:7450-7456.

(56) References Cited

OTHER PUBLICATIONS

Andreu N, Phelan J, de Sessions PF, Cliff JM, Clark TG, Hibberd ML. 2017. Primary macrophages and J774 cells respond differently to infection with Mycobacterium tuberculosis. Scientific Reports 7:42225.
Auffray et al. Blood monocytes: development, heterogeneity, and relationship with dendritic cells, Annual Rev. Immunol. 2009 27:669-92.
Batista FD, Iber D, Neuberger MS. 2001. B cells acquire antigen from target cells after synapse formation. Nature 411:489-494.
Beningo KA, Wang YL. 2002. Fc-receptor-mediated phagocytosis is regulated by mechanical properties of the target. Journal of Cell Science 115:849-856.
Benton et al., Screening lambdagt recombinant clones by hybridization to single plaques in situ, Science, 196(4286):180-182 (1977).
Berger, et al., Efficient Elutriation of monocytes within a closed system (Elutra™) Journal of Immunological Methods 298 (2005) 61-72.
Bhattacharjee, J., et al., "Monocytes isolated by positive and negative magnetic sorting techniques show different molecular characteristics and immunophenotypic behaviour", F100Research (2018) pp. 1-13.
Biglari, A., et al. Human monocytes expressing a CEA-specific chimeric CD64 receptor specifically target CEA-expressing tumour cells in vitro and in vivo, Gene Therapy (2006) 13, 602-610.
Bournazos, et al., "The Role and Function of Fcγ Receptors on Myeloid Cells" Microbiol Spectr (2016) 4(6).
Brooks SR, Kirkham PM, Freeberg L, Carter RH. 2004. Binding of cytoplasmic proteins to the CD19 intracellular domain is high affinity, competitive, and multimeric. The Journal of Immunology 172:7556-7564.
Bu JY, Shaw AS, Chan AC. 1995. Analysis of the interaction of ZAP-70 and syk protein-tyrosine kinases with the T-cell antigen receptor by plasmon resonance. PNAS 92:5106-5110.
Burgueno-Bucio et al."The multiple faces of CD5" J. Leukoc Bio. (2019) 105:891-904.
Calderwood, David, "Integrin Activation" Journal of Cell Science (2004) 117, pp. 657-666.
Chao MP, Alizadeh AA, Tang C, Myklebust JH, Varghese B, Gill S, Jan M, Cha AC, Chan CK, Tan BT, Park CY,Zhao F, Kohrt HE, Malumbres R, Briones J, Gascoyne RD, Losses IS, Levy R, Weissman IL, Majeti R. 2010. Anti-CD47 antibody synergizes with rituximab to promote phagocytosis and eradicate non-Hodgkin lymphoma. Cell 142:699-713.
Chen, et al., "Functional Interrogation of Primary Human T Cells via CRISPR Genetic Editing" The Journal of Immunology 2018; 201:1586-1598.
Chen J, Zhong MC, Guo H, Davidson D, Mishel S, Lu Y, Rhee I, Pe rez-Quintero LA, Zhang S, Cruz-Munoz ME, Wu N, Vinh DC, Sinha M, Calderon V, Lowell CA, Danska JS, Veillette A. 2017. SLAMF7 is critical for phagocytosis of haematopoietic tumour cells via Mac-1 integrin. Nature 544:493-497.
Cros, et al., "Human CD14dim) Monocytes Patrol and Sense Nucleic Acids and viruses via TLR7 and TLR8 Receptors", Immunity 33, 375-386, Sep. 24, 2010.
Cross SE, Jin YS, Rao J, Gimzewski JK. 2007. Nanomechanical analysis of cells from cancer patients. Nature Nanotechnology 2:780-783.
Da Silva et al.: MICA/B antibody induces macrophage-mediated immunity against acute myeloid leukemia. Blood 139(2):205-216 doi:10.1182/blood.2021011619 (2022).
Davis SJ, van der Merwe PA. 2006. The kinetic-segregation model: TCR triggering and beyond. Nature Immunology 7:803-809.
De Oliveria, S, et al., "Modification of Hematopoietic Stem/Progenitor Cells with CD19-Specific Chimeric Antigen Receptros as a Novel Approach for Cancer Immunotherapy" Human Gene Therapy 24:824-839 (Oct. 2013).
Devereux et al., A comprehensive set of sequence analysis programs for the VAX. Nucleic Acids Res. Jan. 11, 1984;12(1 Pt 1):387-95.

Edelstein A, Amodaj N, Hoover K, Vale R, Stuurman N. 2010. Computer control of microscopes using mmanager. Current Protocols in Molecular Biology 14:Unit14.20.
Engel P, Zhou LJ, Ord DC, Sato S, Koller B, Tedder TF. 1995. Abnormal B lymphocyte development, activation, and differentiation in mice that lack or overexpress the CD19 signal transduction molecule. Immunity 3:39-50.
Senju, Satoru, et al., "Generation and genetic modification of dendritic cells derived from mouse embryonic stem cells derived from mouse embryonics stem cells", Blood, May 1, 2003, vol. 101, No. 9, pp. 3501-3508.
Fesnak AD, June CH, Levine BL. 2016. Engineered T cells: the promise and challenges of cancer immunotherapy. Nature Reviews Cancer 16:566-581.
Fix. Oral controlled release technology for peptides: status and future prospects. Pharm Res. 13(12):1760-1764 (1996).
Fong et al.: High expression of TROP2 correlates with poor prognosis in pancreatic cancer. Br J Cancer 99(8):1290-5. doi: 10.1038/sj.bjc.6604677 (2008).
Fraser, A., et al., "Development, functional characterization and validation of methodology for GMP-compliant manufacture of phagocytic macrophages: A novel cellular therapeutic for liver cirrhosis", Cyotherapy, 2017, ISSN 1465-3249.
Freeman SA, Goyette J, Furuya W, Woods EC, Bertozzi CR, Bergmeier W, Hinz B, van der Merwe PA, Das R, Grinstein S. 2016. Integrins Form an Expanding Diffusional Barrier that Coordinates Phagocytosis. Cell 164: 128-140.
Freeman SA, Grinstein S. 2014. Phagocytosis: receptors, signal integration, and the cytoskeleton. Immunological Reviews 262:193-215.
Gardai SJ, McPhillips KA, Frasch SC, Janssen WJ, Starefeldt A, Murphy-Ullrich JE, Bratton DL, Oldenborg PA, Michalak M, Henson PM. 2005. Cell-surface calreticulin initiates clearance of viable or apoptotic cells through trans-activation of LRP on the phagocyte. Cell 123:321-334.
Geissmann, et al., "Blood Monocytes Consist of Two Principal Subsets with Distinct Migratory Properties", Immunity, vol. 19, pp. 71-82, Jul. 2003.
Getts, Daniel R., "Microparticles bearing encephalitogenic peptides induce T-cell tolerance and ameliorate experimental autoimmune encephalomyelitis", Nat Biotechnol. Dec. 2012; 30(12): 1217-1224.
Gordon, Siamon "Phagocytosis: An Immunobiologic Process"(2016) Immunity 44.
Goudot, C. et al., "Aryl Hydrocarbon Receptro Controls Monocyte Differentiation into Dendritic Cells versus Macrophages", Sep. 19, 2017 Immunity 47, 582-596.
Grunstein et al.: Colony hybridization: A method for the isolation of cloned DNAs that contain a specific gene. Proc. Natl. Acad. Sci. USA. 72:3961-3965 (1975).
Harburger, et al., "Integrin signalling at a glance" (2009) Journal of Cell Sciences 122.
Harshyne LA, Zimmer MI, Watkins SC, Barratt-Boyes SM. 2003. A Role for Class A Scavenger Receptor in Dendritic Cell Nibbling from Live Cells. The Journal of Immunology 170:2302-2309.
Harshyne LA, Watkins SC, Gambotto A, Barratt-Boyes SM. 2001. Dendritic cells acquire antigens from live cells for Cross-Presentation to CTL. The Journal of Immunology 166:3717-3723.
Haso W, Lee DW, Shah NN, Stetler-Stevenson M, Yuan CM, Pastan IH, Dimitrov DS, Morgan RA, FitzGerald DJ, Barrett DM, Wayne AS, Mackall CL, Orentas RJ. 2013. Anti-CD22-chimeric antigen receptors targeting B-cell precursor acute lymphoblastic leukemia. Blood 121:1165-1174.
Huang, Min-Nung, et al., "Antigen-loaded monocyte administration induces potent therapeutic antitumor T cell responses", The Journal of Clinical Investigation, Jan. 6, 2020, pp. 1-15.
Hui E, Vale RD. 2014. In vitro membrane reconstitution of the T-cell receptor proximal signaling network. Nature Structural & Molecular Biology 21:133-142.
Hui, et al., "T cell constimulatory receptor CD28 is a primary target for PD-1-mediated inhibition" (2017) Science 355(6332) p. 1428-1433.
Sica, et al., "Fingolimod Immune Effects Beyond Its Sequestration Ability" Neuurol Ther (2019) 8:231-240.

(56) References Cited

OTHER PUBLICATIONS

Silverstein, et al., "Mechanisms of Cell Signaling by The Scavenger Receptor CD36: Implications in Atherosclerosis and Thrombosis" Transactions of the American Clinical and Climatological Association, vol. 121 (2010), vol. 121.
Ingersoll, Ph.D., Brooke, "Brief Report: Pilot Randomized Controlled Trial of Reciprocal Imitation Training for Teaching Elicited and Spontaneous Imitation to Children with Autism", J Autism Dev Disord. Sep. 2010; 40(9): 1154-1160.
International Search Report and Written Opinion for PCT/US2020/030837 dated Oct. 1, 2020.
Jadus MR, Irwin MC, Irwin MR, Horansky RD, Sekhon S, Pepper KA, Kohn DB, Wepsic HT. 1996. Macrophages can recognize and kill tumor cells bearing the membrane isoform of macrophage colony-stimulating factor. Blood 87:5232-5241.
Jaiswal S, Jamieson CH, Pang WW, Park CY, Chao MP, Majeti R, Traver D, van Rooijen N, Weissman IL. 2009. CD47 is upregulated on circulating hematopoietic stem cells and leukemia cells to avoid phagocytosis. Cell 138:271-285.
James JR, Vale RD. 2012. Biophysical mechanism of T-cell receptor triggering in a reconstituted system. Nature 487:64-69.
Jarrosson-Wuilleme et al.: Transduction of nondividing human macrophages with gammaretrovirus-derived vectors. J Virol. 80(3):1152-1159 doi:10.1128/JVI.80.3.1152-1159.2006 (2006).
Joly E, Hudrisier D. 2003. What is trogocytosis and what is its purpose? Nature Immunology 4:815.
Kao G, Huang CC, Hedgecock EM, Hall DH, Wadsworth WG. 2006. The role of the laminin beta subunit in laminin heterotrimer assembly and basement membrane function and development in C. elegans. Developmental Biology 290:211-219.
Kim, et al., "Monocyte Enrichment from Leukapheresis products by using the Elutra cell separator" Transfusion, vol. 47, Dec. 2007 pp. 2290-2296.
Kimmel et al., [54] Identification and characterization of specific clones: Strategy for confirming the validity of presumptive clones, Methods in enzymology, 152:507-511 (1987).
Kochenderfer JN, Feldman SA, Zhao Y, Xu H, Black MA, Morgan RA, Wilson WH, Rosenberg SA. 2009. Construction and preclinical evaluation of an anti-CD19 chimeric antigen receptor. Journal of Immunotherapy 32:689-702.
Lacerna LV, Stevenson GW, Stevenson HC. 1988. Adoptive cancer immunotherapy utilizing lymphokine activated killer cells and gamma interferon activated killer monocytes. Pharmacology & Therapeutics 38:453-465.
Laird et al. (J. Leukocyte Biology 2009, 85: 966-977).
Lee S, Kivimae S, Dolor A, Szoka FC. 2016. Macrophage-based cell therapies: the long and winding road. Journal of Controlled Release 240:527-540.
Lim, et al., "Antisense oligonucleotide modulation of non-productive alternative splicing upregulates gene expression" (2020) Nature Communication.
Lim WA, June CH, Huang J, Hodes RJ. 2017. The Principles of Engineering Immune Cells to Treat Cancer. Cell 168:724-740.
Liu et al.: Overexpression of TROP2 predicts poor prognosis of patients with cervical cancer and promotes the proliferation and invasion of cervical cancer cells by regulating ERK signaling pathway. PLoS One 8(9):e75864, pp. 1-14 doi:10.1371/journal.pone.0075864 (2013).
Liu X, Pu Y, Cron K, Deng L, Kline J, Frazier WA, Xu H, Peng H, Fu YX, Xu MM. 2015. CD47 blockade triggers T cell-mediated destruction of immunogenic tumors. Nature Medicine 21:1209-1215.
Majeti R, Chao MP, Alizadeh AA, Pang WW, Jaiswal S, Gibbs KD, van Rooijen N, Weissman IL. 2009. CD47 is an adverse prognostic factor and therapeutic antibody target on human acute myeloid leukemia stem cells. Cell 138:286-299.
Matsuyoshi, Hidetake, et al., "Enchanced Priming of Antigen-Specific CTL's In Vivo by Embryonic Stem Cell-Derived Dendritic Cells Expressing Chemokine Along with Antigenic Protein: Application to Antitumor Vaccination", The Journal of Immunology (2004) 172:776-786.
Mayordomo JI, Zorina T, Storkus WJ, Zitvogel L, Celluzzi C, Falo LD, Melief CJ, Ildstad ST, Kast WM, Deleo AB. 1995. Bone marrow-derived dendritic cells pulsed with synthetic tumour peptides elicit protective and therapeutic antitumour immunity. Nature Medicine 1:1297-1302.
McEver, et al., "Selectins: initiators of leucocyte adhesion and signalling at the vascular wall" Cardovascular Research (2015) 107, pp. 331-339.
Mildner, A., et al., "Distinct and Non-Redundant Roles of Microglia and Myeloid Subsets in Mouse Models of Alzheimer's Disease" Neurobiology of Disease, J. Neurosci., Aug. 3, 2011, 31(31):11159-11171.
Morrissey, M., et al., "Chimeric antigen receptros that trigger phagocytosis", eLife 2018, pp. 1/21.
Mukherjee, R et al., "Non-Classical monocytes display inflammatory features: Validation in Sepsis and Systemic Lupus Erythematous", Scientific Reports, (2015) pp. 1-14.
Murshid, Ayesha, et al., "Hsp90-peptide complexes stimulate antigen presentation through the class II pathway after binding scavenger receptor SREC-1", Immunobiology, Dec. 2014; 219(12); 924-931.
Ning et al.: TROP2 correlates with microvessel density and poor prognosis in hilar cholangiocarcinoma. J Gastrointest Surg 17(2):360-368 doi:10.1007/s11605-012-2105-1 (2013).
Soderberg et al. (J. Virology 1993 67(6): 3166-3175).
Oviedo-Boyso, et al., "The Phosphoinositide-3-Kinase-Akt Signaling Pathway Is Important for *Staphylococcus aureus* Internalization by Endothelial Cells" (2011) Infection and Immunity, vol. 79, No. 11, p. 4569-4577.
Passlick, et al., "Identification and Characterization of a Novel Monocyte Subpopulation in Human Peripheral Blood", Article in Blood, Dec. 1989, 74: 2527-2534.
Patel, et al., "The fate and lifespan of human monocyte subsets in steady state and systemic inflammation" J.Exp. Med. (2017), vol. 214, No. 7 p. 1913-1923.
PCT/US2019/060052 International Search Report and Written Opinion dated Apr. 30, 2020.
PCT/US2020/037312 International Search Report dated Nov. 30, 2020.
PCT/US2020/049240 International Search Report dated Mar. 26, 2021.
Penberthy KK, Ravichandran KS. 2016. Apoptotic cell recognition receptors and scavenger receptors. Immunological Reviews 269:44-59.
Ralston KS, Solga MD, Mackey-Lawrence NM, Somlata , Bhattacharya A, Petri WA. 2014. Trogocytosis by Entamoeba histolytica contributes to cell killing and tissue invasion. Nature 508:526-530.
Ravin. Chapter 76: Preformulation. Remington's Pharmaceutical Sciences, 17th ed., Mack Publishing Company, Easton, Pa. (pp. 1409-1423) (1985).
Roberts EW, Broz ML, Binnewies M, Headley MB, Nelson AE, Wolf DM, Kaisho T, Bogunovic D, Bhardwaj N, Krummel MF. 2016. Critical Role for CD103(+)/CD141(+) Dendritic Cells Bearing CCR7 for Tumor Antigen Trafficking and Priming of T Cell Immunity in Melanoma. Cancer Cell 30:324-336.
Roberts, Margo R., et al."Antigen-Specific Cytolysis by Neutrophils and NK Cells Expressing Chimeric Immune Receptros Bearing xx Signaling Domains", J Immunol 1998; 161:375-384.
Rosales, C. et al., "Phagocytosis: A Fundamental Process in Immunity", BioMed Research International, vol. 2017, Article ID 9042851, 18 pages.
Ruiz-Aguilar, S., et al., "Human CD16+ and CD16+ monocyte subsets display unique effector properties in inflammatory conditions in vivo", Journal of Leukocyte Biology, (2011) vol. 90, pp. 1119-1131.
Samanen et al. Chemical approaches to improve the oral bioavailability of peptidergic molecules. J. Pharm. Pharmacol. 48:119-135 (1996).
Schlam D, Bagshaw RD, Freeman SA, Collins RF, Pawson T, Fairn GD, Grinstein S. 2015. Phosphoinositide 3-kinase enables phagocytosis

(56) References Cited

OTHER PUBLICATIONS of large particles by terminating actin assembly through Rac/Cdc42 GTPase-activating proteins. Nature Communications 6:8623.
Senju, et al., "Generation of dendritic cells and macrophages from human induced pluripotent stem cells aiming at cell therapy" Gene Therapy (2011) 18, 874-883.
Su X, et al., Phase separation of signaling molecules promotes T cell receptor signal transduction, Science. Apr. 29, 2016; 352(6285): 595-599.
Tippet et al. (J. Leukocyte Biology 2013 93: 913-920).
Strauss, et al., "The immunophenotype of antigen presenting cells of the mononuclear phagocyte system in a normal human liver—A systematic review" Journal of Hepatology, (2015) vol. 62, pp. 458-468.
Tseng D, Volkmer JP, Willingham SB, Contreras-Trujillo H, Fathman JW, Fernhoff NB, Seita J, Inlay MA, Weiskopf K, Miyanishi M, Weissman IL. 2013. Anti-CD47 antibody-mediated phagocytosis of cancer by macrophages primes an effective antitumor T-cell response. PNAS 110:11103-11108.
Tsutsui, et al. "The use of microbubbles to target drug delivery" Cardiovascular Ultrasound (2004) 2:23.
Tuveson DA, Carter RH, Soltoff SP, Fearon DT. 1993. CD19 of B cells as a surrogate kinase insert region to bindphosphatidylinositol 3-kinase. Science 260:986-989.
Wahl et al., [43] Molecular hybridization of immobilized nucleic acids: Theoretical concepts and practical considerations, Methods in enzymology, Academic Press, 152:399-407 (1987).
Wang et al.: Innate Immune Cells: A Potential and Promising Cell Population for Treating Osteosarcoma. Front Immunol. 10(1114):1-14 doi:10.3389/fimmu.2019.01114 (2019).
Weischenfeldt J, Porse B. 2008. Bone Marrow-Derived Macrophages (BMM): Isolation and Applications. Cold Spring Harbor Protocols 2008:pdb.prot5080.
Wilkinson et al. (Med. Microbio. Immunol. 2015 204:273-284).
Xiao, et al., 1997, Electrophysiological Characteristics of Primary Afferent Fibers After Systemic Administration of Anti-GC2 Ganglioside Antibody, Pain69: 145-151.
Xiao X, Ho M, Zhu Z, Pastan I, Dimitrov DS. 2009. Identification and characterization of fully human anti-CD22 monoclonal antibodies. mAbs 1:297-303.
Yong, C., et al., "A role for multiple chimeric antigen receptor-expressing leukocytes in antigen-specific responses to cancer" (2016) Oncotarget, vol. 7, No. 23 pp. 34582-34598.
Zhao et al.: Trop2 is overexpressed in gastric cancer and predicts poor prognosis. Oncotarget 7(5):6136-6145 doi:10.18632/oncotarget. 6733 (2016).
Azad et al. γ-Tilmanocept, a New Radiopharmaceutical Tracer for Cancer Sentinel Lymph Nodes, Binds to the Mannose Receptor (CD206). J. Immunol. 195:2019-2029 (2015). Epub Jul. 22, 2015.
Baeuerle et al. Synthetic TRuC receptors engaging the complete T cell Receptor for potent anti-tumor response. Nat Commun 10:2087 (2019).
De Kleer I, et al. Ontogeny of myeloid cells. Front Immunol. Sep. 3, 2014;5:423.
Flynn RA, et al. Small RNAs are modified with N-glycans and displayed on the surface of living cells. Cell. Jun. 10, 2021;184(12):3109-3124.e22. Epub May 17, 2021.
Ham JS, et al. Elevated serum interleukin-10 level and M2 macrophage infiltration are associated with poor survival in angioimmunoblastic T-cell lymphoma. Oncotarget. Jul. 17, 2017;8(44):76231-76240.
Hou X, et al. Lipid nanoparticles for mRNA delivery. Nat Rev Mater. 2021;6(12):1078-1094. Epub Aug. 10, 2021.
Kwon B. CD137-CD137 Ligand Interactions in Inflammation. Immune Netw. Jun. 2009;9(3):84-9. Epub Jun. 30, 2009.
Milatz S, et al. Claudin-3 acts as a sealing component of the tight junction for ions of either charge and uncharged solutes. Biochim Biophys Acta. Nov. 2010;1798(11):2048-57. Epub Jul. 22, 2010.
Mo F, et al. Engineered off-the-shelf therapeutic T cells resist host immune rejection. Nat Biotechnol. Jan. 2021;39(1):56-63. Epub Jul. 13, 2020.
PCT/US2021/058104 International Search Report and Written Opinion dated Apr. 28, 2022.
Salmon H, et al. Expansion and Activation of CD103(+) Dendritic Cell Progenitors at the Tumor Site Enhances Tumor Responses to Therapeutic PD-L1 and BRAF Inhibition. Immunity. Apr. 19, 2016;44(4):924-38.
Singh P, et al. Anti-claudin 18.2 antibody as new targeted therapy for advanced gastric cancer. J Hematol Oncol. May 12, 2017;10(1):105.
Yang M, et al. Stromal Infiltration of Tumor-Associated Macrophages Conferring Poor Prognosis of Patients with Basal-Like Breast Carcinoma. J Cancer. Jun. 6, 2018;9(13):2308-2316.

* cited by examiner

2/4 treated have complete response by histology
No tumor detected

Non-treated group show large tumors, with little to no cell infiltration. Necrotic core is present

ENGINEERED CHIMERIC FUSION PROTEIN COMPOSITIONS AND METHODS OF USE THEREOF

CROSS REFERENCE

This application is a continuation application of PCT application PCT/US21/58104, filed on Nov. 4, 2021, and claims the benefit of U.S. Provisional Application No. 63/109,445, filed on Nov. 4, 2020; U.S. Provisional Application No. 63/251,400, filed on Oct. 1, 2021; U.S. Provisional Application No. 63/196,994 filed on Jun. 4, 2021; and U.S. Provisional Application No. 63/162,205 filed on Mar. 17, 2021; each of which is incorporated herein by reference in its entirety.

SEQUENCE LISTING

The instant application contains a Sequence Listing which has been submitted electronically in ASCII format and is hereby incorporated by reference in its entirety. Said ASCII copy, created on Dec. 8, 2021, is named 56371-712_601_SL.txt and is 84,863 bytes in size.

BACKGROUND

Cellular immunotherapy is a promising new technology for fighting difficult to treat diseases, such as cancer, and persistent infections and also certain diseases that are refractory to other forms of treatment. A major breakthrough has come across with the discovery of CAR-T cell and their potential use in immunotherapy. CAR-T cells are T lymphocytes expressing a chimeric antigen receptor which helps target the T cell to specific diseased cells such as cancer cells, and can induce cytotoxic responses intended to kill the target cancer cell or immunosuppression and/or tolerance depending on the intracellular domain employed and co-expressed immunosuppressive cytokines. However, several limitations along the way has slowed the progress on CAR-T cells and dampened its promise in clinical trials.

Understanding the limitations of CAR-T cells is the key to leveraging the technology and continue innovations towards better immunotherapy models. Specifically, in T cell malignancies, CAR-T cells appear to have faced a major problem. CAR-T cells and malignant T cells share surface antigen in most T cell lymphomas (TCL), therefore, CAR-T cells are subject to cytotoxicity in the same way as cancer cells. In some instances, the CAR-T products may be contaminated by malignant T cells. Additionally, T cell aplasia is a potential problem due to prolonged persistence of the CAR-T cells. Other limitations include the poor ability for CAR-T cells to penetrate into solid tumors and the potent tumor microenvironment which acts to downregulate their anti-tumor potential. CAR-T cell function is also negatively influenced by the immunosuppressive tumor microenvironment (TME) that leads to endogenous T cell inactivation and exhaustion.

Myeloid cells, including macrophages, are cells derived from the myeloid lineage and belong to the innate immune system. They are derived from bone marrow stem cells which egress into the blood and can migrate into tissues. Some of their main functions include phagocytosis, the activation of T cell responses, and clearance of cellular debris and extracellular matrices. They also play an important role in maintaining homeostasis, and initiating and resolving inflammation. Moreover, myeloid cells can differentiate into numerous downstream cells, including macrophages, which can display different responses ranging from pro-inflammatory to anti-inflammatory depending on the type of stimuli they receive from the surrounding microenvironment. Furthermore, tissue macrophages have been shown to play a broad regulatory and activating role on other immune cell types including CDT effector cells, NK cells and T regulatory cells. Macrophages have been shown to be a main immune infiltrate in malignant tumors and have been shown to have a broad immunosuppressive influence on effector immune infiltration and function.

Myeloid cells are a major cellular compartment of the immune system comprising monocytes, dendritic cells, tissue macrophages, and granulocytes. Models of cellular ontogeny, activation, differentiation, and tissue-specific functions of myeloid cells have been revisited during the last years with surprising results. However, their enormous plasticity and heterogeneity, during both homeostasis and disease, are far from understood. Although myeloid cells have many functions, including phagocytosis and their ability to activate T cells, production of soluble factors, harnessing these functions for therapeutic uses has remained elusive. Newer avenues are therefore sought for using other cell types towards development of improved therapeutics, including but not limited to T cell malignancies.

In vivo or ex vivo engineered myeloid cells can also be short-lived in vivo, phenotypically diverse, sensitive, plastic, and are often found to be difficult to manipulate in vitro. For example, exogenous gene expression in monocytes has been difficult compared to exogenous gene expression in non-hematopoietic cells. There are significant technical difficulties associated with transfecting myeloid cells (e.g., monocytes/macrophages). As professional phagocytes, myeloid cells, such as monocytes/macrophages, comprise many potent degradative enzymes that can disrupt nucleic acid integrity and make gene transfer into these cells an inefficient process. This is especially true of activated macrophages which undergo a dramatic change in their physiology following exposure to immune or inflammatory stimuli. Viral transduction of these cells has been hampered because macrophages are end-stage cells that generally do not divide; therefore, some of the vectors that depend on integration into a replicative genome have met with limited success. Furthermore, macrophages are quite responsive to "danger signals," and therefore several of the original viral vectors that were used for gene transfer induced potent anti-viral responses in these cells making these vectors inappropriate for gene delivery.

SUMMARY

The diverse functionality of myeloid cells makes them an ideal cell therapy candidate that can be engineered to have numerous therapeutic effects. The present disclosure is related to immunotherapy using myeloid cells (e.g., CD14+ cells) of the immune system, particularly phagocytic cells. A number of therapeutic indications could be contemplated using myeloid cells. For example, myeloid cell immunotherapy could be exceedingly important in cancer, autoimmunity, fibrotic diseases and infections. The present disclosure is related to immunotherapy using myeloid cells, including phagocytic cells of the immune system, particularly macrophages. It is an object of the invention disclosed herein to harness one or more of these functions of myeloid cells for therapeutic uses. For example, it is an object of the invention disclosed herein to harness the phagocytic activity of myeloid cells, including engineered myeloid cells, for therapeutic uses. For example, it is an object of the invention disclosed herein to harness the ability of myeloid cells, including engineered myeloid cells, to promote T cell activation. For example, it is an object of the invention disclosed herein to harness the ability of myeloid cells, including engineered myeloid cells, to promote secretion of tumoricidal molecules. For example, it is an object of the invention disclosed herein to harness the ability of myeloid cells, including engineered myeloid cells, to promote recruitment and trafficking of immune cells and molecules. The present disclosure provides innovative methods and compositions that can successfully transfect or transduce a myeloid cell, or otherwise induce a genetic modification in a myeloid cell, with the purpose of augmenting a functional aspect of a myeloid cell, additionally, without compromising the cell's differentiation capability, maturation potential, and/or its plasticity. The myeloid cell may reside in vivo inside the body or be engineered ex vivo.

The present disclosure involves programming myeloid cells in vivo or ex vivo, making and using engineered myeloid cells (e.g., CD14+ cells, such as macrophages or other phagocytic cells, which can attack and kill (ATAK) diseased cells directly and/or indirectly, such as cancer cells and infected cells. Engineered myeloid cells, such as macrophages and other phagocytic cells, can be prepared by incorporating nucleic acid sequences (e.g., mRNA, plasmids, viral constructs) encoding a chimeric fusion protein (CFP), that has an extracellular binding domain specific to disease associated antigens (e.g., cancer antigens), into the cells using, for example, ex vivo using recombinant nucleic acid technology, synthetic nucleic acids, gene editing techniques (e.g., CRISPR), transduction (e.g., using viral constructs), electroporation, or nucleofection, or in vivo using mRNA delivery technology including but not limited to LNP technology. It has been found that myeloid cells can be engineered to have a broad and diverse range of activities. For example, it has been found that myeloid cells can be engineered to express a chimeric fusion protein (CFP) containing an antigen binding domain to have a broad and diverse range of activities. For example, it has been found that myeloid cells can be engineered to have enhanced phagocytic activity such that upon binding of the CFP to an antigen on a target cell, the cell exhibits increased phagocytosis of the target cell. It has also been found that myeloid cells can be engineered to promote T cell activation such that upon binding of the CFP to an antigen on a target cell, the cell promotes activation of T cells, such as T cells in the tumor microenvironment. Myeloid cells can be engineered to promote secretion of tumoricidal molecules such that upon binding of the CFP to an antigen on a target cell, the cell promotes secretion of tumoricidal molecules from nearby cells. Myeloid cells can be engineered to promote recruitment and trafficking of immune cells and molecules such that upon binding of the CFP to an antigen on a target cell, the cell promotes recruitment and trafficking of immune cells and molecules to the target cell or a tumor microenvironment.

The present disclosure is based on the important finding that engineered myeloid cells overcome at least some of the limitations of CAR-T cells, including being readily recruited to solid tumors; having short, as well as engineerable duration of survival, therefore lowering the risk of prolonged persistence resulting in aplasia and immunodeficiency; myeloid cells cannot be contaminated with T cells; myeloid cells can avoid fratricide, at least because they do not express the same antigens as malignant T cells; and myeloid cells have a plethora of anti-tumor functions that can be deployed. In some respects, engineered myeloid derived cells can be safer immunotherapy tools to target and destroy diseased cells.

Moreover, myeloid cells, such as macrophages, have been ubiquitously found in the tumor environment (TME) and are notably the most abundant cells in some tumor types. As part of their role in the immune system, myeloid cells, such as macrophages, are naturally engaged in clearing diseased cells. The present invention relates too harnessing myeloid cell function and specifically for targeting, killing and directly and/or indirectly clearing diseased cells as well as the delivery payloads such as antigens and cytokines.

The present disclosure is also based on the important finding that engineered myeloid cells can promote endogenous T cell activity. The present disclosure involves, in addition to the programming of myeloid cells. Engineered myeloid cells can be achieved through the in vivo incorporation of nucleic acid sequences (e.g., mRNA, plasmids, viral constructs) encoding a chimeric fusion protein (CFP), that has an extracellular binding domain specific to disease associated antigens (e.g., cancer antigens), into the cells using, for example, ex vivo using recombinant nucleic acid technology, synthetic nucleic acids, gene editing techniques (e.g., CRISPR), transduction (e.g., using viral constructs), electroporation, or nucleofection, or in vivo using mRNA delivery technology including but not limited to LNP technology.

Engineered myeloid cells can also be short-lived in vivo, phenotypically diverse, sensitive, plastic, and are often found to be difficult to manipulate in vitro. For example, exogenous gene expression in monocytes has been difficult compared to exogenous gene expression in non-hematopoietic cells. There are significant technical difficulties associated with transfecting myeloid cells (e.g., monocytes/macrophages). As professional phagocytes, myeloid cells, such as monocytes/macrophages, comprise many potent degradative enzymes that can disrupt nucleic acid integrity and make gene transfer into these cells an inefficient process. This is especially true of activated macrophages which undergo a dramatic change in their physiology following exposure to immune or inflammatory stimuli. Viral transduction of these cells has been hampered because macrophages are end-stage cells that generally do not divide; therefore, some of the vectors that depend on integration into a replicative genome have met with limited success. Furthermore, macrophages are quite responsive to "danger signals," and therefore several of the original viral vectors that were used for gene transfer induced potent anti-viral responses in these cells making these vectors inappropriate for gene delivery. The present disclosure provides innovative methods and compositions that can successfully transfect or transduce a myeloid cell, or otherwise induce a genetic modification in a myeloid cell, with the purpose of augmenting a functional aspect of a myeloid cell, additionally, without compromising the cell's differentiation capability, maturation potential, and/or its plasticity.

Provided herein are therapeutic agents directed to bind to certain antigens that are expressed on a diseased cell, for example, a cancer cell, and binding of the therapeutic agents (e.g., targeted "binders") to a target antigen on a target diseased cells initiates the process of destruction of the target cell. A therapeutic agent described herein may be a recombinant nucleic acid that can be expressed in a suitable cell, such as a mammalian cell, such as a human cell, wherein the suitable cell may be a myeloid cell. In some embodiments, a therapeutic agent described herein may be a recombinant protein that can bind to the target antigen on a target cell. In some a therapeutic agent described herein may be a cell, for example, a myeloid cell, wherein the myeloid cell comprises a recombinant nucleic acid described herein, and/or expresses a recombinant protein described herein, such that the myeloid cell can be targeted to a diseased cell, expressing the target antigen on the surface of the cell; and the myeloid cell lyses or phagocytizes the diseased cell.

In some embodiments, the therapeutic agent is a myeloid cell such as described herein. In some embodiments, the myeloid cell is a myeloid precursor cell. In some embodiments, the myeloid cell is an undifferentiated and/or unpolarized myeloid cell. In some embodiments, the myeloid cell is a phagocytic cell. In some embodiments, the myeloid cell is a CD14+/CD16− cell.

In some embodiments, the therapeutic agent is a recombinant or engineered nucleic acid. In some embodiments, the nucleic acid is RNA.

In some embodiments, the engineered nucleic acid is an mRNA. In some embodiments, the therapeutic agent that is a recombinant or engineered nucleic acid encodes a chimeric fusion receptor protein (CFP).

In some embodiments, the recombinant nucleic acid encodes an extracellular or soluble protein, which is also known as an "engager" that binds to a target antigen on a diseased cell with a target binder domain, located for example, at one end of the protein; and is capable of binding to an effector cell such as an effector myeloid cell, e.g., an active phagocytic cell with at least another domain that binds to a molecule on the structure of the effector cell, such as the myeloid cell. Exemplary engagers are bi-specific engagers (BiMEs), or trispecific engagers (TRiMEs) as described herein.

In one aspect, disclosed herein is a composition comprising a recombinant nucleic acid encoding a chimeric fusion protein (CFP) comprising: (a) a phagocytic or tethering receptor (PR) subunit comprising: (i) a transmembrane domain, or (ii) an intracellular domain comprising an intracellular signaling domain; and (b) an extracellular domain comprising a CD137 antigen binding domain that can bind specifically to CD137 on a target cell; wherein the extracellular and the transmembrane domains are operably linked.

In one aspect, disclosed herein is a composition comprising a recombinant nucleic acid encoding a chimeric fusion protein comprising: (a) a first CD137 antigen binding domain that specifically binds to CD137 antigen on a target cell, and (b) a second binding domain that specifically binds to a surface agent on a myeloid cell; wherein, binding of the first antigen binding domain to CD137 antigen on a target cell and binding of the second binding domain on a surface agent on a myeloid cell.

In one aspect, disclosed herein is a composition comprising a recombinant nucleic acid encoding a chimeric fusion protein (CFP) comprising: (a) a phagocytic or tethering receptor (PR) subunit comprising: (i) a transmembrane domain, or (ii) an intracellular domain comprising an intracellular signaling domain; and (b) an extracellular domain comprising a Claudin 18.2 antigen binding domain that can bind specifically to Claudin 18.2 on a target cell; wherein the extracellular and the transmembrane domains are operably linked.

In one aspect, disclosed herein is a composition comprising a recombinant nucleic acid encoding a chimeric fusion protein comprising: (a) a first Claudin 18.2 antigen binding domain that specifically binds to Claudin 18.2 antigen on a target cell, and (b) a second binding domain that specifically binds to a surface agent on a myeloid cell; wherein, binding of the first antigen binding domain to Claudin 18.2 antigen on a target cell and binding of the second binding domain on a surface agent on a myeloid cell.

In one aspect, disclosed herein is a composition comprising a recombinant nucleic acid encoding a chimeric fusion protein (CFP) comprising: (a) a phagocytic or tethering receptor (PR) subunit comprising: (i) a transmembrane domain, or (ii) an intracellular domain comprising an intracellular signaling domain; and (b) an extracellular domain comprising a Claudin 3 antigen binding domain that can bind specifically to Claudin 3 on a target cell; wherein the extracellular and the transmembrane domains are operably linked.

In one aspect, disclosed herein is a composition comprising a recombinant nucleic acid encoding a chimeric fusion protein comprising: (a) a first Claudin 3 antigen binding domain that specifically binds to Claudin 3 antigen on a target cell, and (b) a second binding domain that specifically binds to a surface agent on a myeloid cell; wherein, binding of the first antigen binding domain to Claudin 18.2 antigen on a target cell and binding of the second binding domain on a surface agent on a myeloid cell.

In one aspect, disclosed herein is a composition comprising a recombinant nucleic acid encoding a chimeric fusion protein (CFP) comprising: (a) a phagocytic or tethering receptor (PR) subunit comprising: (i) a transmembrane domain, or (ii) an intracellular domain comprising an intracellular signaling domain; and (b) an extracellular domain comprising a CD70 antigen binding domain that can bind specifically to CD70 on a target cell; wherein the extracellular and the transmembrane domains are operably linked.

In one aspect, disclosed herein is a composition comprising a recombinant nucleic acid encoding a chimeric fusion protein comprising: (a) a first CD70 antigen binding domain that specifically binds to CD70 antigen on a target cell, and (b) a second binding domain that specifically binds to a surface agent on a myeloid cell; wherein, binding of the first antigen binding domain to CD70 antigen on a target cell and binding of the second binding domain on a surface agent on a myeloid cell.

In one aspect, disclosed herein is a composition comprising a recombinant nucleic acid encoding a chimeric fusion protein (CFP) comprising: (a) a phagocytic or tethering receptor (PR) subunit comprising: (i) a transmembrane domain, or (ii) an intracellular domain comprising an intracellular signaling domain; and (b) an extracellular domain comprising a TROP2 antigen binding domain that can bind specifically to TROP2 on a target cell; wherein the extracellular and the transmembrane domains are operably linked.

In one aspect, disclosed herein is a composition comprising a recombinant nucleic acid encoding a chimeric fusion protein comprising: (a) a first TROP2 antigen binding domain that specifically binds to TROP2 antigen on a target cell, and (b) a second binding domain that specifically binds to a surface agent on a myeloid cell; wherein, binding of the first antigen binding domain to TROP2 antigen on a target cell and binding of the second binding domain on a surface agent on a myeloid cell.

In one aspect, disclosed herein is a composition comprising a recombinant nucleic acid encoding a chimeric fusion protein (CFP) comprising: (a) a phagocytic or tethering receptor (PR) subunit comprising: (i) a transmembrane domain, or (ii) an intracellular domain comprising an intracellular signaling domain; and (b) an extracellular domain comprising a TMPRSS antigen binding domain that can bind specifically to TMPRSS on a target cell; wherein the extracellular and the transmembrane domains are operably linked.

In one aspect, disclosed herein is a composition comprising a recombinant nucleic acid encoding a chimeric fusion protein comprising: (a) a first TMPRSS antigen binding domain that specifically binds to TMPRSS antigen on a target cell, and (b) a second binding domain that specifically binds to a surface agent on a myeloid cell; wherein, binding of the first antigen binding domain to TMPRSS antigen on a target cell and binding of the second binding domain on a surface agent on a myeloid cell.

In one aspect, disclosed herein is a composition comprising a recombinant nucleic acid encoding a phagocytic or tethering receptor (PR) fusion protein (PFP) comprising: (a) a PR subunit comprising: (i) a transmembrane domain, and (ii) an intracellular domain comprising an intracellular signaling domain; and (b) an extracellular domain comprising an antigen binding domain of any one of the described above, having a strong binding affinity to an antigen of a target cell; wherein the transmembrane domain and the extracellular domain are operatively linked; and wherein upon binding of the PFP to the antigen of the target cell, the killing or phagocytosis activity of a cell expressing the PFP is increased by at least greater than 20% compared to a cell not expressing the PFP.

In some embodiments, the intracellular signaling domain of any one of the PFPs described herein is derived from a phagocytic or tethering receptor or wherein the intracellular signaling domain comprises a phagocytosis activation domain.

In some embodiments, the intracellular signaling domain comprises a pro-inflammatory signaling domain.

In some embodiments, the pro-inflammatory signaling domain comprises a kinase activation domain or a kinase binding domain.

In some embodiments, the intracellular signaling domain comprises a PI3 kinase recruitment domain.

In some embodiments, the pro-inflammatory signaling domain comprises an IL-1 signaling cascade activation domain.

In some embodiments, the pro-inflammatory signaling domain comprises an intracellular signaling domain derived from TLR3, TLR4, TLR7, TLR 9, TRIF, RIG-1, MYD88, MAL, IRAK1, MDA-5, an IFN-receptor, an NLRP family member, NLRP1-14, NOD1, NOD2, Pyrin, AIM2, NLRC4, FCGR3A, FCERIG, CD40, a caspase domain or a pro-caspase binding domain or any combination thereof.

In some embodiments, any one of the PFPs described herein further comprises a transmembrane domain derived from a CD2, CD8, CD28, CD64 or CD68 protein TM domain.

In some embodiments, any one of the PFPs described herein further comprises further comprises a hinge domain.

In some embodiments, upon binding of the PFP to the antigen of the target cell, the killing activity of a cell expressing the PFP is increased by at least greater than 20% compared to a cell not expressing the PFP.

In some embodiments, upon binding of the PFP to the antigen of the target cell, the killing activity of a cell expressing the PFP is increased by at least 1.1-fold compared to a cell not expressing the PFP.

In some embodiments, the composition comprises a first therapeutic agent, wherein the therapeutic agent comprises: a first binding domain, wherein the first binding domain is a first antibody or functional fragment thereof that specifically interacts with an antigen on a target cell, and a second binding domain, wherein the second binding domain is a second antibody or functional fragment thereof that specifically interacts with a myeloid cell; wherein, (i) the first therapeutic agent is coupled to a first component, wherein the first component is an additional therapeutic agent or a third binding domain, or (ii) In some embodiments, the composition comprises an additional therapeutic agent.

In some embodiments, the therapeutic agent comprises: (a) a first binding domain that specifically interacts with an antigen of a target cell, (b) a second binding domain that specifically interacts with a myeloid cell, and (c) a third binding domain that specifically interacts with the myeloid cell.

In some embodiments, any one of binding domains of the therapeutic agent comprises the binding domain of an antibody, a functional fragment of an antibody, a variable domain thereof, a $V_H$ domain, a $V_L$ domain, a VNAR domain, a $V_{HH}$ domain, a single chain variable fragment (scFv), an Fab, a single-domain antibody (sdAb), a nanobody, a bispecific antibody, a diabody, or a functional fragment or a combination thereof.

In some embodiments, the antigen on the target cell to which the first binding domain binds, is a cancer antigen or a pathogenic antigen on the target cell or an autoimmune antigen.

In some embodiments, the first therapeutic agent comprises a polypeptide that is less than 1000 amino acids or 1000 nm in length. In some embodiments, the first therapeutic agent comprises a polypeptide that is less than 500 amino acids or 500 nm in length. In some embodiments, the first therapeutic agent comprises a polypeptide that is 200-1000 amino acids or 200-1000 nm in length.

In some embodiments, engagement of the binding domains of the first therapeutic agent contacts the cancer cell to the myeloid cell.

In some embodiments, the second binding domain specifically interacts with a myeloid cell and promotes phagocytosis activity of the myeloid cell.

In some embodiments, the second binding domain specifically interacts with a myeloid cell and promotes inflammatory signaling of the myeloid cell.

In some embodiments, the second binding domain specifically interacts with a myeloid cell or an adhesion molecule and promotes adhesion of the myeloid cell to the target cell.

In some embodiments, the second binding domain specifically interacts with a myeloid cell and inhibits anti-phagocytic activity of the myeloid cell mediated by the target cell.

In some embodiments, the second binding domain specifically interacts with a myeloid cell and inhibits anti-inflammatory activity of the myeloid cell mediated by the target cell.

In some embodiments, the second and/or the third binding domain promotes phagocytic activity of the myeloid cell.

In some embodiments, the second and/or the third binding domain promotes inflammatory signaling of the myeloid cell.

In some embodiments, the second and/or the third binding domain specifically interacts with a myeloid cell or an adhesion molecule and promotes adhesion of the myeloid cell to the target cell.

In some embodiments, the second and/or the third binding domain inhibits anti-phagocytic activity of the myeloid cell mediated by the target cell.

In some embodiments, the second and/or the third binding domain inhibits anti-inflammatory activity of the myeloid cell mediated by the target cell.

In some embodiments, the third binding domain or the additional therapeutic agent comprises a CD47 antagonist, a CD47 blocker, an antibody, a chimeric CD47 receptor, a sialidase, a cytokine, a proinflammatory gene, a procaspase, or an anti-cancer agent.

In some embodiments, the third binding domain or the additional therapeutic agent comprises a SIRP-alpha antagonist, a SIRPA blocker, an antibody, a chimeric SIRPA receptor, a cytokine, a proinflammatory gene, a procaspase, or an anti-cancer agent.

In some embodiments, the third binding domain or the additional therapeutic agent comprises a PD1 antagonist, a PD1 blocker, an antibody, a chimeric PD1 receptor, a cytokine, a proinflammatory gene, a procaspase, or an anti-cancer agent.

In some embodiments, the second binding domain and the third binding domain bind to distinct non-identical target antigens.

In some embodiments, the first binding domain, the second binding domain or the third binding domain is a ligand binding domain.

In some embodiments, the first, the second or the third binding domains are operably linked by one or more linkers.

In some embodiments, the linker is a polypeptide. In some embodiments, the linker is a functional peptide. In some embodiments, the linker is a ligand for a receptor. In some embodiments, the ligand for a monocyte or macrophage receptor. In some embodiments, the linker activates the receptor. In some embodiments, the linker inhibits the receptor.

In some embodiments, the linker is a ligand for a M2 macrophage receptor. In some embodiments, the linker is a ligand for a TLR receptor, such as TLR4. In some embodiments, the linker activates a TLR receptor. In some embodiments, the first, the second and/or the third binding domains are associated with a mask that binds to the binding domain.

In some embodiments, the mask is an inhibitor that inhibits the interaction of binding domain to its target when the mask remains associated with the respective binding domain. In some embodiments, the mask is associated with the binding domain via a peptide linker. In some embodiments, the linker comprises a cleavable moiety.

In some embodiments, the cleavable moiety is cleaved by a protein or an enzyme selectively abundant in the site of the cancer or tumor.

In some embodiments, the therapeutic agent is a nucleic acid, e.g., an engineered nucleic acid, wherein the nucleic acid is an RNA.

In some embodiments, the nucleic acid is an mRNA.

In some embodiments, the nucleic acid is an self-replicating RNA designed to target a myeloid cell.

In some embodiments, the nucleic acid, that is, the engineered nucleic acid is an circRNA designed to target a myeloid cell designed to target a myeloid cell.

In some embodiments, the engineered recombinant nucleic acid is an RNA designed to target a myeloid cell.

In some embodiments, the engineered nucleic acid is an mRNA designed to target a myeloid cell.

In some embodiments, the engineered nucleic acid is an self-replicating RNA designed to target a myeloid cell.

In some embodiments, the engineered nucleic acid is an circRNA designed to target a myeloid cell.

In some embodiments, the engineered, recombinant nucleic acid is associated with one or more lipids.

In some embodiments, the recombinant nucleic acid is encapsulated in a liposome.

In some embodiments, the liposome is a nanoparticle.

In some embodiments, the recombinant nucleic acid is comprised in a vector.

Provided herein is a pharmaceutical composition comprising any one of the recombinant nucleic acids of the compositions of the embodiments described above, and an acceptable excipient.

Provided herein is a pharmaceutical composition comprising a polypeptide encoded by a recombinant nucleic acid encoding any one of the recombinant proteins described above.

Provided herein is a cell comprising the recombinant nucleic acid encoding any one of the recombinant proteins described above.

In some embodiments, the cell is a myeloid cell.

In some embodiments, the cell is CD14+, CD16−.

Provided herein is a pharmaceutical composition comprising a population of cells that comprise a recombinant nucleic acid of any one of the embodiments described above, wherein at least 50% of the cells are CD14+CD16−.

In some embodiments, less than 10% of the cells of the pharmaceutical composition are dendritic cells.

In some embodiments, the pharmaceutical composition, further comprising a suitable excipient.

Provided herein is a method of making any one of the compositions of any one of the embodiments described above.

In one aspect, provided herein is a method of treating a cancer in a subject, comprising administering to the subject a pharmaceutical composition of any one of the embodiments described above.

In one aspect, provided herein is a method of treating a cancer in a subject, comprising administering to the subject the pharmaceutical composition of any one of the embodiments described above.

In some embodiments, the cancer is selected from a group consisting of gastric cancer, ovarian cancer, renal cancer, breast cancer, prostate cancer, liver cancer, brain cancer, lymphoma, leukemia, skin cancer, pancreatic cancer, colorectal cancer, glioblastoma and lung cancer.

In one aspect, provided herein is a method of making any one of the compositions as described herein.

In one aspect, provided herein is a method of treating a cancer in a subject, comprising administering to the subject a pharmaceutical composition as described herein.

In one aspect, provided herein is a method of treating a cancer in a subject, comprising administering to the subject the pharmaceutical composition as described herein.

In some embodiments, the cancer is selected from a group consisting of gastric cancer, ovarian cancer, renal cancer, breast cancer, prostate cancer, liver cancer, brain cancer, lymphoma, leukemia, skin cancer, pancreatic cancer, colorectal cancer, glioblastoma and lung cancer.

In one aspect, provided herein is a composition comprising a recombinant polynucleic acid comprising a sequence encoding a chimeric fusion protein (CFP), the CFP comprising: (a) an extracellular domain comprising an antigen binding domain, and (b) a transmembrane domain operatively linked to the extracellular domain; wherein the transmembrane domain is a transmembrane domain from a protein that dimerizes with endogenous FcR-gamma receptors in myeloid cells; wherein the recombinant polynucleic acid is encapsulated by a nanoparticle delivery vehicle; and wherein after administration of the composition to a human subject the CFP is expressed on the surface of myeloid cells of the human subject.

In some embodiments, the antigen binding domain comprises a Fab fragment, an scFv domain or an sdAb domain. In some embodiments, the transmembrane domain is an transmembrane domain from CD8, CD16a, CD64, CD68 or CD89.

In some embodiments, the extracellular domain further comprises a hinge domain derived from CD8, wherein the hinge domain is operatively linked to the transmembrane domain and the antigen binding domain.

In some embodiments, the transmembrane domain is a transmembrane domain from a protein that dimerizes with endogenous FcR-gamma receptors in myeloid cells, monocytes or macrophages; wherein after administration of the pharmaceutical composition to a human subject the CFP is specifically expressed in myeloid cells, monocytes or macrophages of the human subject. In some embodiments, the transmembrane domain is a transmembrane domain from CD16a, CD64, CD68 or CD89. In some embodiments, the CFP further comprises an intracellular domain, wherein the intracellular domain comprises one or more intracellular signaling domains, and wherein the one or more intracellular signaling domains comprises an intracellular signaling domain from FcγR, FcαR, FcεR, CD40 or CD3 zeta. In some embodiments, the one or more intracellular signaling domains further comprises a phosphoinositide 3-kinase (PI3K) recruitment domain. In some embodiments, the PI3K recruitment domain comprises a sequence with at least 90% sequence identity to SEQ ID NO: 26. In some embodiments, the intracellular domain comprises an intracellular domain from CD16a, CD64, CD68 or CD89.

In some embodiments, the intracellular domain of a CFP described herein comprises an immunoreceptor tyrosine-based activation motif (ITAM) domain. In some embodiments, the intracellular domain of a CFP described herein comprises more than one ITAM domains. In some embodiments, the ITAM domain is from the intracellular domain of a protein or polypeptide selected from a group CD3 zeta TCR subunit, CD3 epsilon TCR subunit, CD3 gamma TCR subunit, CD3 delta TCR subunit, TCR zeta chain, Fc epsilon receptor 1 chain, Fc epsilon receptor 2 chain, Fc gamma receptor 1 chain, Fc gamma receptor 2a chain, Fc gamma receptor 2b 1 chain, Fc gamma receptor 2b2 chain, Fc gamma receptor 3a chain, Fc gamma receptor 3b chain, Fc beta receptor 1 chain, TYROBP (DAP12), CD5, CD16a, CD16b, CD22, CD23, CD32, CD64, CD79a, CD79b, CD89, CD278, CD66d, functional fragments thereof, and amino acid sequences thereof having at least one but not more than 20 modifications thereto.

In some embodiments, the at least one ITAM domain comprises a Src-family kinase phosphorylation site.

In some embodiments, the at least one ITAM domain comprises a Syk recruitment domain.

The composition of any one of the claims 107-110, wherein the intracellular signaling subunit further comprises a DAP12 recruitment domain.

In some embodiments, the intracellular domain comprises at least 1, 2, 3, 4, 5, 6, 7, 8, 9, or 10 ITAM domains.

In some embodiments, the recombinant polynucleic acid is an mRNA. In some embodiments, the mRNA is delivered into a cell via a nanoparticle delivery vehicle. In some embodiments, the nanoparticle delivery vehicle comprises a lipid nanoparticle. In some embodiments, the lipid nanoparticle comprises a polar lipid. In some embodiments, the lipid nanoparticle comprises a non-polar lipid. In some embodiments, the lipid nanoparticle is from 100 to 300 nm in diameter. In some embodiments, the antigen binding domain binds to an antigen selected from the group consisting of TROP2, GPC3, CD5, HER2, CD137, CD70, Claudin 3, Claudin 18.2, TMPRSS, CD19, CD22, CD7 and GP75.

Provided herein is a pharmaceutical composition comprising the composition as described above, and a pharmaceutically acceptable excipient. In some embodiments, the pharmaceutical composition comprises an effective amount of the composition as described herein, wherein to inhibit growth of a cancer when administered to a human subject with the cancer.

In one aspect, provided herein is a method of treating cancer in a subject in need thereof comprising administering the pharmaceutical composition described herein.

In one aspect, provided herein is a method of introducing the composition described herein into a myeloid cell comprising: electroporating a myeloid cell in the presence of a recombinant polynucleic acid comprising a sequence encoding a chimeric fusion protein (CFP), the CFP comprising: (a) an extracellular domain comprising an anti-TROP2 binding domain, and (b) a transmembrane domain operatively linked to the extracellular domain; wherein the recombinant polynucleic acid is (i) present in a myeloid cell, or (ii) is encapsulated by a nanoparticle delivery vehicle; wherein the recombinant polynucleic acid is configured for expression of the recombinant polynucleic acid in a myeloid cell of a human subject.

In one aspect, provided herein is a composition comprising a recombinant polynucleic acid comprising a sequence encoding a chimeric fusion protein (CFP), the CFP comprising: (a) an extracellular domain comprising an anti-TROP2 binding domain comprising at least one of the sequences set forth SEQ ID NO: 34 and SEQ ID NO: 35, or a sequence that is at least 85% identical to SEQ ID NO: 34 or SEQ ID NO: 35; (b) a transmembrane domain operably linked with the extracellular domain, comprising a sequence from transmembrane domain of an FcγR1 molecule (CD64), an FcγRIIIA molecule (CD16), or an FcαR1 molecule (CD89); and (c) optionally, a hinge domain operably linked to the extracellular domain and the transmembrane domain, wherein the hinge domain comprises an amino acid sequence from CD8α hinge domain.

In some embodiments, the composition further comprises an intracellular domain comprising an amino acid sequence selected from the sequences set forth in SEQ ID NOs: 26, 27 or 28; or a sequence that is at least 80% identical to the amino acid sequence selected from the sequences set forth in SEQ ID NOs: 26, 27 or 28. In some embodiments, the recombinant polynucleic acid is an mRNA.

Provided herein is a cell comprising the recombinant polynucleic acid comprising a sequence encoding a chimeric fusion protein with an extracellular domain comprising an anti-TROP2 binding domain, wherein the cell is a CD14+ cell.

Provided herein is a use of any one of the compositions described herein or a pharmaceutical composition herein, or the cell as described herein, in treating a disease or a disorder.

Provided herein is a use of the pharmaceutical composition described herein in treating a cancer in a subject, wherein the cancer is selected from a group consisting of gastric cancer, ovarian cancer, renal cancer, breast cancer, prostate cancer, liver cancer, brain cancer, lymphoma, leukemia, skin cancer, pancreatic cancer, colorectal cancer, glioblastoma and lung cancer.

Provided herein is a use of any one of the composition described herein, or the pharmaceutical composition described herein, or the cell described herein in making a medicament for treating a cancer in a subject, wherein the cancer is selected from a group consisting of gastric cancer, ovarian cancer, renal cancer, breast cancer, prostate cancer, liver cancer, brain cancer, lymphoma, leukemia, skin cancer, pancreatic cancer, colorectal cancer, glioblastoma and lung cancer.

Also provided herein is a composition comprising one or more recombinant nucleic acid sequences comprising: (A) a first nucleic acid sequence encoding an exogenous polypeptide; (B) a second nucleic acid sequence encoding a chimeric antigen receptor fusion protein (CFP), wherein the CFP comprises: (a) an intracellular signaling subunit comprising an intracellular signaling domain having one or more tyrosine residues that are phosphorylated upon antigen binding by the receptor; (b) a transmembrane domain, (c) an extracellular binding domain having binding specificity for a component on the surface of a target cell, wherein the extracellular binding domain is operably linked to the transmembrane domain and the intracellular signaling subunit; and (d) a transcription activator domain operably linked to the intracellular signaling subunit by a protease cleavage sequence, wherein the transcription activator domain promotes transcription of the first nucleic acid sequence encoding the exogenous polypeptide; and (C) a third nucleic acid sequence encoding (i) a protease that cleaves the protease cleavage sequence that operably links the transcription activator domain to the intracellular signaling subunit; (ii) a domain that binds to the tyrosine residues that are phosphorylated upon activation of the CFP; wherein the protease that cleaves the protease cleavage sequence and the domain that binds to the tyrosine residues are operably linked.

In some embodiments, the third nucleic acid sequence further encodes (iii) a stimulus responsive element.

In some embodiments, the stimulus responsive element (iii) is fused to the domain that binds to the phosphorylated tyrosine residues.

In some embodiments, the stimulus responsive element (iii) is responsive to the microenvironment of the cell that expresses the nucleic acid sequence.

In some embodiments, the one or more recombinant nucleic acid is expressed in a myeloid cell.

In some embodiments, the transcription activator domain further comprises a DNA binding domain.

In some embodiments, the DNA binding domain is selected from the DNA binding domain (DB) of Gal4, ZFHD1 or tet-R.

In some embodiments, the transcription activator domain comprises a VP64 transactivation domain.

In some embodiments, the protease that cleaves the protease cleavage sequence that operably links the transcription activator domain to the intracellular signaling subunit is a hepatitis C virus (HCV) NS3 protease.

In some embodiments, the domain that binds to the tyrosine residues that are phosphorylated upon activation of the CFP is a phosphotyrosine binding (PTB) domain.

In some embodiments, the PTB is an Shc PTB.

In some embodiments, (iii) is a degron, operably linked with (ii).

In some embodiments, the degron is an HIF-1a degron.

Provided herein is a pharmaceutical composition comprising the composition listed in the preceding paragraphs and a pharmaceutically acceptable excipient. Provided herein is a cell comprising the composition listed in the paragraphs. In some embodiments, the cell is CD14+. Provided herein is a method of treating a disease in a subject, comprising, administering to the subject any one of: (i) the pharmaceutical composition; or (ii) the cell described herein.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings.

FIG. 61A also specifically demonstrates that the protease fused to PTB-HIF-degron is readily degraded as is initiated by the degron complex fused to the PTB, when the PTB is not bound to the phosphotyrosine residues of the ITAM motif of the chimeric receptor intracellular domain.

DETAILED DESCRIPTION

Figure 1:
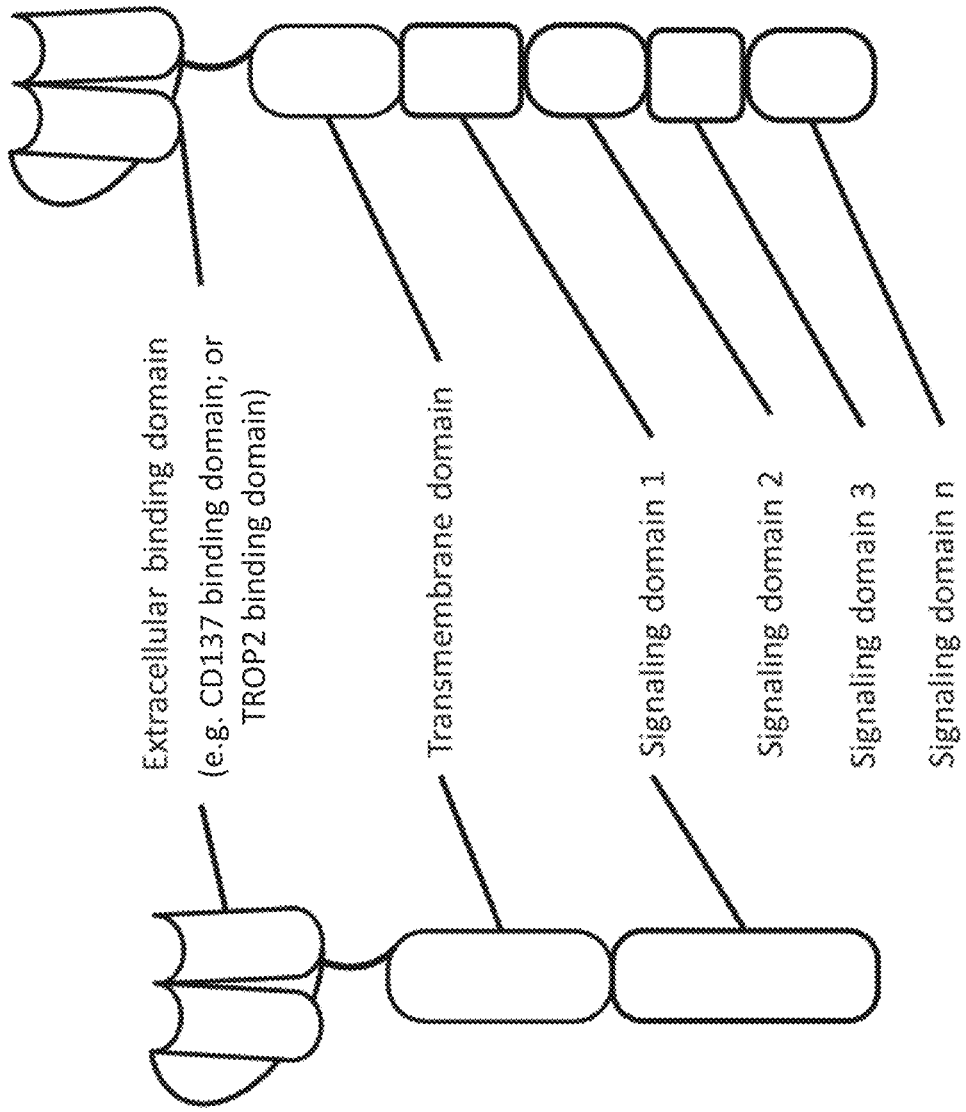
FIG. 1 depicts a schematic showing two exemplary CFPs, the CFP on the left containing an extracellular binding domain, a transmembrane domain, and an intracellular signaling domain, and a CFP on the right containing an extracellular binding domain, a transmembrane domain, a first intracellular signaling domain, a second intracellular signaling domain, a third intracellular signaling domain, and one or more additional intracellular signaling domains. The signaling domains can be derived from other receptors and be designed to elicit any number of cell functions. An exemplary binding domain is a CD137 binding domain. An exemplary binding domain is a TROP2 binding domain.

All terms are intended to be understood as they would be understood by a person skilled in the art. Unless defined otherwise, all technical and scientific terms used herein have the same meaning as commonly understood by one of ordinary skill in the art to which the disclosure pertains.

The section headings used herein are for organizational purposes only and are not to be construed as limiting the subject matter described.

Although various features of the present disclosure can be described in the context of a single embodiment, the features can also be provided separately or in any suitable combination. Conversely, although the present disclosure can be described herein in the context of separate embodiments for clarity, the disclosure can also be implemented in a single embodiment.

Reference in the specification to "some embodiments," "an embodiment," "one embodiment" or "other embodiments" means that a feature, structure, or characteristic described in connection with the embodiments is included in at least some embodiments, but not necessarily all embodiments, of the present disclosure.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. It is contemplated that any embodiment discussed in this specification can be implemented with respect to any method or composition of the disclosure, and vice versa. Furthermore, compositions of the disclosure can be used to achieve methods of the disclosure.

The term "about" or "approximately" as used herein when referring to a measurable value such as a parameter, an amount, a temporal duration, and the like, is meant to encompass variations of +/−30% or less, +/−20% or less, +/−10% or less, +/−5% or less, or +/−1% or less of and from the specified value, insofar such variations are appropriate to perform in the present disclosure. It is to be understood that the value to which the modifier "about" or "approximately" refers is itself also specifically disclosed.

An "agent" can refer to any cell, small molecule chemical compound, antibody or fragment thereof, nucleic acid molecule, or polypeptide.

An "alteration" or "change" can refer to an increase or decrease. For example, an alteration can be an increase or decrease of 1%, 2%, 3%, 4%, 5%, 10%, 20%, 30%, or by 40%, 50%, 60%, or even by as much as 70%, 75%, 80%, 90%, or 100%. For example, an alteration can be an increase or decrease of 1-fold, 2-fold, 3-fold, 4-fold, 5-fold, 10-fold, 20-fold, 30-fold, or by 40-fold, 50-fold, 60-fold, or even by as much as 70-fold, 75-fold, 80-fold, 90-fold, or 100-fold.

An "antigen presenting cell" or "APC" as used herein includes professional antigen presenting cells (e.g., B lymphocytes, macrophages, monocytes, dendritic cells, Langerhans cells), as well as other antigen presenting cells (e.g., keratinocytes, endothelial cells, astrocytes, fibroblasts, oligodendrocytes, thymic epithelial cells, thyroid epithelial cells, glial cells (brain), pancreatic beta cells, and vascular endothelial cells). An APC can express Major Histocompatibility complex (MHC) molecules and can display antigens complexed with MHC on its surface which can be recognized by T cells and trigger T cell activation and an immune response. Professional antigen-presenting cells, notably dendritic cells, play a key role in stimulating naive T cells. Nonprofessional antigen-presenting cells, such as fibroblasts, may also contribute to this process. APCs can also cross-present peptide antigens by processing exogenous antigens and presenting the processed antigens on class I MHC molecules. Antigens that give rise to proteins that are recognized in association with class I MHC molecules are generally proteins that are produced within the cells, and these antigens are processed and associate with class I MHC molecules.

A "biological sample" can refer to any tissue, cell, fluid, or other material derived from an organism.

The term "epitope" can refer to any protein determinant, such as a sequence or structure or amino acid residues, capable of binding to an antibody or binding fragment thereof, a T cell receptor, and/or an antibody-like molecule. Epitopic determinants typically consist of chemically active surface groups of molecules such as amino acids or sugar side chains and generally have specific three dimensional structural characteristics as well as specific charge characteristics. A "T cell epitope" can refer to peptide or peptide-MHC complex recognized by a T cell receptor.

An engineered cell, such as an engineered myeloid cell, can refer to a cell that has at least one exogenous nucleic acid sequence in the cell, even if transiently expressed. Expressing an exogenous nucleic acid may be performed by various methods described elsewhere, and encompasses methods known in the art. The present disclosure relates to preparing and using engineered cells, for example, engineered myeloid cells, such as engineered phagocytic cells. The present disclosure relates to, inter alia, an engineered cell comprising an exogenous nucleic acid encoding, for example, a chimeric fusion protein (CFP).

The term "immune response" includes, but is not limited to, T cell mediated, NK cell mediated and/or B cell mediated immune responses. These responses may be influenced by modulation of T cell costimulation and NK cell costimulation. Exemplary immune responses include T cell responses, e.g., cytokine production, and cellular cytotoxicity. In addition, immune responses include immune responses that are indirectly affected by NK cell activation, B cell activation and/or T cell activation, e.g., antibody production (humoral responses) and activation of cytokine responsive cells, e.g., macrophages. Immune responses include adaptive immune responses. The adaptive immune system can react to foreign molecular structures, such as antigens of an intruding organism. Unlike the innate immune system, the adaptive immune system is highly specific to a pathogen. Adaptive immunity can also provide long-lasting protection. Adaptive immune reactions include humoral immune reactions and cell-mediated immune reactions. In humoral immune reactions, antibodies secreted by B cells into bodily fluids bind to pathogen-derived antigens leading to elimination of the pathogen through a variety of mechanisms, e.g. complement-mediated lysis. In cell-mediated immune reactions, T cells capable of destroying other cells are activated. For example, if proteins associated with a disease are present in a cell, they can be fragmented proteolytically to peptides within the cell. Specific cell proteins can then attach themselves to the antigen or a peptide formed in this manner, and transport them to the surface of the cell, where they can be presented to molecular defense mechanisms, such as T cells. Cytotoxic T cells can recognize these antigens and kill cells that harbor these antigens.

A "ligand" can refer to a molecule which is capable of binding or forming a complex with another molecule, such as a receptor. A ligand can include, but is not limited to, a protein, a glycoprotein, a carbohydrate, a lipoprotein, a hormone, a fatty acid, a phospholipid, or any component that binds to a receptor. In some embodiments, a receptor has a specific ligand. In some embodiments, a receptor may have promiscuous binding to a ligand, in which case it can bind to several ligands that share at least a similarity in structural configuration, charge distribution or any other physicochemical characteristic. A ligand may be a biomolecule. A ligand may be an abiotic material. For example, a ligand may be a negative charged particle that is a ligand for scavenger receptor MARCO. For example, a ligand may be $TiO_2$, which is a ligand for the scavenger receptor SRA1.

The term "major histocompatibility complex (MHC)", "MHC molecule", or "MHC protein" refers to a protein capable of binding an antigenic peptide and present the antigenic peptide to T lymphocytes. Such antigenic peptides can represent T cell epitopes. The human MHC is also called the HLA complex. Thus, the terms "human leukocyte antigen (HLA)", "HLA molecule" or "HLA protein" are used interchangeably with the terms "major histocompatibility complex (MHC)", "MHC molecule", and "MHC protein". HLA proteins can be classified as HLA class I or HLA class II. The structures of the proteins of the two HLA classes are very similar; however, they have very different functions. Class I HLA proteins are present on the surface of almost all cells of the body, including most tumor cells. Class I HLA proteins are loaded with antigens that usually originate from endogenous proteins or from pathogens present inside cells, and are then presented to naïve or cytotoxic T-lymphocytes (CTLs). HLA class II proteins are present on antigen presenting cells (APCs), including but not limited to dendritic cells, B cells, and macrophages. They mainly present peptides which are processed from external antigen sources, e.g. outside of cells, to helper T cells.

In the HLA class II system, phagocytes such as macrophages and immature dendritic cells can take up entities by phagocytosis into phagosomes—though B cells exhibit the more general endocytosis into endosomes—which fuse with lysosomes whose acidic enzymes cleave the uptaken protein into many different peptides. Autophagy is another source of HLA class II peptides. The most studied subclass II HLA genes are: HLA-DPA1, HLA-DPB1, HLA-DQA1, HLA-DQB1, HLA-DRA, and HLA-DRB1.

Presentation of peptides by HLA class II molecules to CD4+ helper T cells can lead to immune responses to foreign antigens. Once activated, CD4+ T cells can promote B cell differentiation and antibody production, as well as CD8+ T cell (CTL) responses. CD4+ T cells can also secrete cytokines and chemokines that activate and induce differentiation of other immune cells. HLA class II molecules are typically heterodimers of α- and β-chains that interact to form a peptide-binding groove that is more open than class I peptide-binding grooves.

HLA alleles are typically expressed in codominant fashion. For example, each person carries 2 alleles of each of the 3 class I genes, (HLA-A, HLA-B and HLA-C) and so can express six different types of class II HLA. In the class II HLA locus, each person inherits a pair of HLA-DP genes (DPA1 and DPB1, which encode α and β chains), HLA-DQ (DQA1 and DQB1, for α and β chains), one gene HLA-DRα (DRA1), and one or more genes HLA-DRβ (DRB1 and DRB3, -4 or -5). HLA-DRB1, for example, has more than nearly 400 known alleles. That means that one heterozygous individual can inherit six or eight functioning class II HLA alleles: three or more from each parent. Thus, the HLA genes are highly polymorphic; many different alleles exist in the different individuals inside a population. Genes encoding HLA proteins have many possible variations, allowing each person's immune system to react to a wide range of foreign invaders. Some HLA genes have hundreds of identified versions (alleles), each of which is given a particular number. In some embodiments, the class I HLA alleles are HLA-A*02:01, HLA-B*14:02, HLA-A*23:01, HLA-E*01:01 (non-classical). In some embodiments, class II HLA alleles are HLA-DRB*01:01, HLA-DRB*01:02, HLA-DRB*11:01, HLA-DRB*15:01, and HLA-DRB*07:01.

A "myeloid cell" can refer broadly to cells of the myeloid lineage of the hematopoietic cell system, and can exclude, for example, the lymphocytic lineage. Myeloid cells comprise, for example, cells of the granulocyte lineage and monocyte lineages. Myeloid cells are differentiated from common progenitors derived from the hematopoietic stem cells in the bone marrow. Commitment to myeloid cell lineages may be governed by activation of distinct transcription factors, and accordingly myeloid cells may be characterized as cells having a level of plasticity, which may be described as the ability to further differentiate into terminal cell types based on extracellular and intracellular stimuli. Myeloid cells can be rapidly recruited into local tissues via various chemokine receptors on their surface. Myeloid cells are responsive to various cytokines and chemokines.

A myeloid cell, for example, may be a cell that originates in the bone marrow from a hematopoietic stem cell under the influence of one or more cytokines and chemokines, such as G-CSF, GM-CSF, Flt3L, CCL2, VEGF and S100A8/9. In some embodiments, the myeloid cell is a precursor cell. In some embodiments, the myeloid cell may be a cell having characteristics of a common myeloid progenitor, or a granulocyte progenitor, a myeloblast cell, or a monocyte-dendritic cell progenitor or a combination thereof. A myeloid can include a granulocyte or a monocyte or a precursor cell thereof. A myeloid can include an immature granulocyte, an immature monocyte, an immature macrophage, an immature neutrophil, and an immature dendritic cell. A myeloid can include a monocyte or a pre-monocytic cell or a monocyte precursor. In some cases, a myeloid cell as used herein may refer to a monocyte having an M0 phenotype, an M1 phenotype or an M2 phenotype. A myeloid can include a dendritic cell (DC), a mature DC, a monocyte derived DC, a plasmacytoid DC, a pre-dendritic cell, or a precursor of a DC. A myeloid can include a neutrophil, which may be a mature neutrophil, a neutrophil precursor, or a polymorphonucleocyte (PMN). A myeloid can include a macrophage, a monocyte-derived macrophage, a tissue macrophage, a macrophage of an M0, an M1 or an M2 phenotype. A myeloid can include a tumor infiltrating monocyte (TIM). A myeloid can include a tumor associated monocyte (TAM). A myeloid can include a myeloid derived suppressor cell (MDSC). A myeloid can include a tissue resident macrophage. A myeloid can include a tumor associated DC (TADC). Accordingly, a myeloid cell may express one or more cell surface markers, for example, CD11b, CD14, CD15, CD16, CD38, CCR5, CD66, Lox-1, CD11c, CD64, CD68, CD163, CCR2, CCR5, HLA-DR, CD1c, CD83, CD141, CD209, CD205, P selectin, integrins, ICAMS, VCAMS, MHC-II, CD123, CD303, CD304, a SIGLEC family protein and a CLEC family protein. In some cases, a myeloid cell may be characterized by a high or a low expression of one or more of cell surface markers, for example, CD11b, CD14, CD15, CD16, CD66, Lox-1, CD11c, CD64, CD68, CD163, CCR2, CCR5, HLA-DR, CD1c, CD83, CD141, CD209, MHC-II, CD123, CD303, CD304 or a combination thereof.

"Phagocytosis" is used interchangeably with "engulfment" and can refer to a process by which a cell engulfs a particle, such as a cancer cell or an infected cell. This process can give rise to an internal compartment (phagosome) containing the particle. This process can be used to ingest and or remove a particle, such as a cancer cell or an infected cell from the body. A phagocytic receptor may be involved in the process of phagocytosis. The process of phagocytosis can be closely coupled with an immune response and antigen presentation. The processing of exogenous antigens follows their uptake into professional antigen presenting cells by some type of endocytic event. Phagocytosis can also facilitate antigen presentation. For example, antigens from phagocytosed cells or pathogens, including cancer antigens, can be processed and presented on the cell surface of APCs.

A "polypeptide" can refer to a molecule containing amino acids linked together via a peptide bond, such as a glycoprotein, a lipoprotein, a cellular protein or a membrane protein. A polypeptide may comprise one or more subunits of a protein. A polypeptide may be encoded by a recombinant nucleic acid. In some embodiments, polypeptide may comprise more than one peptide sequence in a single amino acid chain, which may be separated by a spacer, a linker or peptide cleavage sequence. A polypeptide may be a fused polypeptide. A polypeptide may comprise one or more domains, modules or moieties.

A "receptor" can refer to a chemical structure composed of a polypeptide, which transduces a signal, such as a polypeptide that transduces an extracellular signal to a cell. A receptor can serve to transmit information in a cell, a cell formation or an organism. A receptor comprises at least one receptor unit and can contain two or more receptor units, where each receptor unit comprises a protein molecule, e.g., a glycoprotein molecule. A receptor can contain a structure that binds to a ligand and can form a complex with the ligand. Signaling information can be transmitted by a conformational change of the receptor following binding with the ligand on the surface of a cell.

The term "antibody" refers to a class of proteins that are generally known as immunoglobulins, including, but not limited to IgG1, IgG2, IgG3, and IgG4), IgA (including IgA1 and IgA2), IgD, IgE, IgM, and IgY, The term "antibody" includes, but is not limited to, full length antibodies, single-chain antibodies, single domain antibodies (sdAb) and antigen-binding fragments thereof. Antigen-binding antibody fragments include, but are not limited to, Fab, Fab' and F(ab')2, Fd (consisting of $V_H$ and $C_H1$), single-chain variable fragment (scFv), single-chain antibodies, disulfide-linked variable fragment (dsFv) and fragments comprising a $V_L$ and/or a $V_H$ domain. Antibodies can be from any animal origin. Antigen-binding antibody fragments, including single-chain antibodies, can comprise variable region(s) alone or in combination with tone or more of a hinge region, a CH1 domain, a CH2 domain, and a CH3 domain. Also included are any combinations of variable region(s) and hinge region, CH1, CH2, and CH3 domains. Antibodies can be monoclonal, polyclonal, chimeric, humanized, and human monoclonal and polyclonal antibodies which, e.g., specifically bind an HLA-associated polypeptide or an HLA-peptide complex. As used herein, a "binder" represents a polypeptide that comprises a binding domain that can bind to a target, wherein target for the binder can be a protein e.g. a cancer antigen, a glycoprotein etc. A binder is often used to represent a CFP, e.g., a CAR, and designated by the target it binds, e.g. CD5-binder that comprises a binding domain for CD5 antigen. In some cases, the same is alternatively or interchangeably termed, anti-CD5 binder, or anti-TROP2 binder. As generally used, the term binder refers to any molecule that has a binding domain. In some cases, when described in context, a binder may be a BiME or a TRiME.

The term "recombinant nucleic acid" refers a nucleic acid prepared, expressed, created or isolated by recombinant means. A recombinant nucleic acid can contain a nucleotide sequence that is not naturally occurring. A recombinant nucleic acid may be synthesized in the laboratory. A recombinant nucleic acid may be prepared by using recombinant DNA technology, for example, enzymatic modification of DNA, such as enzymatic restriction digestion, ligation, and DNA cloning. A recombinant nucleic acid can be DNA, RNA, analogues thereof, or a combination thereof. A recombinant DNA may be transcribed ex vivo or in vitro, such as to generate a messenger RNA (mRNA). A recombinant mRNA may be isolated, purified and used to transfect a cell. A recombinant nucleic acid may encode a protein or a polypeptide.

The process of introducing or incorporating a nucleic acid into a cell can be via transformation, transfection or transduction. Transformation is the process of uptake of foreign nucleic acid by a bacterial cell. This process is adapted for propagation of plasmid DNA, protein production, and other applications. Transformation introduces recombinant plasmid DNA into competent bacterial cells that take up extracellular DNA from the environment. Some bacterial species are naturally competent under certain environmental conditions, but competence is artificially induced in a laboratory setting. Transfection is the introduction of small molecules such as DNA, RNA, or antibodies into eukaryotic cells. Transfection may also refer to the introduction of bacteriophage into bacterial cells. 'Transduction' is mostly used to describe the introduction of recombinant viral vector particles into target cells, while 'infection' refers to natural infections of humans or animals with wild-type viruses.

The term "vector", can refer to a nucleic acid molecule capable of autonomous replication in a host cell, and which allow for cloning of nucleic acid molecules. As known to those skilled in the art, a vector includes, but is not limited to, a plasmid, cosmid, phagemid, viral vectors, phage vectors, yeast vectors, mammalian vectors and the like. For example, a vector for exogenous gene transformation may be a plasmid. In certain embodiments, a vector comprises a nucleic acid sequence containing an origin of replication and other elements necessary for replication and/or maintenance of the nucleic acid sequence in a host cell. In some embodiments, a vector or a plasmid provided herein is an expression vector. Expression vectors are capable of directing the expression of genes and/or nucleic acid sequence to which they are operatively linked. In some embodiments, an expression vector or plasmid is in the form of circular double stranded DNA molecules. A vector or plasmid may or may not be integrated into the genome of a host cell. In some embodiments, nucleic acid sequences of a plasmid are not integrated in a genome or chromosome of the host cell after introduction. For example, the plasmid may comprise elements for transient expression or stable expression of the nucleic acid sequences, e.g. genes or open reading frames harbored by the plasmid, in a host cell. In some embodiments, a vector is a transient expression vector. In some embodiments, a vector is a stably expressed vector that replicates autonomously in a host cell. In some embodiments, nucleic acid sequences of a plasmid are integrated into a genome or chromosome of a host cell upon introduction into the host cell. Expression vectors that can be used in the methods as disclosed herein include, but are not limited to, plasmids, episomes, bacterial artificial chromosomes, yeast artificial chromosomes, bacteriophages or viral vectors. A vector can be a DNA or RNA vector. In some embodiments, a vector provide herein is a RNA vector that is capable of integrating into a host cell's genome upon introduction into the host cell (e.g., via reverse transcription), for example, a retroviral vector or a lentiviral vector. Other forms of expression vectors known by those skilled in the art which serve the equivalent functions can also be used, for example, self-replicating extrachromosomal vectors or vectors capable of integrating into a host genome. Exemplary vectors are those capable of autonomous replication and/or expression of nucleic acids to which they are linked.

The terms "spacer" or "linker" as used in reference to a fusion protein refers to a peptide sequence that joins two other peptide sequences of the fusion protein. In some embodiments, a linker or spacer has no specific biological activity other than to join or to preserve some minimum distance or other spatial relationship between the proteins or RNA sequences. In some embodiments, the constituent amino acids of a spacer can be selected to influence some property of the molecule such as the folding, flexibility, net charge, or hydrophobicity of the molecule. Suitable linkers for use in an embodiment of the present disclosure are well known to those of skill in the art and include, but are not limited to, straight or branched-chain carbon linkers, heterocyclic carbon linkers, or peptide linkers. In some embodiments, a linker is used to separate two or more polypeptides, e.g. two antigenic peptides by a distance sufficient to ensure that each antigenic peptide properly folds. Exemplary peptide linker sequences adopt a flexible extended conformation and do not exhibit a propensity for developing an ordered secondary structure. Amino acids in flexible linker protein region may include Gly, Asn and Ser, or any permutation of amino acid sequences containing Gly, Asn and Ser. Other near neutral amino acids, such as Thr and Ala, also can be used in the linker sequence.

The terms "treat," "treated," "treating," "treatment," and the like are meant to refer to reducing, preventing, or ameliorating a disorder and/or symptoms associated therewith (e.g., a neoplasia or tumor or infectious agent or an autoimmune disease). "Treating" can refer to administration of the therapy to a subject after the onset, or suspected onset, of a disease (e.g., cancer or infection by an infectious agent or an autoimmune disease). "Treating" includes the concepts of "alleviating", which can refer to lessening the frequency of occurrence or recurrence, or the severity, of any symptoms or other ill effects related to the disease and/or the side effects associated with therapy. The term "treating" also encompasses the concept of "managing" which refers to reducing the severity of a disease or disorder in a patient, e.g., extending the life or prolonging the survivability of a patient with the disease, or delaying its recurrence, e.g., lengthening the period of remission in a patient who had suffered from the disease. It is appreciated that, although not precluded, treating a disorder or condition does not require that the disorder, condition, or symptoms associated therewith be completely eliminated. The term "prevent", "preventing", "prevention" and their grammatical equivalents as used herein, can refer to avoiding or delaying the onset of symptoms associated with a disease or condition in a subject that has not developed such symptoms at the time the administering of an agent or compound commences. In certain embodiments, treating a subject or a patient as described herein comprises administering a therapeutic composition, such as a drug, a metabolite, a preventive component, a nucleic acid, a peptide, or a protein that encodes or otherwise forms a drug, a metabolite or a preventive component. In some embodiments, treating comprises administering a cell or a population of cells to a subject in need thereof. In some embodiments, treating comprises administering to the subject one or more of engineered cells described herein, e.g. one or more engineered myeloid cells, such as phagocytic cells. Treating comprises treating a disease or a condition or a syndrome, which may be a pathological disease, condition or syndrome, or a latent disease, condition or syndrome. In some cases, treating, as used herein may comprise administering a therapeutic vaccine. In some embodiments, the engineered phagocytic cell is administered to a patient or a subject. In some embodiments, a cell administered to a human subject results in reduced immunogenicity. For example, an engineered phagocytic cell may lead to no or reduced graft versus host disease (GVHD) or fratricide effect. In some embodiments, an engineered cell administered to a human subject is immunocompatible to the subject (i.e. having a matching HLA subtype that is naturally expressed in the subject). Subject specific HLA alleles or HLA genotype of a subject can be determined by any method known in the art. In exemplary embodiments, the methods include determining polymorphic gene types that can comprise generating an alignment of reads extracted from a sequencing data set to a gene reference set comprising allele variants of the polymorphic gene, determining a first posterior probability or a posterior probability derived score for each allele variant in the alignment, identifying the allele variant with a maximum first posterior probability or posterior probability derived score as a first allele variant, identifying one or more overlapping reads that aligned with the first allele variant and one or more other allele variants, determining a second posterior probability or posterior probability derived score for the one or more other allele variants using a weighting factor, identifying a second allele variant by selecting the allele variant with a maximum second posterior probability or posterior probability derived score, the first and second allele variant defining the gene type for the polymorphic gene, and providing an output of the first and second allele variant.

A "fragment" can refer to a portion of a protein or nucleic acid. In some embodiments, a fragment retains at least 50%, 75%, or 80%, or 90%, 95%, or even 99% of the biological activity of a reference protein or nucleic acid.

The terms "isolated," "purified", "biologically pure" and their grammatical equivalents refer to material that is free to varying degrees from components which normally accompany it as found in its native state. "Isolate" denotes a degree of separation from original source or surroundings. "Purify" denotes a degree of separation that is higher than isolation. A "purified" or "biologically pure" protein is sufficiently free of other materials such that any impurities do not materially affect the biological properties of the protein or cause other adverse consequences. That is, a nucleic acid or peptide of the present disclosure is purified if it is substantially free of cellular material, viral material, or culture medium when produced by recombinant DNA techniques, or chemical precursors or other chemicals when chemically synthesized. Purity and homogeneity are typically determined using analytical chemistry techniques, for example, polyacrylamide gel electrophoresis or high performance liquid chromatography. The term "purified" can denote that a nucleic acid or protein gives rise to essentially one band in an electrophoretic gel. For a protein that can be subjected to modifications, for example, phosphorylation or glycosylation, different modifications can give rise to different isolated proteins, which can be separately purified.

The terms "neoplasia" or "cancer" refers to any disease that is caused by or results in inappropriately high levels of cell division, inappropriately low levels of apoptosis, or both. Glioblastoma is one non-limiting example of a neoplasia or cancer. The terms "cancer" or "tumor" or "hyperproliferative disorder" refer to the presence of cells possessing characteristics typical of cancer-causing cells, such as uncontrolled proliferation, immortality, metastatic potential, rapid growth and proliferation rate, and certain characteristic morphological features. Cancer cells are often in the form of a tumor, but such cells can exist alone within an animal, or can be a non-tumorigenic cancer cell, such as a leukemia cell.

The term "vaccine" is to be understood as meaning a composition for generating immunity for the prophylaxis and/or treatment of diseases (e.g., neoplasia/tumor/infectious agents/autoimmune diseases). Accordingly, vaccines as used herein are medicaments which comprise recombinant nucleic acids, or cells comprising and expressing a recombinant nucleic acid and are intended to be used in humans or animals for generating specific defense and protective substance by vaccination. A "vaccine composition" can include a pharmaceutically acceptable excipient, carrier or diluent. Aspects of the present disclosure relate to use of the technology in preparing a phagocytic cell-based vaccine.

The term "pharmaceutically acceptable" refers to approved or approvable by a regulatory agency of the Federal or a state government or listed in the U.S. Pharmacopeia or other generally recognized pharmacopeia for use in animals, including humans. A "pharmaceutically acceptable excipient, carrier or diluent" refers to an excipient, carrier or diluent that can be administered to a subject, together with an agent, and which does not destroy the pharmacological activity thereof and is nontoxic when administered in doses sufficient to deliver a therapeutic amount of the agent.

Nucleic acid molecules useful in the methods of the disclosure include, but are not limited to, any nucleic acid molecule with activity or that encodes a polypeptide. Polynucleotides having substantial identity to an endogenous sequence are typically capable of hybridizing with at least one strand of a double-stranded nucleic acid molecule. "Hybridize" refers to when nucleic acid molecules pair to form a double-stranded molecule between complementary polynucleotide sequences, or portions thereof, under various conditions of stringency. (See, e.g., Wahl, G. M. and S. L. Berger (1987) Methods Enzymol. 152:399; Kimmel, A. R. (1987) Methods Enzymol. 152:507). For example, stringent salt concentration can ordinarily be less than about 750 mM NaCl and 75 mM trisodium citrate, less than about 500 mM NaCl and 50 mM trisodium citrate, or less than about 250 mM NaCl and 25 mM trisodium citrate. Low stringency hybridization can be obtained in the absence of organic solvent, e.g., formamide, while high stringency hybridization can be obtained in the presence of at least about 35% formamide, or at least about 50% formamide. Stringent temperature conditions can ordinarily include temperatures of at least about 30° C., at least about 37° C., or at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In an exemplary embodiment, hybridization can occur at 30° C. in 750 mM NaCl, 75 mM trisodium citrate, and 1% SDS. In another exemplary embodiment, hybridization can occur at 37° C. in 500 mM NaCl, 50 mM trisodium citrate, 1% SDS, 35% formamide, and 100 µg/ml denatured salmon sperm DNA (ssDNA). In another exemplary embodiment, hybridization can occur at 42° C. in 250 mM NaCl, 25 mM trisodium citrate, 1% SDS, 50% formamide, and 200 µg/ml ssDNA. Useful variations on these conditions will be readily apparent to those skilled in the art. For most applications, washing steps that follow hybridization can also vary in stringency. Wash stringency conditions can be defined by salt concentration and by temperature. As above, wash stringency can be increased by decreasing salt concentration or by increasing temperature. For example, stringent salt concentration for the wash steps can be less than about 30 mM NaCl and 3 mM trisodium citrate, or less than about 15 mM NaCl and 1.5 mM trisodium citrate. Stringent temperature conditions for the wash steps can include a temperature of at least about 25° C., of at least about 42° C., or at least about 68° C. In exemplary embodiments, wash steps can occur at 25° C. in 30 mM NaCl, 3 mM trisodium citrate, and 0.1% SDS. In other exemplary embodiments, wash steps can occur at 42° C. in 15 mM NaCl, 1.5 mM trisodium citrate, and 0.1% SDS. In another exemplary embodiment, wash steps can occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196: 180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., Molecular Cloning: A Laboratory Manual, Cold Spring Harbor Laboratory Press, New York.

"Substantially identical" refers to a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Such a sequence can be at least 60%, 80% or 85%, 90%, 95%, 96%, 97%, 98%, or even 99% or more identical at the amino acid level or nucleic acid to the sequence used for comparison. Sequence identity is typically measured using sequence analysis software (for example, Sequence Analysis Software Package of the Genetics Computer Group, University of Wisconsin Biotechnology Center, 1710 University Avenue, Madison, Wis.

53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program can be used, with a probability score between e-3 and e-m° indicating a closely related sequence. A "reference" is a standard of comparison. It will be understood that the numbering of the specific positions or residues in the respective sequences depends on the particular protein and numbering scheme used. Numbering might be different, e.g., in precursors of a mature protein and the mature protein itself, and differences in sequences from species to species may affect numbering. One of skill in the art will be able to identify the respective residue in any homologous protein and in the respective encoding nucleic acid by methods well known in the art, e.g., by sequence alignment to a reference sequence and determination of homologous residues.

The term "subject" or "patient" refers to an organism, such as an animal (e.g., a human) which is the object of treatment, observation, or experiment. By way of example only, a subject includes, but is not limited to, a mammal, including, but not limited to, a human or a non-human mammal, such as a non-human primate, murine, bovine, equine, canine, ovine, or feline.

The term "therapeutic effect" refers to some extent of relief of one or more of the symptoms of a disorder (e.g., a neoplasia, tumor, or infection by an infectious agent or an autoimmune disease) or its associated pathology. "Therapeutically effective amount" as used herein refers to an amount of an agent which is effective, upon single or multiple dose administration to the cell or subject, in prolonging the survivability of the patient with such a disorder, reducing one or more signs or symptoms of the disorder, preventing or delaying, and the like beyond that expected in the absence of such treatment. "Therapeutically effective amount" is intended to qualify the amount required to achieve a therapeutic effect. A physician or veterinarian having ordinary skill in the art can readily determine and prescribe the "therapeutically effective amount" (e.g., ED50) of the pharmaceutical composition required.

Provided herein are engineered myeloid cells (including, but not limited to, neutrophils, monocytes, myeloid dendritic cells (mDCs), mast cells and macrophages), designed to specifically bind a target cell. The engineered myeloid cells can attack and kill target cells directly (e.g., by phagocytosis) and/or indirectly (e.g., by activating T cells). In some embodiments, the target cell is a cancer cell.

While cancer is one exemplary embodiment described in detail in the instant disclosure, the methods and technologies described herein are contemplated to be useful in targeting an infected or otherwise diseased cell inside the body. Similarly, therapeutic and vaccine compositions using the engineered cells are described herein.

Provided herein are compositions and methods for treating diseases or conditions, such as cancer. The compositions and methods provided herein utilize human myeloid cells, including, but not limited to, neutrophils, monocytes, myeloid dendritic cells (mDCs), mast cells and macrophages, to target diseased cells, such as cancer cells. The compositions and methods provided herein can be used to eliminate diseased cells, such as cancer cells and or diseased tissue, by a variety of mechanisms, including T cell activation and recruitment, effector immune cell activation (e.g., CD8 T cell and NK cell activation), antigen cross presentation, enhanced inflammatory responses, reduction of regulatory T cells and phagocytosis. For example, the myeloid cells can be used to sustain immunological responses against cancer cells.

Provided herein are compositions comprising a recombinant nucleic acid encoding a chimeric fusion protein (CFP), such as a phagocytic receptor (PR) fusion protein (PFP), a scavenger receptor (SR) fusion protein (SFP), an integrin receptor (IR) fusion protein (IFP) or a caspase-recruiting receptor (caspase-CAR) fusion protein. A CFP encoded by the recombinant nucleic acid can comprise an extracellular domain (ECD) comprising an antigen binding domain that binds to an antigen of a target cell. The extracellular domain can be fused to a hinge domain or an extracellular domain derived from a receptor, such as CD2, CD8, CD28, CD68, a phagocytic receptor, a scavenger receptor or an integrin receptor. The CFP encoded by the recombinant nucleic acid can further comprise a transmembrane domain, such as a transmembrane domain derived from CD2, CD8, CD28, CD68, a phagocytic receptor, a scavenger receptor or an integrin receptor. In some embodiments, a CFP encoded by the recombinant nucleic acid further comprises an intracellular domain comprising an intracellular signaling domain, such as an intracellular signaling domain derived from a phagocytic receptor, a scavenger receptor or an integrin receptor. For example, the intracellular domain can comprise one or more intracellular signaling domains derived from a phagocytic receptor, a scavenger receptor or an integrin receptor. For example, the intracellular domain can comprise one or more intracellular signaling domains that promote phagocytic activity, inflammatory response, nitric oxide production, integrin activation, enhanced effector cell migration (e.g., via chemokine receptor expression), antigen presentation, and/or enhanced cross presentation. In some embodiments, the CFP is a phagocytic receptor fusion protein (PFP). In some embodiments, the CFP is a phagocytic scavenger receptor fusion protein (PFP). In some embodiments, the CFP is an integrin receptor fusion protein (IFP). In some embodiments, the CFP is an inflammatory receptor fusion protein. In some embodiments, a CFP encoded by the recombinant nucleic acid further comprises an intracellular domain comprising a recruitment domain. For example, the intracellular domain can comprise one or more PI3K recruitment domains, caspase recruitment domains or caspase activation and recruitment domains (CARDs).

Provided herein is a composition comprising a recombinant nucleic acid encoding a CFP comprising a phagocytic or tethering receptor (PR) subunit (e.g., a phagocytic receptor fusion protein (PFP)) comprising: (i) a transmembrane domain, and (ii) an intracellular domain comprising a phagocytic receptor intracellular signaling domain; and an extracellular antigen binding domain specific to an antigen, e.g., an antigen of or presented on a target cell; wherein the transmembrane domain and the extracellular antigen binding domain are operatively linked such that antigen binding to the target by the extracellular antigen binding domain of the fused receptor activated in the intracellular signaling domain of the phagocytic receptor.

In some embodiments, the extracellular domain of a CFP comprises an Ig binding domain. In some embodiments, the extracellular domain comprises an IgA, IgD, IgE, IgG, IgM, FcRγI, FcRγIIA, FcRγIIB, FcRγIIC, FcRγIIIA, FcRγIIIB, FcRn, TRIM21, FcRL5 binding domain. In some embodiments, the extracellular domain of a CFP comprises an FcR extracellular domain. In some embodiments, the extracellular domain of a CFP comprises an FcRα, FcRβ, FcRε or FcRγ extracellular domain. In some embodiments, the extracellular domain comprises an FcRα (FCAR) extracellular domain. In some embodiments, the extracellular domain comprises an FcRβ extracellular domain. In some embodiments, the extracellular domain comprises an FCER1A extracellular domain. In some embodiments, the extracellular domain comprises an FDGR1A, FCGR2A, FCGR2B, FCGR2C, FCGR3A, or FCGR3B extracellular domain. In some embodiments, the extracellular domain comprises an integrin domain or an integrin receptor domain. In some embodiments, the extracellular domain comprises one or more integrin α1, α2, αIIb, α3, α4, α5, α6, α7, α8, α9, α10, α11, αD, αE, αL, αM, αV, αX, β1, β2, β3, β4, β5, β6, β7, or β8 domains.

In some embodiments, the CFP further comprises an extracellular domain operatively linked to the transmembrane domain and the extracellular antigen binding domain. In some embodiments, the extracellular domain further comprises an extracellular domain of a receptor, a hinge, a spacer and/or a linker. In some embodiments, the extracellular domain comprises an extracellular portion of a phagocytic receptor. In some embodiments, the extracellular portion of the CFP is derived from the same receptor as the receptor from which the intracellular signaling domain is derived. In some embodiments, the extracellular domain comprises an extracellular domain of a scavenger receptor. In some embodiments, the extracellular domain comprises an immunoglobulin domain. In some embodiments, the immunoglobulin domain comprises an extracellular domain of an immunoglobulin or an immunoglobulin hinge region. In some embodiments, the extracellular domain comprises a phagocytic engulfment domain. In some embodiments, the extracellular domain comprises a structure capable of multimeric assembly. In some embodiments, the extracellular domain comprises a scaffold for multimerization. In some embodiments, the extracellular domain is at least 10, 20, 30, 40, 50, 60, 70, 80, 90, 100, 150, 200, 300, 300, 400, or 500 amino acids in length. In some embodiments, the extracellular domain is at most 500, 400, 300, 200, or 100 amino acids in length. In some embodiments, the extracellular antigen binding domain specifically binds to the antigen of a target cell. In some embodiments, the extracellular antigen binding domain comprises an antibody domain. In some embodiments, the extracellular antigen binding domain comprises a receptor domain, antibody domain, wherein the antibody domain comprises a functional antibody fragment, a single chain variable fragment (scFv), an Fab, a single-domain antibody (sdAb), a nanobody, a $V_H$ domain, a $V_L$ domain, a VNAR domain, a $V_{HH}$ domain, a bispecific antibody, a diabody, or a functional fragment or a combination thereof. In some embodiments, the extracellular antigen binding domain comprises a ligand, an extracellular domain of a receptor or an adaptor. In some embodiments, the extracellular antigen binding domain comprises a single extracellular antigen binding domain that is specific for a single antigen. In some embodiments, the extracellular antigen binding domain comprises at least two extracellular antigen binding domains, wherein each of the at least two extracellular antigen binding domains is specific for a different antigen.

In some embodiments, the antigen is a cancer associated antigen, a lineage associated antigen, a pathogenic antigen or an autoimmune antigen. In some embodiments, the antigen comprises a viral antigen. In some embodiments, the antigen is a T lymphocyte antigen. In some embodiments, the antigen is an extracellular antigen. In some embodiments, the antigen is an intracellular antigen. In some embodiments, the antigen is selected from the group consisting of an antigen from Thymidine Kinase (TK1), Hypoxanthine-Guanine Phosphoribosyltransferase (HPRT), Receptor Tyrosine Kinase-Like Orphan Receptor 1 (ROR1), Mucin-1, Mucin-16 (MUC16), MUC1, Epidermal Growth Factor Receptor vIII (EGFRvIII), Mesothelin, Human Epidermal Growth Factor Receptor 2 (HER2), EBNA-1, LEMD1, Phosphatidyl Serine, Carcinoembryonic Antigen (CEA), B-Cell Maturation Antigen (BCMA), Glypican 3 (GPC3), Follicular Stimulating Hormone receptor, Fibroblast Activation Protein (FAP), Erythropoietin-Producing Hepatocellular Carcinoma A2 (EphA2), EphB2, a Natural Killer Group 2D (NKG2D) ligand, Disialoganglioside 2 (GD2), CD2, CD3, CD4, CD5, CD7, CD8, CD19, CD20, CD22, CD24, CD30, CD33, CD38, CD44v6, CD45, CD56CD79b, CD97, CD117, CD123, CD133, CD138, CD171, CD179a, CD213A2, CD248, CD276, PSCA, CS-1, CLECL1, GD3, PSMA, FLT3, TAG72, EPCAM, IL-1, an integrin receptor, PRSS21, VEGFR2, PDGFRβ, SSEA-4, EGFR, NCAM, prostase, PAP, ELF2M, GM3, TEM7R, CLDN6, TSHR, GPRCSD, ALK, Dsg1, Dsg3, IGLL1 and combinations thereof. In some embodiments, the antigen is an antigen of a protein selected from the group consisting of CD2, CD3, CD4, CD5, CD7, CCR4, CD8, CD30, CD45, and CD56. In some embodiments, the antigen is an ovarian cancer antigen or a T lymphoma antigen. In some embodiments, the antigen is an antigen of an integrin receptor. In some embodiments, the antigen is an antigen of an integrin receptor or integrin selected from the group consisting of α1, α2, αIIb, α3, α4, α5, α6, α7, α8, α9, α10, α11, αD, αE, αL, αM, αV, αX, β 1, β 2, β 3, β 4, β 5, β 6, β 7, and β8. In some embodiment, the antigen is an antigen of an integrin receptor ligand. In some embodiments, the antigen is an antigen of fibronectin, vitronectin, collagen, or laminin. In some embodiments, the antigen binding domain can bind to two or more different antigens.

In some embodiments, the antigen binding domain comprises an autoantigen or fragment thereof, such as Dsg1 or Dsg3. In some embodiments, the extracellular antigen binding domain comprises a receptor domain or an antibody domain wherein the antibody domain binds to an auto antigen, such as Dsg1 or Dsg3.

In some embodiments, the transmembrane domain and the extracellular antigen binding domain are operatively linked through a linker. In some embodiments, the transmembrane domain and the extracellular antigen binding domain are operatively linked through a linker such as a hinge region of CD8α, IgG1 or IgG4.

In some embodiments, the extracellular domain comprises a multimerization scaffold.

In some embodiments, the transmembrane domain comprises a CD8 transmembrane domain. In some embodiments, the transmembrane domain comprises a CD28 transmembrane domain. In some embodiments, the transmembrane domain comprises a CD68 transmembrane domain. In some embodiments, the transmembrane domain comprises a CD2 transmembrane domain. In some embodiments, the transmembrane domain comprises an FcR transmembrane domain. In some embodiments, the transmembrane domain comprises an FcRγ transmembrane domain. In some embodiments, the transmembrane domain comprises an FcRα transmembrane domain. In some embodiments, the transmembrane domain comprises an FcRβ transmembrane domain. In some embodiments, the transmembrane domain comprises an FGRε transmembrane domain. In some embodiments, the transmembrane domain comprises a transmembrane domain from a syntaxin, such as syntaxin 3 or syntaxin 4 or syntaxin 5. In some embodiments, the transmembrane domain oligomerizes with a transmembrane domain of an endogenous receptor when the CFP is expressed in a cell. In some embodiments, the transmembrane domain oligomerizes with a transmembrane domain of an exogenous receptor when the CFP is expressed in a cell. In some embodiments, the transmembrane domain dimerizes with a transmembrane domain of an endogenous receptor when the CFP is expressed in a cell. In some embodiments, the transmembrane domain dimerizes with a transmembrane domain of an exogenous receptor when the CFP is expressed in a cell. In some embodiments, the transmembrane domain is derived from a protein that is different than the protein from which the intracellular signaling domain is derived. In some embodiments, the transmembrane domain is derived from a protein that is different than the protein from which the extracellular domain is derived. In some embodiments, the transmembrane domain comprises a transmembrane domain of a phagocytic receptor. In some embodiments, the transmembrane domain and the extracellular domain are derived from the same protein. In some embodiments, the transmembrane domain is derived from the same protein as the intracellular signaling domain. In some embodiments, the recombinant nucleic acid encodes a DAP12 recruitment domain. In some embodiments, the transmembrane domain comprises a transmembrane domain that oligomerizes with DAP12.

In some embodiments, the transmembrane domain is at least 12, 13, 14, 15, 16, 17, 18, 19, 20, 21, 22, 23, 24, 25, 26, 27, 28, 29, 30, 31 or 32 amino acids in length. In some embodiments, the transmembrane domain is at most 12, 13, 14, 15, 16, 17, 18, 19, 20, 21, 22, 23, 24, 25, 26, 27, 28, 29, 30, 31 or 32 amino acids in length.

In some embodiments, the intracellular signaling domain comprises an intracellular signaling domain derived from a phagocytic receptor. In some embodiments, the intracellular signaling domain comprises an intracellular signaling domain derived from a phagocytic receptor other than a phagocytic receptor selected from Megf10, MerTk, FcRα, or Bai1. In some embodiments, the intracellular signaling domain comprises an intracellular signaling domain derived from a phagocytic receptor selected from the group consisting of TNFR1, MDA5, CD40, lectin, dectin 1, CD206, scavenger receptor A1 (SRA1), MARCO, CD36, CD163, MSR1, SCARA3, COLEC12, SCARA5, SCARB1, SCARB2, CD68, OLR1, SCARF1, SCARF2, CXCL16, STAB1, STAB2, SRCRB4D, SSC5D, CD205, CD207, CD209, RAGE, CD14, CD64, F4/80, CCR2, CX3CR1, CSF1R, Tie2, HuCRIg(L), CD64, CD32a, CD16a, CD89, Fc-alpha receptor I, CR1, CD35, CD3ζ, CR3, CR4, Tim-1, Tim-4 and CD169. In some embodiments, the intracellular signaling domain comprises a PI3K recruitment domain. In some embodiments, the intracellular signaling domain comprises an intracellular signaling domain derived from a scavenger receptor. In some embodiments, the intracellular domain comprises a CD47 inhibition domain. In some embodiments, the intracellular domain comprises a Rac inhibition domain, a Cdc42 inhibition domain or a GTPase inhibition domain. In some embodiments, the Rac inhibition domain, the Cdc42 inhibition domain or the GTPase inhibition domain inhibits Rac, Cdc42 or GTPase at a phagocytic cup of a cell expressing the PFP. In some embodiments, the intracellular domain comprises an F-actin disassembly activation domain, a ARHGAP12 activation domain, a ARHGAP25 activation domain or a SH3BP1 activation domain. In some embodiments, the intracellular domain comprises a phosphatase inhibition domain. In some embodiments, the intracellular domain comprises an ARP2/3 inhibition domain. In some embodiments, the intracellular domain comprises at least one ITAM domain. In some embodiments, the intracellular domain comprises at least 1, 2, 3, 4, 5, 6, 7, 8, 9, 10, or more ITAM domains. In some embodiments, the intracellular domain comprises at least one ITAM domain select from an ITAM domain of CD3 zeta, CD3 epsilon, CD3 gamma, CD3 delta, Fc epsilon receptor 1 chain, Fc epsilon receptor 2 chain, Fc gamma receptor 1 chain, Fc gamma receptor 2a chain, Fc gamma receptor 2b 1 chain, Fc gamma receptor 2b2 chain, Fc gamma receptor 3a chain, Fc gamma receptor 3b chain, Fc beta receptor 1 chain, TYROBP (DAP12), CD5, CD16a, CD16b, CD22, CD23, CD32, CD64, CD79a, CD79b, CD89, CD278, CD66d, functional fragments thereof, and amino acid sequences thereof having at least one but not more than 20 modifications thereto. In some embodiments, the at least one ITAM domain comprises a Src-family kinase phosphorylation site. In some embodiments, the at least one ITAM domain comprises a Syk recruitment domain. In some embodiments, the intracellular domain comprises an F-actin depolymerization activation domain. In some embodiments, the intracellular domain lacks enzymatic activity.

In some embodiments, the intracellular domain does not comprise a domain derived from a CD3 zeta intracellular domain. In some embodiments, the intracellular domain does not comprise a domain derived from a MerTK intracellular domain. In some embodiments, the intracellular domain does not comprise a domain derived from a TLR4 intracellular domain. In some embodiments, the intracellular domain comprises a CD47 inhibition domain. In some embodiments, the intracellular signaling domain comprises a domain that activates integrin, such as the intracellular region of PSGL-1

In some embodiments, the intracellular signaling domain comprises a domain that activates Rap1 GTPase, such as that from EPAC and C3G. In some embodiments, the intracellular signaling domain is derived from paxillin. In some embodiments, the intracellular signaling domain activates focal adhesion kinase. In some embodiments, the intracellular signaling domain is derived from a single phagocytic receptor. In some embodiments, the intracellular signaling domain is derived from a single scavenger receptor. In some embodiments, the intracellular domain comprises a phagocytosis enhancing domain.

In some embodiments, the intracellular domain comprises a pro-inflammatory signaling domain. In some embodiments, the pro-inflammatory signaling domain comprises a kinase activation domain or a kinase binding domain. In some embodiments, the pro-inflammatory signaling domain comprises an IL-1 signaling cascade activation domain. In some embodiments, the pro-inflammatory signaling domain comprises an intracellular signaling domain derived from TLR3, TLR4, TLR7, TLR 9, TRIF, RIG-1, MYD88, MAL, IRAK1, MDA-5, an IFN-receptor, STING, an NLRP family member, NLRP1-14, NOD1, NOD2, Pyrin, AIM2, NLRC4, FCGR3A, FCERIG, CD40, Tank1-binding kinase (TBK), a caspase domain, a procaspase binding domain or any combination thereof.

In some embodiments, the intracellular domain comprises a signaling domain, such as an intracellular signaling domain, derived from a connexin (Cx) protein. For example, the intracellular domain can comprise a signaling domain, such as an intracellular signaling domain, derived from Cx43, Cx46, Cx37, Cx40, Cx33, Cx50, Cx59, Cx62, Cx32, Cx26, Cx31, Cx30.3, Cx31.1, Cx30, Cx25, Cx45, Cx47, Cx31.3, Cx36, Cx31.9, Cx39, Cx40.1 or Cx23. For example, the intracellular domain can comprise a signaling domain, such as an intracellular signaling domain, derived from Cx43.

In some embodiments, the intracellular domain comprises a signaling domain, such as an intracellular signaling domain, derived from a SIGLEC protein. For example, the intracellular domain can comprise a signaling domain, such as an intracellular signaling domain, derived from Siglec-1 (Sialoadhesin), Siglec-2 (CD22), Siglec-3 (CD33), Siglec-4 (MAG), Siglec-5, Siglec-6, Siglec-7, Siglec-8, Siglec-9, Siglec-10, Siglec-11, Siglec-12, Siglec-13, Siglec-14, Siglec-15, Siglec-16 or Siglec-17.

In some embodiments, the intracellular domain comprises a signaling domain, such as an intracellular signaling domain, derived from a C-type lectin protein. For example, the intracellular domain can comprise a signaling domain, such as an intracellular signaling domain, derived from a mannose receptor protein. For example, the intracellular domain can comprise a signaling domain, such as an intracellular signaling domain, derived from an asialoglycoprotein receptor protein. For example, the intracellular domain can comprise a signaling domain, such as an intracellular signaling domain, derived from macrophage galactose-type lectin (MGL), DC-SIGN (CLEC4L), Langerin (CLEC4K), Myeloid DAP12 associating lectin (MDL)-1 (CLEC5A), a DC associated C type lectin 1 (Dectin1) subfamily protein, dectin 1/CLEC7A, DNGR1/CLEC9A, Myeloid C type lectin like receptor (MICL) (CLEC12A), CLEC2 (CLEC1B), CLEC12B, a DC immunoreceptor (DCIR) subfamily protein, DCIR/CLEC4A, Dectin 2/CLEC6A, Blood DC antigen 2 (BDCA2) (CLEC4C), Mincle (macrophage inducible C type lectin) (CLEC4E), a NOD-like receptor protein, NOD-like receptor MHC Class II transactivator (CIITA), IPAF, BIRC1, a RIG-I-like receptor (RLR) protein, RIG-I, MDA5, LGP2, NAIP5/Birc1e, an NLRP protein, NLRP1, NLRP2, NLRP3, NLRP4, NLRP5, NLRP6, NLRP7, NLRP89, NLRP9, NLRP10, NLRP11, NLRP12, NLRP13, NLRP14, an NLR protein, NOD1 or NOD2, or any combination thereof.

In some embodiments, the intracellular domain comprises a signaling domain, such as an intracellular signaling domain, derived from a cell adhesion molecule. For example, the intracellular domain can comprise a signaling domain, such as an intracellular signaling domain, derived from an IgCAMs, a cadherin, an integrin, a C-type of lectin-like domains protein (CTLD) and/or a proteoglycan molecule. For example, the intracellular domain can comprise a signaling domain, such as an intracellular signaling domain, derived from an E-cadherin, a P-cadherin, an N-cadherin, an R-cadherin, a B-cadherin, a T-cadherin, or an M-cadherin. For example, the intracellular domain can comprise a signaling domain, such as an intracellular signaling domain, derived from a selectin, such as an E-selectin, an L-selectin or a P-selectin.

In some embodiments, the CFP does not comprise a full length intracellular signaling domain. In some embodiments, the intracellular domain is at least 5, 10, 20, 30, 40, 50, 60, 70, 80, 90, 100, 150, 200, 300, 300, 400, or 500 amino acids in length. In some embodiments, the intracellular domain is at most 10, 20, 30, 40, 50, 60, 70, 80, 90, 100, 150, 200, 300, 300, 400, or 500 amino acids in length.

In some embodiments, the recombinant nucleic acid encodes an FcRα chain extracellular domain, an FcRα chain transmembrane domain and/or an FcRα chain intracellular domain. In some embodiments, the recombinant nucleic acid encodes an FcRβ chain extracellular domain, an FcRβ chain transmembrane domain and/or an FcRβ chain intracellular domain. In some embodiments, the FcRα chain or the FcRβ chain forms a complex with FcRγ when expressed in a cell. In some embodiments, the FcRα chain or FcRβ chain forms a complex with endogenous FcRγ when expressed in a cell. In some embodiments, the FcRα chain or the FcRβ chain does not incorporate into a cell membrane of a cell that does not express FcRγ. In some embodiments, the CFP does not comprise an FcRα chain intracellular signaling domain. In some embodiments, the CFP does not comprise an FcRβ chain intracellular signaling domain. In some embodiments, the recombinant nucleic acid encodes a TREM extracellular domain, a TREM transmembrane domain and/or a TREM intracellular domain. In some embodiments, the TREM is TREM1, TREM 2 or TREM 3.

Provided herein are methods and compositions to generate therapeutic myeloid cells, such as that are engineered to target and kill a diseased cell, such as a cancer cell. Although the disclosure abundantly exemplifies compositions and methods for killing cancer or tumor cell, one of skill in the art would be able to design such macrophages to target another diseased cell, such as an infected cell, without undue experimentation.

In some embodiments, a macrophage is isolated from a subject in need thereof, engineered to express a protein or more than one proteins of interest, and is then administered into the subject. In some embodiments, the subject has a cancer or a tumor. The macrophage that is isolated from the subject, is engineered to express a protein or more than one proteins of interest, and is then administered into the subject is a therapeutic macrophage that can target and kill a cancer cell or a tumor cell of the subject.

In one aspect, provided herein is a composition comprising one or more recombinant nucleic acid sequences comprising: (A) a first nucleic acid sequence encoding an exogenous polypeptide; (B) a second nucleic acid sequence encoding a myeloid cell chimeric antigen receptor fusion protein (CFP), wherein the CFP comprises: (a) an intracellular signaling subunit comprising an intracellular signaling domain having tyrosine residues that are phosphorylated upon antigen binding by the receptor; (b) a transmembrane domain, and (c) an extracellular binding domain having binding specificity for a component on the surface of a target cell, wherein the extracellular binding domain is operably linked to the transmembrane domain and the intracellular signaling subunit; and (d) a transcription activator domain operably linked to the intracellular signaling subunit by a protease cleavage sequence, wherein the transcription activator domain promotes transcription of the first nucleic acid sequence encoding the exogenous polypeptide; and (C) a third nucleic acid sequence encoding (a) a protease that cleaves the protease cleavage sequence that operably links the transcription activator domain to the intracellular signaling subunit; (b) a domain that binds to the tyrosine residues that are phosphorylated upon activation of the CFP; wherein the protease that cleaves the protease cleavage sequence and the domain that binds to the tyrosine residues are operably linked.

In some embodiments, the third nucleic acid sequence further encodes (c) an stimulus responsive element. In some embodiments, the stimulus responsive element (c) is fused to the domain that binds to the phosphorylated tyrosine residues. In some embodiments, the stimulus responsive element is responsive to the microenvironment of the cell that expresses the nucleic acid sequence. In some embodiments, the (c) is a degron, operably linked with (b). In some embodiments, the degron is an HIF-1a degron.

In some embodiments, the one or more recombinant nucleic acid is expressed in a myeloid cell. In some embodiments, the myeloid cell is a macrophage cell. In some embodiments, the target cell is a cancer cell.

In some embodiments, the first nucleic acid encodes a pro-phagocytic or pro-inflammatory polypeptide, or both. In some embodiments, the CFP is a phagocytic receptor fusion protein, having one or more phagocytic receptor domains or fragments thereof. In some embodiments, the one or more phagocytic receptor domains or fragments thereof is selected from the group consisting of lectin, dectin 1, CD206, scavenger receptor A1 (SRA1), MARCO, CD36, CD163, MSR1, SCARA3, COLEC12, SCARA5, SCARB1, SCARB2, CD68, OLR1, SCARF1, SCARF2, CXCL16, STAB1, STAB2, SRCRB4D, SSC5D, CD205, CD207, CD209, RAGE, CD14, CD64, F4/80, CCR2, CX3CR1, CSF1R, Tie2, HuCRIg(L), CD64, CD32a, CD16a, CD89, Fc-alpha receptor I, CR1, CD35, CR3, CR4, Tim-1, Tim-4 and CD169.

In some embodiments, the intracellular domain of the CFP is derived from the phagocytic receptor.

In some embodiments, the intracellular signaling domain is derived from a receptor other than a phagocytic receptor selected from Megf10, MerTk, FcR-alpha, or Bai1. In some embodiments, the intracellular signaling subunit comprising an intracellular signaling domain having tyrosine residues comprise at least one ITAM domain. In some embodiments, the intracellular signaling subunit comprises more than one ITAM domains. In some embodiments, the at least one ITAM domain select from a group CD3 zeta TCR subunit, CD3 epsilon TCR subunit, CD3 gamma TCR subunit, CD3 delta TCR subunit, TCR zeta chain, Fc epsilon receptor 1 chain, Fc epsilon receptor 2 chain, Fc gamma receptor 1 chain, Fc gamma receptor 2a chain, Fc gamma receptor 2b1 chain, Fc gamma receptor 2b2 chain, Fc gamma receptor 3a chain, Fc gamma receptor 3b chain, Fc beta receptor 1 chain, TYROBP (DAP12), CD5, CD16a, CD16b, CD22, CD23, CD32, CD64, CD79a, CD79b, CD89, CD278, CD66d, functional fragments thereof, and amino acid sequences thereof having at least one but not more than 20 modifications thereto. In some embodiments, the at least one ITAM domain comprises a Src-family kinase phosphorylation site. In some embodiments, the at least one ITAM domain comprises a Syk recruitment domain.

In some embodiments of the various aspects described herein, the intracellular signaling subunit further comprises a DAP12 recruitment domain. In some embodiments, the intracellular domain comprises at least 1, 2, 3, 4, 5, 6, 7, 8, 9, or 10 ITAM domains.

In some embodiments, the intracellular signaling subunit further comprises a pro-inflammatory signaling domain comprising an IL-1 signaling cascade activation domain. In some embodiments, the pro-inflammatory signaling domain comprises an intracellular signaling domain derived from TLR3, TLR4, TLR7, TLR 9, TRIF, RIG-1, MYD88, MAL, IRAK1, MDA-5, an IFN-receptor, an NLRP family member, NLRP1-14, NOD1, NOD2, Pyrin, AIM2, NLRC4, FCGR3A, FCERIG, CD40, a caspase domain or a procaspase binding domain or any combination thereof.

In some embodiments, the intracellular signaling domain further comprises a domain that activate integrin such as the intracellular region of PSGL-1.

In some embodiments, the intracellular signaling domain further comprises a domain that activate Rap1 GTPase, such as that from EPAC and C3G. In some embodiments, the intracellular signaling domain further comprises a domain from paxillin.

In some embodiments, the intracellular signaling domain activates focal adhesion kinase.

In some embodiments, the extracellular binding domain having binding specificity for a component on the surface of a target cell comprises an antibody or a functional fragment thereof. In some embodiments, the extracellular binding domain comprises a single chain variable fragment (scFv).

In some embodiments, the component on the surface of the target cell is an antigen selected from the group consisting of Thymidine Kinase (TK1), Hypoxanthine-Guanine Phosphoribosyltransferase (HPRT), Receptor Tyrosine Kinase-Like Orphan Receptor 1 (ROR1), Mucin-1, Mucin-16 (MUC16), MUC1, Epidermal Growth Factor Receptor vIII (EGFRvIII), Mesothelin, Human Epidermal Growth Factor Receptor 2 (HER2), Mesothelin, EBNA-1, LEMD1, Phosphatidyl Serine, Carcinoembryonic Antigen (CEA), B-Cell Maturation Antigen (BCMA), Glypican 3 (GPC3), Follicular Stimulating Hormone receptor, Fibroblast Activation Protein (FAP), Erythropoietin-Producing Hepatocellular Carcinoma A2 (EphA2), EphB2, a Natural Killer Group 2D (NKG2D) ligand, Disialoganglioside 2 (GD2), CD2, CD3, CD4, CD5, CD7, CD8, CD19, CD20, CD22, CD24, CD30, CD33, CD38, CD44v6, CD45, CD56CD79b, CD97, CD117, CD123, CD133, CD138, CD171, CD179a, CD213A2, CD248, CD276, PSCA, CS-1, CLECL1, GD3, PSMA, FLT3, TAG72, EPCAM, IL-1, an integrin receptor, PRSS21, VEGFR2, PDGFR-beta, SSEA-4, EGFR, NCAM, prostase, PAP, ELF2M, GM3, TEM7R, CLDN6, TSHR, GPRC5D, ALK, IGLL1 and combinations thereof.

In some embodiments, the component on the surface of the target cell is an antigen selected from the group consisting of CD2, CD3, CD4, CD5, CD7, CCR4, CD8, CD30, CD45, CD56.

In some embodiments, the component on the surface of the target cell is an ovarian cancer antigen or a T lymphoma antigen.

In some embodiments, the component on the surface of the target cell is an integrin receptor.

In some embodiments, the component on the surface of the target cell is an integrin receptor selected from the group consisting of α1, α2, αIIb, α3, α4, α5, α6, α7, α8, α9, α10, α11, αD, αE, αL, αM, αV, αX, β 1, β 2, β 3, β 4, β 5, β 6, β 7, and β8.

In some embodiments, the component on the surface of the target cell comprises 2 or more distinct antigens.

In some embodiments, the transmembrane domain is at least 12, 13, 14, 15, 16, 17, 18, 19, 20, 21, 22, 23, 24, 25, 26, 27, 28, 29, 30, 31 or 32 amino acids in length. In some embodiments, the transmembrane domain is at most 12, 13, 14, 15, 16, 17, 18, 19, 20, 21, 22, 23, 24, 25, 26, 27, 28, 29, 30, 31 or 32 amino acids in length. In some embodiments, the transmembrane domain comprises a transmembrane domain that oligomerizes with DAP12. In some embodiments, the transmembrane domain and the extracellular antigen binding domain are operatively linked through a linker. In some embodiments, the linker comprises a peptide. In some embodiments, the linker comprises a hinge region of CD8α, IgG1 or IgG4. In some embodiments, the linker is a synthetic linker. In some embodiments, the transmembrane domain comprises an FcR transmembrane domain.

The composition of any embodiment described above, wherein the transcription activator domain further comprises a DNA binding domain. In some embodiments, the DNA binding domain is selected from the DNA binding domain (DB) of Gal4, ZFHD1 or tet-R. In some embodiments, the transcription activator domain comprises a VP64 transactivation domain.

In some embodiments, the protease that cleaves the protease cleavage sequence that operably links the transcription activator domain to the intracellular signaling subunit is a hepatitis C virus (HCV) NS3 protease. In some embodiments, the domain that binds to the tyrosine residues that are phosphorylated upon activation of the CFP is a phosphotyrosine binding (PTB) domain. In some embodiments, the PTB is an Shc PTB.

In some embodiments, the recombinant nucleic acid is DNA.

In some embodiments, the recombinant nucleic acid is RNA. In some embodiments, the recombinant nucleic acid is mRNA. In some embodiments, the recombinant nucleic acid is a circRNA. In some embodiments, the recombinant nucleic acid is associated with a replicon RNA.

In one aspect, provided herein is a vector, encoding the one or more recombinant nucleic acid of any one of the embodiments described above.

In one aspect, provided herein is a myeloid cell expressing the vector of an embodiment described above.

In one aspect, provided herein is a pharmaceutical composition comprising the myeloid cell of an embodiment described above.

In one aspect, provided herein is a cell comprising a recombinant nucleic acid encoding a chimeric protein comprising: (a) a cytotoxic polypeptide; (b) a protease cleavage sequence; and (c) an inhibitory polypeptide domain, wherein the inhibitory polypeptide domain inhibits the cytotoxic polypeptide; wherein the cytotoxic polypeptide, protease cleavage sequence and the inhibitory polypeptide domain are operably linked.

In some embodiments, the cell is a myeloid cell.

In some embodiments, the cytotoxic polypeptide is a human eosinophil major basic protein cytotoxic domain. In some embodiments, the cytotoxic polypeptide is a human eosinophil major basic protein acidic domain.

In some embodiments, the protease cleavage sequence is an MMP recognition sequence.

In some embodiments, the protease cleavage sequence is cleaved by MMP.

In one aspect, provided herein is a pharmaceutical composition comprising any one of the cells of the embodiments described herein.

In one aspect, provided herein is a recombinant nucleic acid of any one of the embodiments described herein.

In one aspect, provided herein is a vector, encoding the recombinant nucleic acid of the embodiments described herein.

In one aspect, provided herein is a method for preparing a myeloid cell therapeutic against cancer, the method comprising expressing in the myeloid cell a recombinant nucleic acid comprising: (A) a first nucleic acid sequence encoding an exogenous polypeptide; (B) a second nucleic acid sequence encoding a myeloid cell chimeric antigen receptor (CFP), wherein the CFP comprises: (a) an intracellular signaling subunit comprising an intracellular signaling domain having tyrosine residues that are phosphorylated upon activation of the CFP; (b) a transmembrane domain, and (c) an extracellular binding domain having binding specificity for a component on the surface of a target cell, wherein the extracellular binding domain is operably linked to the transmembrane domain and the intracellular signaling subunit; and (d) a transcription activator domain operably linked to the intracellular signaling subunit by a protease cleavage sequence, wherein the transcription activator domain promotes transcription of the first nucleic acid sequence encoding the exogenous polypeptide; and (C) a third nucleic acid sequence encoding (a) a protease that cleaves the protease cleavage sequence that operably links the transcription activator domain to the intracellular signaling subunit; (b) a domain that binds to the tyrosine residues that are phosphorylated upon activation of the CAR; wherein the protease that cleaves the protease cleavage sequence and the domain that binds to the tyrosine residues are operably linked.

In one aspect, provided herein is a method for preparing a myeloid cell therapeutic against cancer, the method comprising expressing in the myeloid cell a recombinant nucleic acid encoding a chimeric protein comprising: (a) a human eosinophil major basic protein acidic domain; (b) an MMP recognition sequence; and (c) a human eosinophil major basic protein cytotoxic domain.

In one aspect, provided herein is a method for treating a subject having a cancer, the method comprising, administering to the subject in need thereof the pharmaceutical composition of any one of the embodiments described herein.

In one aspect, provided herein is a method of inducing a tumor regression in a subject in need thereof, the method comprising administering intravenously to the subject a pharmaceutical composition comprising myeloid cells, wherein the myeloid cells express one or more recombinant nucleic acids encoding one or more polypeptides, and wherein at least one of the one or more polypeptides is functionally active in the tumor microenvironment, and not functionally active in a non-tumor environment. In some embodiments of several aspects described herein, the pharmaceutical composition is the pharmaceutical composition of the embodiments described herein. In some embodiments of several aspects described herein, the pharmaceutical composition is the pharmaceutical composition of claim the embodiments described herein.

In some embodiments of several aspects described herein, the target cell is a cancer cell that is a glioblastoma cell.

Provided herein is a method for treating a subject having a cancer, the method comprising, administering to the subject in need thereof, the method comprising, administering to the subject in need thereof the pharmaceutical composition described above.

In some embodiments, the recombinant nucleic acid comprises a sequence encoding a pro-inflammatory polypeptide. In some embodiments, the composition further comprises a proinflammatory nucleotide or a nucleotide in the recombinant nucleic acid, for example, an ATP, ADP, UTP, UDP, and/or UDP-glucose. In some embodiments, the transcription activator domain comprises a VP64 transactivation domain. In some embodiments, the protease that cleaves the protease cleavage sequence that operably links the transcription activator domain to the intracellular signaling subunit is a hepatitis C virus (HCV) NS3 protease. In some embodiments, the domain that binds to the tyrosine residues that are phosphorylated upon activation of the CFP is a phosphotyrosine binding (PTB) domain. In some embodiments, the PTB is an Shc PTB. In some embodiments, the third nucleic acid encodes a degron, that can be operably linked to the CFP. In some embodiments, the degron is an HIF-1a degron. In some embodiments, the recombinant nucleic acid is DNA. In some embodiments, the recombinant nucleic acid is RNA. In some embodiments, the recombinant nucleic acid is mRNA. In some embodiments, the recombinant nucleic acid is a circRNA.

In some embodiments, recombinant nucleic acid is associated with a replicon RNA. Provided herein is a method for preparing a myeloid cell therapeutic against cancer, the method comprising expressing in the myeloid cell a recombinant nucleic acid comprising: (A) a first nucleic acid sequence encoding an exogenous polypeptide; (B) a second nucleic acid sequence encoding a myeloid cell chimeric antigen receptor (CFP), wherein the CFP comprises: (a) an intracellular signaling subunit comprising an intracellular signaling domain having tyrosine residues that are phosphorylated upon activation of the CFP; (b) a transmembrane domain, and (c) an extracellular binding domain having binding specificity for a component on the surface of a target cell, wherein the extracellular binding domain is operably linked to the transmembrane domain and the intracellular signaling subunit; and (d) a transcription activator domain operably linked to the intracellular signaling subunit by a protease cleavage sequence, wherein the transcription activator domain promotes transcription of the first nucleic acid sequence encoding the exogenous polypeptide; and (C) a third nucleic acid sequence encoding (a) a protease that cleaves the protease cleavage sequence that operably links the transcription activator domain to the intracellular signaling subunit; (b) a domain that binds to the tyrosine residues that are phosphorylated upon activation of the CFP; wherein the protease that cleaves the protease cleavage sequence and the domain that binds to the tyrosine residues are operably linked. Provided herein is a method for preparing a myeloid cell therapeutic against cancer, the method comprising expressing in the myeloid cell a recombinant nucleic acid encoding a chimeric protein comprising: (a) a human eosinophil major basic protein acidic domain; (b) an MMP recognition sequence; and (c) a human eosinophil major basic protein cytotoxic domain.

Provided herein is a method for treating a subject having a cancer, the method comprising, administering to the subject in need thereof the pharmaceutical composition of described above. Provided herein is a method for treating a subject having a cancer, the method comprising, administering to the subject in need thereof the pharmaceutical composition described herein. Provided herein is a method of inducing a tumor regression in a subject in need thereof, the method comprising administering intravenously to the subject a pharmaceutical composition comprising myeloid cells, wherein the myeloid cells express one or more recombinant nucleic acids encoding one or more polypeptides, and wherein at least one of the one or more polypeptides is functionally active in the tumor microenvironment, and not functionally active in a non-tumor environment.

In some embodiments, the composition further comprises a pro-inflammatory polypeptide. In some embodiments, the pro-inflammatory polypeptide is a chemokine, cytokine. In some embodiments, the chemokine is selected from the group consisting of IL-1, IL3, IL5, IL-6, IL-8, IL-12, IL-13, IL-23, TNF, CCL2, CXCL9, CXCL10, CXCL11, IL-18, IL-23, IL-27, CSF, MCSF, GMCSF, IL17, IP-10, RANTES, and interferon. In some embodiments, the cytokine is selected from the group consisting of IL-1, IL3, IL5, IL-6, IL-12, IL-13, IL-23, TNF, CCL2, CXCL9, CXCL10, CXCL11, IL-18, IL-23, IL-27, CSF, MCSF, GMCSF, IL17, IP-10, RANTES, and interferon.

In some embodiments, the myeloid cells are specifically targeted for delivery. Myeloid cells can be targeted using specialized biodegradable polymers, such as PLGA (poly (lactic-co-glycolic) acid and/or polyvinyl alcohol (PVA). In some embodiments, one or more compounds can be selectively incorporated in such polymeric structures to affect the myeloid cell function. In some embodiments, the targeting structures are multilayered, e.g., of one or more PLGA and one or more PVA layers. In some embodiments, the targeting structures are assembled in an order for a layered activity. In some embodiments, the targeted polymeric structures are organized in specific shaped components, such as labile structures that can adhere to a myeloid cell surface and deliver one or more components such as growth factors and cytokines, such as to maintain the myeloid cell in a microenvironment that endows a specific polarization. In some embodiments, the polymeric structures are such that they are not phagocytosed by the myeloid cell, but they can remain adhered on the surface. In some embodiments the one or more growth factors may be M1 polarization factors, such as a cytokine. In some embodiments the one or more growth factors may be an M2 polarization factor, such as a cytokine. In some embodiments, the one or more growth factors may be a macrophage activating cytokine, such as IFNγ. In some embodiments the polymeric structures are capable of sustained release of the one or more growth factors in an in vivo environment, such as in a solid tumor.

In some embodiments, the recombinant nucleic acid comprises a sequence encoding a homeostatic regulator of inflammation. In some embodiments, the homeostatic regulator of inflammation is a sequence in an untranslated region (UTR) of an mRNA. In some embodiments, the sequence in the UTR is a sequence that binds to an RNA binding protein. In some embodiments, translation is inhibited or prevented upon binding of the RNA binding protein to the sequence in an untranslated region (UTR). In some embodiments, the sequence in the UTR comprises a consensus sequence of WWWU(AUUUA)UUUW, wherein W is A or U (SEQ ID NO: 85). In some embodiments, the recombinant nucleic acid is expressed on a bicistronic vector.

In some embodiments, the target cell is a mammalian cell. In some embodiments, the target cell is a human cell. In some embodiments, the target cell comprises a cell infected with a pathogen. In some embodiments, the target cell is a cancer cell. In some embodiments, the target cell is a cancer cell that is a lymphocyte. In some embodiments, the target cell is a cancer cell that is an ovarian cancer cell. In some embodiments, the target cell is a cancer cell that is a breast cell. In some embodiments, the target cell is a cancer cell that is a pancreatic cell. In some embodiments, the target cell is a cancer cell that is a glioblastoma cell.

In some embodiments, the recombinant nucleic acid is DNA. In some embodiments, the recombinant nucleic acid is RNA. In some embodiments, the recombinant nucleic acid is mRNA. In some embodiments, the recombinant nucleic acid is an unmodified mRNA. In some embodiments, the recombinant nucleic acid is a modified mRNA. In some embodiments, the recombinant nucleic acid is a circRNA. In some embodiments, the recombinant nucleic acid is a tRNA. In some embodiments, the recombinant nucleic acid is a microRNA. In some embodiments, the recombinant nucleic acid is a self-replicating RNA.

Also provided herein is a vector comprising a recombinant nucleic acid sequence encoding a CFP described herein. In some embodiments, the vector is viral vector. In some embodiments, the viral vector is retroviral vector or a lentiviral vector. In some embodiments, the vector further comprises a promoter operably linked to at least one nucleic acid sequence encoding one or more polypeptides. In some embodiments, the vector is polycistronic. In some embodiments, each of the at least one nucleic acid sequence is operably linked to a separate promoter. In some embodiments, the vector further comprises one or more internal ribosome entry sites (IRESs). In some embodiments, the vector further comprises a 5'UTR and/or a 3'UTR flanking the at least one nucleic acid sequence encoding one or more polypeptides. In some embodiments, the vector further comprises one or more regulatory regions.

Also provided herein is a polypeptide encoded by the recombinant nucleic acid of a composition described herein.

Provided herein is a composition comprising a recombinant nucleic acid sequence encoding a CFP comprising a phagocytic or tethering receptor (PR) subunit (e.g., a phagocytic receptor fusion protein (PFP)) comprising: a PR subunit comprising: a transmembrane domain, and an intracellular domain comprising an intracellular signaling domain; and an extracellular domain comprising an antigen binding domain specific to an antigen of a target cell; wherein the transmembrane domain and the extracellular domain are operatively linked; and wherein upon binding of the CFP to the antigen of the target cell, the killing or phagocytosis activity of a myeloid cell, such as a neutrophil, monocyte, myeloid dendritic cell (mDC), mast cell or macrophage expressing the CFP is increased by at least greater than 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 100%, 150%, 200%, 250%, 300%, 350%, 400%, 450%, 500%, 550%, 600%, 650%, 700%, 750%, 800%, 850%, 900%, 950%, or 1000% compared to a cell not expressing the CFP.

Table 1 shows exemplary sequences of chimeric fusion protein domains and/or fragments thereof that are meant to be non-limiting for the disclosure.

TABLE 1

EXEMPLARY CHIMERIC FUSION PROTEINS AND RECEPTOR DOMAINS

| SEQ ID NO | CFP/Domain | Sequence |
|---|---|---|
| 1 | CD5-FcR-PI3K | MWLQSLLLLGTVACSISEIQLVQSGGGLVKPGGSVRISCAASGYTFTNYGMNWVRQAPGKGLEWMGWINTHTGEPTYADSFKGRFTFSLDDSKNTAYLQINSLRAEDTAVYFCTRRGYDWYFDVWGQGTTVTV*SSGGGGSGGGGSGGGGS*DIQMTQSPSSLSASVGDRVTITCRASQDINSYLSWFQQKPGKAPKTLIYRANRLESGVPSRF*SGSGSG*TDYTLTISSLQYEDFGIYYCQQYDESPWTFGGGTKLEIK*SGGGGS*GALSNSIMYFSHFVPVFLPAKPTTTPAPRPPTPAPTIASQPLSLRPEACRPAAGGAVHTRGLDIYIWAPLAGTCGVLLLSLVITLYCRRLKIQVRKAAITSYEKSDGVYTGLSTRNQETYETLKHEKPPQ*GSGS*YEDMRGILYAAPQLRSIRGQPGPNHEEDADSYENM |
| 2 | HER2-FcR-PI3K | MWLQSLLLLGTVACSISDIQMTQSPSSLSASVGDRVTITCRASQDVNTAVAWYQQKPGKAPKLLIYSASFLYSGVPSRFSGSRSGTDFTLTISSLQPEDFATYYCQQHYTTPPTFGQGTKVEIKRTGSTSGSGKPGSGEGSEVQLVE*SGGGL*VQPGGSLRLSCAASGFNIKDTYIHWVRQAPGKGLEWVARIYPTNGYTRYADSVKGRFTISADTSKNTAYLQMNSLRAEDTAVYYCSRWGGDGFYAMDVWGQGTLVTV*SSSGGGGS*GALSNSIMYFSHFVPVFLPAKPTTTPAPRPPTPAPTIASQPLSLRPEACRPAAGGAVHTRGLDIYIWAPLAGTCGVLLLSLVITLYCRRLKIQVRKAAITSYEKSDGVYTGLSTRNQETYETLKHEKPPQ*GSGS*YEDMRGILYAAPQLRSIRGQPGPNHEEDADSYENM |
| 3 | CD5-FcR-CD40 | MWLQSLLLLGTVACSISEIQLVQSGGGLVKPGGSVRISCAASGYTFTNYGMNWVRQAPGKGLEWMGWINTHTGEPTYADSFKGRFTFSLDDSKNTAYLQINSLRAEDTAVYFCTRRGYDWYFDVWGQGTTVTV*SSGGGGSGGGGSGGGGS*DIQMTQSPSSLSASVGDRVTITCRASQDINSYLSWFQQKPGKAPKTLIYRANRLESGVPSRFSGSGSGTDYTLTISSLQYEDFGIYYCQQYDESPWTFGGGTKLEIK*SGGGGS*GALSNSIMYFSHFVPVFLPAKPTTTPAPRPPTPAPTIASQPLSLRPEACRPAAGGAVHTRGLDIYIWAPLAGTCGVLLLSLVITLYCRLKIQVRKAAITSYEKSDGVYTGLSTRNQETYETLKHEKPPQKKVAKKPTNKAPHPKQEPQEINFPDDLPGSNTAAPVQETLHGCQPVTQEDGKESRISVQERQ |
| 4 | CD5-FcR-MDA5 | MWLQSLLLLGTVACSISEIQLVQSGGGLVKPGGSVRISCAASGYTFTNYGMNWVRQAPGKGLEWMGWINTHTGEPTYADSFKGRFTFSLDDSKNTAYLQINSLRAEDTAVYFCTRRGYDWYFDVWGQGTTVTVSSGGGGSGGGGSGGGGSDIQMTQSPSSLSASVGDRVTITCRASQDINSYLSWFQQKPGKAPKTLIYRANRLESGVPSRFSGSGSGTDYTLTISSLQYEDFGIYYCQQYDESPWTFGGGTKLEIKSGGGGSGALSNSIMYFSHFVPVFLPAKPTTTPAPRPPTPAPTIASQPLSLRPEACRPAAGGAVHTRGLDIYIWAPLAGTCGVLLLSLVITLYCRLKIQVRKAAITSYEKSDGVYTGLSTRNQETYETLKHEKPPQGSGSMSNGYSTDENFRYLISCFRARVKMYIQVEPVLDYLTFLPAEVKEQIQRTVATSGNMQAVELLLSTLEKGVWHLGWTREFVEALRRTGSPLAARYMNPELTDLPSPSFENAHDEYLQLLNLLQPTLVDKLLVRDVLDKCMEEELLTIEDRNRIAAAENNGNESGVRELLKRIVQKENWFSAFLNVLRQTGNNELVQELTGSDCSESNAEIEN |

TABLE 1-continued

EXEMPLARY CHIMERIC FUSION PROTEINS AND RECEPTOR DOMAINS

| SEQ ID NO | CFP/Domain | Sequence |
|---|---|---|
| 5 | CD5-FcR-TNFR1 | MWLQSLLLLGTVACSISEIQLVQSGGGLVKPGGSVRISCAASGYTFTNYGMNWVRQAPGKGLEWMGWINTHTGEPTYADSFKGRFTFSLDDSKNTAYLQINSLRAEDTAVYFCTRRGYDWYFDVWGQGTTVTVSSGGGGSGGGGSGGGGSDIQMTQSPSSLSASVGDRVTITCRASQDINSYLSWFQQKPGKAPKTLIYRANRLESGVPSRFSGSGSGTDYTLTISSLQYEDFGIYYCQQYDESPWTFGGGTKLEIKSGGGGSGALSNSIMYFSHFVPVFLPAKPTTTPAPRPPTPAPTIASQPLSLRPEACRPAAGGAVHTRGLDIYIWAPLAGTCGVLLLSLVITLYCRLKIQVRKAAITSYEKSDGVYTGLSTRNQETYETLKHEKPPQGSGSQRWKSKLYSIVCGKSTPEKEGELEGTTTKPLAPNPSFSPTPGFTPTLGFSPVPSSTFTSSSTYTPGDCPNFAAPRREVAPPYQGADPILATALASDPIPNPLQKWEDSAHKPQSLDTDDPATLYAVVENVPPLRWKEFVRRLGLSDHEIDRLELQNGRCLREAQYSMLATWRRRTPRREATLELLGRVLRDMDLLGCLEDIEEALCGPAALPPAPSLLR |
| 6 | CD5-FcR-TNFR2 | MWLQSLLLLGTVACSISEIQLVQSGGGLVKPGGSVRISCAASGYTFTNYGMNWVRQAPGKGLEWMGWINTHTGEPTYADSFKGRFTFSLDDSKNTAYLQINSLRAEDTAVYFCTRRGYDWYFDVWGQGTTVTVSSGGGGSGGGGSGGGGSDIQMTQSPSSLSASVGDRVTITCRASQDINSYLSWFQQKPGKAPKTLIYRANRLESGVPSRFSGSGSGTDYTLTISSLQYEDFGIYYCQQYDESPWTFGGGTKLEIKSGGGGSGALSNSIMYFSHFVPVFLPAKPTTTPAPRPPTPAPTIASQPLSLRPEACRPAAGGAVHTRGLDIYIWAPLAGTCGVLLLSLVITLYCRLKIQVRKAAITSYEKSDGVYTGLSTRNQETYETLKHEKPPQGSGSPLCLQREAKVPHLPADKARGTQGPEQQHLLITAPSSSSSSLESSASALDRRAPTRNQPQAPGVEASGAGEARASTGSSDSSPGGHGTQVNVTCIVNVCSSSDHSSQCSSQASSTMGDTDSSPSESPKDEQVPFSKEECAFRSQLETPETLLGSTEEKPLPLGVPDAGMKPS |
| 7 | GMCSF Signal peptide | MWLQSLLLLGTVACSIS |
| 8 | Anti-CD5 heavy chain variable domain | EIQLVQSGGGLVKPGGSVRISCAASGYTFTNYGMNWVRQAPGKGLEWMGWINTHTGEPTYADSFKGRFTFSLDDSKNTAYLQINSLRAEDTAVYFCTRRGYDWYFDVWGQGTTVTV |
| 9 | Anti-CD5 light chain variable domain | DIQMTQSPSSLSASVGDRVTITCRASQDINSYLSWFQQKPGKAPKTLIYRANRLESGVPSRFSGSGSGTDYTLTISSLQYEDFGIYYCQQYDESPWTFGGGTKLEIK |
| 10 | Anti-CD5 scFv | EIQLVQSGGGLVKPGGSVRISCAASGYTFTNYGMNWVRQAPGKGLEWMGWINTHTGEPTYADSFKGRFTFSLDDSKNTAYLQINSLRAEDTAVYFCTRRGYDWYFDVWGQGTTVTV*SSGGGGSGGGGSGGGGS*DIQMTQSPSSLSASVGDRVTITCRASQDINSYLSWFQQKPGKAPKTLIYRANRLESGVPSRFSGSGSGTDYTLTISSLQYEDFGIYYCQQYDESPWTFGGGTKLEIK |
| 11 | Anti-CD5 scFv | MWLQSLLLLGTVACSISEIQLVQSGGGLVKPGGSVRISCAASGYTFTNYGMNWVRQAPGKGLEWMGWINTIITGEPTYADSFKGRFTFSLDDSKNTAYLQINSLRAEDTAVYFCTRRGYDWYFDVWGQGTTVTVSSGGGGSGGGGSGGGGSDIQMTQSPSSLSASVGDRVTITCRASQDINSYLSWFQQKPGKAPKTLIYRANRLESGVPSRFSGSGSGTDYTLTISSLQYEDFGIYYCQQYDESPWTFGGGTKLEIK |
| 12 | Anti-HER2 heavy chain variable domain | DIQMTQSPSSLSASVGDRVTITCRASQDVNTAVAWYQQKPGKAPKLLIYSASFLYSGVPSRFSGSRSGTDFTLTISSLQPEDFATYYCQQHYTTPPTFGQGTKVEIKRTGSTSGSGKPGSGEGSEVQLVE |
| 13 | Anti-HER2 light chain variable domain | LVQPGGSLRLSCAASGFNIKDTYIHWVRQAPGKGLEWVARIYPTNGYTRYADSVKGRFTISADTSKNTAYLQMNSLRAEDTAVYYCSRWGGDGFYAMDVWGQGTLVTV |
| 14 | Anti-HER2 scFv | DIQMTQSPSSLSASVGDRVTITCRASQDVNTAVAWYQQKPGKAPKLLIYSASFLYSGVPSRFSGSRSGTDFTLTISSLQPEDFATYYCQQHYTTPPTFGQGTKVEIKRTGSTSGSGKPGSGEGSEVQLVE*SSGGGGSGGGGSGGGGS*LVQPGGSLRLSCAASGFNIKDTYIHWVRQAPGKGLEWVARIYPTNGYTRYADSVKGRFTISADTSKNTAYLQMNSLRAEDTAVYYCSRWGGDGFYAMDVWGQGTLVTV |

TABLE 1-continued

EXEMPLARY CHIMERIC FUSION PROTEINS AND RECEPTOR DOMAINS

| SEQ ID NO | CFP/Domain | Sequence |
|---|---|---|
| 15 | CD8a transmembrane domain | IYIWAPLAGTCGVLLLSLVIT |
| 16 | CD8a transmembrane domain | IYIWAPLAGTCGVLLLSLVITLYC |
| 17 | CD2 Transmembrane domain | IYLIIGICGGGSLLMVFVALLVFYIT |
| 18 | CD28 transmembrane domain | FWVLVVVGGVLACYSLLVTVAFIIFWV |
| 19 | CD68 transmembrane domain | ILLPLIIGLILLGLLALVLIAFCII |
| 20 | CD8α chain hinge domain + transmembrane domain | ALSNSIMYFSHFVPVFLPAKPTTTPAPRPPTPAPTIASQPLSLRPEACRPAAGGAVHTRGLDIYIWAPLAGTCGVLLLSLVITLYC |
| 21 | CD8α chain hinge domain + transmembrane domain | ALSNSIMYFSHFVPVFLPAKPTTTPAPRPPTPAPTIASQPLSLRPEACRPAAGGAVHTRGLDIYIWAPLAGTCGVLLLSLVIT |
| 22 | FcRγ-chain intracellular signaling domain | LYCRRLKIQVRKAAITSYEKSDGVYTGLSTRNQETYETLKHEKPPQ |
| 23 | FcRγ-chain intracellular signaling domain | LYCRLKIQVRKAAITSYEKSDGVYTGLSTRNQETYETLKHEKPPQ |
| 24 | FcRγ-chain intracellular signaling domain | RLKIQVRKAAITSYEKSDGVYTGLSTRNQETYETLKHEKPPQ |
| 25 | FcRγ-chain intracellular signaling domain | RLKIQVRKAAITSYEKSDGVYTGLSTRNQETYETLKHEKPPQ |
| 26 | PI3K recruitment domain | YEDMRGILYAAPQLRSIRGQPGPNHEEDADSYENM |
| 27 | CD40 intracellular domain | KKVAKKPTNKAPHPKQEPQEINFPDDLPGSNTAAPVQETLHGCQPVTQEDGKESRISVQERQ |
| 28 | TNFR1 intracellular domain | QRWKSKLYSIVCGKSTPEKEGELEGTTTKPLAPNPSFSPTPGFTPTLGFSPVPSSTFTSSSTYTPGDCPNFAAPRREVAPPYQGADPILATALASDPIPNPLQKWEDSAHKPQSLDTDDPATLYAVVENVPPLRWKEFVRRLGLSDHEIDRLELQNGRCLREAQYSMLATWRRRTPRREATLELLGRVLRDMDLLGCLEDIEEALCGPAALPPAPSLLR |
| 29 | TNFR2 intracellular domain | PLCLQREAKVPHLPADKARGTQGPEQQHLLITAPSSSSSSLESSSASALDRRAPTRNQPQAPGVEASGAGEARASTGSSDSSPGGHGTQVNVTCIVNVCSSSDHSSQCSSQASSTMGDTDSSPSESPKDEQVPFSKEECAFRSQLETPETLLGSTEEKPLPLGVPDAGMKPS |
| 30 | MDA5 intracellular domain | MSNGYSTDENFRYLISCFRARVKMYIQVEPVLDYLTFLPAEVKEQIQRTVATSGNMQAVELLLSTLEKGVWHLGWTREFVEALRRTGSPLAARYMNPELTDLPSPSFENAHDEYLQLLNLL |

TABLE 1-continued

EXEMPLARY CHIMERIC FUSION PROTEINS AND RECEPTOR DOMAINS

| SEQ ID NO | CFP/Domain | Sequence |
|---|---|---|
| | | QPTLVDKLLVRDVLDKCMEEELLTIEDRNRIAAAENNGNE SGVRELLKRIVQKENWFSAFLNVLRQTGNNELVQELTGSD CSESNAEIEN |
| 31 | Anti-CD137 extracellular binding domain | MEFGLSWLFLVAILKGVQCGLLDLRQGMFAQLVAQNVLLI DGPLSWYSDPGLAGVSLTGGLSYKEDTKELVVAKAGVYY VFFQLELRRVVAGEGSGSVSLALHLQPLRSAAGAAALAT VDLPPASSEARNSAFGFQGRLLHLSAGQRLGVHLHTEARA RHAWQLTQGATVLGLFRVTPEIPAGLPSPRSE |
| 32 | Anti-CD70 extracellular binding domain | QVQLVQSGAEVKKPGASVKVSCKASGYTFTNYGMNWVR QAPGQGLEWMGWINTYTGEPTYADAFKGRVTMTTDTSTS TAYMELRSLRSDDTAVYYCARDYGDYGMDYWGQGTTVT VSSGSTSGSGKPGSSEGSTKGDIVMTQSPDSLAVSLGERATI NCRASKSVSTSGYSFMHWYQQKPGQPPKLLIYLASNLESG VPDRFSGSGSGTDFTLTISSLQAEDVAVYYCQHSREVPWTF GQGTKVEIK |
| 33 | Anti-Claudin18.2 extracellular binding domain | QVQLQESGPGLVKPSQTLSLTCTVSGGSISSGYNWHWIRQP PGKGLEWIGYIHYTGSTNYNPALRSRVTISVDTSKNQFSLK LSSVTAADTAVYYCARIYNGNSFPYWGQGTTVTVSSGGG GSGGGGSGGGGSDIVMTQSPDSLAYSLGERATINCKSSQSL FNSGNQKNYLTWYQQKPGQPPKLLIYWASTRESGVPDRFS GSGSGTDIFITISSLQAEDVAVYYCQNAYSFPYTFGGGTKLE IKR |
| 34 | Anti-TROP2 extracellular binding domain | DIQLTQSPSSLSASVGDRVSITCKASQDVSIAVAWYQQKPG KAPKLLIYSASYRYTGVPDRFSGSGSGTDFTLTISSLQPEDF AVYYCQQHYITPLTFGAGTKVEIKRGGGGSGGGGSGGGGS QVQLQQSGSELKKPGASVKVSCKASGYTFTNYGMNWVK QAPGQGLKWMGWINTYTGEPTYTDDFKGRFAFSLDTSVST AYLQISSLKADDTAVYFCARGGFGSSYVVYFDVWGQGSLV TVSS |
| 35 | Anti-TROP2 extracellular binding domain | QVQLQQSGSELKKPGASVKVSCKASGYTFTNYGMNWVK QAPGQGLKWMGWINTYTGEPTYTDDFKGRFAFSLDTSVST AYLQISSLKADDTAVYFCARGGFGSSYWYFDVWGQGSLV TVSSGGGGSGGGGSGGGGSDIQLTQSPSSLSASVGDRVSIT CKASQDVSIAVAWYQQKPGKAPKLLIYSASYRYTGVPDRF SGSGSGTDFTLTISSLQPEDFAVYYCQQHYITPLTFGAGTKV EIKR |

Provided herein is a composition comprising a recombinant nucleic acid sequence encoding a CFP comprising a phagocytic or tethering receptor (PR) subunit (e.g., a phagocytic receptor fusion protein (PFP)) comprising: a PR subunit comprising: a transmembrane domain, and an intracellular domain comprising an intracellular signaling domain; and an extracellular domain comprising an antigen binding domain specific to an antigen of a target cell; wherein the transmembrane domain and the extracellular domain are operatively linked; and wherein upon binding of the CFP to the antigen of the target cell, the killing or phagocytosis activity of a myeloid cell, such as a neutrophil, monocyte, myeloid dendritic cell (mDC), mast cell or macrophage expressing the CFP is increased by at least 1.1-fold, 1.5-fold, 2-fold, 2.5-fold, 3-fold, 3.5-fold, 4-fold, 4.5-fold, 5-fold, 5.5-fold, 6-fold, 6.5-fold, 7-fold, 7.5-fold, 8-fold, 8.5-fold, 9-fold, 9.5-fold, 10-fold, 11-fold, 12-fold, 13-fold, 14-fold, 15-fold, 16-fold, -fold, 17-fold, 18-fold, 19-fold, 20-fold, 25-fold, 30-fold, 40-fold, 50-fold, 75-fold, or 100-fold compared to a cell not expressing the CFP.

CD137 Binder Protein and Domains

In one aspect, provided herein are recombinant proteins that can bind to CD137 on a target cell. As used herein, such recombinant proteins capable of binding a CD137 on a target cell is termed a CD137 binder. In some embodiments, the CD137 binders comprise an extracellular domain of a chimeric fusion protein (CFP). In some embodiments, provided herein are recombinant nucleic acid sequence that encodes the chimeric CD137-binder receptor fusion protein (CFP), termed CD137-CFP, as used herein. In some embodiments, the recombinant nucleic acid encoding such as a chimeric receptor fusion protein, e.g. the CD137-binder receptor fusion protein can be expressed in a suitable cell, such as a myeloid cell. In some embodiments, the CD137-CFP when expressed on a suitable cell, such as a myeloid cell, the CD137 binder can bind to a target cell which expresses CD137, and the myeloid cell expressing the binder is activated. In some embodiments the CD137-CFP, upon engaging with a CD137 activated the intracellular signaling domain of the CD137-CFP, that activates the myeloid cell expressing the recombinant nucleic acid encoding the CD137-CFP. In some embodiments, the myeloid cell is a phagocytic cell. In some embodiments, a myeloid cell that is a phagocytic cell, and expressing a CD137 binder, may be activated when the CD137 binder binds to CD137 expressed on another cell (a target cell), and phagocytizes the target cell. In some embodiments, the target cell may be any cell that expresses CD137. In some embodiments, the target cell is a lymphocyte. In some embodiments, the target cell is a T lymphocyte (T cell). In some embodiments, the target cell may be a malignant cell. In some embodiments, the target cell may be a malignant T cell. In some embodiments, the CD137-binder CFP-expressing myeloid cell may be used to generate a therapeutic composition against T cell lymphoma.

Provided herein is a recombinant polynucleic acid comprises a sequence encoding a chimeric fusion protein (CFP), wherein the CFP protein can bind to CD137 on a T lymphocyte. In some embodiments, provided herein is a CFP that can bind to a target on a T cell, the target being CD137. In some embodiments, the target T cell is an activated T cell. In some embodiments, the CFP targets an activated T cell that is expressed in a T cell lymphoma. Provided herein is a recombinant nucleic acid, encoding a CD137 targeting CFP, wherein the CFP comprises: (i) an extracellular domain comprising an anti-CD137 binding domain, and (ii) a transmembrane domain operatively linked to the extracellular domain; and (b) a pharmaceutically acceptable carrier; wherein the myeloid cell expresses the CFP and exhibits at least a 1.1-fold increase in phagocytosis of a target cell expressing CD137 compared to a myeloid cell not expressing the CFP. In some embodiments, the CD137 binding domain is a CD137 binding protein that comprises an antigen binding fragment of an antibody, an Fab fragment, an scFv domain or an sdAb domain. In some embodiments, the CD137 binding domain comprises a CD137 ligand sequence of SEQ ID NO: 31 or with at least 90% sequence identity to SEQ ID NO: 31.

Provided herein is a recombinant protein which is a chimeric fusion protein that can bind to CD137. CD137 is an activated T cell surface marker. The chimeric fusion protein that can bind to CD137 can therefore specifically bind to an activated T cell, wherein the CFP comprises: (i) an extracellular domain comprising an anti-CD137 binding domain, and (ii) a transmembrane domain operatively linked to the extracellular domain. In some embodiments, the CD137 binding domain is a CD137 binding protein that comprises an antigen binding fragment of an antibody, an Fab fragment, an scFv domain or an sdAb domain. In some embodiments, the CD137 binding domain comprises an scFv. Provided herein is a myeloid cell expressing a recombinant protein which is a chimeric fusion protein that can bind to CD137 expressed on a T cell, wherein the CFP comprises: (i) an extracellular domain comprising an anti-CD137 binding domain, and (ii) a transmembrane domain operatively linked to the extracellular domain; the myeloid cell is capable of specifically targeting a CD137-expressing T cell and phagocytose, lyse and therefore lyse the CD137-expressing T cell. In some embodiments, the myeloid cell expressing a recombinant protein, which is a chimeric fusion protein that can bind to CD137, is a therapeutic for CD137+ve cancer, such as, a T cell lymphoma.

Generally, CD137 is expressed on an activated immune cell. CD137 is expressed in both innate and adaptive cells of the immune cascade. In healthy individuals, T cell may be abundant in lymph nodes (e.g., tonsils where T cells are found in activated state). CD137+ve T cells are also abundant in tumors.

It is noted that CD137±ve T cells may be responsible for graft-versus-host and host-versus-graft rejections. In case of allogeneic cell therapy, CD137 may be additionally targeted for destruction to reduce the host-versus-graft rejections. In some embodiments, the method and compositions described herein comprises (i) using an allogeneic myeloid cell expressing a chimeric receptor that binds to a cancer antigen and lyses a cancer cell expressing the cancer antigen; and (ii) administering a myeloid cell that expresses a chimeric antigen that can bind to CD137, and lyse a CD137+ve T cell, thereby reducing killing of the allogeneic myeloid cell by host's CD137+ve T lymphocytes.

In one aspect, provided herein is a recombinant protein which is a chimeric fusion protein that can bind to CD137, and also comprises a second, a third or additional binding domain that binds to a second, a third or additional extracellular moieties, wherein a extracellular moiety may be a cell surface molecule. In some embodiments, any one of the second, or the third or additional binding domain may comprise a binding domain for an additional cell surface molecule on a target cell, e.g., a cell surface molecule other than CD137, such as a cell surface molecule on a cancer cell or an activated T cell. The second, or the third or additional binding domain may comprise a binding domain for any additional cell surface molecule on a target cell, such as CD5, or any other antigen on a target cell described anywhere in the specification.

In some embodiments, any one of the second, or the third or additional binding domains may comprise a binding domain for a cell surface molecule on a myeloid cell. In some embodiments, any one of the second, or the third or additional binding domains that comprise a binding domain for a myeloid cell may activate the myeloid cell upon binding.

In some embodiments, the CD137-binding protein is a chimeric fusion protein comprising the extracellular domain capable of binding to CD137, and further comprises a hinge domain derived from CD8, wherein the hinge domain is operatively linked to a transmembrane domain at the cytoplasmic side, and to the CD137-binding domain on the extracellular side. In some embodiments, the transmembrane domain comprises a sequence set forth in any one of the sequences in SEQ ID NO: 15, 16, 17, 18 or 19. In some embodiments, the transmembrane domain comprises a sequence derived from CD8 alpha (CD8α) transmembrane domain. In some embodiments, the transmembrane domain comprises a sequence set forth in SEQ ID NO: 15 or a sequence that has at least 70%, 75%, 80%, 85%, 90%, 91%, 92%, 93%, 94%, 95%, 96%, 97%, 98% or 99% sequence identity to SEQ ID NO: 15. In some embodiments, the transmembrane domain comprises a sequence set forth in SEQ ID NO: 16 or a sequence that has at least 70%, 75%, 80%, 85%, 90%, 91%, 92%, 93%, 94%, 95%, 96%, 97%, 98% or 99% sequence identity to SEQ ID NO: 16. In some embodiments, the transmembrane domain comprises a sequence derived from CD2 transmembrane domain. In some embodiments, the transmembrane domain comprises a sequence set forth in SEQ ID NO: 17 or a sequence that has at least 70%, 75%, 80%, 85%, 90%, 91%, 92%, 93%, 94%, 95%, 96%, 97%, 98% or 99% sequence identity to SEQ ID NO: 17. In some embodiments, the transmembrane domain comprises a sequence derived from CD28 transmembrane domain. In some embodiments, the transmembrane domain comprises a sequence set forth in SEQ ID NO: 18 or a sequence that has at least 70%, 75%, 80%, 85%, 90%, 91%, 92%, 93%, 94%, 95%, 96%, 97%, 98% or 99% sequence identity to SEQ ID NO: 18. In some embodiments, the transmembrane domain comprises a sequence derived from CD68 transmembrane domain. In some embodiments, the transmembrane domain comprises a sequence set forth in SEQ ID NO: 19 or a sequence that has at least 70%, 75%, 80%, 85%, 90%, 91%, 92%, 93%, 94%, 95%, 96%, 97%, 98% or 99% sequence identity to SEQ ID NO: 19. In some embodiments, the ECD of the CFP comprises an amino acid sequence depicted in SEQ ID NO: 31 or a sequence that is 70%, 75%, 80%, 85%, 90%, 91%, 92%, 93%, 94%, 95%, 96%, 97%, 98% or 99% sequence identity to SEQ ID NO: 31, fused to a transmembrane domain selected from any one of sequences set forth in SEQ ID NO: 15, 16, 17, 18 or 19 or a transmembrane domain having an amino acid sequence that is at least 70%, 75%, 80%, 85%, 90%, 91%, 92%, 93%, 94%, 95%, 96%, 97%, 98% or 99% sequence identity to any one of SEQ ID NO: 15, 16, 17, 18 or 19.

In some embodiments, the extracellular hinge domain and transmembrane domain comprises a sequence of SEQ ID NO: 20 or SEQ ID NO: 21 or with at least 70%, 75%, 80%, 85%, 90%, 91%, 92%, 93%, 94%, 95%, 96%, 97%, 98% or 99% sequence identity to SEQ ID NO: 20 or SEQ ID NO: 21 respectively. In some embodiments, the CFP comprises an extracellular domain fused to a transmembrane domain of SEQ ID NO: 20 or with at least 70%, 75%, 80%, 85%, 90%, 91%, 92%, 93%, 94%, 95%, 96%, 97%, 98% or 99% sequence identity to SEQ ID NO: 20. In some embodiments, the CFP comprises an extracellular domain fused to a transmembrane domain of SEQ ID NO: 21 or with at least 70%, 75%, 80%, 85%, 90%, 91%, 92%, 93%, 94%, 95%, 96%, 97%, 98% or 99% sequence identity to SEQ ID NO: 21. In some embodiments, the CFP comprises an ECD binder domain having at least 70%, 75%, 80%, 85%, 90%, 91%, 92%, 93%, 94%, 95%, 96%, 97%, 98%, 99% or 100% sequence identity to SEQ ID NO: 31 fused to a hinge and transmembrane domain having an amino acid sequence that is at least 70%, 75%, 80%, 85%, 90%, 91%, 92%, 93%, 94%, 95%, 96%, 97%, 98%, 99% or 100% sequence identity to SEQ ID NO: 20 or 21.

In some embodiments, the CFP comprises an extracellular domain comprising a sequence as set forth in SEQ ID NO: 31, or a sequence having at least 80% identity to SEQ ID NO: 31; operably linked to a TM domain comprising a sequence of CD16 transmembrane domain (e.g. comprising a short hinge domain) as set forth in Table 4. In some embodiments, the CFP comprises an extracellular domain comprising a sequence as set forth in SEQ ID NO: 31, or a sequence having at least 80% identity to SEQ ID NO: 31; operably linked to a TM domain comprising a CD64 transmembrane domain sequence. In some embodiments, the CFP comprises an extracellular domain comprising a sequence as set forth in SEQ ID NO: 31; operably linked to a TM domain comprising a sequence of a CD89 transmembrane domain (e.g. comprising a short hinge domain) as set forth in Table 4. In some embodiments, the CFP comprises an ECD with a sequence set forth in SEQ ID NO: 31, or a sequence having at least 80% identity to SEQ ID NO: 31; a TM domain comprising a sequence from the TM domain of a CD16 protein, or the TMD of a CD64 protein or a TMD of a CD89 protein, and a corresponding intracellular domain (ICD), or a portion thereof, e.g., from a CD16 protein, a CD64 protein or a CD89 protein respectively, optionally, in addition to other distinct ICDs described herein. Exemplary CD16 and CD89 ICD sequences are provided in Table 4.

In some embodiments, the CFP comprises one or more intracellular signaling domains that comprise an intracellular signaling domain. In some embodiments, the intracellular signaling domain comprises a phagocytosis signaling domain. In some embodiments, the phagocytosis signaling domain comprises an intracellular signaling domain derived from a receptor other than Megf10, MerTk, FcRα, and Bai1. In some embodiments, the phagocytosis signaling domain comprises an intracellular signaling domain derived from a receptor other than Megf10, MerTk, an FcR, and Bai1. In some embodiments, the intracellular signaling domain comprises a domain derived from a receptor other than CD3ζ. In some embodiments, the phagocytosis signaling domain comprises an intracellular signaling domain derived from FcRγ, FcRα or FcRε.

In some embodiments, the CFP comprises an intracellular signaling domain derived from an FcRgamma protein (FcRγ chain) comprising an amino acid sequence of any one of SEQ ID NOs: 22, 23, 24 or 25 or a sequence with at least 70%, 75%, 80%, 85%, 90%, 91%, 92%, 93%, 94%, 95%, 96%, 97%, 98% or 99% sequence identity to any one of SEQ ID NOs: 22, 23, 24 or 25. In some embodiments, the one or more intracellular signaling domains further comprises a proinflammatory signaling domain. In some embodiments, the proinflammatory signaling domain comprises a PI3-kinase (PI3K) recruitment domain. In some embodiments, the proinflammatory signaling domain comprises a sequence of SEQ ID NO: 26 or with at least 70%, 75%, 80%, 85%, 90%, 91%, 92%, 93%, 94%, 95%, 96%, 97%, 98% or 99% sequence identity to SEQ ID NO: 26. In some embodiments, the proinflammatory signaling domain is derived from an intracellular signaling domain of CD40. In some embodiments, the proinflammatory signaling domain comprises a sequence of SEQ ID NO: 27 or with at least 70%, 75%, 80%, 85%, 90%, 91%, 92%, 93%, 94%, 95%, 96%, 97%, 98% or 99% sequence identity to SEQ ID NO: 27. In some embodiments, the CFP comprises an intracellular signaling domain of SEQ ID NO: 28 or with at least 70%, 75%, 80%, 85%, 90%, 91%, 92%, 93%, 94%, 95%, 96%, 97%, 98% or 99% sequence identity to SEQ ID NO: 28. In some embodiments, the CFP comprises an intracellular signaling domain of SEQ ID NO: 29 or with at least 70%, 75%, 80%, 85%, 90%, 91%, 92%, 93%, 94%, 95%, 96%, 97%, 98% or 99% sequence identity to SEQ ID NO: 29. In some embodiments, the CFP comprises an intracellular signaling domain of SEQ ID NO: 30 or with at least 70%, 75%, 80%, 85%, 90%, 91%, 92%, 93%, 94%, 95%, 96%, 97%, 98% or 99% sequence identity to SEQ ID NO: 30.

In some embodiments, the CFP comprises: (a) an extracellular domain comprising: (i) a scFv that specifically binds CD137, and (ii) a hinge domain derived from CD8; a hinge domain derived from CD28 or at least a portion of an extracellular domain from CD68; (b) a CD8 transmembrane domain, a CD28 transmembrane domain, a CD2 transmembrane domain or a CD68 transmembrane domain; and (c) an intracellular domain comprising at least two intracellular signaling domains, wherein the at least two intracellular signaling domains comprise: (i) a first intracellular signaling domain derived from FcRα, FcRγ or FcRε, and (ii) a second intracellular signaling domain: (A) comprising a PI3K recruitment domain, or (B) derived from CD40. In some embodiments, the CFP comprises as an alternative (c) to the above: an intracellular domain comprising at least two intracellular signaling domains, wherein the at least two intracellular signaling domains comprise: (i) a first intracellular signaling domain derived from a phagocytic receptor intracellular domain, and (ii) a second intracellular signaling domain derived from a scavenger receptor phagocytic receptor intracellular domain comprising: (A) comprising a PI3K recruitment domain, or (B) derived from CD40. In some embodiments, the CFP comprises and intracellular signaling domain derived from an intracellular signaling domain of an innate immune receptor.

In some embodiments, the chimeric fusion protein may have more than one extracellular antigen binding domain.

In some embodiments, the chimeric fusion protein may comprise a CD137 binding domain and a second binding domain for a second cell surface molecule, such as an extracellular protein or glycoprotein, a membrane protein or glycoprotein that is present on the surface of the cancer cell or the target cell. In some embodiments, the second binding domain binds to any target described herein. In some embodiment, the second binding domain may be designed such that the second binding domain binds to a protein on the extracellular matrix of the target cell or the neighboring cell. In some embodiments, the extracellular domain may comprise a second binding domain that can bind to a soluble target, such as a molecule released in the extracellular space of a neighboring cell, or a target cell.

In one aspect, provided herein is a chimeric fusion protein that can bind to CD137 (also known as 4-1BB) on a target cell. In some embodiment, a recombinant nucleic acid encoding a CFP that can bind to CD137 may be incorporated in a myeloid cell such that the myeloid cell expresses the CD137-binding CFP. In some embodiments, the myeloid cell may be a CD14+ cell. In some embodiments the myeloid cell may be CD14+/CD16−. In some embodiments, the myeloid cell may be CD14+/CD16low. A CD137 binding CFP-expressing myeloid cell may be used in various ways, either alone; or in combination with other CFP expressing myeloid cells in a therapeutic composition; or separately a combination therapeutic regimen; and may be used alone or in combination with other therapeutics comprising other nucleic acid-, peptide-, protein- or small molecule-therapeutics.

CD137 is a member of the tumor necrosis factor receptor superfamily member 9 (TNFRSF9) and is expressed on the surface of certain immune cells. CD137 is a cell surface protein that is expressed on activated T cells. Interaction of CD137 with its ligand (CD137L, also known as TNFSF9 or 4-1BBL) on activated antigen-presenting cells (APCs) may lead to bidirectional activation that promotes immunity against cancer. For instance, it has been shown that signals through the CD137 receptor may lead to T cell activation and survival. Reversely, engaged CD137L may impact the cells expressing it, such as a myeloid cell, a dendritic cells, leading to their activation and maturation. Use of agonistic CD137 antibodies such as urelumab and utomilumab is considered as a promising immunotherapeutic approach to treat various types of tumors. In some embodiments, a CFP comprising a CD137L may be expressed in a myeloid cell and used for anti-tumor therapy, signaling of CD137L into monocytes induces their differentiation to CD137L-DCs. CD137L-DCs preferentially induce type 1 T helper (Th1) cell polarization and strong type 1 CD8+ T cell (Tc1) responses against tumor CD137 agonistic antibodies or CD137-binding regions thereof may be used to design CFP to activate immune response in vivo. Alternatively, CD137L or fragments thereof may be used to design CFP to activate immune response in vivo. In certain embodiments, CD137-binding CFP comprising a CD137-agonist antibody or fragment thereof or a CD137L as the extracellular domain may be used to activate immune response or as an antineoplastic agent. Provided herein is a chimeric fusion protein that comprises a CD137-binding extracellular domain that comprises a CD137 agonistic antibody or a fragment thereof, wherein the antibody may be an scFv, a bispecific antibody, a Fab, Fab fragments, F(ab')2 fragments, monovalent antibody, scFv fragments, scRv-Fc fragments, IgNARs, hcIgGs, Vnm antibodies, nanobodies, and alphabodies. In some embodiments the CD137 agonistic antibody is a human or humanized antibody or fragments thereof. In some embodiments the CD137 agonistic antibody is urelumab or fragments thereof. Provided herein is a nucleic acid construct encoding chimeric fusion protein that comprises a CD137-binding extracellular domain that comprises a CD137 agonistic antibody or a fragment thereof, wherein the antibody may be an scFv, a bispecific antibody, a Fab, Fab fragments, F(ab')2 fragments, monovalent antibody, scFv fragments, scRv-Fc fragments, IgNARs, hcIgGs, $V_{HH}$ antibodies, nanobodies, and alphabodies. Provided herein is a chimeric fusion protein that comprises a CD137-binding extracellular domain that comprising a CD137L or a fragment thereof. In some embodiments, a therapeutic cell may be generated by expressing a full length CD137L protein may be expressed in the cell, such as a myeloid cell, such that the myeloid cell binds to and activates lymphocytes. In some embodiments, a therapeutic cell may be generated by designing and expressing a CFP that expresses at least an extracellular fragment of the CD137L. In some embodiments the CFP comprising the extracellular CD137L as CD137-binding domain may further comprise an intracellular domain of CD137L. The CFP described in the paragraph can be used in any therapeutic purpose to stimulate immune response when administered in a subject either as a therapeutic cell expressing the CFP, or a nucleic acid construct encoding the CFP, wherein the nucleic acid construct is administered such that it is taken up by a cell in vivo and the cell expresses the CFP. In some embodiments, the nucleic acid construct that is administered may comprise a targeting moiety to target and be taken up by a specific cell type or tissue. In some embodiments, the nucleic acid construct may encode an extracellular protein comprising a CD137-binding domain, such as a soluble extracellular protein. In some embodiments, the CFP comprising a CD137-binding domain can be a soluble extracellular protein and can function as an immunostimulatory CD137 agonistic protein, thereby activating lymphocytes when administered and expressed in vivo in a subject. In some embodiments, the chimeric fusion protein is a receptor protein. Accordingly, a CFP receptor comprising a CD137-binding extracellular domain comprises a transmembrane domain, and may optionally comprise an intracellular domain. A cell expressing a fusion protein having a CD137-agonist-binding domain and/or a transmembrane domain can activate T lymphocytes and can be used to activate antitumor response in vivo.

In some embodiments, a CD137-binding fusion protein may be designed and expressed in a myeloid cell, such as a DC cell to generate a DC vaccine, such as an anticancer DC vaccine. Provided herein is a myeloid cell (e.g., a DC) expressing a CFP comprising an extracellular domain that comprises a CD137-binding ligand, such as a human CD137L or a binding fragment thereof.

However, CD137 may be targeted in CD137+ve cancers, such as T cell lymphomas. CD137-targeted myeloid cells designed to express CD137-binding chimeric fusion proteins as described herein can act as potent, safe and efficacious tumoricidal agents in CD137+ tumors and can be used in adoptive cell therapy in T cell lymphoma, as well as other cancers, such as lung, pancreatic, leukocytic and other cancers.

In some embodiments, the chimeric fusion protein described herein is targeted to bind to CD137 receptor on lymphocyte and NK cells. When expressed in a suitable myeloid cell, a killer myeloid cell may be generated, further by nurturing the cell in suitable culture conditions for a limited period of time and development of the cell ex vivo as a therapeutic. The killer myeloid cell described herein, expressing CD137-binding CFP may be used for therapy in a subject having a CD137 cell malignancy, or a possibility for a disease or condition arising from CD137 cell function.

In some embodiments, the chimeric fusion protein described herein is a therapeutic that can be administered in the form of a nucleic acid construct in a therapeutic composition, such that when a suitable cell in vivo takes up the nucleic acid, the chimeric fusion protein is expressed by the cell in vivo, and the cell can bind to a cell expressing CD137 in vivo. Additional domains in the CD137-binding CFP fusion protein (e.g. intracellular signaling domains) can render the cell in which the protein is expressed a potent cytotoxic cell, for example, a cell with enhanced phagocytic activity, therefore rendering the cell that expresses the protein "an attack cell" or a killer cell targeted for destruction of a CD137 expressing cell, such as a lymphocyte or an NK cell.

In some embodiments, the CD137-binding chimeric fusion protein may comprise a heterologous transmembrane domain and/or one or more heterologous intracellular domains, and can be expressed in a suitable cell, such as a myeloid cell to generate a potent immunoreactive cell. In some embodiments, binding of the CFP having a CD137-binder activates the chimeric fusion protein (receptor) intracellular domains, that activates a phagocytic response, an inflammatory response, and/or a cytotoxic response in the cell that expresses the CFP such that the CFP-expressing cell destroys a target cell expressing the CD137. Examples of target cell expressing CD137 can be a lymphocyte, such as T lymphocyte or NK cell, such as in a CD137+ve cell cancer, for example, lung cancer, leukemia, pancreatic cancer, colorectal cancer and lymphoma.

In some embodiments the CD137-binding CFP can be expressed in a suitable cell (e.g., a myeloid cell) such that the CD137-expressing cell can act as a regulator of immune response by binding to and killing activated CD137+ lymphocytes. In such embodiments, CD137-targeted CFP is used therapeutically to reduce activated immune response, such as an allogeneic immune response.

In some embodiments, a killer cell, such as an active phagocytic cell engineered to express an anti-CD137 extracellular moiety may be used as an adjoining therapy to several non-autologous cell-based immunotherapy. Such a combination therapy may be employed in a large variety of cancers, including but not limited to melanoma, glioblastoma, sarcoma, renal cell carcinoma, ovarian cancer, lung cancer, pancreatic cancer breast cancer and many others.

In some embodiments, a CD137-targeted CFP nucleic acid construct may be incorporated in a myeloid cell for expression of the CFP, and the myeloid cell expressing the CD137-binding CFP may to be used as a helper cell in a CAR-P (e.g., phagocytic cell expressing a CAR or CFP) therapy or a CAR-T (CAR-expressing T cell) therapy, where the cell expressing the CAR targets a cancer antigen other than CD137, such as CD5, CD19, CD40 etc., such that the CD137 CFP expressing cell reduces the CD137 expressing tumor suppressor lymphocytes are reduced or eliminated, enhancing the tumoricidal function of the cancer targeted CAR expressing cell (CAR-P or CAR-T). The CD137-binding CFP may therefore be used to develop helper cells for co-administration in any adoptive cell therapy, where the helper cell is a cytotoxic cell in which the CD137-binding CFP-encoding nucleic acid construct is incorporated and the cell expresses a CD137-binder CFP extracellular domain. The CD137-binder CFP expressing cell may be a myeloid cell. The CD137-binder CFP expressing cell may be a phagocytic myeloid cell. The CD137-binder CFP expressing cell may be a lymphoid cell. The CD137-binder CFP expressing cell may be a cytotoxic cell.

In some embodiments, the CD137-binding CFP can be expressed in a suitable cell (e.g., a myeloid cell) such that the CD137-expressing cell can act as a regulator of immune response, such as in an allogeneic cell therapy response, host-versus-graft disease or an autoimmune disease or condition. For example, a CD137-binding CFP may be used in combination with a CAR-P or CAR-T therapy where the CAR-P or a CAR-T is an allogeneic cell, that targets a disease cell such as a cancer cell expressing a cancer antigen other than CD137, such as CD5, CD19, CD40. In some embodiments, the CD137-binding CFP may be used to develop helper cells for co-administration in any adoptive cell therapy, where the helper cell is a cytotoxic cell that comprises the CD137-binding CFP and expresses a CD137-binder CFP extracellular domain. The CD137-binder CFP expressing cell may be a myeloid cell. The CD137-binder CFP expressing cell may be a phagocytic myeloid cell. The CD137-binder CFP expressing cell may be a lymphoid cell. The CD137-binder CFP expressing cell may be a cytotoxic cell.

In some embodiments, the CD137-targeted CFP may be expressed in a myeloid cell, and used in conjunction with a CART therapy, where the CART cell may be allogeneic or autogeneic. In some embodiments, the CD137-targeted CFP may be expressed in a myeloid cell, and used in conjunction with a CART therapy targeting a cancer cell other than a CD137+ cell, where the CART cell may be allogeneic or autogeneic. In some embodiments, the CD137-targeted CFP may be expressed in a myeloid cell, and used in conjunction with a CART therapy, where the CART cell and/or the myeloid cell may be allogeneic or autogeneic. In some embodiments the CD137-targeted CFP expressing cell may be allogeneic or autogeneic relative to the subject the cell is administered to, as a therapy.

In some embodiments, the CD137-targeted CFP may comprise an extracellular CD137-binding domain comprised of a CD137-agonist antibody or a fragment thereof. In some embodiments, an extracellular CD137-binding domain comprises of a CD137-agonist antibody or fragment thereof may comprise an scFv, a VHH, a diabody, a bispecific antibody or a CD137 ligand or fragment thereof. In some embodiments, the CD137-targeted CFP may further comprise a transmembrane domain (TMD) derived from CD3ζ, CD2, CD8α CD28, CD68, FcgR, FcG, FcR gamma, FcR alpha transmembrane domains or any other suitable domains. In some embodiments, the CD137-targeted CFP described above may further comprise an intracellular domain comprising one or more signal transduction domains. In some embodiments, the CD137-targeted CFP may comprise an intracellular domain derived from a PI3K recruitment domain, an intracellular signaling domain of a scavenger receptor, a CD40 intracellular domain, a FcR-derived signaling domain, a TLR intracellular domain, an NLRP3 intracellular domain, a CD3 derived intracellular domain and others. The instant disclosure at Table 1 and 4 exhibit sequence information for various individual domains described herein in the various embodiments, and it is contemplated to be within the scope of the disclosure that various combinations of the same may be incorporated into a single biomolecule to develop a chimeric fusion protein, using sequence information in Table 1 and 4 and utilizing molecular biology techniques known in the art.

In some embodiments, the chimeric fusion protein (CFP) comprises an extracellular domain (ECD) targeted to bind to CD137 that may comprise an amino acid sequence of SEQ ID NO: 31, or a sequence that has at least 80%, 85%, 90%, 95%, 96%, 97%, 98%, 99% sequence identity to SEQ ID NO: 31.

(SEQ ID NO: 31)
MEFGLSWLFLVAILKGVQCGLLDLRQGMFAQLVAQNVLLIDGPLSWYSDP

GLAGVSLTGGLSYKEDTKELVVAKAGVYYVFFQLELRRVVAGEGSGSVSL

ALHLQPLRSAAGAAALALTVDLPPASSEARNSAFGFQGRLLHLSAGQRLG

VHLHTEARARHAWQLTQGATVLGLFRVTPEIPAGLPSPRSE

In one aspect, the chimeric fusion protein may comprise a soluble protein, having a binding domain that binds to CD137. In one embodiment, the chimeric fusion protein may comprise a soluble protein, having at least one binding domain that binds to CD137 and one or more additional binding domains, at least one of which binds to a cell surface molecule on a myeloid cell. In some embodiments, the chimeric fusion protein comprises a binding domain that can bind CD137, and a binding domain that can bind to a cell surface molecule on a myeloid cell. In some embodiments, the chimeric fusion protein comprises a binding domain that can bind CD137, and a binding domain that can bind to a cell surface molecule on a myeloid cell. In some embodiments, the CFP also comprises a third or any number of additional binding domains that binds to a third or additional extracellular moieties, wherein a extracellular moiety may be a cell surface molecule or a soluble component in the extracellular environment. In some embodiments, the chimeric fusion protein described herein may be termed a bi-specific engager, (e.g., a bi-specific myeloid cell engager, BiME) wherein the bispecific engager comprises two "engager" moieties, wherein the engager moieties are the binding domains for two different targets, wherein a first binding domain binds, e.g., a CD137 on any CD137+ cell, such as on an activated T cell, an activated NK cell or a cancer cell, and wherein the second binding domain binds a surface molecule on a myeloid cell. In some aspects, the chimeric fusion protein described herein is termed a tri-specific engager (a tri-specific myeloid cell engager, TRiME), wherein the trispecific engager comprises three engager moieties, which are binding domains for three different targets, wherein a first binding domain binds, e.g., CD137 on any CD137+ cell, such as an activated T cell, an activated NK cell or a CD137-expressing cancer cell, and wherein the second binding domain binds a cell surface molecule on a myeloid cell, and a third binding domain binds to a third element, wherein the third element may be a different cell surface molecule other than CD137 or the cell surface molecule on a myeloid cell that the second binding domain binds to. In some embodiments the third binding domain binds to a cell surface molecule other than CD137 on the CD137+ cell. In some embodiments the third binding domain binds to a cell surface molecule on the myeloid cell, and binds to a molecule other than the one that the second binding domain binds to. In some embodiments the BiME or the TriME juxtaposes a target cell to a myeloid cell, such that the myeloid cell can attack, phagocytose and lyse the target cell. In some embodiments, the BiME or TRiME engagement to a myeloid cell can not only bring the myeloid cell and the target cell in close proximity, but also activates the myeloid cell to engage and kill the target cell efficiently. In some embodiments, the second and/or the third binding domain described herein, activates the myeloid cell upon binding. In some embodiments, the BiME or TriME is a secreted fusion protein. In some embodiment, an engager, or any binding domain described herein may be an antigen-binding fragment (Fab), a single-chain variable fragment (scFv), a nanobody, a $V_H$ domain, a $V_L$ domain, a single domain antibody (sdAb), a VNAR domain, and a $V_{HH}$ domain, a bispecific antibody, a diabody, or a functional fragment of any thereof. In some embodiment, an engager may be a ligand such as a CD137 ligand (SEQ ID NO: 31), or a fragment thereof that binds to CD137.

In some embodiments, a CFP comprising a binding domain capable of binding to CD137 on a tumor cell is designed for use in anti-tumor activity. A recombinant nucleic acid encoding the fusion protein comprising a binding domain capable of binding to CD137 is expressed in a myeloid cell, wherein the chimeric fusion protein is a transmembrane protein and the myeloid cell is a phagocytic cell; upon engagement of the CFP to the target CD137 expressed on a cell e.g., a tumor cell, the myeloid cell is activated, phagocytoses and lyses the target cell, .g. tumor cell, and thereby slows down or stalls tumor growth, reduces tumor size and/or eliminates the tumor.

In some embodiments, a CFP comprising a binding domain capable of binding to CD137 on an activated CD137-expressing cell is designed for use in immunosuppression, such as to treat host-versus-graph-disease (HVGD) or a condition related to allogeneic reaction, or an acute or sustained severe inflammation. In some embodiments, the CD137-expressing cell is an activated T cell, or an NK cell. In some embodiments, the CD137 ligand or fragment thereof on an extracellular domain of the CFP expressed in a myeloid cell activates the myeloid cell upon binding to CD137 on an activated T cell or NK cell activates phagocytosis and lyses the activated T cell or NK cell and reduces inflammation.

In some embodiments, a therapeutic, such as a pharmaceutical composition is described herein, wherein the pharmaceutical composition may comprise: (i) a CFP comprising a binding domain capable of binding to CD137; (ii) a recombinant nucleic acid encoding the CFP comprising a binding domain capable of binding to CD137; or (iii) a cell expressing a CFP comprising a binding domain capable of binding to CD137.

In some embodiments, a therapeutic, such as a pharmaceutical composition described herein, comprising a CFP comprising a binding domain capable of binding to CD137; a recombinant nucleic acid encoding the CFP comprising a binding domain capable of binding to CD137; or a cell expressing a CFP comprising a binding domain capable of binding to CD137 may be used in combination with (i) one or more additional CFPs; or (ii) a recombinant nucleic acid encoding the one or more additional CFPs; or, (iii) cell expressing the one or more additional CFPs, respectively, or any combination thereof. As one example of the above, a pharmaceutical composition may be described herein, comprising myeloid cells expressing a CFP comprising a binding domain capable of binding to CD137, may be used in combination with myeloid cells expressing a CFP comprising a binding domain capable of binding to CD5, or any other binding domain described anywhere in the specification. Similarly, any combinations of the compositions described herein are contemplated to be combined or mixed in a therapeutic, and will be within the scope of the disclosure.

CD70 Binder Proteins and Domains

CD70 may be highly expressed in certain cancers, including, but not limited to, colorectal cancer (CRC), lung cancer, T cell lymphoma, glioma, thyroid cancer, head and neck cancer, stomach, liver, pancreatic, urothelial, ovarian cancers, and melanoma. Provided herein are chimeric fusion proteins that can bind to CD70 on a cancer cell, and designed for a therapeutic use against a disease involving overexpression of CD70, such as a cancer.

In one aspect, provided herein is a chimeric fusion protein having an extracellular binding domain that can bind to CD70 (CD70 binder CFP). In some embodiments, the CD70 binder CFP may comprise an extracellular binding domain having an amino acid sequence of SEQ ID NO: 32 or a sequence that has at least 80% sequence identity to the amino acid sequence of SEQ ID NO: 32. A CD70 binding domain may comprise an antigen-binding fragment (Fab), a single-chain variable fragment (scFv), a nanobody, a $V_H$ domain, a $V_L$ domain, a single domain antibody (sdAb), a VNAR domain, and a $V_{HH}$ domain, a bispecific antibody, a diabody, or a functional fragment of any thereof.

In some embodiments, the extracellular domain further comprises a hinge domain derived from CD8, wherein the hinge domain is operatively linked to a transmembrane domain at the cytoplasmic side, and to the CD70-binding domain on the extracellular side. In some embodiments, the transmembrane domain comprises a sequence set forth in any one of the sequences in SEQ ID NO: 15, 16, 17, 18 or 19. In some embodiments, the transmembrane domain comprises a sequence derived from CD8 alpha (CD8a) transmembrane domain. In some embodiments, the transmembrane domain comprises a sequence set forth in SEQ ID NO: 15 or a sequence that has at least 70%, 75%, 80%, 85%, 90%, 91%, 92%, 93%, 94%, 95%, 96%, 97%, 98% or 99% sequence identity to SEQ ID NO: 15. In some embodiments, the transmembrane domain comprises a sequence set forth in SEQ ID NO: 16 or a sequence that has at least 70%, 75%, 80%, 85%, 90%, 91%, 92%, 93%, 94%, 95%, 96%, 97%, 98% or 99% sequence identity to SEQ ID NO: 16. In some embodiments, the transmembrane domain comprises a sequence derived from CD2 transmembrane domain. In some embodiments, the transmembrane domain comprises a sequence set forth in SEQ ID NO: 17 or a sequence that has at least 70%, 75%, 80%, 85%, 90%, 91%, 92%, 93%, 94%, 95%, 96%, 97%, 98% or 99% sequence identity to SEQ ID NO: 17. In some embodiments, the transmembrane domain comprises a sequence derived from CD28 transmembrane domain. In some embodiments, the transmembrane domain comprises a sequence set forth in SEQ ID NO: 18 or a sequence that has at least 70%, 75%, 80%, 85%, 90%, 91%, 92%, 93%, 94%, 95%, 96%, 97%, 98% or 99% sequence identity to SEQ ID NO: 18. In some embodiments, the transmembrane domain comprises a sequence derived from CD68 transmembrane domain. In some embodiments, the transmembrane domain comprises a sequence set forth in SEQ ID NO: 19 or a sequence that has at least 70%, 75%, 80%, 85%, 90%, 91%, 92%, 93%, 94%, 95%, 96%, 97%, 98% or 99% sequence identity to SEQ ID NO: 19. In some embodiments, the ECD of the CFP comprises an amino acid sequence depicted in SEQ ID NO: 32 or a sequence that is 70%, 75%, 80%, 85%, 90%, 91%, 92%, 93%, 94%, 95%, 96%, 97%, 98% or 99% sequence identity to SEQ ID NO: 32, fused to a transmembrane domain selected from any one of sequences set forth in SEQ ID NO: 15, 16, 17, 18 or 19 or a transmembrane domain having an amino acid sequence that is at least 70%, 75%, 80%, 85%, 90%, 91%, 92%, 93%, 94%, 95%, 96%, 97%, 98% or 99% sequence identity to any one of SEQ ID NO: 15, 16, 17, 18 or 19.

In some embodiments, the extracellular hinge domain and transmembrane domain comprises a sequence of SEQ ID NO: 20 or SEQ ID NO: 21 or with at least 70%, 75%, 80%, 85%, 90%, 91%, 92%, 93%, 94%, 95%, 96%, 97%, 98% or 99% sequence identity to SEQ ID NO: 20 or SEQ ID NO: 21 respectively. In some embodiments, the CFP comprises an extracellular domain fused to a transmembrane domain of SEQ ID NO: 20 or with at least 70%, 75%, 80%, 85%, 90%, 91%, 92%, 93%, 94%, 95%, 96%, 97%, 98% or 99% sequence identity to SEQ ID NO: 20. In some embodiments, the CFP comprises an extracellular domain fused to a transmembrane domain of SEQ ID NO: 21 or with at least 70%, 75%, 80%, 85%, 90%, 91%, 92%, 93%, 94%, 95%, 96%, 97%, 98% or 99% sequence identity to SEQ ID NO: 21. In some embodiments, the CFP comprises an ECD binder domain having at least 70%, 75%, 80%, 85%, 90%, 91%, 92%, 93%, 94%, 95%, 96%, 97%, 98%, 99% or 100% sequence identity to SEQ ID NO: 32 fused to a hinge and transmembrane domain having an amino acid sequence that is at least 70%, 75%, 80%, 85%, 90%, 91%, 92%, 93%, 94%, 95%, 96%, 97%, 98%, 99% or 100% sequence identity to SEQ ID NO: 20 or 21.

In some embodiments, the CFP comprises an extracellular domain comprising a sequence as set forth in SEQ ID NO: 32, or a sequence having at least 80% identity to SEQ ID NO: 32; operably linked to a TM domain comprising a sequence of CD16 transmembrane domain (e.g. comprising a short hinge domain) as set forth in Table 4. In some embodiments, the CFP comprises an extracellular domain comprising a sequence as set forth in SEQ ID NO: 32, or a sequence having at least 80% identity to SEQ ID NO: 32; operably linked to a TM domain comprising a CD64 transmembrane domain sequence. In some embodiments, the CFP comprises an extracellular domain comprising a sequence as set forth in SEQ ID NO: 32; operably linked to a TM domain comprising a sequence of a CD89 transmembrane domain (e.g. comprising a short hinge domain) as set forth in Table 4. In some embodiments, the CFP comprises an ECD with a sequence set forth in SEQ ID NO: 32, or a sequence having at least 80% identity to SEQ ID NO: 32; a TM domain comprising a sequence from the TM domain of a CD16 protein, or the TMD of a CD64 protein or a TMD of a CD89 protein, and a corresponding intracellular domain (ICD), or a portion thereof, e.g., from a CD16 protein, a CD64 protein or a CD89 protein respectively, optionally, in addition to other distinct ICDs described herein. Exemplary CD16 and CD89 ICD sequences are provided in Table 4.

In some embodiments, the CFP comprises one or more intracellular signaling domains that comprise an intracellular signaling domain. In some embodiments, the intracellular signaling domain comprises a phagocytosis signaling domain. In some embodiments, the phagocytosis signaling domain comprises an intracellular signaling domain derived from a receptor other than Megf10, MerTk, FcRα, and Bai1. In some embodiments, the phagocytosis signaling domain comprises an intracellular signaling domain derived from a receptor other than Megf10, MerTk, an FcR, and Bai1. In some embodiments, the intracellular signaling domain comprises a domain derived from a receptor other than CD3ζ. In some embodiments, the phagocytosis signaling domain comprises an intracellular signaling domain derived from FcRγ, FcRα or FcRε.

In some embodiments, the CFP comprises an intracellular signaling domain derived from an FcRgamma protein (FcRγ chain) comprising an amino acid sequence of any one of SEQ ID NOs: 22, 23, 24 or 25 or a sequence with at least 70%, 75%, 80%, 85%, 90%, 91%, 92%, 93%, 94%, 95%, 96%, 97%, 98% or 99% sequence identity to any one of SEQ ID NOs: 22, 23, 24 or 25. In some embodiments, the one or more intracellular signaling domains further comprises a proinflammatory signaling domain. In some embodiments, the proinflammatory signaling domain comprises a PI3-kinase (PI3K) recruitment domain. In some embodiments, the proinflammatory signaling domain comprises a sequence of SEQ ID NO: 26 or with at least 70%, 75%, 80%, 85%, 90%, 91%, 92%, 93%, 94%, 95%, 96%, 97%, 98% or 99% sequence identity to SEQ ID NO: 26. In some embodiments, the proinflammatory signaling domain is derived from an intracellular signaling domain of CD40. In some embodiments, the proinflammatory signaling domain comprises a sequence of SEQ ID NO: 27 or with at least 70%, 75%, 80%, 85%, 90%, 91%, 92%, 93%, 94%, 95%, 96%, 97%, 98% or 99% sequence identity to SEQ ID NO: 27. In some embodiments, the CFP comprises an intracellular signaling domain of SEQ ID NO: 28 or with at least 70%, 75%, 80%, 85%, 90%, 91%, 92%, 93%, 94%, 95%, 96%, 97%, 98% or 99% sequence identity to SEQ ID NO: 28. In some embodiments, the CFP comprises an intracellular signaling domain of SEQ ID NO: 29 or with at least 70%, 75%, 80%, 85%, 90%, 91%, 92%, 93%, 94%, 95%, 96%, 97%, 98% or 99% sequence identity to SEQ ID NO: 29. In some embodiments, the CFP comprises an intracellular signaling domain of SEQ ID NO: 30 or with at least 70%, 75%, 80%, 85%, 90%, 91%, 92%, 93%, 94%, 95%, 96%, 97%, 98% or 99% sequence identity to SEQ ID NO: 30.

Provided herein is a recombinant nucleic acid encoding a CFP comprising a CD70 binding domain (A CD70 binder) as described above, which may be expressed in a suitable cell, such as a myeloid cell. The myeloid cell may be a phagocytic cell. In some embodiments, the CD70 binder upon binding CD70 on a cell activates the myeloid cell expressing the CD70-binding CFP. Provided herein are recombinant nucleic acid sequence that encodes the chimeric CD70-binder receptor fusion protein (CFP), termed CD70-CFP, as used herein. In some embodiments, the recombinant nucleic acid encoding such as a chimeric receptor fusion protein, e.g. the CD70-binder receptor fusion protein can be expressed in a suitable cell, such as a myeloid cell. In some embodiments, the CD70-CFP when expressed on a suitable cell, such as a myeloid cell, the CD70 binder can bind to a target cell which expresses CD70, and the myeloid cell expressing the binder is activated. In some embodiments the CD70-CFP, upon engaging with a CD70 activated the intracellular signaling domain of the CD70-CFP, that activates the myeloid cell expressing the recombinant nucleic acid encoding the CD70-CFP. In some embodiments, the myeloid cell is a phagocytic cell. In some embodiments, a myeloid cell that is a phagocytic cell, and expressing a CD70 binder, may be activated when the CD70 binder binds to CD70 expressed on another cell (a target cell), and phagocytizes the target cell. In some embodiments, the target cell may be any cell that expresses CD70. In some embodiments, the target cell is a lymphocyte. In some embodiments, the target cell is a T lymphocyte (T cell). In some embodiments, the target cell may be a malignant cell. In some embodiments, the target cell may be a malignant T cell. In some embodiments, the CD70-binding CFP expressing myeloid cell may be used to generate a therapeutic composition against T cell lymphoma.

In another embodiment, provided herein is a recombinant protein such as an extracellular protein, such as a soluble protein that can bind to the extracellular domain of CD70. In some embodiments, the chimeric fusion protein, such as the soluble protein described herein may be termed a bi-specific engager, (e.g., a bi-specific myeloid cell engager, BiME) wherein the bispecific engager comprises two "engager" moieties, wherein the engager moieties are the binding domains for two different targets, wherein a first binding domain binds, e.g., a CD70 on any CD70+ cell, such as on an activated T cell, an activated NK cell or a cancer cell, and wherein the second binding domain binds a surface molecule on a myeloid cell. In some aspects, the chimeric fusion protein described herein is termed a tri-specific engager (a tri-specific myeloid cell engager, TRiME), wherein the trispecific engager comprises three engager moieties, which are binding domains for three different targets, wherein a first binding domain binds CD70. In some embodiments, the recombinant extracellular protein (BiME or a TRiME) having a domain that can bind to CD70, further comprises a second domain that can bind to a surface protein of a myeloid cell, such as a phagocytic cell. The surface protein of a myeloid cell may be a protein expressed on the membrane of a myeloid cell, for example, a phagocytic receptor, a pattern recognition molecule or a scavenger receptor. Provided herein is a recombinant nucleic acid encoding an extracellular protein, such as a soluble protein that can bind to the extracellular domain of CD70 as described herein.

Provided herein is a therapeutic for treating a disease in a subject, wherein the disease is associated with the overexpression of CD70 protein, the therapeutic comprising at least a recombinant protein having an extracellular binding domain that can bind to CD70, such as any of the CD70 binder proteins described above. In some embodiments, provided herein is a cell that expresses a CD70 binder protein. In some embodiments, provided herein is a therapeutic for treating a disease in a subject, wherein the disease is associated with the overexpression of CD70, the therapeutic comprising at least a recombinant nucleic acid encoding a CD70 binder as described herein. In some embodiments, provided herein is a therapeutic for treating a disease in a subject, wherein the disease is associated with the overexpression of a CD70 protein, the therapeutic comprising a cell comprising a recombinant nucleic acid encoding a CD70 binder as described herein. In some embodiments, the cell is a myeloid cell. In some embodiments, the diseases is a cancer, for example a T cell lymphoma or a colorectal cancer (CRC).

An exemplary CD70 binder sequence is SEQ ID NO: 32:

```
(SEQ ID NO: 32)
QVQLVQSGAEVKKPGASVKVSCKASGYTFTNYGMNWVRQAPGQGLEWMGW

INTYTGEPTYADAFKGRVTMTTDTSTSTAYMELRSLRSDDTAVYYCARDY

GDYGMDYWGQGTTVTVSSGSTSGSGKPGSSEGSTKGDIVMTQSPDSLAVS

LGERATINCRASKSVSTSGYSFMHWYQQKPGQPPKWYLASNLESGVPDRF

SGSGSGTDFTLTISSLQAEDVAVYYCQHSREVPWTFGQGTKVEIK
```

In some embodiments, the chimeric fusion protein (CFP) comprises an extracellular domain (ECD) targeted to bind to CD70 comprising an amino acid sequence of SEQ ID NO: 32, or a sequence that has at least 80%, 85%, 90%, 95%, 96%, 97%, 98%, 99% sequence identity to SEQ ID NO: 32.

Claudin 18.2 and claudin 3 binder proteins and domains

The claudin family of proteins are components of tight cell junctions and they establish a paracellular barrier which controls the flow of molecules between the cells. The transmembrane domains of claudins include a N-terminus and a C-terminus in the cytoplasm. Claudin proteins exhibit tissue specific expression and are their altered function are often related to cancer of the specific tissues. Claudin-1 expression has been shown to have prognostic value in colon cancer. Claudin-1 is a strong prognostic indicator in stage II colonic cancer and claudin-18 is a strong prognostic indicator in gastric cancer. Down-regulation of the claudin-18 gene has been demonstrated through serial analysis of gene expression data analysis in gastric cancer with an intestinal phenotype and down-regulation of claudin-10 has been demonstrated in hepatocellular carcinoma. Claudins, being surface proteins, represent a useful target for various therapeutic strategies.

Claudin 18 isoform 2 (claudin 18.2) is a highly selective cell lineage marker. Claudin-18 splice variant 2 is a pan-cancer target suitable for therapeutic antibody development and exhibits a highly restricted expression pattern in normal tissues, with frequent ectopic activation in a diversity of human cancers, including, gastric cancers, ovarian and pancreatic cancers.

Claudin-3 is expressed in tight junctions and is shown to be regulated during tumorigenesis in a number of organs and tissues, such as breast, ovaries, uterus, prostrate and oesophagus. Claudin 3 overexpression increases epithelial resistance measured by paracellular resistance, whereas transcellular resistance was not significantly changed. Claudin-3 overexpression results in decreased permeabilities to both, sodium and chloride and the expression of the Claudin 3 molecule is elevated in many cancer tissues such as ovarian cancer, prostate cancer, breast cancer, uterine cancer, liver cancer, lung cancer, pancreatic cancer, stomach cancer, bladder cancer, and colon cancer tissues. It has been shown that the expression of Claudin 3 and Claudin 4 is particularly elevated in chemotherapy resistant uterine cancer. Claudin 3 is a protein with four transmembrane regions, and has a structure that exposes two peptide loops to the outside of the cell.

In one aspect, provided herein is a chimeric fusion protein having an extracellular binding domain that can bind to claudin 18.2 (Claudin 18.2 binder CFP).

In another aspect, provided herein is a chimeric fusion protein that has an extracellular binding domain that can bind to claudin 3.0.

In one embodiment, the extracellular binding domain comprises a scFv, that is specific to human claudin 18.2, or a fragment thereof. in some embodiments the ECD of the chimeric fusion receptor protein comprises a binding domain that binds to an extracellular loop of Claudin 18.2 on a target cell.

In some embodiments, an exemplary Claudin 18.2 binder domain may comprise a sequence of SEQ ID NO: 33; or a sequence that has at least 80%, 85%, 90%, 95%, 96%, 97%, 98%, 99% sequence identity to SEQ ID NO: 31

(SEQ ID NO: 33)
QVQLQESGPGLVKPSQTLSLTCTVSGGSISSGYNWHWIRQPPGKGLEWIG

YIHYTGSTNYNPALRSRVTISVDTSKNQFSLKLSSVTAADTAVYYCARIY

NGNSFPYWGQGTTVTVSSGGGGSGGGGSGGGGSDIVMTQSPDSLAYSLGE

RATINCKSSQSLFNSGNQKNYLTWYQQKPGQPPKLLIYWASTRESGVPDR

FSGSGSGTDIFITISSLQAEDVAVYYCQNAYSFPYTFGGGTKLEIKR

In some embodiments, the chimeric fusion protein (CFP) comprises an extracellular domain (ECD) targeted to bind to Claudin 18.2 comprising an amino acid sequence of SEQ ID NO: 33, or a sequence that has at least 80%, 85%, 90%, 95%, 96%, 97%, 98%, 99% sequence identity to SEQ ID NO: 33.

In some embodiments, the CFP comprises an extracellular domain comprising a sequence as set forth in SEQ ID NO: 33, or a sequence having at least 80% identity to SEQ ID NO: 33; operably linked to a TM domain comprising a sequence of CD16 transmembrane domain (e.g. comprising a short hinge domain) as set forth in Table 4. In some embodiments, the CFP comprises an extracellular domain comprising a sequence as set forth in SEQ ID NO: 33, or a sequence having at least 80% identity to SEQ ID NO: 33; operably linked to a TM domain comprising a CD64 transmembrane domain sequence. In some embodiments, the CFP comprises an extracellular domain comprising a sequence as set forth in SEQ ID NO: 33; operably linked to a TM domain comprising a sequence of a CD89 transmembrane domain (e.g. comprising a short hinge domain) as set forth in Table 4. In some embodiments, the CFP comprises an ECD with a sequence set forth in SEQ ID NO: 33, or a sequence having at least 80% identity to SEQ ID NO: 33; a TM domain comprising a sequence from the TM domain of a CD16 protein, or the TMD of a CD64 protein or a TMD of a CD89 protein, and a corresponding intracellular domain (ICD), or a portion thereof, e.g., from a CD16 protein, a CD64 protein or a CD89 protein respectively, optionally, in addition to other distinct ICDs described herein. Exemplary CD16 and CD89 ICD sequences are provided in Table 4.

In on embodiment, the extracellular binding domain comprises a scFv that is specific to human claudin 3.0. In some embodiments, the extracellular binding domain comprises a claudin 3 binding domain comprising a sequence as shown in Table 2. Table 2 shows exemplary sequences of human claudin 3.0 binding domains and/or fragments thereof that are meant to be non-limiting for the disclosure.

TABLE 2

| Domain | Sequence | SEQ ID NO: | Domain | Sequence | SEQ ID NO: |
|---|---|---|---|---|---|
| 1HC-CDR1 | GYTMN | 38 | 1LC-CDR1 | KSSQSLLYGSNQKNYL | 57 |
| 1HC-CDR2 | LINPYNGGTSYNQKFKD | 39 | 1LC-CDR2 | WASTRES | 58 |
| 1HC-CDR3 | GSYGSSYFDY | 40 | 1LC-CDR3 | QQYYNFPYT | 59 |
| Heavy chain-1 | ELVKPGASMKISCKASGYSFTGYTMNWMKQGHGKNLEWIGLINPYNGGTSYNQKFKDKATLTLDKSSSSAYMELLSLTSEDSAVYYCARGSY | 41 | Light Chain-1 | DIVMSQSPSSLAVSVGEKVTMSCKSSQSLLYGSNQKNYLAWYQQKPGQSPKLLIYWASTRESGVPDRFTGSGSGTDFTLTISSVKAE | 60 |

TABLE 2-continued

| Domain | Sequence | SEQ ID NO: | Domain | Sequence | SEQ ID NO: |
|---|---|---|---|---|---|
| | GSSYFDYWGQGTTLTVSS | | | DLAVYYCQQYYNFPYTFGGGTKLEIKR | |
| 2HC-CDR1 | DYYMN | 42 | 2LC-CDR1 | RASESVDSYGNSFMH | 61 |
| 2HC-CDR2 | RVNPSNGGTSYNQKFK | 43 | 2LC-CDR2 | RASNLES | 62 |
| 2HC-CDR3 | GLAYYSNSFVY | 44 | 2LC-CDR3 | QQNNEDPWT | 63 |
| Heavy chain-2 | EVQLQQSGPELVKPGASVKMSCKASGYTFTDYYMNWVKQSHGKSLEWIGRVNPSNGGTSYNQKFKGKATLTVDKSLSTAYMQLNSLTSEDSAVYYCARGLAYYSNSFVYWGQGTLVTVSA | 45 | Light Chain-2 | KIVLTQSPASLAVSLRQRATISCRASESVDSYGNSFMHWYQQKPGQPPKLLIYRASNLESGVPARFSGSGSRTDFTLTIDPVEADDAATYYCQQNNEDPWTFGGGTKLEIKR | 64 |
| 3HC-CDR1 | GYFMN | 46 | 3LC-CDR1 | RASKSVSTSSYSYMH | 65 |
| 3HC-CDR2 | RINPYNGDTFYNQKFKG | 47 | 3LC-CDR2 | FASYLES | 66 |
| 3HC-CDR3 | SGDWYFDV | 48 | 3LC-CDR3 | PVEEEFPRT | 67 |
| Heavy chain-3 | EVQLQQSGPELVKPGASVKISCKASGYSFTGYFMNWVKQSHGKSLEWIGRINPYNGDTFYNQKFKGKATLTVDKSSSTAHMELRSLTSEDSAVYYCARSGDWYFDVWGAGTTVTVSS | 49 | Light Chain-3 | DIVLTQSPASLAVSLGQRATISCRASKSVSTSSYSYMHWYQQKPGQPPKLLIKFASYLESGVPARFSGSGSGTDFTLNIHPVEEEDAATYYCQHSREFPRTFGGGTKLEIKR | 68 |
| 4HC-CDR1 | GYFMN | 46 | 4LC-CDR1 | KASENVVSYVS | 69 |
| 4HC-CDR2 | RINPYNGDTFYNQKFKG | 47 | 4LC-CDR2 | GASNRYT | 70 |
| 4HC-CDR3 | GDGYYVTSLAY | 50 | 4LC-CDR3 | GQSYSYPLT | 71 |
| Heavy chain-4 | EVQLQQSGPELVKPGASVKISCKASGYSFTGYFMNWVKQSHGKSLEWLGRINPYNGDTFYNQKFKGKATLTVDKSSNTAHMELRSLTSEDSAVYYCARGDGYYVTSLAYWGQGTLVTVSA | 51 | Light Chain-4 | NIVMTQSPKSMSMSVGERVTLSCKASENVVSYVSWFQQKPEQSPKLLIYGASNRYTGVPDRFTGSGSATDFTLTISSVQAEDLADYYCGQSYSYPLTFGAGTKLELKR | 72 |
| 5HC-CDR1 | DYYMN | 42 | 5LC-CDR1 | RASESVDSYGNSFMH | 61 |
| 5HC-CDR2 | RVNPSNGGTSYNQKFKG | 52 | 5LC-CDR2 | RASNLES | 62 |
| 5HC-CDR3 | GLAYYSNSFTY | 53 | 5LC-CDR3 | QQNNEDPWT | 63 |
| Heavy chain-5 | EVQLQQSGPELVKPGASVKMSCKASGYTFTDYYMNWVKQSHGKSLEWIGRVNPSNGGTSYNQKFKGKATLT | 54 | Light Chain-5 | KIVLTQSPASLAVSLRQRATISCRASESVDSYGNSFMHWYQQKPGQPPKLLIYRASNLESGVPARFSGSGS | 64 |

TABLE 2-continued

| Domain | Sequence | SEQ ID NO: | Domain | Sequence | SEQ ID NO: |
|---|---|---|---|---|---|
| | VDKSLSTAYMQ LNSLTSEDSAVY YCARGLAYYSN SFTYWGQGTLV TVSA | | | RTDFTLTIDPVE ADDAATYYCQ QNNEDPWTFG GGTKLEIKR | |
| 6HC-CDR1 | GYFMN | 46 | 6LC-CDR1 | RASESVEYYGT SLMQ | 73 |
| 6HC-CDR2 | RINPYNGDTFYN QKFKG | 47 | 6LC-CDR2 | GASNVES | 74 |
| 6HC-CDR3 | SGNYVMDY | 55 | 6LC-CDR3 | QQSRKVPWT | 75 |
| Heavy chain-6 | EVQLQQSGPELV KPGASVKMSCK ASGYSFTGYFMN WVKQSHGKSLE WIGRINPYNGDT FYNQKFKGKAT LTVDKSSSTAHM ELRSLTSEDSAL YYCARSGNYVM DYWGQGTSVTV SS | 56 | Light Chain-6 | DIVLTQSPASL AVSLGQSVTIS CRASESVEYYG TSLMQWYQQK PGQPPKLLIYG ASNVESGVPAR FSGSGSGTDFS LNIHPVEEDDI AMYFCQQSRK VPWTFGGGTK LEIKR | 76 |

A claudin 3 binding domain can comprises one or more of the sequences from Table 2. In some embodiments the claudin 3 binding domain comprises an ScFv, comprising a sequence of Table 2. In some embodiments, the binding domain comprises an antigen-binding fragment (Fab), a single-chain variable fragment (scFv), a nanobody, a VH domain, a VL domain, a single domain antibody (sdAb), a VNAR domain, and a VHH domain, a bispecific antibody, a diabody, or a functional fragment of any thereof, comprising a sequence of Table 2. In some embodiments, the antigen-binding fragment (Fab), a single-chain variable fragment (scFv), a nanobody, a VH domain, a VL domain, a single domain antibody (sdAb), a VNAR domain, and a VHH domain, a bispecific antibody, a diabody, or a functional fragment of any thereof specifically bind to one or more antigens.

In some embodiments the chimeric fusion protein is a receptor, comprising an extracellular binding domain, such as an antigen binding domain; wherein the extracellular binding domain may comprises a sequence that can bind to claudin 18.2 protein as described herein; or can bind a claudin 3 protein as described herein; and may further comprise a transmembrane domain with or without a hinge domain in between the extracellular antigen binding domain and an intracellular domain. In some embodiments, the extracellular domain further comprises a hinge domain derived from CD8, wherein the hinge domain is operatively linked to a transmembrane domain at the cytoplasmic side, and to the Claudin 18.2-binding domain on the extracellular side. In some embodiments, the transmembrane domain comprises a sequence set forth in any one of the sequences in SEQ ID NO: 15, 16, 17, 18 or 19. In some embodiments, the transmembrane domain comprises a sequence derived from CD8 alpha (CD8a) transmembrane domain. In some embodiments, the transmembrane domain comprises a sequence set forth in SEQ ID NO: 15 or a sequence that has at least 70%, 75%, 80%, 85%, 90%, 91%, 92%, 93%, 94%, 95%, 96%, 97%, 98% or 99% sequence identity to SEQ ID NO: 15. In some embodiments, the transmembrane domain comprises a sequence set forth in SEQ ID NO: 16 or a sequence that has at least 70%, 75%, 80%, 85%, 90%, 91%, 92%, 93%, 94%, 95%, 96%, 97%, 98% or 99% sequence identity to SEQ ID NO: 16. In some embodiments, the transmembrane domain comprises a sequence derived from CD2 transmembrane domain. In some embodiments, the transmembrane domain comprises a sequence set forth in SEQ ID NO: 17 or a sequence that has at least 70%, 75%, 80%, 85%, 90%, 91%, 92%, 93%, 94%, 95%, 96%, 97%, 98% or 99% sequence identity to SEQ ID NO: 17. In some embodiments, the transmembrane domain comprises a sequence derived from CD28 transmembrane domain. In some embodiments, the transmembrane domain comprises a sequence set forth in SEQ ID NO: 18 or a sequence that has at least 70%, 75%, 80%, 85%, 90%, 91%, 92%, 93%, 94%, 95%, 96%, 97%, 98% or 99% sequence identity to SEQ ID NO: 18. In some embodiments, the transmembrane domain comprises a sequence derived from CD68 transmembrane domain. In some embodiments, the transmembrane domain comprises a sequence set forth in SEQ ID NO: 19 or a sequence that has at least 70%, 75%, 80%, 85%, 90%, 91%, 92%, 93%, 94%, 95%, 96%, 97%, 98% or 99% sequence identity to SEQ ID NO: 19. In some embodiments, the ECD of the CFP comprises an amino acid sequence depicted in sequences of Table 2 or a sequence that is 70%, 75%, 80%, 85%, 90%, 91%, 92%, 93%, 94%, 95%, 96%, 97%, 98% or 99% sequence identity to any of the sequences in Table 2, fused to a transmembrane domain selected from any one of sequences set forth in SEQ ID NO: 15, 16, 17, 18 or 19 or a transmembrane domain having an amino acid sequence that is at least 70%, 75%, 80%, 85%, 90%, 91%, 92%, 93%, 94%, 95%, 96%, 97%, 98% or 99% sequence identity to any one of SEQ ID NO: 15, 16, 17, 18 or 19.

In some embodiments, the extracellular hinge domain and transmembrane domain comprises a sequence of SEQ ID NO: 20 or SEQ ID NO: 21 or with at least 70%, 75%, 80%, 85%, 90%, 91%, 92%, 93%, 94%, 95%, 96%, 97%, 98% or 99% sequence identity to SEQ ID NO: 20 or SEQ ID NO: 21 respectively. In some embodiments, the CFP comprises an extracellular domain fused to a transmembrane domain of SEQ ID NO: 20 or with at least 70%, 75%, 80%, 85%, 90%, 91%, 92%, 93%, 94%, 95%, 96%, 97%, 98% or 99% sequence identity to SEQ ID NO: 20. In some embodiments, the CFP comprises an extracellular domain fused to a transmembrane domain of SEQ ID NO: 21 or with at least 70%, 75%, 80%, 85%, 90%, 91%, 92%, 93%, 94%, 95%, 96%, 97%, 98% or 99% sequence identity to SEQ ID NO: 21. In some embodiments, the CFP comprises an ECD binder domain having at least 70%, 75%, 80%, 85%, 90%, 91%, 92%, 93%, 94%, 95%, 96%, 97%, 98%, 99% or 100% sequence identity to any of the sequences in Table 2, fused to a hinge and transmembrane domain having an amino acid sequence that is at least 70%, 75%, 80%, 85%, 90%, 91%, 92%, 93%, 94%, 95%, 96%, 97%, 98%, 99% or 100% sequence identity to SEQ ID NO: 20 or 21.

In some embodiments, the CFP comprises one or more intracellular signaling domains that comprise an intracellular signaling domain. In some embodiments, the intracellular signaling domain comprises a phagocytosis signaling domain. In some embodiments, the phagocytosis signaling domain comprises an intracellular signaling domain derived from a receptor other than Megf10, MerTk, FcRα, and Bai1. In some embodiments, the phagocytosis signaling domain comprises an intracellular signaling domain derived from a receptor other than Megf10, MerTk, an FcR, and Bai1. In some embodiments, the intracellular signaling domain comprises a domain derived from a receptor other than CD3ζ. In some embodiments, the phagocytosis signaling domain comprises an intracellular signaling domain derived from FcRγ, FcRα or FcRε.

In some embodiments, the CFP comprises an intracellular signaling domain derived from an FcRgamma protein (FcRγ chain) comprising an amino acid sequence of any one of SEQ ID NOs: 22, 23, 24 or 25 or a sequence with at least 70%, 75%, 80%, 85%, 90%, 91%, 92%, 93%, 94%, 95%, 96%, 97%, 98% or 99% sequence identity to any one of SEQ ID NOs: 22, 23, 24 or 25. In some embodiments, the one or more intracellular signaling domains further comprises a proinflammatory signaling domain. In some embodiments, the proinflammatory signaling domain comprises a PI3-kinase (PI3K) recruitment domain. In some embodiments, the proinflammatory signaling domain comprises a sequence of SEQ ID NO: 26 or with at least 70%, 75%, 80%, 85%, 90%, 91%, 92%, 93%, 94%, 95%, 96%, 97%, 98% or 99% sequence identity to SEQ ID NO: 26. In some embodiments, the proinflammatory signaling domain is derived from an intracellular signaling domain of CD40. In some embodiments, the proinflammatory signaling domain comprises a sequence of SEQ ID NO: 27 or with at least 70%, 75%, 80%, 85%, 90%, 91%, 92%, 93%, 94%, 95%, 96%, 97%, 98% or 99% sequence identity to SEQ ID NO: 27. In some embodiments, the CFP comprises an intracellular signaling domain of SEQ ID NO: 28 or with at least 70%, 75%, 80%, 85%, 90%, 91%, 92%, 93%, 94%, 95%, 96%, 97%, 98% or 99% sequence identity to SEQ ID NO: 28. In some embodiments, the CFP comprises an intracellular signaling domain of SEQ ID NO: 29 or with at least 70%, 75%, 80%, 85%, 90%, 91%, 92%, 93%, 94%, 95%, 96%, 97%, 98% or 99% sequence identity to SEQ ID NO: 29. In some embodiments, the CFP comprises an intracellular signaling domain of SEQ ID NO: 30 or with at least 70%, 75%, 80%, 85%, 90%, 91%, 92%, 93%, 94%, 95%, 96%, 97%, 98% or 99% sequence identity to SEQ ID NO: 30.

Provided herein is a recombinant nucleic acid encoding a CFP comprising a Claudin 18.2 binding domain (A Claudin 18.2 binder) as described above, which may be expressed in a suitable cell, such as a myeloid cell. The myeloid cell may be a phagocytic cell. In some embodiments, the Claudin 18.2 binder upon binding Claudin 18.2 on a cell activates the myeloid cell expressing the Claudin 18.2-binding CFP.

Provided herein are recombinant nucleic acid sequence that encodes the chimeric Claudin 18.2-binder receptor fusion protein (CFP). In some embodiments, the recombinant nucleic acid encoding such as a chimeric receptor fusion protein, e.g. the Claudin 18.2-binder receptor fusion protein can be expressed in a suitable cell, such as a myeloid cell. In some embodiments, the Claudin 18.2-CFP when expressed on a suitable cell, such as a myeloid cell, the Claudin 18.2 binder can bind to a target cell which expresses Claudin 18.2, and the myeloid cell expressing the binder is activated. In some embodiments the Claudin 18.2-CFP, upon engaging with a Claudin 18.2 activated the intracellular signaling domain of the Claudin 18.2-CFP, that activates the myeloid cell expressing the recombinant nucleic acid encoding the Claudin 18.2-CFP. In some embodiments, the myeloid cell is a phagocytic cell. In some embodiments, a myeloid cell that is a phagocytic cell, and expressing a CD137 binder, may be activated when the Claudin 18.2 binder binds to Claudin 18.2 expressed on another cell (a target cell), and phagocytizes the target cell. In some embodiments, the target cell may be any cell that expresses Claudin 18.2. In some embodiments, the target cell is a lymphocyte. In some embodiments, the target cell is a T lymphocyte (T cell). In some embodiments, the target cell may be a malignant cell. In some embodiments, the target cell may be a malignant T cell. In some embodiments, the Claudin 18.2-binding CFP expressing myeloid cell may be used to generate a therapeutic composition against T cell lymphoma.

In some embodiments, the claudin 18.2 binder chimeric fusion protein is an extracellular protein comprising an antigen binding domain that binds to claudin 18.2. Provided herein is a recombinant protein such as an extracellular protein, such as a soluble protein that can bind to claudin 18.2. In some embodiments the extracellular protein comprises an antibody of a fragment thereof that can bind to claudin 18.2 as described above. In some embodiments the extracellular protein or the soluble protein further comprises a second domain that can bind to a surface protein of a myeloid cell, such as a phagocytic cell. The surface protein of a myeloid cell may be a protein expressed on the membrane of a myeloid cell, for example, a phagocytic receptor, a pattern recognition molecule or a scavenger receptor.

Provided herein is a recombinant nucleic acid encoding an extracellular protein, such as a soluble protein that can bind to the extracellular domain of claudin 18.2 as described herein.

In some embodiments, the claudin 3 binder is an extracellular protein. Provided herein is a recombinant protein such as an extracellular protein, such as a soluble protein that can bind to claudin 3. In some embodiments the extracellular protein comprises an antibody of a fragment thereof that can bind to claudin 3, such as any one or more of the sequences depicted in Table 2. In some embodiments, the extracellular claudin 3 binder protein further comprises a second domain that can bind to a surface protein of a myeloid cell, such as a phagocytic cell. The surface protein of a myeloid cell may be a protein expressed on the membrane of a myeloid cell, for example, a phagocytic receptor, a pattern recognition molecule or a scavenger receptor. Provided herein is a recombinant nucleic acid encoding an extracellular protein, such as a soluble protein that can bind to the extracellular domain of claudin 3 as described herein.

Provided herein is a therapeutic for treating a disease in a subject, wherein the disease is associated with the overexpression of a claudin protein, e.g. a claudin 18.2 protein or a claudin 3 protein, the therapeutic comprising at least a recombinant protein having an extracellular binding domain that can bind to claudin 18.2 or claudin 3 respectively, such as any of the claudin 18.2 or claudin 3 binder proteins described above. In some embodiments, provided herein is a cell that expresses a claudin 18.2 binder or a claudin 3 binding. In some embodiments, provided herein is a therapeutic for treating a disease in a subject, wherein the disease is associated with the overexpression of a claudin protein, e.g. a claudin 18.2 protein or a claudin 3 protein, the therapeutic comprising at least a recombinant nucleic acid encoding a claudin 18.2 binder or claudin 3 binder as described herein. In some embodiments, provided herein is a therapeutic for treating a disease in a subject, wherein the disease is associated with the overexpression of a claudin protein, e.g. a claudin 18.2 protein or a claudin 3 protein, the therapeutic comprising a cell comprising a recombinant nucleic acid encoding a claudin 18.2 binder or claudin 3 binder as described herein. In some embodiments, the cell is a myeloid cell.

TROP2 Binder Proteins and Domains

TROP2, also known as epithelial glycoprotein-1, gastrointestinal antigen 733-1, membrane component surface marker-1, and tumor-associated calcium signal transducer-2, is the protein product of the TACSTD2 gene. It is a transmembrane glycoprotein that functions in a variety of cell signaling pathways and was first elucidated as a transducer of an intracellular calcium signal. TROP2 expression has been demonstrated to depend on a large variety of transcription factors. TROP2 regulates proliferation and self-renewal through b-catenin signaling and TROP2 signaling enhances stem cell-like properties of cancer cells. TROP2 may play a role in tumor progression given the involvement in several molecular pathways traditionally associated with cancer development. High TROP2 expression correlates with poor prognosis in pancreatic, hilar cholangiocarcinoma, cervical cancer, gastric cancer, and others (Fong D et al., Br J Cancer. 2008; 99(8):1290-1295; Ning S. et al., J Gastrointest Surg. 2013; 17(2):360-368; Liu T, et al., PLoS One. 2013; 8(9): e75864; Zhao W, et al., Oncotarget. 2016; 7(5):6136-6145). TROP2 is overexpressed on a wide variety of tumors, with upregulated expression relative to normal cells it can be targeted for novel therapeutic development.

Provided herein is a chimeric protein that can bind to a cancer cell expressing TROP2. Provided herein is a chimeric protein that binds to the extracellular domain of TROP2 (TROP2 binder). In some embodiments, the chimeric protein is a chimeric receptor protein with an extracellular protein capable of binding to the extracellular domain of TROP2, a transmembrane domain and/or a cytoplasmic domain. In some embodiments, the chimeric protein is a protein that is an extracellular soluble protein that can bind to the extracellular domain of TROP2. In some embodiments, the extracellular soluble chimeric protein capable of binding to the extracellular domain of TROP2 may comprise another domain that is capable of binding to an extracellular domain of a protein expressed on the surface of a myeloid cell, such as a phagocytic cell. The chimeric protein described herein (TROP2 binder) as described herein may be used to prepare a therapeutic, comprising a pharmaceutical composition comprising the TROP2 binder for the treatment of a disease related to the overexpression of TROP2 proteins such as cancer. Such cancers include but are not limited to pancreatic, hilar cholangiocarcinoma, cervical cancer, and gastric cancers.

In one aspect, provided herein is a chimeric fusion receptor (CFP) protein having an extracellular TROP2 binding domain (TROP2 binder CFP). In some embodiments the extracellular binding domain is an antigen binding domain of an antibody capable of binding to TROP2, or a fragment a single-chain variable fragment (scFv), a nanobody, a VH domain, a VL domain, a single domain antibody (sdAb), a VNAR domain, and a VHH domain, a bispecific antibody, a diabody, or a functional fragment of any thereof. In some embodiments, the antigen-binding fragment (Fab), a single-chain variable fragment (scFv), a nanobody, a VH domain, a VL domain, a single domain antibody (sdAb), a VNAR domain, and a VHH domain, a bispecific antibody, a diabody, or a functional fragment of any thereof specifically bind to one or more antigens. In some embodiments, the binder is the natural ligand for the TROP2 receptor.

In some embodiments, the extracellular domain further comprises a hinge domain derived from CD8, wherein the hinge domain is operatively linked to a transmembrane domain at the cytoplasmic side, and to the TROP2 binding domain on the extracellular side. In some embodiments, the transmembrane domain comprises a sequence set forth in any one of the sequences in SEQ ID NO: 15, 16, 17, 18 or 19. In some embodiments, the transmembrane domain comprises a sequence derived from CD8 alpha (CD8a) transmembrane domain. In some embodiments, the transmembrane domain comprises a sequence set forth in SEQ ID NO: 15 or a sequence that has at least 70%, 75%, 80%, 85%, 90%, 91%, 92%, 93%, 94%, 95%, 96%, 97%, 98% or 99% sequence identity to SEQ ID NO: 15. In some embodiments, the transmembrane domain comprises a sequence set forth in SEQ ID NO: 16 or a sequence that has at least 70%, 75%, 80%, 85%, 90%, 91%, 92%, 93%, 94%, 95%, 96%, 97%, 98% or 99% sequence identity to SEQ ID NO: 16. In some embodiments, the transmembrane domain comprises a sequence derived from CD2 transmembrane domain. In some embodiments, the transmembrane domain comprises a sequence set forth in SEQ ID NO: 17 or a sequence that has at least 70%, 75%, 80%, 85%, 90%, 91%, 92%, 93%, 94%, 95%, 96%, 97%, 98% or 99% sequence identity to SEQ ID NO: 17. In some embodiments, the transmembrane domain comprises a sequence derived from CD28 transmembrane domain. In some embodiments, the transmembrane domain comprises a sequence set forth in SEQ ID NO: 18 or a sequence that has at least 70%, 75%, 80%, 85%, 90%, 91%, 92%, 93%, 94%, 95%, 96%, 97%, 98% or 99% sequence identity to SEQ ID NO: 18. In some embodiments, the transmembrane domain comprises a sequence derived from CD68 transmembrane domain. In some embodiments, the transmembrane domain comprises a sequence set forth in SEQ ID NO: 19 or a sequence that has at least 70%, 75%, 80%, 85%, 90%, 91%, 92%, 93%, 94%, 95%, 96%, 97%, 98% or 99% sequence identity to SEQ ID NO: 19. In some embodiments, the ECD of the CFP comprises an amino acid sequence depicted in sequences of Table 2 or a sequence that is 70%, 75%, 80%, 85%, 90%, 91%, 92%, 93%, 94%, 95%, 96%, 97%, 98% or 99% sequence identity to any of the sequences in Table 2, fused to a transmembrane domain selected from any one of sequences set forth in SEQ ID NO: 15, 16, 17, 18 or 19 or a transmembrane domain having an amino acid sequence that is at least 70%, 75%, 80%, 85%, 90%, 91%, 92%, 93%, 94%, 95%, 96%, 97%, 98% or 99% sequence identity to any one of SEQ ID NO: 15, 16, 17, 18 or 19.

In some embodiments, the extracellular hinge domain and transmembrane domain comprises a sequence of SEQ ID NO: 20 or SEQ ID NO: 21 or with at least 70%, 75%, 80%, 85%, 90%, 91%, 92%, 93%, 94%, 95%, 96%, 97%, 98% or 99% sequence identity to SEQ ID NO: 20 or SEQ ID NO: 21 respectively. In some embodiments, the CFP comprises an extracellular domain fused to a transmembrane domain of SEQ ID NO: 20 or with at least 70%, 75%, 80%, 85%, 90%, 91%, 92%, 93%, 94%, 95%, 96%, 97%, 98% or 99% sequence identity to SEQ ID NO: 20. In some embodiments, the CFP comprises an extracellular domain fused to a transmembrane domain of SEQ ID NO: 21 or with at least 70%, 75%, 80%, 85%, 90%, 91%, 92%, 93%, 94%, 95%, 96%, 97%, 98% or 99% sequence identity to SEQ ID NO: 21. In some embodiments, the CFP comprises an ECD binder domain having at least 70%, 75%, 80%, 85%, 90%, 91%, 92%, 93%, 94%, 95%, 96%, 97%, 98%, 99% or 100% sequence identity to any of the sequences in Table 2, fused to a hinge and transmembrane domain having an amino acid sequence that is at least 70%, 75%, 80%, 85%, 90%, 91%, 92%, 93%, 94%, 95%, 96%, 97%, 98%, 99% or 100% sequence identity to SEQ ID NO: 20 or 21.

In some embodiments, the CFP comprises an extracellular domain comprising a sequence as set forth in SEQ ID NO: 34 or SEQ ID NO: 35 or both, or a sequence having at least 80% identity to SEQ ID NO: 34 or SEQ ID NO: 35; operably linked to a TM domain comprising a sequence of CD16 transmembrane domain (e.g. comprising a short hinge domain) as set forth in Table 4. In some embodiments, the CFP comprises an extracellular domain comprising a sequence as set forth in SEQ ID NO: 34 or 35, or a sequence having at least 80% identity to SEQ ID NO: 34 or 35; operably linked to a TM domain comprising a CD64 transmembrane domain sequence. In some embodiments, the CFP comprises an extracellular domain comprising a sequence as set forth in SEQ ID NO: 34 or 35; operably linked to a TM domain comprising a sequence of a CD89 transmembrane domain (e.g. comprising a short hinge domain) as set forth in Table 4. In some embodiments, the CFP comprises an ECD with a sequence set forth in SEQ ID NO: 34 or 35, or a sequence having at least 80% identity to SEQ ID NO: 34 or 35; a TM domain comprising a sequence from the TM domain of a CD16 protein, or the TMD of a CD64 protein or a TMD of a CD89 protein, and a corresponding intracellular domain (ICD), or a portion thereof, e.g., from a CD16 protein, a CD64 protein or a CD89 protein respectively, optionally, in addition to other distinct ICDs described herein. Exemplary CD16 and CD89 ICD sequences are provided in Table 4.

In some embodiments, the CFP comprises one or more intracellular signaling domains that comprise an intracellular signaling domain. In some embodiments, the intracellular signaling domain comprises a phagocytosis signaling domain. In some embodiments, the phagocytosis signaling domain comprises an intracellular signaling domain derived from a receptor other than Megf10, MerTk, FcRα, and Bai1. In some embodiments, the phagocytosis signaling domain comprises an intracellular signaling domain derived from a receptor other than Megf10, MerTk, an FcR, and Bai1. In some embodiments, the intracellular signaling domain comprises a domain derived from a receptor other than CD3ζ. In some embodiments, the phagocytosis signaling domain comprises an intracellular signaling domain derived from FcRγ, FcRα or FcRε.

In some embodiments, the CFP comprises an intracellular signaling domain derived from an FcRgamma protein (FcRγ chain) comprising an amino acid sequence of any one of SEQ ID NOs: 22, 23, 24 or 25 or a sequence with at least 70%, 75%, 80%, 85%, 90%, 91%, 92%, 93%, 94%, 95%, 96%, 97%, 98% or 99% sequence identity to any one of SEQ ID NOs: 22, 23, 24 or 25. In some embodiments, the one or more intracellular signaling domains further comprises a proinflammatory signaling domain. In some embodiments, the proinflammatory signaling domain comprises a PI3-kinase (PI3K) recruitment domain. In some embodiments, the proinflammatory signaling domain comprises a sequence of SEQ ID NO: 26 or with at least 70%, 75%, 80%, 85%, 90%, 91%, 92%, 93%, 94%, 95%, 96%, 97%, 98% or 99% sequence identity to SEQ ID NO: 26. In some embodiments, the proinflammatory signaling domain is derived from an intracellular signaling domain of CD40. In some embodiments, the proinflammatory signaling domain comprises a sequence of SEQ ID NO: 27 or with at least 70%, 75%, 80%, 85%, 90%, 91%, 92%, 93%, 94%, 95%, 96%, 97%, 98% or 99% sequence identity to SEQ ID NO: 27. In some embodiments, the CFP comprises an intracellular signaling domain of SEQ ID NO: 28 or with at least 70%, 75%, 80%, 85%, 90%, 91%, 92%, 93%, 94%, 95%, 96%, 97%, 98% or 99% sequence identity to SEQ ID NO: 28. In some embodiments, the CFP comprises an intracellular signaling domain of SEQ ID NO: 29 or with at least 70%, 75%, 80%, 85%, 90%, 91%, 92%, 93%, 94%, 95%, 96%, 97%, 98% or 99% sequence identity to SEQ ID NO: 29. In some embodiments, the CFP comprises an intracellular signaling domain of SEQ ID NO: 30 or with at least 70%, 75%, 80%, 85%, 90%, 91%, 92%, 93%, 94%, 95%, 96%, 97%, 98% or 99% sequence identity to SEQ ID NO: 30.

Provided herein is a recombinant nucleic acid encoding a CFP comprising a TROP2 binding domain (a TROP2 binder) as described above, which may be expressed in a suitable cell, such as a myeloid cell. The myeloid cell may be a phagocytic cell. In some embodiments, the recombinant nucleic acid encoding a CFP comprising a TROP2 binding domain as described above, an intracellular domain which comprises one or more of the sequences from SEQ ID NOs: 21-30; and a transmembrane domain comprising a sequence having a sequence selected from any one of SEQ ID NO: 15-21.

In another embodiment, provided herein is a recombinant protein such as an extracellular protein, such as a soluble protein that can bind to the extracellular domain of TROP2. In some embodiments, the recombinant extracellular protein having a domain that can bind to TROP2, e.g., a domain that can bind to the extracellular domain of TROP2, further comprises a second domain that can bind to a surface protein of a myeloid cell, such as a phagocytic cell. The surface protein of a myeloid cell may be a protein expressed on the membrane of a myeloid cell, for example, a phagocytic receptor, a pattern recognition molecule or a scavenger receptor. Provided herein is a recombinant nucleic acid encoding an extracellular protein, such as a soluble protein that can bind to the extracellular domain of TROP2 as described herein.

Provided herein is a therapeutic for treating a disease in a subject, wherein the disease is associated with the overexpression of TROP2 protein, the therapeutic comprising at least a recombinant polynucleic acid encoding a protein having an extracellular binding domain that can bind to TROP2, such as any of the TROP2 binder proteins described above. In some embodiments, the recombinant polynucleic acid encoding the protein is an mRNA. In some embodiments, the recombinant polynucleic acid encoding the protein is DNA. In some embodiments, the recombinant polynucleic acid encodes a TROP2 binder protein that is a chimeric fusion receptor protein (CFP) comprising an extracellular TROP2 binding domain, an optional transmembrane domain and one or more intracellular domains. In some embodiments, the one or more intracellular domains comprise one or more cell signaling domains. In some embodiments the one or more intracellular signaling domains comprise a PI3-kinase recruitment domain, a CD40 intracellular domain, a FcR domain, as described in the specification. In some embodiments the recombinant polynucleic acid is comprised in a cell. In some embodiments, the recombinant mRNA comprising a sequence encoding a TROP2-binder CFP is expressed in a myeloid cell. In some embodiments, provided herein is a cell that expresses a TROP2 binder protein. In some embodiments, provided herein is a therapeutic for treating a disease in a subject, wherein the disease is associated with the overexpression of TROP2, the therapeutic comprising at least a recombinant nucleic acid encoding a TROP2 binder as described herein. In some embodiments, provided herein is a therapeutic for treating a disease in a subject, wherein the disease is associated with the overexpression of a TROP2 protein, the therapeutic comprising a cell comprising a recombinant nucleic acid encoding a TROP2 binder as described herein. In some embodiments, the cell is a myeloid cell. In some embodiments, the diseases is a cancer including but not limited to pancreatic, hilar cholangiocarcinoma, cervical cancer, gastric cancer, lung cancer. In some embodiments, the diseases is a non-small cell lung carcinoma.

In some embodiments, the therapeutic described herein comprises at least a recombinant chimeric fusion protein (CFP) or a polynucleotide encoding the recombinant CFP having an extracellular binding domain that can bind to TROP2, optionally a CD8 hinge domain, and a transmembrane domain that can bind to an endogenous protein in a myeloid cell in order to be properly expressed and localized on the membrane of a myeloid cell. For example, in some embodiments, the TROP2 binder comprises a transmembrane region that dimerizes or oligomerizes with another transmembrane protein of a myeloid cell. In some embodiments, the TROP2 binder comprises a transmembrane protein that dimerizes with an Fc-gamma receptor on the myeloid cell membrane and thereby can express only in a myeloid cell. In some embodiments, the TROP2 binder is designed such that the protein is functional only if it dimerizes (or oligomerizes) with an endogenous protein that is expressed only in a myeloid cell. In some embodiments, the TROP2 binder comprises an Fc-alpha transmembrane domain. In some embodiments, the TROP2 binder comprises a transmembrane domain selected from a CD64 (FcγR1) protein transmembrane domain, a CD89 (FcαR1) protein transmembrane domain, a CD16a (FcγRIIIA) transmembrane domain. In some embodiments, the TROP2 binder comprises an Fc-epsilon transmembrane domain. In some embodiments, provided herein is a TROP2 binding CFP (TROP2 binder), that comprises an extracellular TROP2 binding domain, optionally a short hinge region, e.g., comprising a CD8 hinge domain, a CD89 transmembrane domain, optionally a CD89 intracellular region, fused to one or more intracellular signaling domains, such as CD40 intracellular domain and a PI3-kinase recruitment domain. In some embodiments, provided herein is a TROP2 binding CFP (TROP2 binder), that comprises an extracellular TROP2 binding domain, optionally a short hinge region, e.g., comprising a CD8 hinge domain, a CD64 transmembrane domain, optionally a CD64 intracellular region, fused to one or more intracellular signaling domains, such as CD40 intracellular domain and a PI3-kinase recruitment domain. The TROP2 CFP can comprise one or more human or humanized domains. Provided herein is a polynucleotide, e.g. an mRNA or a DNA, comprising a sequence encoding the TROP2 CFP construct, comprising the anti-TROP2 ScFv (TROP2 antigen binder) fused to a CD8 hinge domain, that is operably linked to a CD89 transmembrane domain, and an intracellular domain.

In some embodiments, the TROP2 CFP described herein shows myeloid cell specific expression. In some embodiments, the TROP2 CFP described herein shows Fc-gamma-dependent expression. In some embodiments, the TROP2 CFP described herein exhibits undetectable expression in a T cell, a B cell, an epithelial cell, a muscle cell, a neuronal cell or any non-myeloid cell, when the polynucleotide is administered in vivo. In one embodiment, the TROP2 binder having a CD16, CD89 or a CD64 transmembrane domain as described herein, encoded by the polynucleotide described herein expresses predominantly in a CD14+ cell when the polynucleotide is administered in vivo. In one embodiment, the TROP2 binder having a CD16, CD89 or a CD64 transmembrane domain, encoded by the polynucleotide described herein expresses only in a CD14+ cell when the polynucleotide is administered in vivo.

Provided herein is a pharmaceutical composition comprising a CD14+ cell expressing a CFP having a TROP2 binding domain. In some embodiments, the pharmaceutical composition comprises a cell population of which at least 50% cells are CD14+ cells that express the TROP2 binder CFP. In some embodiments, the pharmaceutical composition comprises at least 50% cells that are CD14+ and CD16−. In some embodiments, the pharmaceutical composition comprises at least 50% cells that express CD14+ cells that are CD16− and express TROP2-CFP (CFP having a TROP2 binding extracellular domain).

Provided herein is a pharmaceutical composition comprising a recombinant polynucleotide (polynucleic acid) encoding a transmembrane polypeptide comprising a CD64, or CD89 or CD16a transmembrane domain, and wherein the recombinant polynucleotide is encapsulated within an LNP. In some embodiments, the transmembrane polypeptide is a CFP, having an extracellular binding domain specific for binding an antigen on a cancer cell. In some embodiments the CFP, comprises an extracellular binding domain specific for binding TROP2.

Provided herein is a pharmaceutical composition for treatment of a cancer in a human subject that comprises a cell, e.g. a CD14+ myeloid cell, expressing a TROP2 binder CFP as described herein, wherein the cancer is a lung cancer. In some embodiments, the lung cancer is a NSCLC.

Provided herein is a pharmaceutical composition for treatment of a cancer in a human subject that comprises a recombinant polynucleic acid encoding CFP comprising a TROP2 binding extracellular domain capable of being expressed in a myeloid cell in vivo; wherein the CFP comprising a TROP2 binding extracellular domain comprises a CD64, a CD16a or a CD89 transmembrane domain as described herein, wherein the recombinant polynucleic acid is encapsulated in an LNP, wherein the cancer is a lung cancer. In some embodiments, the lung cancer is a NSCLC.

An exemplary TROP2 binding domain sequence may be the amino acid sequence of SEQ ID NO: 34, or a sequence that shares at least 80% identity to SEQ ID NO: 34.

(SEQ ID NO: 34)
DIQLTQSPSSLSASVGDRVSITCKASQDVSIAVAWYQQKPGKAPKLLIYS

ASYRYTGVPDRFSGSGSGTDFTLTISSLQPEDFAVYYCQQHYITPLTFGA

GTKVEIKRGGGGSGGGGSGGGGSQVQLQQSGSELKKPGASVKVSCKASGY

-continued

TFTNYGMNWVKQAPGQGLKWMGWINTYTGEPTYTDDFKGRFAFSLDTSVS

TAYLQISSLKADDTAVYFCARGGFGSSYWYFDVWGQGSLVTVSS

In some embodiments, the chimeric fusion protein (CFP) comprises an extracellular domain (ECD) targeted to bind to TROP2 comprising an amino acid sequence of SEQ ID NO: 34, or a sequence that has at least 80%, 85%, 90%, 95%, 96%, 97%, 98%, 99% sequence identity to SEQ ID NO: 34.

An exemplary TROP2 binding domain may be the sequence depicted in SEQ ID NO: 35.

(SEQ ID NO: 35)
QVQLQQSGSELKKPGASVKVSCKASGYTFTNYGMNWVKQAPGQGLKWMGW

INTYTGEPTYTDDFKGRFAFSLDTSVSTAYLQISSLKADDTAVYFCARGG

FGSSYWYFDVWGQGSLVTVSSGGGGSGGGGSGGGGSDIQLTQSPSSLSAS

VGDRVSITCKASQDVSIAVAWYQQKPGKAPKLLIYSASYRYTGVPDRFSG

SGSGTDFTLTISSLQPEDFAVYYCQQHYITPLTFGAGTKVEIKR

In some embodiments, the chimeric fusion protein (CFP) comprises an extracellular domain (ECD) targeted to bind to TROP2 comprising an amino acid sequence of SEQ ID NO: 35, or a sequence that has at least 80%, 85%, 90%, 95%, 96%, 97%, 98%, 99% sequence identity to SEQ ID NO: 35.

TMPRSS3 Binder Proteins and Domains

Approximately 50% of prostate cancers harbor a gene fusion linking the androgen-regulated gene transmembrane protease, serine 2 (TMPRSS2) with transcription factors of the erythroblastosis virus E26 transforming sequence (ETS) family, typically erythroblast transformation-specific-related gene (ERG). It has been recently demonstrated that the TMPRSS2:ERG fusion typically occurs early during tumor development and is often homogeneously distributed across the cancer bulk. In a recent study, discrepant ERG findings were observed in the lymph nodes of 30% of 84 prostate cancers. The TMPRSS2:ERG fusion protein may be an optimal target for a novel therapy, as it is highly specific for prostate cancer cells. In one aspect, provided herein is a chimeric fusion receptor (CFP) protein having an extracellular TMPRSS binding domain (TMPRSS binder CFP).

In some embodiments the extracellular binding domain is an antigen binding domain of an antibody capable of binding to TMPRSS, or a fragment a single-chain variable fragment (scFv), a nanobody, a VH domain, a VL domain, a single domain antibody (sdAb), a VNAR domain, and a VHH domain, a bispecific antibody, a diabody, or a functional fragment of any thereof. In some embodiments, the antigen-binding fragment (Fab), a single-chain variable fragment (scFv), a nanobody, a VH domain, a VL domain, a single domain antibody (sdAb), a VNAR domain, and a VHH domain, a bispecific antibody, a diabody, or a functional fragment of any thereof specifically bind to one or more antigens.

In some embodiments, the extracellular domain further comprises a hinge domain derived from CD8, wherein the hinge domain is operatively linked to a transmembrane domain at the cytoplasmic side, and to the TMPRSS binding domain on the extracellular side. In some embodiments, the transmembrane domain comprises a sequence set forth in any one of the sequences in SEQ ID NO: 15, 16, 17, 18 or 19. In some embodiments, the transmembrane domain comprises a sequence derived from CD8 alpha (CD8α) transmembrane domain. In some embodiments, the transmembrane domain comprises a sequence set forth in SEQ ID NO: 15 or a sequence that has at least 70%, 75%, 80%, 85%, 90%, 91%, 92%, 93%, 94%, 95%, 96%, 97%, 98% or 99% sequence identity to SEQ ID NO: 15. In some embodiments, the transmembrane domain comprises a sequence set forth in SEQ ID NO: 16 or a sequence that has at least 70%, 75%, 80%, 85%, 90%, 91%, 92%, 93%, 94%, 95%, 96%, 97%, 98% or 99% sequence identity to SEQ ID NO: 16. In some embodiments, the transmembrane domain comprises a sequence derived from CD2 transmembrane domain. In some embodiments, the transmembrane domain comprises a sequence set forth in SEQ ID NO: 17 or a sequence that has at least 70%, 75%, 80%, 85%, 90%, 91%, 92%, 93%, 94%, 95%, 96%, 97%, 98% or 99% sequence identity to SEQ ID NO: 17. In some embodiments, the transmembrane domain comprises a sequence derived from CD28 transmembrane domain. In some embodiments, the transmembrane domain comprises a sequence set forth in SEQ ID NO: 18 or a sequence that has at least 70%, 75%, 80%, 85%, 90%, 91%, 92%, 93%, 94%, 95%, 96%, 97%, 98% or 99% sequence identity to SEQ ID NO: 18. In some embodiments, the transmembrane domain comprises a sequence derived from CD68 transmembrane domain. In some embodiments, the transmembrane domain comprises a sequence set forth in SEQ ID NO: 19 or a sequence that has at least 70%, 75%, 80%, 85%, 90%, 91%, 92%, 93%, 94%, 95%, 96%, 97%, 98% or 99% sequence identity to SEQ ID NO: 19. In some embodiments, the ECD of the CFP comprises an amino acid sequence depicted in sequences of Table 2 or a sequence that is 70%, 75%, 80%, 85%, 90%, 91%, 92%, 93%, 94%, 95%, 96%, 97%, 98% or 99% sequence identity to any of the sequences in Table 2, fused to a transmembrane domain selected from any one of sequences set forth in SEQ ID NO: 15, 16, 17, 18 or 19 or a transmembrane domain having an amino acid sequence that is at least 70%, 75%, 80%, 85%, 90%, 91%, 92%, 93%, 94%, 95%, 96%, 97%, 98% or 99% sequence identity to any one of SEQ ID NO: 15, 16, 17, 18 or 19.

In some embodiments, the extracellular hinge domain and transmembrane domain comprises a sequence of SEQ ID NO: 20 or SEQ ID NO: 21 or with at least 70%, 75%, 80%, 85%, 90%, 91%, 92%, 93%, 94%, 95%, 96%, 97%, 98% or 99% sequence identity to SEQ ID NO: 20 or SEQ ID NO: 21 respectively. In some embodiments, the CFP comprises an extracellular domain fused to a transmembrane domain of SEQ ID NO: 20 or with at least 70%, 75%, 80%, 85%, 90%, 91%, 92%, 93%, 94%, 95%, 96%, 97%, 98% or 99% sequence identity to SEQ ID NO: 20. In some embodiments, the CFP comprises an extracellular domain fused to a transmembrane domain of SEQ ID NO: 21 or with at least 70%, 75%, 80%, 85%, 90%, 91%, 92%, 93%, 94%, 95%, 96%, 97%, 98% or 99% sequence identity to SEQ ID NO: 21. In some embodiments, the CFP comprises an ECD binder domain having at least 70%, 75%, 80%, 85%, 90%, 91%, 92%, 93%, 94%, 95%, 96%, 97%, 98%, 99% or 100% sequence identity to any of the sequences in Table 2, fused to a hinge and transmembrane domain having an amino acid sequence that is at least 70%, 75%, 80%, 85%, 90%, 91%, 92%, 93%, 94%, 95%, 96%, 97%, 98%, 99% or 100% sequence identity to SEQ ID NO: 20 or 21.

In some embodiments, the CFP comprising an ECD domain that can bind to a TMPRSS protein or portion thereof comprises a TMD and a hinge domain, optionally a short cytoplasmic domain of a CD16, a CD64 or a CD89 protein, optionally with one or more other ICDs described herein.

In some embodiments, the CFP comprises one or more intracellular signaling domains that comprise an intracellular signaling domain. In some embodiments, the intracellular signaling domain comprises a phagocytosis signaling domain. In some embodiments, the phagocytosis signaling domain comprises an intracellular signaling domain derived from a receptor other than Megf10, MerTk, FcRα, and Bai1. In some embodiments, the phagocytosis signaling domain comprises an intracellular signaling domain derived from a receptor other than Megf10, MerTk, an FcR, and Bai1. In some embodiments, the intracellular signaling domain comprises a domain derived from a receptor other than CD3ζ. In some embodiments, the phagocytosis signaling domain comprises an intracellular signaling domain derived from FcRγ, FcRα or FcRε.

In some embodiments, the CFP comprises an intracellular signaling domain derived from an FcRgamma protein (FcRγ chain) comprising an amino acid sequence of any one of SEQ ID NOs: 22, 23, 24 or 25 or a sequence with at least 70%, 75%, 80%, 85%, 90%, 91%, 92%, 93%, 94%, 95%, 96%, 97%, 98% or 99% sequence identity to any one of SEQ ID NOs: 22, 23, 24 or 25. In some embodiments, the one or more intracellular signaling domains further comprises a proinflammatory signaling domain. In some embodiments, the proinflammatory signaling domain comprises a PI3-kinase (PI3K) recruitment domain. In some embodiments, the proinflammatory signaling domain comprises a sequence of SEQ ID NO: 26 or with at least 70%, 75%, 80%, 85%, 90%, 91%, 92%, 93%, 94%, 95%, 96%, 97%, 98% or 99% sequence identity to SEQ ID NO: 26. In some embodiments, the proinflammatory signaling domain is derived from an intracellular signaling domain of CD40. In some embodiments, the proinflammatory signaling domain comprises a sequence of SEQ ID NO: 27 or with at least 70%, 75%, 80%, 85%, 90%, 91%, 92%, 93%, 94%, 95%, 96%, 97%, 98% or 99% sequence identity to SEQ ID NO: 27. In some embodiments, the CFP comprises an intracellular signaling domain of SEQ ID NO: 28 or with at least 70%, 75%, 80%, 85%, 90%, 91%, 92%, 93%, 94%, 95%, 96%, 97%, 98% or 99% sequence identity to SEQ ID NO: 28. In some embodiments, the CFP comprises an intracellular signaling domain of SEQ ID NO: 29 or with at least 70%, 75%, 80%, 85%, 90%, 91%, 92%, 93%, 94%, 95%, 96%, 97%, 98% or 99% sequence identity to SEQ ID NO: 29. In some embodiments, the CFP comprises an intracellular signaling domain of SEQ ID NO: 30 or with at least 70%, 75%, 80%, 85%, 90%, 91%, 92%, 93%, 94%, 95%, 96%, 97%, 98% or 99% sequence identity to SEQ ID NO: 30.

Provided herein is a recombinant nucleic acid encoding a CFP comprising a TMPRSS binding domain (a TMPRSS binder) as described above, which may be expressed in a suitable cell, such as a myeloid cell. The myeloid cell may be a phagocytic cell. In some embodiments, the recombinant nucleic acid encoding a CFP comprising a TMPRSS binding domain as described above, an intracellular domain which comprises one or more of the sequences from SEQ ID NOs: 21-30; and a transmembrane domain comprising a sequence having a sequence selected from any one of SEQ ID NO: 15-21.

In another embodiment, provided herein is a recombinant protein such as an extracellular protein, such as a soluble protein that can bind to the extracellular domain of TMPRSS. In some embodiments, the recombinant extracellular protein having a domain that can bind to TMPRSS, e.g., a domain that can bind to the extracellular domain of TMPRSS, further comprises a second domain that can bind to a surface protein of a myeloid cell, such as a phagocytic cell. The surface protein of a myeloid cell may be a protein expressed on the membrane of a myeloid cell, for example, a phagocytic receptor, a pattern recognition molecule or a scavenger receptor. Provided herein is a recombinant nucleic acid encoding an extracellular protein, such as a soluble protein that can bind to the extracellular domain of TMPRSS as described herein.

Provided herein is a therapeutic for treating a disease in a subject, wherein the disease is associated with the overexpression of TMPRSS protein, the therapeutic comprising at least a recombinant protein having an extracellular binding domain that can bind to TMPRSS, such as any of the TMPRSS binder proteins described above. In some embodiments, provided herein is a cell that expresses a TMPRSS binder protein. In some embodiments, provided herein is a therapeutic for treating a disease in a subject, wherein the disease is associated with the overexpression of TMPRSS, the therapeutic comprising at least a recombinant nucleic acid encoding a TMPRSS binder as described herein. In some embodiments, provided herein is a therapeutic for treating a disease in a subject, wherein the disease is associated with the overexpression of a TMPRSS protein, the therapeutic comprising a cell comprising a recombinant nucleic acid encoding a TMPRSS binder as described herein. In some embodiments, the cell is a myeloid cell. In some embodiments, the diseases is a cancer, such as a prostate cancer. BiME and TRiME structures Provided herein are bi-specific engagers (BiMEs) or tri-specific engagers (TRiMEs) comprising any one of binding domains of the therapeutic agents described above, wherein the binding domains comprise the binding domain of an antibody, a functional fragment of an antibody, a variable domain thereof, a $V_H$ domain, a $V_L$ domain, a VNAR domain, a $V_{HH}$ domain, a single chain variable fragment (scFv), an Fab, a single-domain antibody (sdAb), a nanobody, a bispecific antibody, a diabody, or a functional fragment or a combination thereof. In some embodiments, the antigen on the target cell to which the first binding domain binds, is a cancer antigen or a pathogenic antigen on the target cell or an autoimmune antigen. In some embodiments, the first therapeutic agent comprises a polypeptide that is less than 1000 amino acids or 1000 nm in length. In some embodiments, the first therapeutic agent comprises a polypeptide that is less than 500 amino acids or 500 nm in length. In some embodiments, the first therapeutic agent comprises a polypeptide that is 200-1000 amino acids or 200-1000 nm in length.

In some embodiments, engagement of the binding domains of the first therapeutic agent contacts the cancer cell to the myeloid cell. In some embodiments, the second binding domain specifically interacts with a myeloid cell and promotes phagocytosis activity of the myeloid cell. In some embodiments, the second binding domain specifically interacts with a myeloid cell and promotes inflammatory signaling of the myeloid cell. In some embodiments, the second binding domain specifically interacts with a myeloid cell or an adhesion molecule and promotes adhesion of the myeloid cell to the target cell. In some embodiments, the second binding domain specifically interacts with a myeloid cell and inhibits anti-phagocytic activity of the myeloid cell mediated by the target cell. In some embodiments, the second binding domain specifically interacts with a myeloid cell and inhibits anti-inflammatory activity of the myeloid cell mediated by the target cell. In some embodiments, the second and/or the third binding domain promotes phagocytic activity of the myeloid cell. In some embodiments, the second and/or the third binding domain promotes inflammatory signaling of the myeloid cell. In some embodiments, the second and/or the third binding domain specifically interacts with a myeloid cell or an adhesion molecule and promotes adhesion of the myeloid cell to the target cell. In some embodiments, the second and/or the third binding domain inhibits anti-phagocytic activity of the myeloid cell mediated by the target cell. In some embodiments, the second and/or the third binding domain inhibits anti-inflammatory activity of the myeloid cell mediated by the target cell.

In some embodiments, the third binding domain or the additional therapeutic agent comprises a CD47 antagonist, a CD47 blocker, an antibody, a chimeric CD47 receptor, a sialidase, a cytokine, a proinflammatory gene, a procaspase, or an anti-cancer agent. In some embodiments, the first binding domain, the second binding domain and the third binding domain bind to distinct non-identical target antigens. In some embodiments, the first binding domain, the second binding domain or the third binding domain is a ligand binding domain.

In some embodiments, the first, the second or the third binding domains are operably linked by one or more linkers. In some embodiments, the linker is a polypeptide. In some embodiments, the linker is a functional peptide. In some embodiments, the linker is a ligand for a receptor. In some embodiments, the linker is a ligand for a monocyte or macrophage receptor. In some embodiments, the linker activates the receptor. In some embodiments, the linker inhibits the receptor. In some embodiments, the linker is a ligand for a M2 macrophage receptor. In some embodiments, the linker is a ligand for a TLR receptor, such as TLR4. In some embodiments, the linker activates a TLR receptor. In some embodiments, the first, the second and/or the third binding domains are associated with a mask that binds to the binding domain. In some embodiments, the mask is an inhibitor that inhibits the interaction of binding domain to its target when the mask remains associated with the respective binding domain. In some embodiments, the mask is associated with the binding domain via a peptide linker. In some embodiments, the peptide linker comprises a cleavable moiety. In some embodiments, the cleavable moiety is cleaved by a protein or an enzyme selectively abundant in the site of the cancer or tumor.

Therapeutic Compositions

Provided herein, in one aspect, is a myeloid cell, such as a CD14+ cell, a CD14+/CD16− cell, a CD14+/CD16+ cell, a CD14−/CD16+ cell, CD14−/CD16− cell, a dendritic cell, an M0 macrophage, an M2 macrophage, an M1 macrophage or a mosaic myeloid cell/macrophage/dendritic cell. In some embodiments, provided herein is a therapeutic composition comprising at least 20%, at least 30%, at least 40% or at least 50% CD14+ cells. In some embodiments, the therapeutic composition comprises at least 20%, at least 30%, at least 40% or at least 50% CD14+/CD16− cells. In some embodiments, provided herein is a therapeutic composition comprising less than 20%, less than 15%, less than 10% or less than 5% dendritic cells. The myeloid cell for the therapeutic composition as described herein, comprises a recombinant nucleic acid that encodes a chimeric fusion protein encoding a CFP receptor protein or an engager protein as described herein. The myeloid cell for the therapeutic composition as described herein, expresses the CFP encoded by the recombinant nucleic acid or expresses an engager protein encoded by the recombinant nucleic acid as described herein.

In some embodiments, provided herein is a therapeutic composition comprising a chimeric fusion protein, such as a chimeric fusion receptor protein (CFP), the CFP comprises: (a) an extracellular domain comprising: (i) a scFv that specifically binds any one of the targets disclosed herein, and (ii) a hinge domain derived from CD8, a hinge domain derived from CD28 or at least a portion of an extracellular domain from CD68; (b) a CD8 transmembrane domain, a CD28 transmembrane domain, a CD2 transmembrane domain or a CD68 transmembrane domain; and (c) an intracellular domain comprising at least two intracellular signaling domains, wherein the at least two intracellular signaling domains comprise: (i) a first intracellular signaling domain derived from FcRγ or FcRε, and (ii) a second intracellular signaling domain that: (A) comprises a PI3K recruitment domain, or (B) is derived from CD40.

In some embodiments, provided herein is therapeutic composition comprising a bispecific or trispecific engager as disclosed herein.

Provided herein, in one aspect, one or more recombinant polynucleic acid(s) encoding one or more recombinant proteins that can be a chimeric fusion protein such as a receptor, or an engager as described herein. In some embodiments, the recombinant polynucleic acid(s) is an mRNA. In some embodiments, the recombinant polynucleic acid comprises a circRNA. In some embodiments, the recombinant polynucleic acid is encompassed in a viral vector. In some embodiments, the recombinant polynucleic acid is delivered via a viral vector.

In some embodiments, provided herein is a therapeutic composition comprising a recombinant nucleic acid encoding a chimeric fusion protein, such as a chimeric fusion receptor protein (CFP), the CFP comprises: (a) an extracellular domain comprising: (i) a scFv that specifically binds any one of the targets disclosed herein, and (ii) a hinge domain derived from CD8, a hinge domain derived from CD28 or at least a portion of an extracellular domain from CD68; (b) a CD8 transmembrane domain, a CD28 transmembrane domain, a CD2 transmembrane domain or a CD68 transmembrane domain; and (c) an intracellular domain comprising at least two intracellular signaling domains, wherein the at least two intracellular signaling domains comprise: (i) a first intracellular signaling domain derived from FcRγ or FcRε, and (ii) a second intracellular signaling domain that: (A) comprises a PI3K recruitment domain, or (B) is derived from CD40.

In some embodiments, provided herein is therapeutic composition comprising a recombinant nucleic acid encoding a bispecific or trispecific engager as disclosed herein.

Other Therapeutic Compositions for Co-Administration

In some embodiments, the therapeutic composition further comprises an additional therapeutic agent selected from the group consisting of a CD47 agonist, an agent that inhibits Rac, an agent that inhibits Cdc42, an agent that inhibits a GTPase, an agent that promotes F-actin disassembly, an agent that promotes PI3K recruitment to the PFP, an agent that promotes PI3K activity, an agent that promotes production of phosphatidylinositol 3,4,5-trisphosphate, an agent that promotes ARHGAP12 activity, an agent that promotes ARHGAP25 activity, an agent that promotes SH3BP1 activity, an agent that promotes sequestration of lymphocytes in primary and/or secondary lymphoid organs, an agent that increases concentration of naïve T cells and central memory T cells in secondary lymphoid organs, and any combination thereof.

In some embodiments, the myeloid cell further comprises: (a) an endogenous peptide or protein that dimerizes with the CFP, (b) a non-endogenous peptide or protein that dimerizes with the CFP; and/or (c) a second recombinant polynucleic acid sequence, wherein the second recombinant polynucleic acid sequence comprises a sequence encoding a peptide or protein that interacts with the CFP; wherein the dimerization or the interaction potentiates phagocytosis by the myeloid cell expressing the CFP as compared to a myeloid cell that does not express the CFP.

In some embodiments, the myeloid cell exhibits (i) an increase in effector activity, cross-presentation, respiratory burst, ROS production, iNOS production, inflammatory mediators, extra-cellular vesicle production, phosphatidylinositol 3,4,5-trisphosphate production, trogocytosis with the target cell expressing the antigen, resistance to CD47 mediated inhibition of phagocytosis, resistance to LILRB1 mediated inhibition of phagocytosis, or any combination thereof and/or (ii) an increase in expression of a IL-1, IL3, IL-6, IL-10, IL-12, IL-13, IL-23, TNFα, a TNF family of cytokines, CCL2, CXCL9, CXCL10, CXCL11, IL-18, IL-23, IL-27, CSF, MCSF, GMCSF, IL-17, IP-10, RANTES, an interferon, MHC class I protein, MHC class II protein, CD40, CD48, CD58, CD80, CD86, CD112, CD155, a TRAIL/TNF Family death receptor, TGFβ, B7-DC, B7-H2, LIGHT, HVEM, TL1A, 41BBL, OX40L, GITRL, CD30L, TIM1, TIM4, SLAM, PDL1, an MMP (e.g., MMP2, MMP7 and MMP9) or any combination thereof.

In some embodiments, the intracellular signaling domain is derived from a phagocytic or tethering receptor or wherein the intracellular signaling domain comprises a phagocytosis activation domain. In some embodiments, the intracellular signaling domain is derived from a receptor other than a phagocytic receptor selected from Megf10, MerTk, FcR-alpha, or Bai1. In some embodiments, the intracellular signaling domain is derived from a protein, such as receptor (e.g., a phagocytic receptor), selected from the group consisting of TNFR1, MDA5, CD40, lectin, dectin 1, CD206, scavenger receptor A1 (SRA1), MARCO, CD36, CD163, MSR1, SCARA3, COLEC12, SCARA5, SCARB1, SCARB2, CD68, OLR1, SCARF1, SCARF2, CXCL16, STAB1, STAB2, SRCRB4D, SSC5D, CD205, CD207, CD209, RAGE, CD14, CD64, F4/80, CCR2, CX3CR1, CSF1R, Tie2, HuCRIg(L), CD64, CD32a, CD16a, CD89, Fcα receptor I, CR1, CD35, CD3ζ, a complement receptor, CR3, CR4, Tim-1, Tim-4 and CD169. In some embodiments, the intracellular signaling domain comprises a pro-inflammatory signaling domain. In some embodiments, the intracellular signaling domain comprises a pro-inflammatory signaling domain that is not a PI3K recruitment domain.

In some embodiments, the intracellular signaling domain is derived from an ITAM domain containing receptor. In some embodiments, the recombinant intracellular signaling domain comprises a first portion derived from a phagocytic and a second portion derived from non-phagocytic receptor wherein the second portion derived from non-phagocytic receptor comprises a phosphorylation site. In some embodiments, the phosphorylation site comprises amino acid sequences suitable for an autophosphorylation site. In some embodiments, the amino acid residue that is phosphorylated is a tyrosine In some embodiments, the phosphorylation site comprises amino acid sequences suitable phosphorylation by Src family kinases. In some embodiments, the phosphorylation site comprises amino acid sequences, which upon phosphorylation are capable of binding to SH2 domains in a kinase. In some embodiments, a receptor tyrosine kinase domain is fused at the cytoplasmic end of the chimeric receptor in addition to the first cytoplasmic portion.

In some embodiments, the phosphorylation site is a Tyrosine phosphorylation site.

In some embodiments the second intracellular domain is an Immune receptor Tyrosine Activation Motif (ITAM). Exemplary ITAM motifs are present in mammalian α and β immunoglobulin proteins, TCR γ receptors, FCR γ receptors subunits, CD3 chains receptors and NFAT activation molecule.

In some embodiments the chimeric receptor intracellular domain comprises one ITAM motif. In some embodiments the chimeric receptor intracellular domain comprises more than one ITAM motifs. In some embodiments the chimeric receptor intracellular domain comprises two or more ITAM motifs. In some embodiments the chimeric receptor intracellular domain comprises three or more ITAM motifs. In some embodiments the chimeric receptor intracellular domain comprises four or more ITAM motifs. In some embodiments the chimeric receptor intracellular domain comprises five or more ITAM motifs. In some embodiments the chimeric receptor intracellular domain comprises six or more ITAM motifs. In some embodiments the chimeric receptor intracellular domain comprises seven or more ITAM motifs. In some embodiments the chimeric receptor intracellular domain comprises eight or more ITAM motifs. In some embodiments the chimeric receptor intracellular domain comprises nine or more ITAM motifs. In some embodiments the chimeric receptor intracellular domain comprises ten or more ITAM motifs.

Provided herein is a composition comprising a recombinant nucleic acid encoding a CFP, such as a phagocytic or tethering receptor (PR) fusion protein (PFP), comprising: a PR subunit comprising: a transmembrane domain, and an intracellular domain comprising an intracellular signaling domain; and an extracellular domain comprising an antigen binding domain specific to an antigen of a target cell; wherein the transmembrane domain and the extracellular domain are operatively linked; and wherein the intracellular signaling domain is derived from a phagocytic receptor other than a phagocytic receptor selected from Megf10, MerTk, FcRα, or Bai1. 459. In some embodiments, upon binding of the CFP to the antigen of the target cell, the killing activity of a cell expressing the CFP is increased by at least greater than 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 100%, 150%, 200%, 250%, 300%, 350%, 400%, 450%, 500%, 550%, 600%, 650%, 700%, 750%, 800%, 850%, 900%, 950%, or 1000% compared to a cell not expressing the CFP. In some embodiments, the CFP functionally incorporates into a cell membrane of a cell when the CFP is expressed in the cell. In some embodiments, upon binding of the CFP to the antigen of the target cell, the killing activity of a cell expressing the CFP is increased by at least 1.1-fold, 1.5-fold, 2-fold, 2.5-fold, 3-fold, 3.5-fold, 4-fold, 4.5-fold, 5-fold, 5.5-fold, 6-fold, 6.5-fold, 7-fold, 7.5-fold, 8-fold, 8.5-fold, 9-fold, 9.5-fold, 10-fold, 11-fold, 12-fold, 13-fold, 14-fold, 15-fold, 16-fold, -fold, 17-fold, 18-fold, 19-fold, 20-fold, 25-fold, 30-fold, 40-fold, 50-fold, 75-fold, or 100-fold compared to a cell not expressing the CFP.

In some embodiments, the intracellular signaling domain is derived from a receptor, such as a phagocytic receptor, selected from the group consisting of TNFR1, MDA5, CD40, lectin, dectin 1, CD206, scavenger receptor A1 (SRA1), MARCO, CD36, CD163, MSR1, SCARA3, COLEC12, SCARA5, SCARB1, SCARB2, CD68, OLR1, SCARF1, SCARF2, CXCL16, STAB1, STAB2, SRCRB4D, SSC5D, CD205, CD207, CD209, RAGE, CD14, CD64, F4/80, CCR2, CX3CR1, CSF1R, Tie2, HuCRIg(L), CD64, CD32a, CD16a, CD89, Fcα receptor I, CR1, CD35, CD3ζ, CR3, CR4, Tim-1, Tim-4 and CD169. In some embodiments, the intracellular signaling domain comprises a pro-inflammatory signaling domain.

Provided herein is a composition comprising a recombinant nucleic acid encoding a CFP, such as a phagocytic or tethering receptor (PR) fusion protein (PFP), comprising: a PR subunit comprising: a transmembrane domain, and an intracellular domain comprising an intracellular signaling domain; and an extracellular domain comprising an antigen binding domain specific to an antigen of a target cell; wherein the transmembrane domain and the extracellular domain are operatively linked; and wherein the intracellular signaling domain is derived from a receptor, such as a phagocytic receptor, selected from the group consisting of TNFR1, MDA5, CD40, lectin, dectin 1, CD206, scavenger receptor A1 (SRA1), MARCO, CD36, CD163, MSR1, SCARA3, COLEC12, SCARA5, SCARB1, SCARB2, CD68, OLR1, SCARF1, SCARF2, CXCL16, STAB1, STAB2, SRCRB4D, SSC5D, CD205, CD207, CD209, RAGE, CD14, CD64, F4/80, CCR2, CX3CR1, CSF1R, Tie2, HuCRIg(L), CD64, CD32a, CD16a, CD89, Fcα receptor I, CR1, CD35, CD3ζ, CR3, CR4, Tim-1, Tim-4 and CD169.

In some embodiments, upon binding of the CFP to the antigen of the target cell, the killing activity of a cell expressing the CFP is increased by at least greater than 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 100%, 150%, 200%, 250%, 300%, 350%, 400%, 450%, 500%, 550%, 600%, 650%, 700%, 750%, 800%, 850%, 900%, 950%, or 1000% compared to a cell not expressing the CFP. In some embodiments, the intracellular signaling domain is derived from a phagocytic receptor other than a phagocytic receptor selected from Megf10, MerTk, FcRα, or Bai1. In some embodiments, the intracellular signaling domain comprises a pro-inflammatory signaling domain. In some embodiments, the intracellular signaling domain comprises a PI3K recruitment domain, such as a PI3K recruitment domain derived from CD19. In some embodiments, the intracellular signaling domain comprises a pro-inflammatory signaling domain that is not a PI3K recruitment domain.

In some embodiments, a cell expressing the CFP exhibits an increase in phagocytosis of a target cell expressing the antigen compared to a cell not expressing the CFP. In some embodiments, a cell expressing the CFP exhibits at least a 1.1-fold increase in phagocytosis of a target cell expressing the antigen compared to a cell not expressing the CFP. In some embodiments, a cell expressing the CFP exhibits at least a 2-fold, 3-fold, 4-fold, 5-fold, 6-fold, 7-fold, 8-fold, 9-fold, 10-fold, 20-fold, 30-fold or 50-fold increase in phagocytosis of a target cell expressing the antigen compared to a cell not expressing the CFP. In some embodiments, a cell expressing the CFP exhibits an increase in production of a cytokine compared to a cell not expressing the CFP. In some embodiments, the cytokine is selected from the group consisting of IL-1, IL3, IL-6, IL-12, IL-13, IL-23, TNF, CCL2, CXCL9, CXCL10, CXCL11, IL-18, IL-23, IL-27, CSF, MCSF, GMCSF, IL17, IP-10, RANTES, an interferon and combinations thereof. In some embodiments, a cell expressing the CFP exhibits an increase in effector activity compared to a cell not expressing the CFP. In some embodiments, a cell expressing the CFP exhibits an increase in cross-presentation compared to a cell not expressing the CFP. In some embodiments, a cell expressing the CFP exhibits an increase in expression of an MHC class II protein compared to a cell not expressing the CFP. In some embodiments, a cell expressing the CFP exhibits an increase in expression of CD80 compared to a cell not expressing the CFP. In some embodiments, a cell expressing the CFP exhibits an increase in expression of CD86 compared to a cell not expressing the CFP. In some embodiments, a cell expressing the CFP exhibits an increase in expression of MHC class I protein compared to a cell not expressing the CFP. In some embodiments, a cell expressing the CFP exhibits an increase in expression of TRAIL/TNF Family death receptors compared to a cell not expressing the CFP. In some embodiments, a cell expressing the CFP exhibits an increase in expression of B7-H2 compared to a cell not expressing the CFP. In some embodiments, a cell expressing the CFP exhibits an increase in expression of LIGHT compared to a cell not expressing the CFP. In some embodiments, a cell expressing the CFP exhibits an increase in expression of HVEM compared to a cell not expressing the CFP. In some embodiments, a cell expressing the CFP exhibits an increase in expression of CD40 compared to a cell not expressing the CFP. In some embodiments, a cell expressing the CFP exhibits an increase in expression of TL1A compared to a cell not expressing the CFP. In some embodiments, a cell expressing the CFP exhibits an increase in expression of 41BBL compared to a cell not expressing the CFP. In some embodiments, a cell expressing the CFP exhibits an increase in expression of OX40L compared to a cell not expressing the CFP. In some embodiments, a cell expressing the CFP exhibits an increase in expression of GITRL death receptors compared to a cell not expressing the CFP. In some embodiments, a cell expressing the CFP exhibits an increase in expression of CD30L compared to a cell not expressing the CFP. In some embodiments, a cell expressing the CFP exhibits an increase in expression of TIM4 compared to a cell not expressing the CFP. In some embodiments, a cell expressing the CFP exhibits an increase in expression of TIM1 ligand compared to a cell not expressing the CFP. In some embodiments, a cell expressing the CFP exhibits an increase in expression of SLAM compared to a cell not expressing the CFP. In some embodiments, a cell expressing the CFP exhibits an increase in expression of CD48 compared to a cell not expressing the CFP. In some embodiments, a cell expressing the CFP exhibits an increase in expression of CD58 compared to a cell not expressing the CFP. In some embodiments, a cell expressing the CFP exhibits an increase in expression of CD155 compared to a cell not expressing the CFP. In some embodiments, a cell expressing the CFP exhibits an increase in expression of CD112 compared to a cell not expressing the CFP. In some embodiments, a cell expressing the CFP exhibits an increase in expression of PDL1 compared to a cell not expressing the CFP. In some embodiments, a cell expressing the CFP exhibits an increase in expression of B7-DC compared to a cell not expressing the CFP. In some embodiments, a cell expressing the CFP exhibits an increase in respiratory burst compared to a cell not expressing the CFP. In some embodiments, a cell expressing the CFP exhibits an increase in ROS production compared to a cell not expressing the CFP. In some embodiments, a cell expressing the CFP exhibits an increase in iNOS production compared to a cell not expressing the CFP. In some embodiments, a cell expressing the CFP exhibits an increase in iNOS production compared to a cell not expressing the CFP. In some embodiments, a cell expressing the CFP exhibits an increase in extra-cellular vesicle production compared to a cell not expressing the CFP. In some embodiments, a cell expressing the CFP exhibits an increase in trogocytosis with a target cell expressing the antigen compared to a cell not expressing the CFP. In some embodiments, a cell expressing the CFP exhibits an increase in resistance to CD47 mediated inhibition of phagocytosis compared to a cell not expressing the CFP. In some embodiments, a cell expressing the CFP exhibits an increase in resistance to LILRB1 mediated inhibition of phagocytosis compared to a cell not expressing the CFP. In some embodiments, a cell expressing the CFP exhibits an increase in phosphatidylinositol 3,4,5-trisphosphate production.

Also provided herein is a pharmaceutical composition comprising a composition described herein, such as a recombinant nucleic acid described herein, a vector described herein, a polypeptide described herein or a cell described herein; and a pharmaceutically acceptable excipient.

In some embodiments, the pharmaceutical composition further comprises an additional therapeutic agent. In some embodiments, the additional therapeutic agent is selected from the group consisting of a CD47 agonist, an agent that inhibits Rac, an agent that inhibits Cdc42, an agent that inhibits a GTPase, an agent that promotes F-actin disassembly, an agent that promotes PI3K recruitment to the PFP, an agent that promotes PI3K activity, an agent that promotes production of phosphatidylinositol 3,4,5-trisphosphate, an agent that promotes ARHGAP12 activity, an agent that promotes ARHGAP25 activity, an agent that promotes SH3BP1 activity and any combination thereof. In some embodiments, the pharmaceutically acceptable excipient comprises serum free media, a lipid, or a nanoparticle.

In some embodiments, the recombinant nucleic acid is mRNA or circRNA.

In some embodiments, provided herein is a therapeutic composition comprising a cell, the cell comprising a recombinant nucleic acid as described anywhere within the specification. In some embodiments, the therapeutic composition comprising a recombinant nucleic acid expressing a chimeric protein as described anywhere herein. In some embodiments, the myeloid cell is a CD14+ cell, a CD14+/CD16− cell, a CD14+/CD16+ cell, a CD14−/CD16+ cell, CD14−/CD16− cell, a dendritic cell, an M0 macrophage, an M2 macrophage, an M1 macrophage or a mosaic myeloid cell/macrophage/dendritic cell.

Methods for Generation of Novel Chimeric Receptors Fusion Proteins (CFP) Constructs In one aspect, provided herein is a method for generating novel chimeric receptor proteins, including, for example, identification of novel domains that can be useful in augmenting a myeloid cell function such that when the fusion receptor is expressed in a myeloid cell, it functions as an effector myeloid cell of the specifications described herein. Generation of fusion proteins as described herein can be performed using well known molecular cloning techniques, and the sequences can be verified after generating of the recombinant nucleic acid.

Preparation of Recombinant Nucleic Acid Encoding CAR: Recombinant nucleic acid constructs are prepared that encode chimeric antigen receptor (CAR) and are incorporated in plasmid vectors for amplification and/or testing expression in an eukaryotic cell. The recombinant CARs are constructed using molecular cloning techniques known in the art. A recombinant CAR protein comprises an intracellular domain, a transmembrane domain and an extracellular domain. Each domain or subsection of a domain can be encoded by a nucleic acid sequence that is generated by PCR from heterologous source sequences, and pieced together by cloning individually into the vector, or ligated into a longer nucleic acid that is then inserted into the multi-cloning sites of a suitable plasmid or vector with appropriate promoter and 3'-regulatory elements for amplification. Briefly, an exemplary CAR is prepared by incorporating a nucleic sequence encoding one or more signaling domains, (e.g., a PI3Kinase recruiting domain), a nucleic acid sequence encoding the CD8 hinge and transmembrane domain, a nucleic acid sequence encoding an extracellular domain, having a sequence encoding a target antigen binding scFv at the extracellular end. Certain constructs include a FLAG peptide sequence at the extracellular end designed such that it does not pose hindrance to the scFv binding to its target antigen. These components are ligated together into a sequence that encode a fully functional transmembrane CAR. The nucleic acid subunits encoding individual domains of the recombinant protein is designed to include intervening short flexible linker sequences between two domains. The construct is ligated in a plasmid having a promoter and 3' stabilizing structural units. In one variation, the construct is placed within an Alu retrotransposon element that encodes ORF2p and has the respective 5'- and 3'-UTR sequences, a CMV promoter. The plasmid is amplified in $E.\ coli$, validated by sequencing or stored in (−) 80° C. mRNA Preparation: mRNA can be prepared by in vitro transcription using the digested plasmid as template and purified to remove contaminant DNA and polyadenylated. The RNA product is purified, resuspended to 1 mg/ml in RNase free water and stored in cryovials.

Identification of useful CFP ECD, TM, ICD and antigen binding domains for the generation of novel CFPs can be done using the method described herein. Briefly, a large number of potential candidate proteins can be screened for enhanced phagocytic properties and their respective phagocytosis related intracellular signaling. The useful domains can be then used for generation of novel CFPs. The screen can be divided in two parts: A. Screening for the phagocytic receptor (PR) domains; B. Screening for the extracellular antigen binding domains.

Screening for the PR Domains:

In one embodiment, about 5,800 plasma membrane proteins were screened for their phagocytic potential following the general method described herein. J774 macrophage cells can be transiently transfected with the library of 5800 plasma proteins. High-throughput multiplex assays (ranging from 6-well plate assay set up to up to 384-well plate assay with robotic handling) can be set up to evaluate various potential functions of the plasma membranes. Exemplary assays include, but are not limited to phagocytosis assay, cytokine production assay, inflammasome activation assay, and iNOS activation assay. Exemplary simplified methods can be described in the following paragraphs. Variations of each method can be also used and can be understood by a skilled artisan. Variations of each method can be also used and can be understood by a skilled artisan. Exemplary intracellular signaling domains tested for include but are not limited to CD40-FcRγ; FcRγ-CD40; NLRP3; FcRγ-SH2-Procaspase; FcRγ-Myd88; FcRγ-IFN receptor; FcR-TNFR1; FcRγ-TNFR2; FcR-AIM2; FcRγ-TRIFN; FcRγ-Procaspase; TRIFC; RIG1; MDA5; TBK; CD64; CD16A; CD89; FcRε; SIRPβ; (two consecutive intracellular domains can be represented as hyphenated terms, for example, FcRγ-Myd88 refers to an intracellular domain comprising an FcRγ intracellular signaling domain as signaling domain 1; and an Myd88 intracellular signaling domain as signaling domain 2). The extracellular linker domains screened include but are not limited to CD64, CD16A, CD89, SIRPα, FcRε, CD8 hinge. The transmembrane domains tested include but are not limited to CD8, CD64, CD16A, CD89, FcRε, SIRPα, TNFR1 and CD40. MDA5 domains were also screened.

Phagocytosis Assay:

Antigen-linked silica or polysterene beads ranging in diameters 1 nm, 5 nm or 10 nm were used for a screen of macrophages. Inert beads can be coated in a supported lipid bilayer and the antigens can be ligated to the lipid bilayer. J774 macrophage cell lines can be prepare d, each cell line expressing a cloned recombinant plasma membrane protein. The recombinant plasma membrane protein may also express a fluorescent tag. The cell lines can be maintained and propagated in complete RPMI media with heat inactivated serum and antibiotics (Penicillin/Streptomycin). On the day of the assay, cells can be plated at a density of $1 \times 10^{\wedge}6$ cells/ml per well in 6 well plates or in a relative proportion in 12 or 24 well plates, and incubated for 2-6 hours. The cells can be then washed once in Phosphate Buffer Saline, and the beads can be added in serum depleted or complement depleted nutrient media. Cells can be visualized by light microscopy at 30 minutes and 2 hours after addition of the beads. Immunofluorescence reaction may be performed using tagged antibody, and fluorescent confocal microscopy is used to detect the interaction and co-localization of cellular proteins at engulfment. Confidence levels can be determined by Kruskal-Wallis test with Dunn's multiple comparison correction.

In some examples, dye loaded tumor cells can be fed to macrophage cell lines and phagocytosis is assessed by microscopy.

Cytokine Production:

Macrophage cell lines can be cultured as described above. In one assay, each J774 cell line expressing a plasma membrane protein is plated in multi-wells and challenged with antigen-linked beads and cytokine production was assayed by collecting the supernatants at 4 hours and 24 hours. Cytokines can be assayed from the supernatant by ELISA. In another fraction, cells can be collected at 4 and 24 hours after incubation with the beads and flow cytometry is performed for detection of cytokines. In each case, multiple cytokines can be assayed in a multiplex format, which can be selected from: IL-1α, IL-1β, IL-6, IL-12, IL-23, TNF-α, GMCSF, CXCL1, CXCL3, CXCL9, CXCL-10, MIP1-α and MIP-2. Macrophage inflammatory cytokine array kit (R&D Systems) is used.

Intracellular signaling pathway for inflammatory gene and cytokine activation can be identified by western blot analysis for phosphorylation of MAP kinases, JNK, Akt signaling pathway, Interferon activation pathway including phosphorylation and activation of STAT-1.

Functional Assays

Inflammasome Activation Assay:

Activation of NLRP3 inflammasome is assayed by ELISA detection of increased IL-1 production and detection caspase-1 activation by western blot, detecting cleavage of procaspase to generate the shorter caspase. In a microwell plate multiplex setting, Caspase-Glo (Promega Corporation) is used for faster readout of Caspase 1 activation.

iNOS Activation Assay:

Activation of the oxidative burst potential can be measured by iNOS activation and NO production using a fluorimetric assay NOS activity assay kit (AbCAM).

Cancer Cell Killing Assay:

Raji B cells can be used as cancer antigen presenting cells. Raji cells can be incubated with whole cell crude extract of cancer cells, and co-incubated with J774 macrophage cell lines. The macrophages can destroy the cells after 1 hour of infection, which can be detected by microscopy or detected by cell death assay.

Screening for High Affinity Antigen Binding Domains:

Cancer ligands can be subjected to screening for antibody light chain and heavy chain variable domains to generate extracellular binding domains for the CFPs. Human full length antibodies or scFv libraries can be screened. Also potential ligands can be used for immunizing llama for development of novel immunoglobulin binding domains in llama, and preparation of single domain antibodies.

Specific useful domains identified from the screens can be then reverse transcribed, and cloned into lentiviral expression vectors to generate the CFP constructs. A recombinant nucleic acid encoding a CFP can generated using one or more domains from the extracellular, TM and cytoplasmic regions of the highly phagocytic receptors generated from the screen. Briefly plasma membrane receptors showing high activators of pro-inflammatory cytokine production and inflammasome activation can be identified. Bioinformatics studies can be performed to identify functional domains including extracellular activation domains, transmembrane domains and intracellular signaling domains, for example, specific kinase activation sites, SH2 recruitment sites. These screened functional domains can be then cloned in modular constructions for generating novel CFPs. These can be candidate CFPs, and each of these chimeric construct is tested for phagocytic enhancement, production of cytokines and chemokines, and/or tumor cell killing in vitro and/or in vivo. A microparticle based phagocytosis assay was used to examine changes in phagocytosis. Briefly, streptavidin coupled fluorescent polystyrene microparticles (6 µm diameter) can be conjugated with biotinylated recombinantly expressed and purified cancer ligand. Myeloid cells expressing the novel CFP can be incubated with the ligand coated microparticles for 1-4 h and the amount of phagocytosis was analyzed and quantified using flow cytometry. Plasmid or lentiviral constructions of the designer CFPs can be then prepared and tested in macrophage cells for cancer cell lysis.

Specific Designs for Cell-Targeted CFPs

One aspect of developing recombinant nucleic acid encoding chimeric antigen receptor for delivery in vivo is rendering macrophage specific uptake, expression and function of the CFP in monocytic cells, and avoid expression in non-myeloid cells which do not have phagocytic capability. Accordingly, in one aspect, the CFP is designed such that the expression of CFP is dependent on a myeloid specific protein. As for example, contemplated herein is the concept of applying a myeloid specific promoters for expression of the CFP. The myeloid specific promoter can be encoded in a vector or otherwise in the recombinant nucleic acid, at a position upstream of and operatively linked to the sequence encoding the CFP. Certain myeloid cell-specific promoters are disclosed in the art. For example CD68S promoter is a myeloid specific promoter (Scharenberg et al., *Nat Commun* 11, 3327 (2020).)

In one aspect, the recombinant nucleic acid is mRNA. Contemplated herein are methods for myeloid specific expression that can be utilized irrespective of whether the nucleic acid is delivered as mRNA or DNA. Accordingly, in one aspect, the CFP is designed such that it leverages the presence of a myeloid endogenous protein for its own expression and functionality. In one aspect, the myeloid specific expression of the CFP is achieved through a design in which the CFP is expressed in the membrane only when it dimerizes (or multimerizes) with one monocyte specific protein. In some embodiments, the myeloid specific functionality of the CFP is achieved through a design in which the CFP is expressed on the membrane only when it dimerizes (or multimerizes) with a monocyte specific protein. FcR alpha receptors oligomerize with FcR gamma receptors for membrane expression on myeloid cells and/or function. Several Fc receptors (FcRs) are endogenously expressed in monocytes and myeloid cells. Following their crosslinking by immune complexes, FcRs play various roles such as modulation of the immune response by released cytokines or of phagocytosis. FcR alpha receptors a FcR-gamma receptors oligomerize via transmembrane domains.

In some embodiments, the CFP comprises a transmembrane domain and/or an intracellular domain from a Fc receptor, which oligomerize with an endogenous FcR.

FcRs and their cellular expression pattern is shown below in Table 3:

TABLE 3

| Receptor | Expressed in (cell type) | Oligomerization or association characteristic at the cell membrane |
| --- | --- | --- |
| FcγR1 (CD64) | Monocyte/Macrophage | FcR γ-chain dimer |
| FcγRIIA (CD32a) | Monocyte/Macrophage | no |
| FcγRIIB (CD32b) | B cells, DCs, mast cell | no |
| FcγRIIC (CD32c) | NK cells /Monocytes/ Macrophages/neutrophils | no |
| FcγRIIIA (CD16) | NK cells /Monocytes/ Macrophages | FcR γ-chain dimer |
| FcγRIIIB (CD16b) | Neutrophil, Eosinophil, Basophil | no |
| FcαR1 (CD89) | Monocyte/Macrophage/ Neutrophil/DCs/Kupfer cells | FcR γ-chain dimer |
| FcμR | Lymphocytes | no |
| FcεR1 | Basophils, Mast cells | FcR γ-chain dimer and β-chain |

Exemplary FcR domain sequences used in constructing chimeric fusion protein receptors disclosed herein are provided in Table 4.

TABLE 4

| 1a | Human CD16 TM sequence incorporated in a CFP (includes an extracellular hinge domain) GLAVSTISSFFPPGYQVSFCLVMVLLFAVDTGLYFSV (SEQ ID NO: 77) Extracellular hinge domain   GLAVSTISSFFPPGYQV (SEQ ID NO: 78) TM domain   SFCLVMVLLFAVDTGLYFSV (SEQ ID NO: 79) |
| --- | --- |
| 1b | Human CD16 Cytoplasmic domain KTNIRSSTRDWKDHKFKWRKDPQDK (SEQ ID NO: 80) |
| 2a | Human CD89 TM sequence incorporated in a CFP (includes an extracellular hinge domain) IHQDYTTQNLIRMAVAGLVLVALLAILV (SEQ ID NO: 81) Extracellular hinge domain   IHQDYTTQN (SEQ ID NO: 82) TM domain   LIRMAVAGLVLVALLAILV (SEQ ID NO: 83) |
| 2b | Human CD89 cytoplasmic domain ENWHSHTALNKEASADVAEPSWSQQMCQPGLTFARTPSVCK (SEQ ID NO: 84) |

In some embodiments, the CFP is designed to comprise a transmembrane domain derived from the transmembrane domain of protein selected from FcγR1 (CD64). In some embodiments, the CFP is designed to comprise a transmembrane domain derived from the transmembrane domain of protein selected from FcγRIIIA (CD16). In some embodiments, the CFP is designed to comprise a transmembrane domain derived from the transmembrane domain of protein selected from FcγRIIA (CD32a). In some embodiments, the CFP is designed to comprise a transmembrane domain derived from the transmembrane domain of protein selected from FcαR1 (CD89). Any of the domains in the CFP described herein can be from a suitable mammalian origin, either depending on or irrespective of the origin of any other adjoining domains. Non-human mammalian transmembrane domains are contemplated within the scope of the instant disclosure.

In some embodiments, the CFP can comprise 2, 3, 4, 5, 6, 7, 8 9, 10, 11, 12, 13, 14, 15, 16, 17 18, 19 or 20 amino acid residues from the protein from which the TMD is derived, in the extracellular domain. In some embodiments, the CFP can comprise 2, 3, 4, 5, 6, 7, 8 9, 10, 11, 12, 13, 14, 15, 16, 17 18, 19 or 20 or more amino acid residues from the protein from which the TMD is derived, in the intracellular domain.

In some embodiments, the CFP comprises an intracellular domain from the protein FcγR1 (CD64), FcγRIIIA (CD16), or FcγRIIA (CD32a) from which the TMD is derived. In some embodiments, the TMD has a sequence that is identical to the sequence of the TMD of the protein FcγR1 (CD64), FcγRIIIA (CD16), or FcγRIIA (CD32a).

Myeloid cell-specific CFP constructs are designed to comprise a transmembrane domain that dimerizes with an endogenous Fc-gamma receptor that is specifically expressed in a myeloid cell, thereby becoming functionally active as a result of dimerization.

In some embodiments, myeloid cell-specific CFP constructs comprises an FcαR1 (CD89) transmembrane domain. In some embodiments, myeloid cell-specific CFP constructs comprises a human FcαR1 (CD89) transmembrane domain. In some embodiments, myeloid cell-specific CFP constructs comprises a mouse FcαR1 (CD89) transmembrane domain. In some embodiments, myeloid cell-specific CFP constructs comprises a rodent FcαR1 (CD89) transmembrane domain. In some embodiments, myeloid cell-specific CFP constructs comprises a equine FcαR1 (CD89) transmembrane domain. In some embodiments, myeloid cell-specific CFP constructs comprises a porcine FcαR1 (CD89) transmembrane domain. In some embodiments, myeloid cell-specific CFP constructs comprises a ovine FcαR1 (CD89) transmembrane domain. In some embodiments, the CD89 TMD is at least 80% homologous to a human or a mouse CD89 TMD. In some embodiments, the CD89 TMD is at least 85% homologous to a human or a mouse CD89 TMD. In some embodiments, CD89 TMD is at least 90% homologous to a human or a mouse CD89 TMD. In some embodiments, CD89 TMD is at least 95% homologous to a human or a mouse CD89 TMD.

In some embodiments, myeloid cell-specific CFP constructs comprises an FcγRIII (CD16) transmembrane domain. In some embodiments, myeloid cell-specific CFP constructs comprises a human FcγRIII (CD16) transmembrane domain. In some embodiments, myeloid cell-specific CFP constructs comprises a mouse FcγRIII (CD16) transmembrane domain. In some embodiments, myeloid cell-specific CFP constructs comprises a rodent FcγRIII (CD16) transmembrane domain. In some embodiments, myeloid cell-specific CFP constructs comprises a equine FcγRIII (CD16) transmembrane domain. In some embodiments, myeloid cell-specific CFP constructs comprises a porcine FcγRIII (CD16) transmembrane domain. In some embodiments, myeloid cell-specific CFP constructs comprises a ovine FcγRIII (CD16) transmembrane domain. In some embodiments, the CD16 TMD is at least 80% homologous to a human or a mouse CD16 TMD. In some embodiments, the CD16TMD is at least 85% homologous to a human or a mouse CD16 TMD. In some embodiments, CD16 TMD is at least 90% homologous to a human or a mouse CD16 TMD. In some embodiments, CD16 TMD is at least 95% homologous to a human or a mouse CD16 TMD. In one embodiment, the FcγRIII is FcγRIIIA (CD16a).

It is contemplated herein that any myeloid cell specific CFP can be designed or generated using a TMD from a CD89 molecule, a CD16 molecule, a CD64 molecule or a CD32a molecule, and a myeloid cell specific CFP having the desired antigen binding domain can be created based on the compositions and methods described in the instant disclosure. In some embodiments, the CFP exhibits myeloid cell-specific expression. In some embodiments, the myeloid cell-specific expression is an Fc-gamma dependent expression, that is, if the cell that comprises the nucleic acid comprising the CFP construct expresses an Fc-gamma endogenously, the CFP will co-express in the cell. In some embodiments, the CFP, even though it expresses in a cell other than a myeloid cell, does so only transiently, and may not be detectable. In some embodiments, only a myeloid cell expresses a functional CFP in an Fc-gamma dependent manner, that is, the CFP is not functional in a cell that does not express Fc-gamma endogenously. In some embodiments, the myeloid cell specific CFP comprises an antigen binding domain that binds to a cancer cell-specific target antigen, and an intracellular region comprising 1, 2, 3 or more domain, e.g., intracellular cell signaling domain, for example, a PI3 kinase recruitment domain. For example, the myeloid cell specific CFP comprises an antigen binding domain that binds to a CD5 target antigen. The respective CFP is designed herein comprising: an extracellular domain comprising an anti-CD5 antibody or a part thereof, e.g., an anti-CD5 ScFv, a hinge domain, e.g. a CD8 hinge domain, a transmembrane domain capable of dimerizing with an Fc-gamma receptor endogenously expressed by a myeloid cell and an intracellular region comprising 1, 2, 3 or more domain, e.g., intracellular cell signaling domain including, for example, a CD40 intracellular signaling domain, and/or a PI3kinase recruitment domain.

In some embodiments, provided herein is a TROP2 binding CFP (TROP2 binder), that comprises an extracellular TROP2 binding domain, optionally a short hinge region, e.g., comprising a CD8 hinge domain, a CD89 transmembrane domain, optionally a CD89 intracellular region, fused to one or more intracellular signaling domains, such as CD40 intracellular domain and a PI3 kinase recruitment domain. In some embodiments, provided herein is a TROP2 binding CFP (TROP2 binder), that comprises an extracellular TROP2 binding domain, optionally a short hinge region, e.g., comprising a CD8 hinge domain, a CD16 transmembrane domain, optionally a CD16 intracellular region, fused to one or more intracellular signaling domains, such as CD40 intracellular domain and a PI3-kinase recruitment domain. The TROP2 CFP can comprise one or more human or humanized domains. Provided herein is a polynucleotide, e.g. an mRNA or a DNA, comprising a sequence encoding the TROP2 CFP construct, comprising the anti-TROP2 ScFv (TROP2 antigen binder) fused to a CD8 hinge domain, that is operably linked to a CD16 or CD89 transmembrane domain, and an intracellular domain. In some embodiments, the TROP2 CFP described herein shows myeloid cell specific expression. In some embodiments, the TROP2 CFP described herein shows Fc-gamma dependent expression. In some embodiments, the TROP2 CFP described herein exhibits undetectable expression in a T cell, a B cell, an epithelial cell, a muscle cell, a neuronal cell or any non-myeloid cell, when the polynucleotide is administered in vivo. In one embodiment, the TROP2 binder having a CD16, CD89 or a CD64 transmembrane domain as described herein, encoded by the polynucleotide described herein expresses predominantly in a CD14+ cell when the polynucleotide is administered in vivo. In one embodiment, the TROP2 binder having a CD16, CD89 or a CD64 transmembrane domain, encoded by the polynucleotide described herein expresses only in a CD14+ cell when the polynucleotide is administered in vivo.

In some embodiments, provided herein is a GPC3 binding CFP (GPC3 binder), that comprises an extracellular GPC3 binding domain, optionally a short hinge region, e.g., comprising a CD8 hinge domain, a CD89 transmembrane domain, optionally a CD89 intracellular region, fused to one or more intracellular signaling domains, such as CD40 intracellular domain and a PI3-kinase recruitment domain. In some embodiments, provided herein is a GPC3 binding CFP (GPC3 binder), that comprises an extracellular GPC3 binding domain, optionally a short hinge region, e.g., comprising a CD8 hinge domain, a CD16 transmembrane domain, optionally a CD16 intracellular region, fused to one or more intracellular signaling domains, such as CD40 intracellular domain and a PI3-kinase recruitment domain. The GPC3 CFP can comprise one or more human or humanized domains. In some embodiments, the GPC3-CFP comprises further comprising an interferon inducing intracellular domain.

Provided herein is a polynucleotide, e.g. an mRNA or a DNA, comprising a sequence encoding the GPC3 CFP construct, comprising the anti-GPC3 ScFv (GPC3 antigen binder) fused to a CD8 hinge domain, that is operably linked to a CD16 or CD89 transmembrane domain, and an intracellular domain. In some embodiments, the GPC3 CFP described herein shows myeloid cell specific expression. In some embodiments, the GPC3 CFP described herein shows Fc-gamma dependent expression. In some embodiments, the GPC3 CFP described herein exhibits undetectable expression in a T cell, a B cell, an epithelial cell, a muscle cell, a neuronal cell or any non-myeloid cell, when the polynucleotide is administered in vivo. In one embodiment, the GPC3 binder having a CD16, CD89 or a CD64 transmembrane domain as described herein, encoded by the polynucleotide described herein expresses predominantly in a CD14+ cell when the polynucleotide is administered in vivo. In one embodiment, the GPC3 binder having a CD16, CD89 or a CD64 transmembrane domain, encoded by the polynucleotide described herein expresses only in a CD14+ cell when the polynucleotide is administered in vivo. In some embodiments, the GPC3 CFP further comprising an interferon inducing intracellular domain.

Provided herein is a pharmaceutical composition comprising In some embodiments, the GPC3 binder of the specifications described herein is used to treat a cancer in a human subject. In some embodiments, the GPC3 binder is used for treatment of hepatocellular carcinoma (HCC).

In some embodiments, provided herein is a GP75 binding CFP (GP75 binder), that comprises an extracellular GP75 binding domain, optionally a short hinge region, e.g., comprising a CD8 hinge domain, a CD89 transmembrane domain, optionally a CD89 intracellular region, fused to one or more intracellular signaling domains, such as CD40 intracellular domain and a PI3-kinase recruitment domain. In some embodiments, provided herein is a GP75 binding CFP (GP75 binder), that comprises an extracellular GP75 binding domain, optionally a short hinge region, e.g., comprising a CD8 hinge domain, a CD16 transmembrane domain, optionally a CD16 intracellular region, fused to one or more intracellular signaling domains, such as CD40 intracellular domain and a PI3-kinase recruitment domain. The GP75 CFP can comprise one or more human or humanized domains. Provided herein is a polynucleotide, e.g. an mRNA or a DNA, comprising a sequence encoding the GP75 CFP construct, comprising the anti-GP75 ScFv (GP75 antigen binder) fused to a CD8 hinge domain, that is operably linked to a CD16 or CD89 transmembrane domain, and an intracellular domain. In some embodiments, the GP75 CFP described herein shows myeloid cell specific expression. In some embodiments, the GP75 CFP described herein shows Fc-gamma dependent expression. In some embodiments, the GP75 CFP described herein exhibits undetectable expression in a T cell, a B cell, an epithelial cell, a muscle cell, a neuronal cell or any non-myeloid cell, when the polynucleotide is administered in vivo. In one embodiment, the GP75 binder having a CD16, CD89 or a CD64 transmembrane domain as described herein, encoded by the polynucleotide described herein expresses predominantly in a CD14+ cell when the polynucleotide is administered in vivo. In one embodiment, the GP75 binder having a CD16, CD89 or a CD64 transmembrane domain, encoded by the polynucleotide described herein expresses only in a CD14+ cell when the polynucleotide is administered in vivo.

In some embodiments, any one of the CFP constructs described in this section comprises at least a CD40 intracellular signaling domain. In some embodiments, any one of the CFP constructs described in this section comprises at least a PI3-kinase recruitment and signaling domain. In some embodiments, any one of the CFP constructs described in this section comprises at least a CD40 intracellular signaling domain and a PI3-kinase recruitment domain. In some embodiments, a myeloid cell-specific CFP constructs described in this section comprises at least three intracellular domains, comprising, e.g., a CD40 intracellular signaling domain and a PI3-kinase recruitment domain and a third intracellular signaling domain. In some embodiments, any one of the CFP constructs described in this section comprises at least one intracellular domain that induces NF-kappa B activation upon receptor activation. In some embodiments, any one of the CFP constructs described in this section comprises at least one intracellular domain that stimulates interferon production upon receptor activation. In some embodiments, any one of the CFP constructs described in this section comprises at least one intracellular domain that induces NF-kappa B activation and comprises at least one intracellular domain that stimulates interferon production upon receptor activation.

Method of Manufacturing Myeloid Cells from a Subject
Myeloid Cell Isolation from PBMCs:

Peripheral blood mononuclear cells can be separated from normal donor buffy coats by density centrifugation using Histopaque 1077 (Sigma). After washing, CD14+ monocytes can be isolated from the mononuclear cell fraction using CliniMACS GMP grade CD14 microbeads and LS separation magnetic columns (Miltenyi Biotec). Briefly, cells can be resuspended to appropriate concentration in PEA buffer (phosphate-buffered saline [PBS] plus 2.5 mmol/L ethylenediaminetetraacetic acid [EDTA] and human serum albumin [0.5% final volume of Alburex 20%, Octopharma]), incubated with CliniMACS CD14 beads per manufacturer's instructions, then washed and passed through a magnetized LS column. After washing, the purified monocytes can be eluted from the demagnetized column, washed and re-suspended in relevant medium for culture. Isolation of CD14+ cells from leukapheresis: PBMCs can be collected by leukapheresis from cirrhotic donors who gave informed consent to participate in the study. Leukapheresis of peripheral blood for mononuclear cells (MNCs) is carried out using an Optia apheresis system by sterile collection. A standard collection program for MNC is used, processing 2.5 blood volumes. Isolation of CD14 cells is carried out using a GMP-compliant functionally closed system (CliniMACS Prodigy system, Miltenyi Biotec). Briefly, the leukapheresis product is sampled for cell count and an aliquot taken for pre-separation flow cytometry. The percentage of monocytes (CD14+) and absolute cell number can be determined, and, if required, the volume is adjusted to meet the required criteria for selection ($\leq 20\times10^9$ total white blood cells; $<400\times10^6$ white blood cells/mL; $\leq 3.5\times10^9$ CD14 cells, volume 50-300 mL). CD14 cell isolation and separation is carried out using the CliniMACS Prodigy with CliniMACS CD14 microbeads (medical device class III), TS510 tubing set and LP-14 program. At the end of the process, the selected CD14+ positive monocytes can be washed in PBS/EDTA buffer (CliniMACS buffer, Miltenyi) containing pharmaceutical grade 0.5% human albumin (Alburex), then re-suspended in TexMACS (or comparator) medium for culture.

Cell Count and Purity:

Cell counts of total MNCs and isolated monocyte fractions can be performed using a Sysmex XP-300 automated analyzer (Sysmex). Assessment of macrophage numbers is carried out by flow cytometry with TruCount tubes (Becton Dickinson) to determine absolute cell number, as the Sysmex consistently underestimated the number of monocytes. The purity of the separation is assessed using flow cytometry (FACSCanto II, BD Biosciences) with a panel of antibodies against human leukocytes (CD45-VioBlue, CD15-FITC, CD14-PE, CD16-APC), and product quality is assessed by determining the amount of neutrophil contamination (CD45int, CD15pos).

Cell Culture—Development of Cultures with Healthy Donor Samples

Optimal culture medium for macrophage differentiation is investigated, and three candidates can be tested using for the cell product. In addition, the effect of monocyte cryopreservation on deriving myeloid cells and macrophages for therapeutic use is examined. Functional assays can be conducted to quantify the phagocytic capacity of myeloid cells and macrophages and their capacity for further polarization, and phagocytic potential as described elsewhere in the disclosure.

Full-Scale Process Validation with Subject Samples

Monocytes cultured from leukapheresis from Prodigy isolation can be cultured at $2\times10^6$ monocytes per cm$^2$ and per mL in culture bags (MACS GMP differentiation bags, Miltenyi) with GMP-grade TexMACS (Miltenyi) and 100 ng/mL M-CSF. Monocytes can be cultured with 100 ng/mL GMP-compliant recombinant human M-CSF (R&D Systems). Cells can be cultured in a humidified atmosphere at 37° C., with 5% CO$_2$ for 7 days. A 50% volume media replenishment is carried out twice during culture (days 2 and 4) with 50% of the culture medium removed, then fed with fresh medium supplemented with 200 ng/mL M-CSF (to restore a final concentration of 100 ng/mL).

Cell Harvesting:

For normal donor-derived macrophages, cells can be removed from the wells at day 7 using Cell Dissociation Buffer (Gibco, Thermo Fisher) and a pastette. Cells can be resuspended in PEA buffer and counted, then approximately $1\times10^6$ cells per test can be stained for flow cytometry. Leukapheresis-derived macrophages can be removed from the culture bags at day 7 using PBS/EDTA buffer (CliniMACS buffer, Miltenyi) containing pharmaceutical grade 0.5% human albumin from serum (HAS; Alburex). Harvested cells can be resuspended in excipient composed of two licensed products: 0.9% saline for infusion (Baxter) with 0.5% human albumin (Alburex).

Flow Cytometry Characterization:

Monocyte and macrophage cell surface marker expression can be analyzed using either a FACSCanto II (BD Biosciences) or MACSQuant 10 (Miltenyi) flow cytometer. Typically, approximately 20,000 events can be acquired for each sample. Cell surface expression of leukocyte markers in freshly isolated and day 7 matured cells is carried out by incubating cells with specific antibodies (final dilution 1:100). Cells are incubated for 5 min with FcR block (Miltenyi) then incubated at 4° C. for 20 min with antibody cocktails. Cells can be washed in PEA, and dead cell exclusion dye DRAQ7 (BioLegend) is added at 1:100. Cells can be stained for a range of surface markers as follows: CD45-VioBlue, CD14-PE or CD14-PerCP-Vio700, CD163-FITC, CD169-PE and CD16-APC (all Miltenyi), CCR2-BV421, CD206-FITC, CXCR4-PE and CD115-APC (all BioLegend), and 25F9-APC and CD115-APC (eBioscience). Both monocytes and macrophages can be gated to exclude debris, doublets and dead cells using forward and side scatter and DRAQ7 dead cell discriminator (BioLegend) and analyzed using FlowJo softwcan be (Tree Star). From the initial detailed phenotyping, a panel is developed as Release Criteria (CD45-VB/CD206-FITC/CD14-PE/25F9 APC/DRAQ7) that defined the development of a functional macrophage from monocytes. Macrophages can be determined as having mean fluorescence intensity (MFI) five times higher than the level on day 0 monocytes for both 25F9 and CD206. A second panel is developed which assessed other markers as part of an Extended Panel, composed of CCR2-BV421/CD163-FITC/CD169-PE/CD14-PerCP-Vio700/CD16-APC/DRAQ7), but is not used as part of the Release Criteria for the cell product.

Monocytes and macrophages can be isolated from withdrawing a buffy coat layer formed in a sucrose gradient centrifugation sample of isolated peripheral blood cells. CD14 cells can be tested for phagocytic uptake using pHRodo beads, which fluoresce only when taken into acidic endosomes. Briefly, monocytes or macrophages can be cultured with 1-2 uL of pHRodo Escherichia coli bioparticles (Life Technologies, Thermo Fisher) for 1 h, then the medium is taken off and cells are washed to remove non-phagocytosed particles. Phagocytosis is assessed using an EVOS microscope (Thermo Fisher), images captured and cellular uptake of beads quantified using ImageJ software (NIH). The capacity to polarize toward defined differentiated macrophages is examined by treating day 7 macrophages with IFNγ (50 ng/mL) or IL-4 (20 ng/mL) for 48 h to induce polarization to M1 or M2 phenotype (or M[IFNγ] versus M[IL-4], respectively). After 48 h, the cells can be visualized by EVOS bright-field microscopy, then harvested and phenotyped as before. Further analysis is performed on the cytokine and growth factor secretion profile of macrophages after generation and in response to inflammatory stimuli. Macrophages can be generated from healthy donor buffy coats as before, and either left untreated or stimulated with TNFα (50 ng/mL, Peprotech) and polyinosinic:polycytidylic acid (poly I:C, a viral homolog which binds TLR3, 1 g/mL, Sigma) to mimic the conditions present in the inflamed liver, or lipopolysaccharide (LPS, 100 ng/mL, Sigma) plus IFNγ (50 IU/mL, Peprotech) to produce a maximal macrophage activation. Day 7 macrophages can be incubated overnight and supernatants collected and spun down to remove debris, then stored at −80° C. until testing. Secretome analysis is performed using a 27-plex human cytokine kit and a 9-plex matrix metalloprotease kit run on a Magpix multiplex enzyme linked immunoassay plate reader (BioRad).

Product Stability:

Various excipients can be tested during process development including PBS/EDTA buffer; PBS/EDTA buffer with 0.5% HAS (Alburex), 0.9% saline alone or saline with 0.5% HAS. The 0.9% saline (Baxter) with 0.5% HAS excipient is found to maintain optimal cell viability and phenotype (data not shown). The stability of the macrophages from cirrhotic donors after harvest is investigated in three process optimization runs, and a more limited range of time points assessed in the process validation runs (n=3). After harvest and re-suspension in excipient (0.9% saline for infusion, 0.5% human serum albumin), the bags can be stored at ambient temperature (21-22° C.) and samples taken at 0, 2, 4, 6, 8, 12, 24, 30 and 48 h postharvest. The release criteria antibody panel is run on each sample, and viability and mean fold change from day 0 is measured from geometric MFI of 25F9 and CD206.

Statistical Analysis:

Results can be expressed as mean±SD. The statistical significance of differences is assessed where possible with the unpaired two-tailed t-test using GraphPad Prism 6. Results can be considered statistically significant when the P value is <0.05.

Also provided herein is a cell comprising a composition described herein, a vector described herein or a polypeptide described herein. In some embodiments, the cell is a phagocytic cell. In some embodiments, the cell is a stem cell derived cell, a myeloid cell, a macrophage, a dendritic cell, a lymphocyte, a mast cell, a monocyte, a neutrophil, a microglia, or an astrocyte. In some embodiments, the cell is an autologous cell. In some embodiments, the cell is an allogeneic cell. In some embodiments, the cell is an M1 cell. In some embodiments, the cell is an M2 cell. In some embodiments, the cell is an M1 macrophage cell. In some embodiments, the cell is an M2 macrophage cell. In some embodiments, the cell is an M1 myeloid cell. In some embodiments, the cell is an M2 myeloid cell.

Also provided herein is a method of treating a disease in a subject in need thereof comprising administering to the subject a pharmaceutical composition described herein. In some embodiments, the disease is cancer. In some embodiments, the cancer is a solid cancer. In some embodiments, the solid cancer is selected from the group consisting of ovarian cancer, suitable cancers include ovarian cancer, renal cancer, breast cancer, prostate cancer, liver cancer, brain cancer, lymphoma, leukemia, skin cancer, pancreatic cancer, colorectal cancer, lung cancer. In some embodiments, the cancer is a liquid cancer. In some embodiments, the liquid cancer is leukemia or a lymphoma. In some embodiments, the liquid cancer is a T cell lymphoma. In some embodiments, the disease is a T cell malignancy. In some embodiments the cancer is NSCLC. In some embodiments, the cancer is HCC.

In some embodiments, the method further comprises administering an additional therapeutic agent to the subject. In some embodiments, the additional therapeutic agent is selected from the group consisting of a CD47 agonist, an agent that inhibits Rac, an agent that inhibits Cdc42, an agent that inhibits a GTPase, an agent that promotes F-actin disassembly, an agent that promotes PI3K recruitment to the PFP, an agent that promotes PI3K activity, an agent that promotes production of phosphatidylinositol 3,4,5-trisphosphate, an agent that promotes ARHGAP12 activity, an agent that promotes ARHGAP25 activity, an agent that promotes SH3BP1 activity and any combination thereof.

In some embodiments, administering comprises infusing or injecting. In some embodiments, administering comprises administering directly to the solid cancer. In some embodiments, administering comprises a circRNA-based delivery procedure, anon-particle encapsulated mRNA-based delivery procedure, an mRNA-based delivery procedure, viral-based delivery procedure, particle-based delivery procedure, liposome-based delivery procedure, or an exosome-based delivery procedure. In some embodiments, a CD4+ T cell response or a CD8+ T cell response is elicited in the subject.

Also provided herein is a method of preparing a cell, the method comprising contacting a cell with a composition described herein, a vector described herein or a polypeptide described herein. In some embodiments, contacting comprises transducing. In some embodiments, contacting comprises chemical transfection, electroporation, nucleofection, or viral infection or transduction.

Provided herein is a method for administering a therapeutic comprising any one of the compositions described above. In some embodiments, the therapeutic is administered via a parenteral administration route.

In some embodiments, the therapeutic is administered via intramuscular administration route. In some embodiments, the therapeutic is administered via intravenous administration route. In some embodiments, the therapeutic is administered via subcutaneous administration route.

Also provided herein is a method of preparing a pharmaceutical composition comprising the one or more recombinant nucleic acids described herein and a lipid in an aqueous composition described herein. In some embodiments, the composition comprises a vector described herein. In some embodiments, the lipid comprises forming a lipid nanoparticle.

In Vitro and In Vivo Delivery of Recombinant Nucleic Acid

In one aspect, the recombinant nucleic acid encoding a chimeric antigen receptor is encapsulated in a suitable lipid nanoparticle that in a therapeutic composition for delivery in vivo. The recombinant nucleic acid may be DNA, circRNA or mRNA. In some embodiments, naked DNA or messenger RNA (mRNA) may be used to introduce the nucleic acid inside a cell. In some embodiments, DNA or mRNA encoding the chimeric fusion protein is introduced into the phagocytic cell by lipid nanoparticle (LNP) encapsulation. The mRNA can be codon optimized. In some embodiments the mRNA may comprise one or more modified or unnatural bases such as 5'-Methylcytosine, or Pseudouridine. mRNA may be 50-10,000 bases long. In one aspect the transgene is delivered as an mRNA. The mRNA may comprise greater than about 100, 200, 300, 400, 500, 600, 700, 800, 900, 1000, 1100, 1200, 1300, 1400, 1500, 1600, 1700, 1800, 1900, 2000, 3000, 4000, 5000, 6000, 7000, 8000, 9000, 10,000 bases. In some embodiments, the mRNA may be more than 10,000 bases long. In some embodiments, the mRNA may be about 11,000 bases long. In some embodiments, the mRNA may be about 12,000 bases long.

In some embodiments, a pharmaceutical composition delivered locally or systemically in a subject comprises a messenger RNA encoding a chimeric fusion protein described herein, associated with one or more lipid components. In some embodiments, the one or more lipid components can comprise a cationic lipid. In some embodiments, the one or more lipid components may comprise a non-cationic lipid. In some embodiments, the one or more lipid components may comprise a polar lipid, and/or a non-polar lipid. In some embodiments, the one or more lipid components may comprise a neutral lipid. In some embodiments, the one or more lipid components may comprise a conjugated lipid. In some embodiments, the one or more lipid components may comprise a liposome around the mRNA. In some embodiments, the one or more lipid components may comprise a lipid nanoparticle encapsulating the mRNA.

An LNP encapsulated DNA or RNA can be used for transfecting myeloid cells, such as monocytes or macrophages, or can be administered to a subject. The LNP may be designed for targeted delivery for uptake by a myeloid cell when delivered locally or systemically to a subject. In some embodiments, the LNP may comprise one or more targeting moieties, such as an antibody or a ligand, or a biomolecule or part thereof that binds to a surface element of a myeloid cell and facilitates uptake of the mRNA encapsulated LNP by myeloid cells. In some embodiments, the LNP can be targeted to a tissue by one or more antibodies, ligands, binders, aptamers that me be associated or incorporated into the LNP.

In one embodiment, the LNP comprises one or more polymers.

In one embodiments, the LNP comprises a synthetic polymer.

In some embodiments, the LNP comprises a cationic lipid. In some embodiments, the LNP comprises a non-cationic lipid. In some embodiments the LNP comprises a neutral lipid. In some embodiments, the LNP comprises one or more PEGylated lipids. In some embodiments, the LNP is about 100 nm to about 200 nm in diameter. In some embodiments, the LNP is about 150 nm in diameter, such as 80-120 nm, 100-140 nm, 100-130 nm, 70-140 nm, 80-150 nm, or 90-180 nm in diameter. In some embodiments, the LNP is less than 100 nm, such as less than 90 nm, or less than 80 nm in diameter.

In some embodiments, the delivery vehicle is any one of the lipid vehicles as described above, e.g., freely associated lipid components with the recombinant nucleic acids, encapsulating liposomes or LNPs, and wherein the mRNA is designed for preferential expression in myeloid cells, as described elsewhere within the specification.

In some embodiments the mRNA with the delivery vehicle described anywhere in the specification is used for formulating a composition, for in vitro delivery of the mRNA encoding a CFP in a myeloid cell, such as a monocyte in a population of cells comprising a monocyte, wherein the myeloid cell comprising the mRNA encoding the CFP is formulated into a pharmaceutical composition for delivery into a mammalian subject, such as a human subject. In some embodiments, the mRNA comprises a CFP that comprises an extracellular antigen binding domain that binds to TROP2 as described in the specification. In some embodiments, the mRNA with the delivery vehicle described anywhere in the specification is used for formulating a pharmaceutical composition for delivery into a mammalian subject, such as a human subject. In some embodiments, the mRNA comprises a sequence that encodes a CFP that comprises an extracellular antigen binding domain that binds to TROP2 as described in the specification. In some embodiments, the mRNA comprising a sequence that encodes a TROP2 binding CFP and the delivery vehicle is taken up specifically by a myeloid cell in a heterogenous population of cells. In some embodiments, the mRNA comprising a sequence that encodes a TROP2 binding CFP is taken up specifically by myeloid and non-myeloid cells in a heterogenous population of cells, but is only expressed and/or functional in a myeloid cell within the heterogenous population of cells.

In some embodiments, the mRNA described above is electroporated into a cell. In some embodiments, the composition comprising the mRNA is electroporated into a cell in vitro. In some embodiments, the mRNA is associated with one or more lipid components, as described above, e.g., in an LNP. In some embodiments, the composition comprising the mRNA (comprising the one or more lipid components, for example) is electroporated into myeloid cell within a heterogenous population of cells in vitro, designed and optimized for delivery into a myeloid cell.

Modifications in CFP Designs for Functional Enhancements

In one aspect, provided herein is a composition comprising one or more recombinant nucleic acid sequences comprising: (A) a first nucleic acid sequence encoding an exogenous polypeptide; (B) a second nucleic acid sequence encoding a chimeric antigen receptor fusion protein (CFP), wherein the CFP comprises: (a) an intracellular signaling subunit comprising an intracellular signaling domain having one or more tyrosine residues that are phosphorylated upon antigen binding by the receptor; (b) a transmembrane domain, and (c) an extracellular binding domain having binding specificity for a component on the surface of a target cell, wherein the extracellular binding domain is operably linked to the transmembrane domain and the intracellular signaling subunit; and (d) a transcription activator domain operably linked to the intracellular signaling subunit by a protease cleavage sequence, wherein the transcription activator domain promotes transcription of the first nucleic acid sequence encoding the exogenous polypeptide; and (C) a third nucleic acid sequence encoding (i) a protease that cleaves the protease cleavage sequence that operably links the transcription activator domain to the intracellular signaling subunit; (ii) a domain that binds to the tyrosine residues that are phosphorylated upon activation of the CFP; wherein the protease that cleaves the protease cleavage sequence and the domain that binds to the tyrosine residues are operably linked. In some embodiments, the third nucleic acid sequence further encodes (iii) an stimulus responsive element. In some embodiments, the stimulus responsive element (iii) is fused to the domain that binds to the phosphorylated tyrosine residues. In some embodiments, the stimulus responsive element (iii) is responsive to the microenvironment of the cell that expresses the nucleic acid sequence. In some embodiments, the one or more recombinant nucleic acid is expressed in a myeloid cell.

In some embodiments, the stimulus responsive element (iii) is fused to the domain that binds to the phosphorylated tyrosine residues. In some embodiments, the stimulus responsive element is responsive to the microenvironment of the cell that expresses the nucleic acid sequence. In some embodiments, the (iii) is a degron, operably linked with (ii). In some embodiments, the degron is an HIF-1a degron.

In some embodiments, the transcription activator domain comprises a VP64 transactivation domain. In some embodiments, the protease that cleaves the protease cleavage sequence that operably links the transcription activator domain to the intracellular signaling subunit is a hepatitis C virus (HCV) NS3 protease. In some embodiments, the domain that binds to the tyrosine residues that are phosphorylated upon activation of the CFP is a phosphotyrosine binding (PTB) domain. In some embodiments, the PTB is an Shc PTB.

In some embodiments, the recombinant nucleic acid is DNA. In some embodiments, the recombinant nucleic acid is RNA. In some embodiments, the recombinant nucleic acid is mRNA. In some embodiments, the recombinant nucleic acid is a circRNA.

In some embodiments, recombinant nucleic acid is associated with a replicon RNA. Provided herein is a method for preparing a myeloid cell therapeutic against cancer, the method comprising expressing in the myeloid cell a recombinant nucleic acid comprising: (A) a first nucleic acid sequence encoding an exogenous polypeptide; (B) a second nucleic acid sequence encoding a myeloid cell chimeric antigen receptor (CFP), wherein the CFP comprises: (a) an intracellular signaling subunit comprising an intracellular signaling domain having tyrosine residues that are phosphorylated upon activation of the CFP; (b) a transmembrane domain, and (c) an extracellular binding domain having binding specificity for a component on the surface of a target cell, wherein the extracellular binding domain is operably linked to the transmembrane domain and the intracellular signaling subunit; and (d) a transcription activator domain operably linked to the intracellular signaling subunit by a protease cleavage sequence, wherein the transcription activator domain promotes transcription of the first nucleic acid sequence encoding the exogenous polypeptide; and (C) a third nucleic acid sequence encoding (i) a protease that cleaves the protease cleavage sequence that operably links the transcription activator domain to the intracellular signaling subunit; (ii) a domain that binds to the tyrosine residues that are phosphorylated upon activation of the CFP; wherein the protease that cleaves the protease cleavage sequence and the domain that binds to the tyrosine residues are operably linked.

Provided herein is a method for preparing a myeloid cell therapeutic against cancer, the method comprising expressing in the myeloid cell a recombinant nucleic acid encoding a chimeric protein comprising: (a) a human eosinophil major basic protein acidic domain; (b) an MMP recognition sequence; and (c) a human eosinophil major basic protein cytotoxic domain.

Provided herein is a method for treating a subject having a cancer, the method comprising, administering to the subject in need thereof the pharmaceutical composition of described above. Provided herein is a method for treating a subject having a cancer, the method comprising, administering to the subject in need thereof the pharmaceutical composition described herein. Provided herein is a method of inducing a tumor regression in a subject in need thereof, the method comprising administering intravenously to the subject a pharmaceutical composition comprising myeloid cells, wherein the myeloid cells express one or more recombinant nucleic acids encoding one or more polypeptides, and wherein at least one of the one or more polypeptides is functionally active in the tumor microenvironment, and not functionally active in a non-tumor environment.

Chimeric Antigenic Receptors with Modular Sensing and Internally Programmable Switches The salient objectives in designing a immunotherapeutic encompass (1) disease specificity, which comprises that the therapeutic agent will be active at the site of the disease and will act specifically on the diseased cells; (2) programmability, which comprises that the therapeutic can be which comprises that the therapeutic can be programmed or intended to execute its desired function at the time and location desired.

In one aspect, the present disclosure encompasses development of chimeric antigen receptors that can sense and utilize the disease microenvironment and turn it into generating an output function that counters the disease. In one embodiment, this is referred to as a switch function. Principally, the recombinant proteins of interest disclosed herein utilize the signal transduction within the disease system, such as in a tumor microenvironment (TME) for performing the switch. For example, the TME is rich in matrix metalloproteinase (MMP), which is used as a trigger to cleave a peptide that activates a component of the chimeric protein and enables its function. This ensures that the function of the immunotherapeutic cell is specific, and does not apply to all cells in the body, thus reducing the chances of toxicity associated with immunotherapy.

Generation of Target—specific, Programmable Chimeric Constructs for Myeloid Cell Therapeutics Provided herein is a method for making a myeloid cell for immunotherapy, where the myeloid cell expresses an exogenous recombinant nucleic acid encoding a chimeric fusion protein that is inducible in the tumor microenvironment. For example, the myeloid cell for immunotherapy comprises a recombinant nucleic acid, which expresses a chimeric receptor at least a portion of which is activated in the tumor microenvironment (TME). In some embodiments, the myeloid cell for immunotherapy comprises a recombinant nucleic acid, which encodes a proinflammatory protein, or a proapoptotic protein or a lytic protein, the expression of which is under the control of an inducible transcription activator. Under resting conditions, the transcription activator remains fused to a non-nuclear protein. Upon reaching the tumor environment, the transcription activator is released for nuclear localization and transactivation of the nucleic acid encoding encodes a proinflammatory protein, or a proapoptotic protein or a lytic protein, via cleavage from the fused protein. Such a functional outcome can be achieved by modular designing of recombinant proteins and expressing them in the myeloid cell.

In one embodiment, the cleavable transcription activator can be designed by inserting a cleavable sequence that is cleaved by a non-endogenous protease. In some embodiments, the transcriptional activator is fused to a transmembrane protein, for example a chimeric receptor (CFP). In some embodiments, the CFP comprises an ICD with one or more ITAM domains comprising one or more tyrosine residues that are activated upon receptor activation. Receptor activation it is understood to occur upon receptor engagement with the cancer cell via the extracellular binding domain. In some embodiments, an exemplary modular design of an inducible transcription activator can be achieved thus: a transcription activator domain is operably linked to the intracellular signaling subunit by a non-endogenous protease cleavage sequence; wherein the non-endogenous protease is encoded by a recombinant nucleic acid that is expressed in the same cell. The non-endogenous protease can be designed such that it is fused and operably linked to a another protein domain that binds to the tyrosine residues that are phosphorylated upon activation of the CFP for activation. The domain that binds to phosphorylated tyrosine residues is a phosphotyrosine binding domain (PTB). Upon activation of the CFP, the ITAM is phosphorylated, the PTB domain in turn can be activated by the ITAM domains and the activated PTB domain in turn can activate the protease that can cleave the transcription activator domain from the cytoplasmic end of the CFP, thereby releasing the transcription activator for nuclear localization.

Figure 2B:
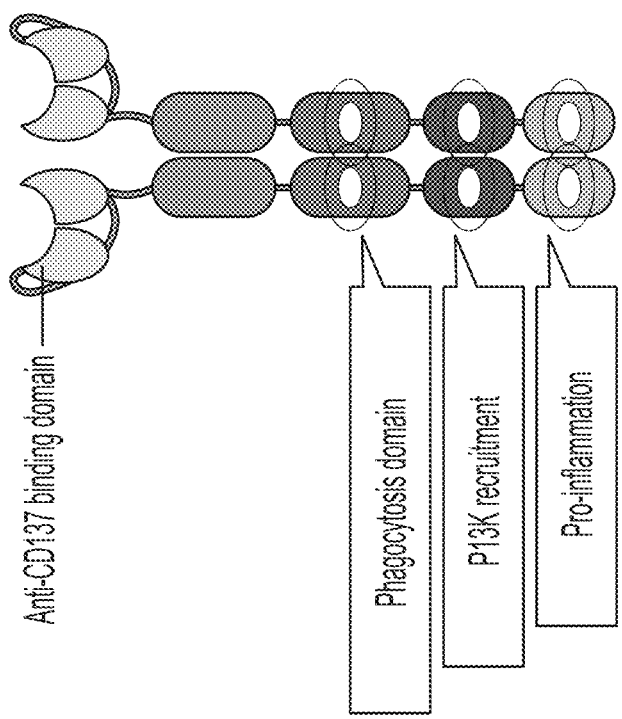
FIG. 2B depicts a schematic showing an exemplary CFP dimer containing an extracellular an anti-CD137 antigen binding domain, a transmembrane domain, and an intracellular signaling domain containing a phagocytosis domain a PI3K recruitment domain and a pro-inflammation domain.
Figure 2A:
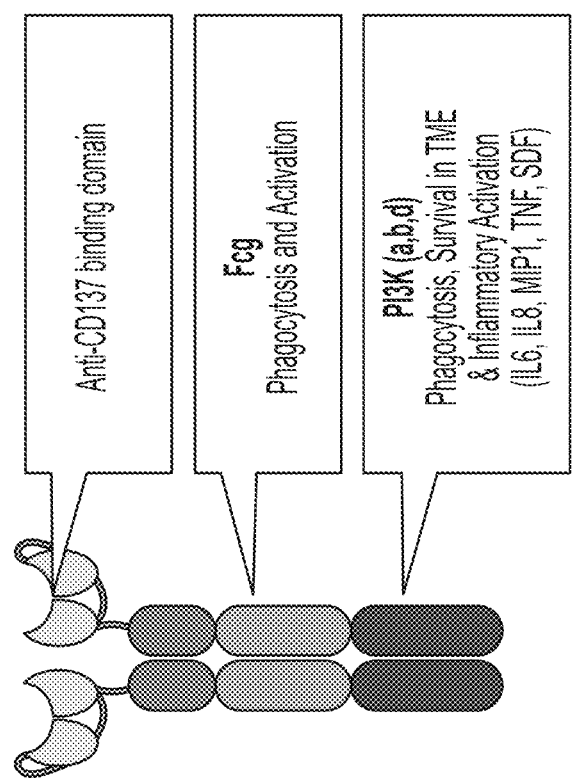
FIG. 2A depicts a schematic showing an exemplary CFP dimer containing an anti-CD137 extracellular binding domain, a transmembrane domain, and an intracellular signaling domain containing an intracellular domain derived from FcRγ fused to a PI3K recruitment domain.
Figure 3:
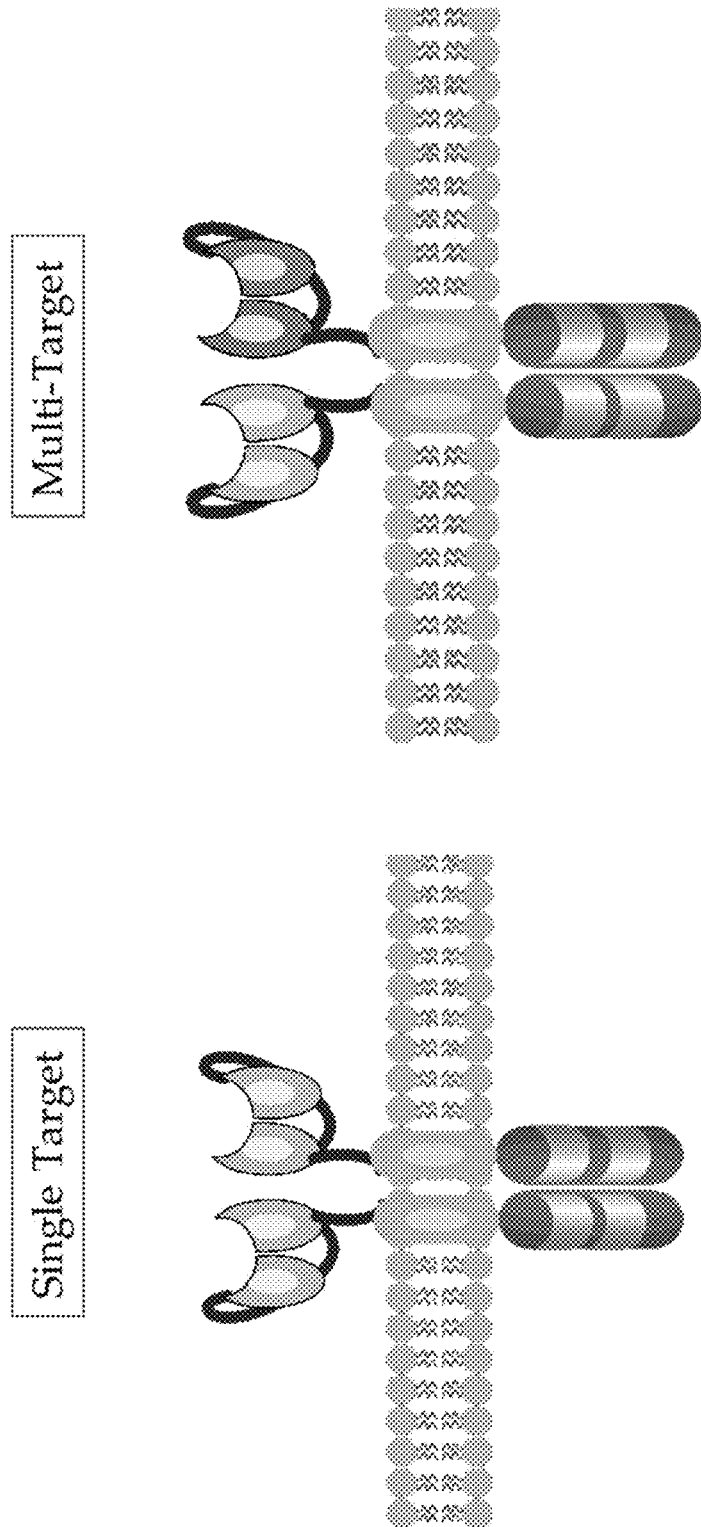
FIG. 3 is a schematic depicting an exemplary CFP homodimer in which each subunit contains an extracellular domain fused to an scFv that binds to a single target (left), and an exemplary CFP heterodimer in which a first subunit of the heterodimer contains an extracellular domain fused to an scFv that binds to a first target and in which a second subunit of the heterodimer subunit contains an extracellular domain fused to an scFv that binds to a second target (right).

In addition, the protease-PTB fusion protein can be fused to a degron, which initiates degradation of the PTB and the protease in an inactive state. In one embodiment, the degron is an HIF 1-alpha (HIF 1-a) degron sequence, which is naturally degraded under normoxic conditions. Therefore, the PTB-protease will be degraded in a cell that is under normoxic condition, that is in circulation or in a normal (non-tumor) tissue. On the other hand, when the cell expressing the proteins is in a hypoxic tissue environment, the PTB-protease no longer is degraded, and finds the cognate phosphorylated residues that are in an activated CFP intracellular sequence. Moreover, upon binding of the degron-PTB complex to the intracellular phosphotyrosine residue in the CFP-ICD, the degron is inactivated by contact with a portion of the ICD (see FIG. 2B). Thus, a recombinant protein can be designed as follows: the recombinant protein comprises (i) a CFP, comprising an extracellular domain that binds to a component on the surface of a cancer cell or a tumor cell and the binding activates the receptor (CFP), wherein the CFP comprises a transmembrane and an intracellular domain (ICD), the ICD comprising ITAM domains that are activated and phosphorylated upon receptor activation; (ii) a degron-PTB-protease complex that may optionally be encoded by the same vector encoding the recombinant nucleic acid, and generates a pre-protein with the degron-PTB-protease flanked with a T2A auto-cleavable sequence; (iii) a transcription activator operably linked to the intracellular domain of the CFP by a cleavable sequence, which is a substrate of the protease. In addition, the myeloid cell co-expresses a nucleic acid under the influence of a promoter or transcriptional activator that is responsive to the transcriptional activator that is operably linked to the intracellular domain of the CFP by a cleavable sequence. Upon activation of the CFP via engagement with the cancer cell, the ITAM in the ICD is phosphorylated, the activated ITAM domain facilitates binding of the PTB and its activation, at the same time, the binding inactivates the degron, which otherwise degrades the free (not bound to the phosphotyrosine residues in the ITAM, inactive) degron-PTB-protease. The activated PTB activates the protease and stabilizes (in absence of the degron activity) which is turn cleaves the transcription activator for nuclear localization.

Exemplary proteases which can be used in the first fusion protein include hepatitis C virus proteases (e.g., NS3 and NS2-3); signal peptidase; proprotein convertases of the subtilisin/kexin family (furin, PC1, PC2, PC4, PACE4, PCS, PC); proprotein convertases cleaving at hydrophobic residues (e.g., Leu, Phe, Val, or Met); proprotein convertases cleaving at small amino acid residues such as Ala or Thr; proopiomelanocortin converting enzyme (PCE); chromaffin granule aspartic protease (CGAP); prohormone thiol protease; carboxypeptidases (e.g., carboxypeptidase E/H, carboxypeptidase D and carboxypeptidase Z); aminopeptidases (e.g., arginine aminopeptidase, lysine aminopeptidase, aminopeptidase B); prolyl endopeptidase; aminopeptidase N; insulin degrading enzyme; calpain; high molecular weight protease; and, caspases 1, 2, 3, 4, 5, 6, 7, 8, and 9. Other proteases include, but are not limited to, aminopeptidase N; puromycin sensitive aminopeptidase; angiotensin converting enzyme; pyroglutamyl peptidase II; dipeptidyl peptidase IV; N-arginine dibasic convertase; endopeptidase 24.15; endopeptidase 24.16; amyloid precursor protein secretases alpha, beta and gamma; angiotensin converting enzyme secretase; TGF alpha secretase; TNF alpha secretase; FAS ligand secretase; TNF receptor-I and -II secretases; CD30 secretase; KL1 and KL2 secretases; IL6 receptor secretase; CD43, CD44 secretase; CD16-I and CD16-II secretases; L-selectin secretase; Folate receptor secretase; MMP 1, 2, 3, 7, 8, 9, 10, 11, 12, 13, 14, and 15; urokinase plasminogen activator; tissue plasminogen activator; plasmin; thrombin; BMP-1 (procollagen C-peptidase); ADAM 1, 2, 3, 4, 5, 6, 7, 8, 9, 10, and 11; and, granzymes A, B, C, D, E, F, G, and H.

In some embodiments the protease is Hepatitis C virus (HCV) nonstructural protein 3 protease NS3. In some embodiments the NS3 cleavable sequence is EDVVCC (SEQ ID NO: 36). In some embodiments, the NS3 cleavable sequence is DEMEEC (SEQ ID NO: 37).

In some embodiments, the transcription activator comprises a DNA binding domain. In some embodiments, the DNA binding domain is GAL4 domain. In some embodiments, the DNA binding domain is that of ZFHD1 or tetR. In some embodiments the transcriptional activator comprises the VP64 transactivation domain (a tetrameric repeat of the minimal activation domain (amino acids 437-447) of the herpes simplex protein VP16).

In some embodiments the degron is a HIF-degron.

In some embodiments, provided herein are one or more recombinant nucleic acid comprising: (A) a first nucleic acid sequence encoding an exogenous polypeptide; (B) a second nucleic acid sequence encoding a chimeric antigen receptor (CFP), wherein the CFP comprises: (a) an intracellular signaling subunit comprising an intracellular signaling domain having tyrosine residues that are phosphorylated upon activation of the CFP; (b) a transmembrane domain, and (c) an extracellular binding domain having binding specificity for a component on the surface of a target cell, wherein the extracellular binding domain is operably linked to the transmembrane domain and the intracellular signaling subunit; and (d) a transcription activator domain operably linked to the intracellular signaling subunit by a protease cleavage sequence, wherein the transcription activator domain promotes transcription of the first nucleic acid sequence encoding the exogenous polypeptide; and (C) a third nucleic acid sequence encoding (i) a protease that cleaves the protease cleavage sequence that operably links the transcription activator domain to the intracellular signaling subunit; (ii) a domain that binds to the tyrosine residues that are phosphorylated upon activation of the CFP; wherein the protease that cleaves the protease cleavage sequence and the domain that binds to the tyrosine residues are operably linked.

In some embodiments, provided herein is a recombinant nucleic acid for a modular polypeptide that can be expressed in a myeloid cell for use in immunotherapy. The recombinant nucleic acid encodes a chimeric protein comprising: (a) a cytotoxic polypeptide; (b) a protease cleavage sequence; and (c) an inhibitory polypeptide domain, wherein the inhibitory polypeptide domain inhibits the cytotoxic polypeptide; wherein the cytotoxic polypeptide, protease cleavage sequence and the inhibitory polypeptide domain are operably linked. In some embodiments, the cytotoxic polypeptide is a human eosinophil major basic protein cytotoxic domain. In some embodiments, the cytotoxic polypeptide is a human eosinophil major basic protein acidic domain. In some embodiments, the protease cleavage sequence is an MMP recognition sequence. In some embodiments, protease cleavage sequence is cleaved by MMP.

In some embodiments one or more domains in the first phagocytic ICD comprises a mutation.

In some embodiments one or more domains in the second ICD comprises a mutation to enhance a kinase binding domain, to generate a phosphorylation site, to generate an SH2 docking site or a combination thereof Co-Expression of an Inflammatory Gene In one aspect, the recombinant nucleic acid comprises a coding sequence for a pro-inflammatory gene, which is co-expressed with the chimeric receptor in the engineered cell. In some embodiments, the pro-inflammatory gene is a cytokine. Examples include but not limited to TNF-α, IL-1α, IL-1β, IL-6, CSF, GMCSF, or IL-12 or interferons.

The recombinant nucleic acid encoding the proinflammatory gene can be monocistronic, wherein the two coding sequences for (a) the CFP and (b) the proinflammatory gene are post-transcriptionally or post-translationally cleaved for independent expression.

In some embodiments, the two coding sequences comprise a self-cleavage domain, encoding a P2A sequence, for example.

In some embodiments the two coding regions are separated by an IRES site.

In some embodiments the two coding sequences are encoded by a bicistronic genetic element. The coding regions for (a) the CFP and (b) the proinflammatory gene can be unidirectional, where each is under a separate regulatory control. In some embodiments the coding regions for both are bidirectional and drive in opposite directions. Each coding sequence is under a separate regulatory control.

Coexpression of the proinflammatory gene is designed to confer strong inflammatory stimulation of the macrophage and activate the surrounding tissue for inflammation.

Chimeric Antigen Receptors for Enhancing Intracellular Signaling and Inflammation Activation In one aspect, the recombinant nucleic acid encodes a chimeric intracellular domain in addition to the extracellular binding domain, the transmembrane domain, and in some cases, part of or an entire intracellular domain of the receptor. The intracellular domain is designed with the capability of potent pro-inflammatory immune activation, such as, when macrophages engage in fighting infection. The chimeric intracellular domain (or the second ICD, as the case may be) is fused to the cytoplasmic terminus of the chimeric receptor, such that the ICD is operably linked to the extracellular domain, and activation of the extracellular domain can activate the fused ICD. This ICD provides a second signal which is necessary to trigger pro-inflammatory signals. In one embodiment, a proinflammatory signal is a signal for activation of inflammasome. Nod-like receptors (NLRs) are a subset of receptors that form components of the inflammasome pathway. These receptors are activated in innate immune response, and oligomerize to form multi-protein complexes that serve as platforms to recruit proinflammatory caspases and induce their cleavage and activation. This leads to direct activation of ROS, and often result in a violent cell death known as pyroptosis. There are four inflammasome complexes, NLRP1m, NLRP3, IPAF and AIM2. The tumor microenvironment (TME) constitutes an immunosuppressive environment.

Influence of IL-10, glucocorticoid hormones, apoptotic cells, and immune complexes can interfere with innate immune cell function. Immune cells, including phagocytic cells settle into a tolerogenic phenotype. In macrophages, this phenotype, commonly known as the M2 phenotype is distinct from the M1 phenotype, where the macrophages are potent and capable of killing pathogens. Macrophages exposed to LPS or IFN-gamma, for example, can polarize towards an M1 phenotype, whereas macrophages exposed to IL-4 or IL-13 will polarize towards an M2 phenotype. LPS or IFN-gamma can interact with Toll-like receptor 4 (TLR4) on the surface of macrophages inducing the Trif and MyD88 pathways, inducing the activation of transcription factors IRF3, AP-1, and NFKB and thus activating TNFs genes, interferon genes, CXCL10, NOS2, IL-12, etc., which are necessary in a pro-inflammatory M1 macrophage response. Similarly, IL-4 and IL-13 bind to IL-4R, activation the Jak/Stat6 pathway, which regulates the expression of CCL17, ARG1, IRF4, IL-10, SOCS3, etc., which are genes associated with an anti-inflammatory response (M2 response). Expression of CD14, CD80, D206 and low expression of CD163 are indicators of macrophage polarization towards the M1 phenotype.

In some embodiments, the recombinant nucleic acid encodes one or more additional intracellular domains, comprising a cytoplasmic domain for inflammatory response. In some embodiments, expression of the recombinant nucleic acid encoding the chimeric receptor fusion protein comprising the cytoplasmic domain for inflammatory response in the engineered macrophages confers potent pro-inflammatory response similar to the M1 phenotype.

In some embodiments, the cytoplasmic domain for inflammatory response can be the signal transducing domains or regions of TLR3, 4, 9, MYD88, TRIF, RIG-1, MDA5, CD40, IFN receptor, NLRP-1-14, NOD1, NOD2, Pyrin, AIM2, NLRC4, CD40.

In some embodiments, the expression of the recombinant nucleic acid encoding the chimeric receptor fusion protein comprises a pro-inflammatory cytoplasmic domain for activation of IL-1 signaling cascade.

In some embodiments, the cytoplasmic portion of the chimeric receptor comprises a cytoplasmic domain from a toll-like receptor, such as the intracellular signaling domains of toll-like receptor 3 (TLR3), toll-like receptor 4 (TLR4), toll-like receptor 7 (TLR7), toll-like receptor 8 (TLR8), toll-like receptor 9 (TLR9).

In some embodiments, the cytoplasmic portion of the chimeric receptor comprises a suitable region from interleukin-1 receptor-associated kinase 1 (IRAK1).

In some embodiments, the cytoplasmic portion of the chimeric receptor comprises a suitable region from differentiation primary response protein (MYD88).

In some embodiments, the cytoplasmic portion of the chimeric receptor comprises a suitable region from myelin and lymphocyte protein (MAL).

In some embodiments, the cytoplasmic portion of the chimeric receptor comprises a suitable region from retinoic acid inducible gene (RIG-1).

In some embodiments the transmembrane domain of the chimeric receptor comprises the transmembrane domain of any one of MYD88, TLR3, TLR4, TLR7, TLR8, TLR9, MAL, IRAK1, proteins.

In some embodiments, the recombinant intracellular signaling domain comprises a first portion derived from a phagocytic and a second portion derived from non-phagocytic receptor wherein the second portion derived from non-phagocytic receptor comprises a phosphorylation site. In some embodiments, the phosphorylation site comprises amino acid sequences suitable for an autophosphorylation site. In some embodiments, the amino acid residue that is phosphorylated is a tyrosine In some embodiments, the phosphorylation site comprises amino acid sequences suitable phosphorylation by Src family kinases. In some embodiments, the phosphorylation site comprises amino acid sequences, which upon phosphorylation are capable of binding to SH2 domains in a kinase. In some embodiments, a receptor tyrosine kinase domain is fused at the cytoplasmic end of the chimeric receptor in addition to the first cytoplasmic portion.

In some embodiments, the phosphorylation site is a Tyrosine phosphorylation site.

In some embodiments the second intracellular domain is an Immune receptor Tyrosine Activation Motif (ITAM). Exemplary ITAM motifs are present in mammalian α and β immunoglobulin proteins, TCR γ receptors, FCR γ receptors subunits, CD3 chains receptors and NFAT activation molecule.

In some embodiments the chimeric receptor intracellular domain comprises one ITAM motif. In some embodiments the chimeric receptor intracellular domain comprises more than one ITAM motifs. In some embodiments the chimeric receptor intracellular domain comprises two or more ITAM motifs. In some embodiments the chimeric receptor intracellular domain comprises three or more ITAM motifs. In some embodiments the chimeric receptor intracellular domain comprises four or more ITAM motifs. In some embodiments the chimeric receptor intracellular domain comprises five or more ITAM motifs. In some embodiments the chimeric receptor intracellular domain comprises six or more ITAM motifs. In some embodiments the chimeric receptor intracellular domain comprises seven or more ITAM motifs. In some embodiments the chimeric receptor intracellular domain comprises eight or more ITAM motifs. In some embodiments the chimeric receptor intracellular domain comprises nine or more ITAM motifs. In some embodiments the chimeric receptor intracellular domain comprises ten or more ITAM motifs.

In some embodiments one or more domains in the first phagocytic ICD comprises a mutation.

In some embodiments one or more domains in the second ICD comprises a mutation to enhance a kinase binding domain, to generate a phosphorylation site, to generate an SH2 docking site or a combination thereof.

Myeloid Cell Specific Chimeric Antigen Receptor-Encoding Polynucleic Acid as "Off-the Shelf" Therapeutic Compositions Provided herein for the first time, therapeutically effective compositions that can be prepared and stored for use one a subject in need thereof at any point of time. The therapeutically effective compositions comprise nucleic acid compositions having a sequence encoding a chimeric fusion protein (CFP). The polynucleotide encoding the CFP comprises (i) a sequence encoding an extracellular antigen binding domain, e.g., an ScFv, (ii) a sequence encoding a transmembrane domain capable of dimerizing with an Fc-gamma receptor transmembrane domain upon expression in a cell, and (iii) a sequence encoding an intracellular domain. In some embodiments, the therapeutically effective composition comprises, in addition to the above, a delivery vehicle. In some embodiments, the delivery vehicle comprises a lipid nanoparticle. In some embodiments, the nucleic acid, i.e., the polynucleotide is an mRNA.

Provided herein are myeloid cell-specific expression constructs encoding a CFP, wherein the CFP comprises (i) a sequence encoding an extracellular antigen binding domain that binds to a target antigen, where the binding domain comprises a target-specific antibody or a fragment thereof, e.g., an scFv, for example, an scFv that binds to a target antigen expressed on a cancer cell, (ii) a sequence encoding a transmembrane domain capable of dimerizing with an Fc-gamma receptor transmembrane domain upon expression in a cell, and (iii) a sequence encoding one or more intracellular domains comprising a signaling domain that can activate intracellular signal transduction for phagocytosis activation, inflammatory cytokine secretion and/or immune activation in the cell expressing the construct; wherein the expression constructs is a polynucleotide, encapsulated in a lipid nanoparticle for delivery. In some embodiments, the polynucleotide is an mRNA.

Provided herein are myeloid cell-specific expression constructs encoding a CFP, wherein the CFP comprises (i) a sequence encoding an extracellular antigen binding domain that binds to a target antigen, e.g., a target antigen expressed on a cancer cell, for example, CD5, HER2, TROP2, GPC3, GP75, CD19, CD7, CD22 or any other conceivable target antigen, (ii) a sequence encoding a transmembrane domain capable of dimerizing with an Fc-gamma receptor transmembrane domain upon expression in a cell, for example, a CD89 TMD, a CD16 TMD, a CD64 TMD or a CD32a TMD, and (iii) a sequence encoding one or more intracellular domains comprising a signaling domain that can activate intracellular signal transduction for phagocytosis activation, inflammatory cytokine secretion and/or immune activation in the cell expressing the construct; wherein the expression constructs is a polynucleotide, wherein the expression construct is encapsulated in a lipid nanoparticle for delivery. In some embodiments, the polynucleotide is an mRNA.

The therapeutically effective composition is a pharmaceutical composition. The pharmaceutical composition is suitable for delivery in vivo for example, suitable for delivery to a human in need thereof.

In some embodiments, the pharmaceutical composition comprising the myeloid cell-specific expression constructs encoding the CFP is required to be stored at proper temperature and conditions for preservation of the composition therein.

The therapeutically effective composition described herein can be delivered intravenously, intramuscularly, subcutaneously, intra-orbitally, intracranially, intrathecally, intranasally, or by any suitable route of administration.

Also contemplated herein are myeloid cells comprising the myeloid cell-specific expression constructs encoding the CFP, as a therapeutic composition that can be formulated as an "off the shelf" product for a subject in need thereof. In some embodiments the myeloid cells are electroporated with a construct encoding a CFP, wherein the CFP comprises (i) a sequence encoding an extracellular antigen binding domain that binds to a target antigen, e.g., a target antigen expressed on a cancer cell, for example, CD5, HER2, TROP2, GPC3, GP75, CD19, CD7, CD22 or any other conceivable target antigen, (ii) a sequence encoding a transmembrane domain capable of dimerizing with an Fc-gamma receptor transmembrane domain upon expression in a cell, for example, a CD89 TMD, a CD16 TMD, a CD64 TMD or a CD32a TMD, and (iii) a sequence encoding one or more intracellular domains comprising a signaling domain that can activate intracellular signal transduction for phagocytosis activation, inflammatory cytokine secretion and/or immune activation. The myeloid cells are formulated in a composition for in vivo delivery. In some embodiments, such compositions are suitable for delivery in vivo to a human in need thereof.

ENUMERATED EMBODIMENTS

1. A composition comprising a recombinant nucleic acid encoding a chimeric fusion protein (CFP) comprising:
   (a) a phagocytic or tethering receptor (PR) subunit comprising:
     (i) a transmembrane domain, or
     (ii) an intracellular domain comprising an intracellular signaling domain; and
   (b) an extracellular domain comprising a CD137 antigen binding domain that can bind specifically to CD137 on a target cell; wherein the extracellular and the transmembrane domains are operably linked.
2. A composition comprising a recombinant nucleic acid encoding a chimeric fusion protein comprising: (a) a first CD137 antigen binding domain that specifically binds to CD137 antigen on a target cell, and (b) a second binding domain that specifically binds to a surface agent on a myeloid cell; wherein, binding of the first antigen binding domain to CD137 antigen on a target cell and binding of the second binding domain on a surface agent on a myeloid cell.
3. A composition comprising a recombinant nucleic acid encoding a chimeric fusion protein (CFP) comprising: (a) a phagocytic or tethering receptor (PR) subunit comprising: (i) a transmembrane domain, or (ii) an intracellular domain comprising an intracellular signaling domain; and (b) an extracellular domain comprising a Claudin 18.2 antigen binding domain that can bind specifically to Claudin 18.2 on a target cell; wherein the extracellular and the transmembrane domains are operably linked.
4. A composition comprising a recombinant nucleic acid encoding a chimeric fusion protein comprising: (a) a first Claudin 18.2 antigen binding domain that specifically binds to Claudin 18.2 antigen on a target cell, and (b) a second binding domain that specifically binds to a surface agent on a myeloid cell; wherein, binding of the first antigen binding domain to Claudin 18.2 antigen on a target cell and binding of the second binding domain on a surface agent on a myeloid cell.
5. A composition comprising a recombinant nucleic acid encoding a chimeric fusion protein (CFP) comprising: (a) a phagocytic or tethering receptor (PR) subunit comprising: (i) a transmembrane domain, or (ii) an intracellular domain comprising an intracellular signaling domain; and (b) an extracellular domain comprising a Claudin 3 antigen binding domain that can bind specifically to Claudin 3 on a target cell; wherein the extracellular and the transmembrane domains are operably linked.
6. A composition comprising a recombinant nucleic acid encoding a chimeric fusion protein comprising: (a) a first Claudin 3 antigen binding domain that specifically binds to Claudin 3 antigen on a target cell, and (b) a second binding domain that specifically binds to a surface agent on a myeloid cell; wherein, binding of the first antigen binding domain to Claudin 18.2 antigen on a target cell and binding of the second binding domain on a surface agent on a myeloid cell.
7. A composition comprising a recombinant nucleic acid encoding a chimeric fusion protein (CFP) comprising: (a) a phagocytic or tethering receptor (PR) subunit comprising: (i) a transmembrane domain, or (ii) an intracellular domain comprising an intracellular signaling domain; and (b) an extracellular domain comprising a CD70 antigen binding domain that can bind specifically to CD70 on a target cell; wherein the extracellular and the transmembrane domains are operably linked.
8. A composition comprising a recombinant nucleic acid encoding a chimeric fusion protein comprising: (a) a first CD70 antigen binding domain that specifically binds to CD70 antigen on a target cell, and (b) a second binding domain that specifically binds to a surface agent on a myeloid cell; wherein, binding of the first antigen binding domain to CD70 antigen on a target cell and binding of the second binding domain on a surface agent on a myeloid cell.
9. A composition comprising a recombinant nucleic acid encoding a chimeric fusion protein (CFP) comprising: (a) a phagocytic or tethering receptor (PR) subunit comprising: (i) a transmembrane domain, or (ii) an intracellular domain comprising an intracellular signaling domain; and (b) an extracellular domain comprising a TROP2 antigen binding domain that can bind specifically to TROP2 on a target cell; wherein the extracellular and the transmembrane domains are operably linked.
10. A composition comprising a recombinant nucleic acid encoding a chimeric fusion protein comprising: (a) a first TROP2 antigen binding domain that specifically binds to TROP2 antigen on a target cell, and (b) a second binding domain that specifically binds to a surface agent on a myeloid cell; wherein, binding of the first antigen binding domain to TROP2 antigen on a target cell and binding of the second binding domain on a surface agent on a myeloid cell.
11. A composition comprising a recombinant nucleic acid encoding a chimeric fusion protein (CFP) comprising: (a) a phagocytic or tethering receptor (PR) subunit comprising: (i) a transmembrane domain, or (ii) an intracellular domain comprising an intracellular signaling domain; and (b) an extracellular domain comprising a TMPRSS antigen binding domain that can bind specifically to TMPRSS on a target cell; wherein the extracellular and the transmembrane domains are operably linked.
12. A composition comprising a recombinant nucleic acid encoding a chimeric fusion protein comprising: (a) a first TMPRSS antigen binding domain that specifically binds to TMPRSS antigen on a target cell, and (b) a second binding domain that specifically binds to a surface agent on a myeloid cell; wherein, binding of the first antigen binding domain to TMPRSS antigen on a target cell and binding of the second binding domain on a surface agent on a myeloid cell.
13. A composition comprising a recombinant nucleic acid encoding a phagocytic or tethering receptor (PR) fusion protein (PFP) comprising: (a) a PR subunit comprising: (i) a transmembrane domain, and (ii) an intracellular domain comprising an intracellular signaling domain; and (b) an extracellular domain comprising an antigen binding domain of any one of the embodiments 1, 3, 5, 7, 9 or 11 having a strong binding affinity to an antigen of a target cell; wherein the transmembrane domain and the extracellular domain are operatively linked; and wherein upon binding of the PFP to the antigen of the target cell, the killing or phagocytosis activity of a cell expressing the PFP is increased by at least greater than 20% compared to a cell not expressing the PFP.
14. The composition of any one of the embodiments 1, 3, 5, 7, 9, 11 or 13, wherein the intracellular signaling domain is derived from a phagocytic or tethering receptor or wherein the intracellular signaling domain comprises a phagocytosis activation domain.
15. The composition of any one of the embodiments 1, 3, 5, 7, 9, 11, 13 or 14, wherein the intracellular signaling domain comprises a pro-inflammatory signaling domain.
16. The composition of any one of the embodiments 1, 3, 5, 7, 9, 11 or 13-15, wherein the pro-inflammatory signaling domain comprises a kinase activation domain or a kinase binding domain.
17. The composition of any one of the embodiments 1, 3, 5, 7, 9, 11 or 13-16, wherein the intracellular signaling domain comprises a PI3 kinase recruitment domain.
18. The composition of any one of the embodiments 1, 3, 5, 7, 9, 11 or 13-17, wherein the pro-inflammatory signaling domain comprises an IL-1 signaling cascade activation domain.
19. The composition of any one of the embodiments 1, 3, 5, 7, 9, 11 or 13-18, wherein the pro-inflammatory signaling domain comprises an intracellular signaling domain derived from TLR3, TLR4, TLR7, TLR 9, TRIF, RIG-1, MYD88, MAL, IRAK1, MDA-5, an IFN-receptor, an NLRP family member, NLRP1-14, NOD1, NOD2, Pyrin, AIM2, NLRC4, FCGR3A, FCERIG, CD40, a caspase domain or a procaspase binding domain or any combination thereof
20. The composition of any one of the embodiments 1, 3, 5, 7, 9, 11 and 13-19, further comprising a transmembrane domain derived from a CD2, CD8, CD28 or CD68 protein TM domain.
21. The composition of any one of the embodiments 1, 3, 5, 7, 9, 11 and 13-20, further comprising a hinge domain.
22. The composition of any one of the embodiments 1, 3, 5, 7, 9, 11 or 13-22, wherein upon binding of the PFP to the antigen of the target cell, the killing activity of a cell expressing the PFP is increased by at least greater than 20% compared to a cell not expressing the PFP.
23. The composition of any one of the embodiments 1, 3, 5, 7, 9, 11 or 13-22, wherein upon binding of the PFP to the antigen of the target cell, the killing activity of a cell expressing the PFP is increased by at least 1.1-fold compared to a cell not expressing the PFP.
24. The composition of any one of the embodiments 2, 4, 6, 8, 10 or 12 comprising a first therapeutic agent, wherein the therapeutic agent comprises:
   a. a first binding domain, wherein the first binding domain is a first antibody or functional fragment thereof that specifically interacts with an antigen on a target cell, and
   b. a second binding domain, wherein the second binding domain is a second antibody or functional fragment thereof that specifically interacts with a myeloid cell;

wherein, (i) the first therapeutic agent is coupled to a first component, wherein the first component is an additional therapeutic agent or a third binding domain, or
   (ii) the composition comprises an additional therapeutic agent.
25. The composition of any one of the embodiments 2, 4, 6, 8, 10, 12 or 24, wherein the therapeutic agent comprises: (a) a first binding domain that specifically interacts with an antigen of a target cell, (b) a second binding domain that specifically interacts with a myeloid cell, and (c) a third binding domain that specifically interacts with the myeloid cell.
26. The composition of any one of embodiments 1-25, wherein any one of binding domains of the therapeutic agent comprises the binding domain of a an antibody, a functional fragment of an antibody, a variable domain thereof, a $V_H$ domain, a $V_L$ domain, a VNAR domain, a $V_{HH}$ domain, a single chain variable fragment (scFv), an Fab, a single-domain antibody (sdAb), a nanobody, a bispecific antibody, a diabody, or a functional fragment or a combination thereof
27. The composition of any one of embodiments 1-26, wherein the antigen on the target cell to which the first binding domain binds, is a cancer antigen or a pathogenic antigen on the target cell or an autoimmune antigen.
28. The composition of any one of embodiments 2, 4, 6, 8, 10, 12 or 24, wherein the first therapeutic agent comprises a polypeptide that is less than 1000 amino acids or 1000 nm in length.
29. The composition of any one of embodiments 2, 4, 6, 8, 10, 12, 24, or 28, wherein the first therapeutic agent comprises a polypeptide that is less than 500 amino acids or 500 nm in length.

30. The composition of any one of embodiments 2, 4, 6, 8, 10, 12, 24, 28, or 29, wherein the first therapeutic agent comprises a polypeptide that is 200-1000 amino acids or 200-1000 nm in length.
31. The composition of any one of embodiments 2, 4, 6, 8, 10, 12, 24, or 28-30, wherein engagement of the binding domains of the first therapeutic agent contacts the cancer cell to the myeloid cell.
32. The composition of any one of embodiments 2, 4, 6, 8, 10, 12, 24, or 28-31, wherein the second binding domain specifically interacts with a myeloid cell and promotes phagocytosis activity of the myeloid cell.
33. The composition of any one of embodiments 2, 4, 6, 8, 10, 12, 24, or 28-32, wherein the second binding domain specifically interacts with a myeloid cell and promotes inflammatory signaling of the myeloid cell.
34. The composition of any one of embodiments 2, 4, 6, 8, 10, 12, 24, or 28-33, wherein the second binding domain specifically interacts with a myeloid cell or an adhesion molecule and promotes adhesion of the myeloid cell to the target cell.
35. The composition of any one of embodiments 2, 4, 6, 8, 10, 12, 24, or 28-34, wherein the second binding domain specifically interacts with a myeloid cell and inhibits anti-phagocytic activity of the myeloid cell mediated by the target cell.
36. The composition of any one of embodiments 2, 4, 6, 8, 10, 12, 24, or 28-35, wherein the second binding domain specifically interacts with a myeloid cell and inhibits anti-inflammatory activity of the myeloid cell mediated by the target cell.
37. The composition of any one of embodiments 2, 4, 6, 8, 10, 12, 24, or 28-36, wherein the second and/or the third binding domain promotes phagocytic activity of the myeloid cell.
38. The composition of any one of embodiments 2, 4, 6, 8, 10, 12, 24, or 28-37, wherein the second and/or the third binding domain promotes inflammatory signaling of the myeloid cell.
39. The composition of any one of embodiments 2, 4, 6, 8, 10, 12, 24, or 28-38, wherein the second and/or the third binding domain specifically interacts with a myeloid cell or an adhesion molecule and promotes adhesion of the myeloid cell to the target cell.
40. The composition of any one of embodiments 2, 4, 6, 8, 10, 12, 24, or 28-39, wherein the second and/or the third binding domain inhibits anti-phagocytic activity of the myeloid cell mediated by the target cell.
41. The composition of any one of embodiments 2, 4, 6, 8, 10, 12, 24, or 28-40, wherein the second and/or the third binding domain inhibits anti-inflammatory activity of the myeloid cell mediated by the target cell.
42. The composition of any one of embodiments 2, 4, 6, 8, 10, 12, 24, or 28-41, wherein the third binding domain or the additional therapeutic agent comprises a CD47 antagonist, a CD47 blocker, an antibody, a chimeric CD47 receptor, a sialidase, a cytokine, a proinflammatory gene, a procaspase, or an anti-cancer agent.
43. The composition of any one of the preceding embodiments, wherein the first binding domain, the second binding domain and the third binding domain bind to distinct non-identical target antigens.
44. The composition of any one of the embodiments 2, 4, 6, 8, 10, 12, 24, or 28-43, wherein the first binding domain, the second binding domain or the third binding domain is a ligand binding domain.
45. The composition of any one of the preceding embodiments, wherein the first, the second or the third binding domains are operably linked by one or more linkers.
46. The composition of embodiment 45, wherein the linker is a polypeptide.
47. The composition of embodiment 46, wherein the linker is a functional peptide.
48. The composition of any one of the embodiments 45-47, wherein the linker is a ligand for a receptor.
49. The composition of embodiment 45, wherein the linker is a ligand for a monocyte or macrophage receptor.
50. The composition of any one of the embodiments 45-49, wherein the linker activates the receptor.
51. The composition of any one of the embodiments 45-50, wherein the linker inhibits the receptor.
52. The composition of embodiment 51, wherein the linker is a ligand for a M2 macrophage receptor.
53. The composition of embodiment 48 or 49, wherein the linker is a ligand for a TLR receptor, such as TLR4.
54. The composition of embodiment any of the embodiments 48, 49 or 50, wherein the linker activates a TLR receptor.
55. The composition of any one of the embodiments 45-54, wherein the first, the second and/or the third binding domains are associated with a mask that binds to the binding domain.
56. The composition of embodiment 55, wherein the mask is an inhibitor that inhibits the interaction of binding domain to its target when the mask remains associated with the respective binding domain.
57. The composition of embodiment 56, wherein the mask is associated with the binding domain via a peptide linker.
58. The composition of embodiment 57, wherein the peptide linker comprises a cleavable moiety.
59. The composition of embodiment 57, wherein the cleavable moiety is cleaved by a protein or an enzyme selectively abundant in the site of the cancer or tumor.
60. The composition of any one of the embodiments 1-59, wherein the recombinant nucleic acid is an RNA.
61. The composition of any one of the embodiments 1-60, wherein the recombinant nucleic acid is an mRNA.
62. The composition of any one of the embodiments 1-61, wherein the recombinant nucleic acid is associated with one or more lipids.
63. The composition of any one of the embodiments 1-61, wherein the recombinant nucleic acid is encapsulated in a liposome.
64. The composition of embodiment 63, wherein the liposome is a nanoparticle.
65. The composition of any one of the embodiments 1-64, wherein the recombinant nucleic acid is comprised in a vector.
66. A pharmaceutical composition comprising any one of the recombinant nucleic acids of the compositions of embodiment 1-65, and an acceptable excipient.
67. A pharmaceutical composition comprising a polypeptide encoded by a recombinant nucleic acid of any one of the embodiments 2, 4, 6, 8, 10, 12, 24, or 28-59.
68. A cell comprising the recombinant nucleic acid of any one of the embodiments 1-67.
69. The cell of embodiment 68, wherein the cell is a myeloid cell, e.g. a CD14+ cell.
70. The cell of embodiment 69, wherein the cell is CD14+, CD16−.

71. A pharmaceutical composition comprising a population of cells that comprise a recombinant nucleic acid of any one of the embodiments 1-66, wherein at least 50% of the cells are CD14+CD16−.

72. The pharmaceutical composition of embodiment 71, wherein less than 10% of the cells are dendritic cells.

73. The pharmaceutical composition of embodiment 71 or 72, further comprising a suitable excipient.

74. A method of making any one of the compositions of embodiments 1-73.

75. A method of treating a cancer in a subject, comprising administering to the subject a pharmaceutical composition of any one of the embodiments 71-73.

76. A method of treating a cancer in a subject, comprising administering to the subject the pharmaceutical composition of embodiment 66; or the pharmaceutical composition of embodiment 67.

77. The method of embodiment 75 or 76, wherein the cancer is selected from a group consisting of gastric cancer, ovarian cancer, renal cancer, breast cancer, prostate cancer, liver cancer, brain cancer, lymphoma, leukemia, skin cancer, pancreatic cancer, colorectal cancer, glioblastoma and lung cancer.

78. A composition comprising a recombinant polynucleic acid comprising a sequence encoding a chimeric fusion protein (CFP), the CFP comprising: (a) an extracellular domain comprising an anti-tumor-associated antigen binding domain, and (b) a transmembrane domain operatively linked to the extracellular domain; wherein the transmembrane domain is a transmembrane domain from a protein that dimerizes with an endogenous FcR-gamma receptor in a myeloid cell, and wherein the recombinant polynucleic acid comprising a sequence encoding a chimeric fusion protein (CFP) when expressed in a cell is functional in a myeloid cell, and not functional in a non-myeloid cell.

79. The composition of embodiment 78, wherein the expression of the CFP is detectable in a myeloid cell at 24 h, 36 h, 48 h, or 72 h after transfection with the recombinant nucleic acid comprising a sequence encoding the CFP, and is not detectable in a non-myeloid cell at 24 h, 36 h, 48 h, or 72 h after transfection with the same.

80. A composition comprising a recombinant polynucleic acid comprising a sequence encoding a chimeric fusion protein (CFP), the CFP comprising:
(a) an extracellular domain comprising an anti-tumor-associated antigen binding domain, and
(b) a transmembrane domain operatively linked to the extracellular domain;
wherein the recombinant polynucleic acid is encapsulated by a nanoparticle delivery vehicle; and wherein after administration of the composition to a human subject the CFP is expressed on the surface of myeloid cells of the human subject.

81. A composition comprising a recombinant polynucleic acid comprising a sequence encoding a chimeric fusion protein (CFP), the CFP comprising:
(a) an extracellular domain comprising an anti-tumor-associated calcium signal transducer-2 (anti-TROP2) binding domain, and
(b) a transmembrane domain operatively linked to the extracellular domain;
wherein the transmembrane domain is a transmembrane domain from a protein that dimerizes with endogenous FcR-gamma receptors in myeloid cells; wherein the recombinant polynucleic acid is encapsulated by a nanoparticle delivery vehicle; and wherein after administration of the composition to a human subject the CFP is expressed on the surface of myeloid cells of the human subject.

82. The composition of embodiment 1, wherein the anti-TROP2 binding domain comprises a Fab fragment, an scFv domain or an sdAb domain.

83. The composition of embodiment 1, wherein the extracellular domain or the transmembrane domain is an extracellular domain or the transmembrane domain from CD8, CD16a, CD64, CD68 or CD89.

84. The composition of embodiment 1, wherein the extracellular domain further comprises a hinge domain derived from CD8, wherein the hinge domain is operatively linked to the transmembrane domain and the anti-TROP2 binding domain.

85. The composition of embodiment 78, wherein the transmembrane domain is a transmembrane domain from a protein that dimerizes with endogenous FcR-gamma receptors in myeloid cells, monocytes or macrophages; wherein after administration of the pharmaceutical composition to a human subject the CFP is specifically expressed in myeloid cells, monocytes or macrophages of the human subject.

86. The composition of embodiment 85, wherein the transmembrane domain is a transmembrane domain from CD16a, CD64, CD68 or CD89.

87. The composition of embodiment 78, wherein the CFP further comprises an intracellular domain.

88. The composition of embodiment 87, wherein the intracellular domain comprises one or more intracellular signaling domains, and wherein the one or more intracellular signaling domains comprises an intracellular signaling domain from FcγR, FcαR, FcεR, CD40 or CD3 zeta.

89. The composition of embodiment 87, wherein the one or more intracellular signaling domains further comprises a phosphoinositide 3-kinase (PI3K) recruitment domain.

90. The composition of embodiment 89, wherein the PI3K recruitment domain comprises a sequence with at least 90% sequence identity to SEQ ID NO: 26.

91. The composition of embodiment 87, wherein the intracellular domain comprises an intracellular domain from CD16a, CD64, CD68 or CD89.

92. The composition of embodiment 78, wherein the recombinant polynucleic acid is an mRNA.

93. The composition of embodiment 78, wherein the nanoparticle delivery vehicle comprises a lipid nanoparticle.

94. The composition of embodiment 93, wherein the lipid nanoparticle comprises a polar lipid 95. The composition of embodiment 93, wherein the lipid nanoparticle comprises a non-polar lipid.

96. The composition of embodiment 93, wherein the lipid nanoparticle is from 100 to 300 nm in diameter.

97. A pharmaceutical composition comprising the composition of embodiment 78 and a pharmaceutically acceptable excipient.

98. The pharmaceutical composition of embodiment 97, wherein pharmaceutical composition comprises an effective amount of the composition of embodiment 78 to inhibit growth of a cancer when administered to a human subject with the cancer.

99. A method of treating cancer in a subject in need thereof comprising administering the pharmaceutical composition of embodiment 97 or 98 to the subject.

100. A method of introducing the composition of embodiment 78 into a myeloid cell comprising:

electroporating a myeloid cell in the presence of a recombinant polynucleic acid comprising a sequence encoding a chimeric fusion protein (CFP), the CFP comprising:
- (a) an extracellular domain comprising an anti-TROP2 binding domain, and
- (b) a transmembrane domain operatively linked to the extracellular domain;

wherein the recombinant polynucleic acid is
- (i) present in a myeloid cell, or
- (ii) is encapsulated by a nanoparticle delivery vehicle;

wherein the recombinant polynucleic acid is configured for expression of the recombinant polynucleic acid in a myeloid cell of a human subject.

101. The composition of embodiments 81-84, further comprising an interferon inducing intracellular domain.

EXAMPLES

Example 1. CD137-FcR-PI3K CFP Construct

Figure 4A:
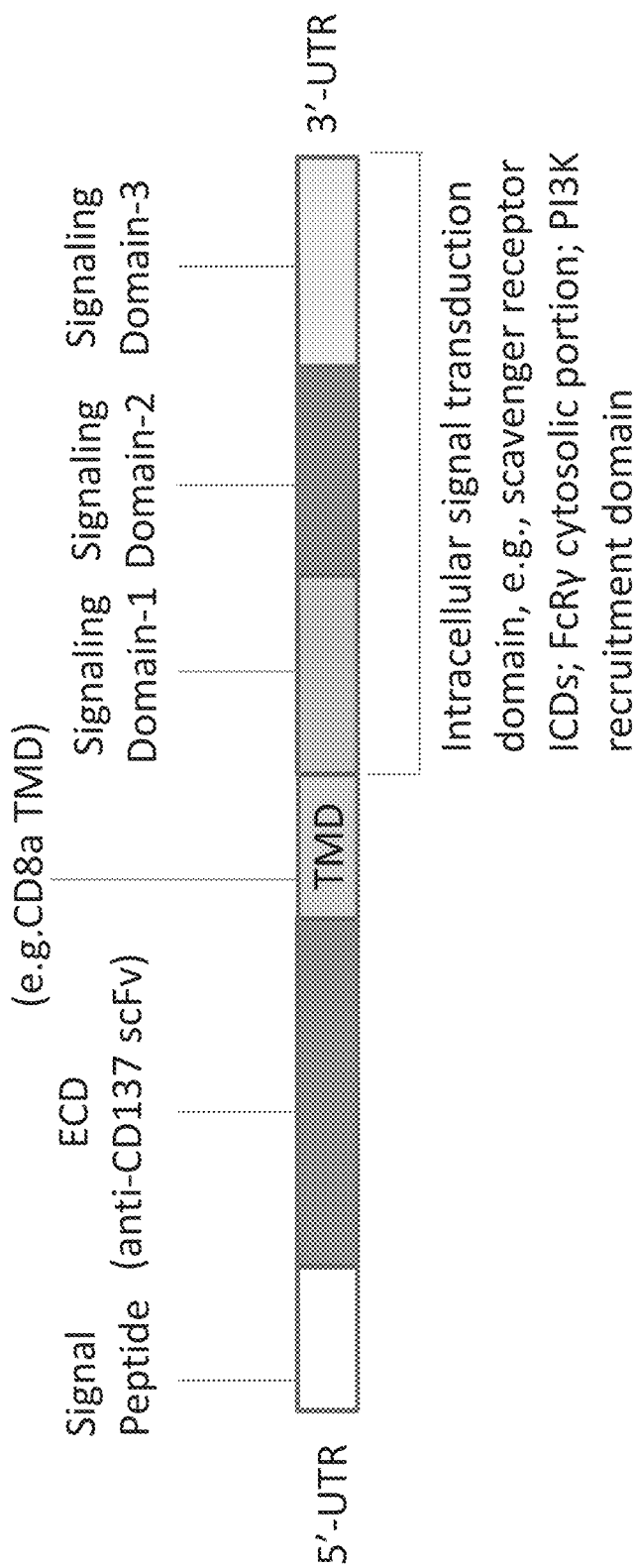
FIG. 4A is a schematic depicting an exemplary recombinant nucleic acid encoding a CFP containing a signal peptide fused to an antigen-specific scFv that is fused to an extracellular domain (ECD), transmembrane domain (TMD) and intracellular domain (ICD) of a scavenger receptor with signaling domains 1, 2, and 3. Additionally, the exemplary recombinant nucleic acid is mRNA, with 5'- and 3'UTRs.

In this section, design and functional analysis of an exemplary chimeric fusion protein (CFP) receptor having an extracellular binding domain that binds to an antigen, such as a cancer antigen, e.g., CD37, in short, a CD137-binder CFP receptor protein is provided as an exemplary case for the binders described herein (Graphically represented in FIGS. 1, 2A, 2B, and FIG. 3). The procedures and methods can be used with some modifications as necessary for generating any one of the other constructs described herein. CD137-targeted CFP is constructed using known molecular biology techniques. The nucleic acid construct comprises a sequence encoding a signal peptide fused upstream of a sequence encoding the extracellular CD137-binding domain derived from the ligand-binding fragment of human CD137L. Ligand-binding domain of human CD137L was PCR amplified from a human complementary DNA library and fused with a backbone containing transmembrane region, attached to a CD8α chain hinge and CD8α chain TM domain via a short linker. The TM domain is fused at the cytosolic end with an FcRγ cytosolic portion, and a PI3K recruitment domain. A graphical representation is provided in FIG. 4A. The construct is prepared in a vector having a fluorescent marker and a drug (ampicillin) resistance and amplified by transfecting a bacterial host.

Figure 4B:
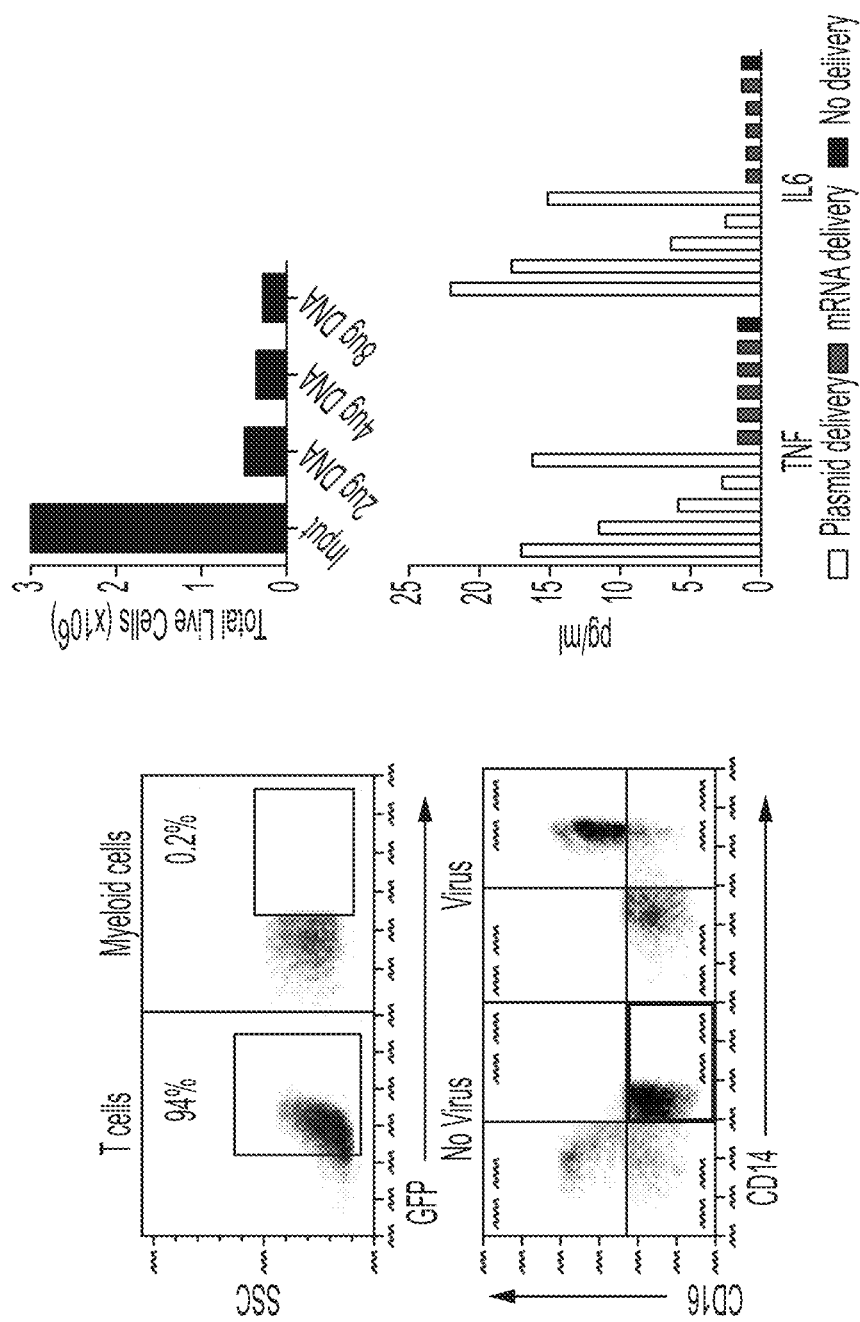
FIG. 4B demonstrates data that with viral gene delivery (left panel) some cell types show poor transduction and cell differentiation which could negatively affect the potential effect of the therapeutic cell function and longevity; plasmid mediated delivery (upper right) could induce differentiation and ell death; whereas mRNA delivery is both safe and causes almost negligible immune response in the cell post-delivery (lower right).

The constructs are delivered into a non-dividing mammalian cell as mRNA, and is accompanied by a delivery vehicle, e.g. a lipid, a liposome, a lipid nanoparticle or a synthetic compound such as a polymer etc. It was found and previously reported by the group that several cell types, such as myeloid cells are affected by introduction of foreign DNA, either by viral transduction or by plasmid delivery. Myeloid cells poorly express a foreign DNA, and often undergo cellular transformations, such as maturation, differentiation upon manipulation of the cells as simple as expressing a foreign DNA. (FIG. 4B, left). In some cases viability of the cells are affected (upper right). On the other hand, as shown in FIG. 4B, lower right, delivery via mRNA does not lead to cellular progression, aging or transformation, in that the cells do not release cytokines such as TNF and IL6 which are indicators of cellular activation.

Figure 5:
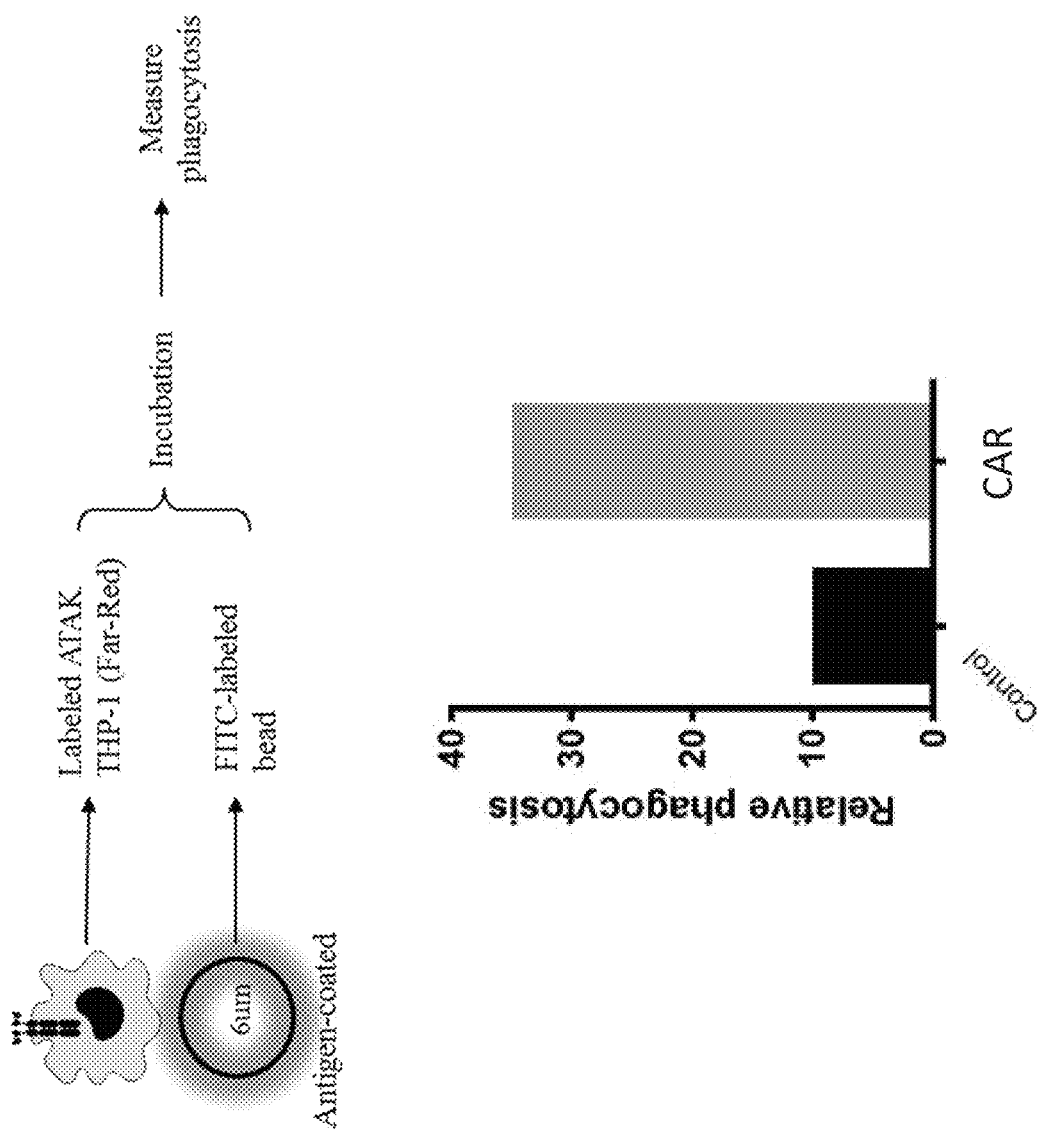
FIG. 5 is an exemplary data depicting expected results of relative phagocytosis in human primary myeloid cells transduced with empty vector (control) or a vector encoding a CFP co-cultured with antigen coated beads, as depicted in the graphical diagram on the top. Phagocytosis is quantified using flow cytometry.

Example 2. Efficacy of CD137-Targeting Chimeric Antigen Receptor Expressing Monocytes In this example, chimeric fusion proteins (CARs) having an extracellular CD137 antigen binding domain of the exemplary design described in the disclosure are analyzed for functional efficacy as potential anti-cancer agents. First generation lentiviral vector can be used to generate lentiviruses used to transduce the myeloid THP1 cell line. Transduction efficiency in PMA treated THP1 cells ranges from 67-90% for CFP constructs similar to the CD137 binder with other binding domains. The experimental set up is depicted in the schematic diagram of FIG. 5, upper panel, and expected results for phagocytosis are depicted in FIG. 5 lower panel. Target cell death can be calculated by the formula: [(#SKOV3 alone−#SKOV3 with effectors)/#SKOV3 alone]×100.

Figure 6A:
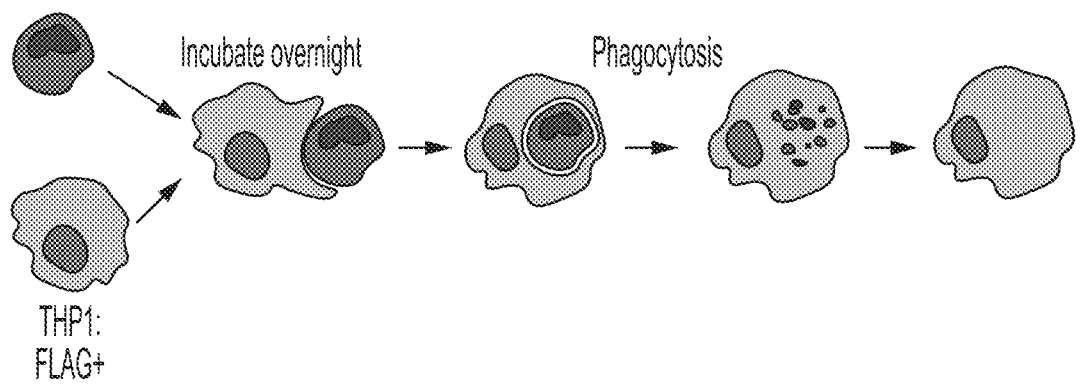
FIG. 6A is an exemplary data depicting expected results of relative phagocytosis in human primary myeloid cells transduced with empty vector (control) or a vector encoding a CFP co-cultured with antigen expressing target cells labeled with a fluorescent dye, as depicted in the graphical diagram on the top. Phagocytosis is quantified using flow cytometry. Effect of different myeloid cell to target ratios is depicted as expected.
Figure 6A:
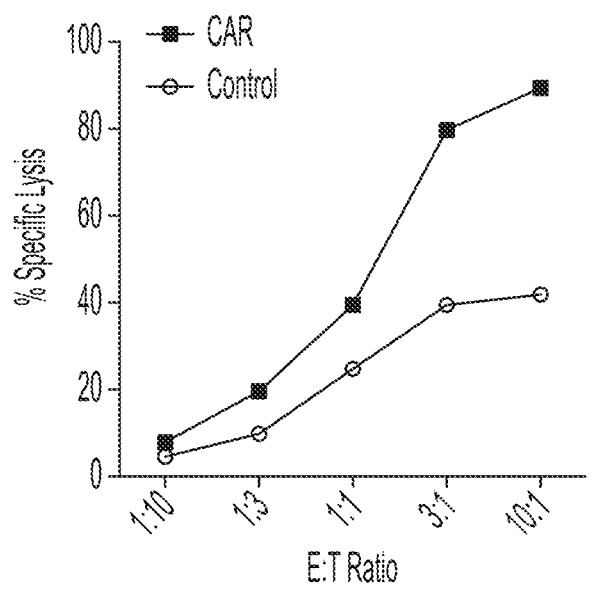

CD14+ cells isolated from healthy donor is transduced with a lentiviral CD137 targeted CFP constructs encoding FcRγ+PI3K intracellular domain are analyzed for phagocytosis and killing of CSFE labeled SCOV3 tumor cells (FIG. 6A).

Figure 6B:
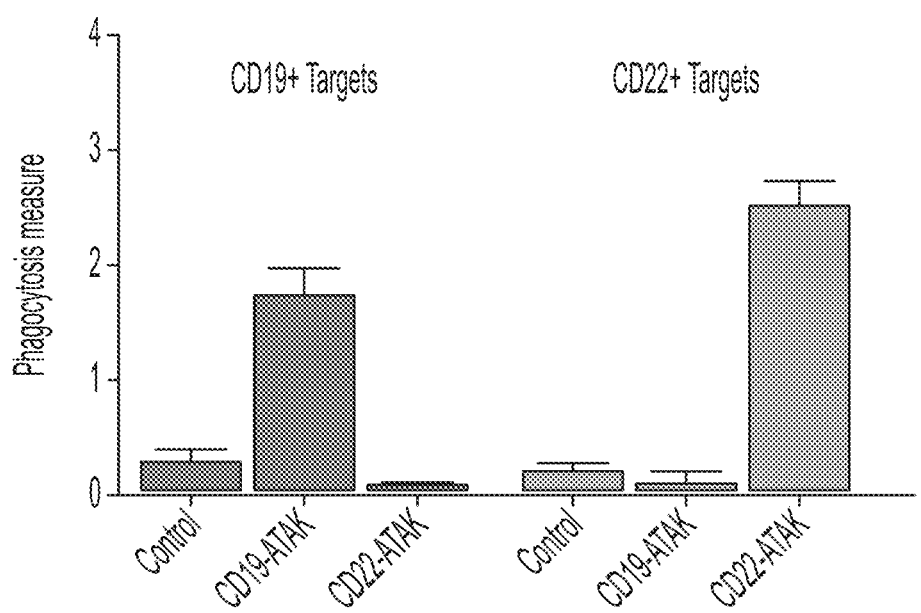
FIG. 6B shows data demonstrating specificity of the CFP binding domains (binders), the cells expressing CD19 binding CFP construct (CD19-ATAK) show high phagocytosis only in the presence of CD19+ targets, and not in the presence of CD22+ targets that do not bear CD19 on the surface, and vice versa.
Figure 6C:
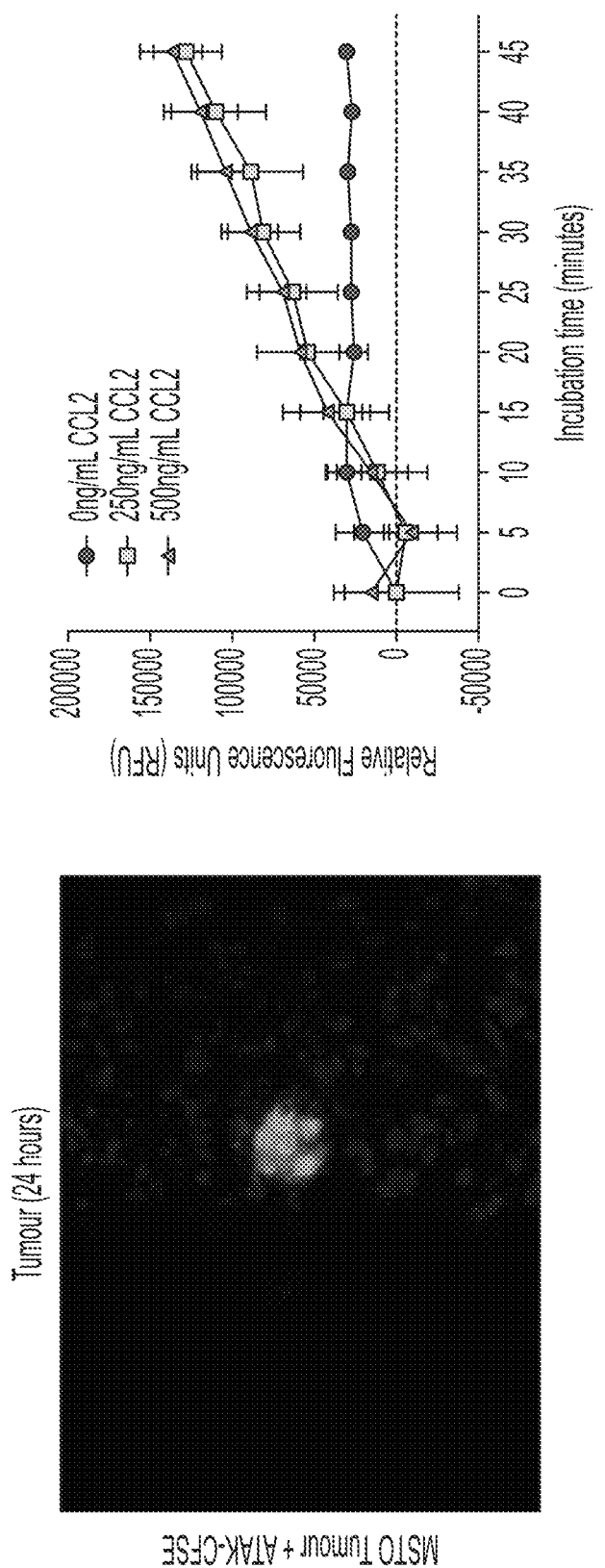
FIG. 6C shows data showing successful chemotaxis and localization of myeloid cells expressing fluorescent CFP constructs in the tumor (by imaging, left panel); the graph on the right shows chemotaxis of in vitro in the presence varying concentrations of CCL2.

The ATAK constructs render target specificity to the cells expressing the construct (FIG. 6B). For example, cells expressing CD19 binder did not phagocytose targets that present CD22 on their surface, not CD19. FIG. 6C illustrates that incorporating the constructs in myeloid cells do not affect migration of the cells to a tumor cite (e.g. left image, cells expressing the CAR construct are GFP+ in a tumor, the cells have migrated following introduction of the mRNA into a mouse.) CAR expressing cells are responsive to chemokines in vitro—as shown in the data (right).

Figure 7A:
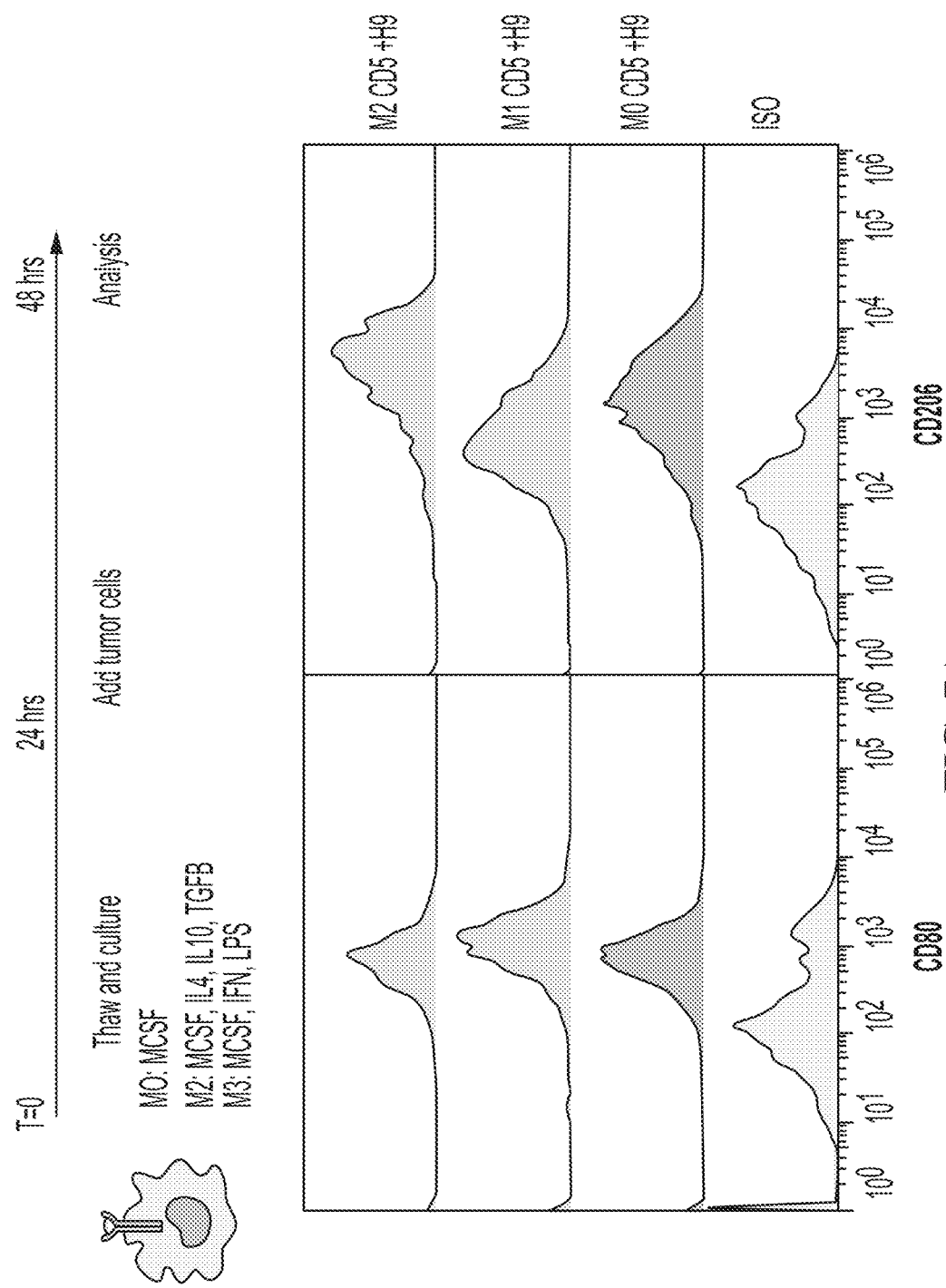
FIG. 7A depicts an exemplary graph from flow cytometry analysis depicting in primary human monocyte cells expressing an anti-CD5 CFP that were incubated under different polarization conditions (shown in the upper panel), e.g., in the presence of MCSF alone (M0 conditions); or additionally with IL-10, IL-4 and TGFβ (M2 conditions) or in the presence of IFN and LPS for 24 hours and then incubated with H9 T cell lymphoma cells, the results indicate that expression of the CFP did not alter the ability of the cells to be polarized under these conditions. Additionally, co-incubation with tumor cells did not alter the polarization. Further, the same culture conditions were used to test and demonstrate that the primary human monocyte cells expressing the anti-CD5 CFP had a potent tumor cell phagocytosis and killing activity in an M2 environment (not shown here). The same approach can be used to test in vitro efficacy of any of the binders described herein in an M1 or M2 promoting environment.

In order to test whether these cells expressing the CD137 constructs can be capable of differentiating into M0, M1, M2 phenotypes in a tumor environment, CAR expressing myeloid cells were subjected to M0, M1 or M2 polarization signal and incubated in the presence of tumor cells or non-tumor control cells in culture for 18 hours. M0 (100 ng/ml MCSF); M1 (5 ng/ml LPS+100 ng/ml IFNγ); M2 (100 ng/ml MCSF+20 ng/ml IL-10+20 ng/ml TGFβ); DC (100 ng/ml GMCSF+20 ng/ml IL-4); and control. FIG. 7A shows expected CD80 and CD206 expression profiles under different conditions described, indicating differential potential of these cells. For some of these experiments, a sequence encoding a FLAG peptide is incorporated in between the scFv and the transmembrane domain, in the extracellular region of the chimeric CD137 construct. Cells can be harvested and cell viability can be tested and found to be greater than 80%. The phenotype of the cells can be examined by flow cytometry at 24 hours. The expression of several cell markers at 24, 48 and 72 hours can be determined. CD16 expression does not increase by CAR expression alone.

Figure 7B:
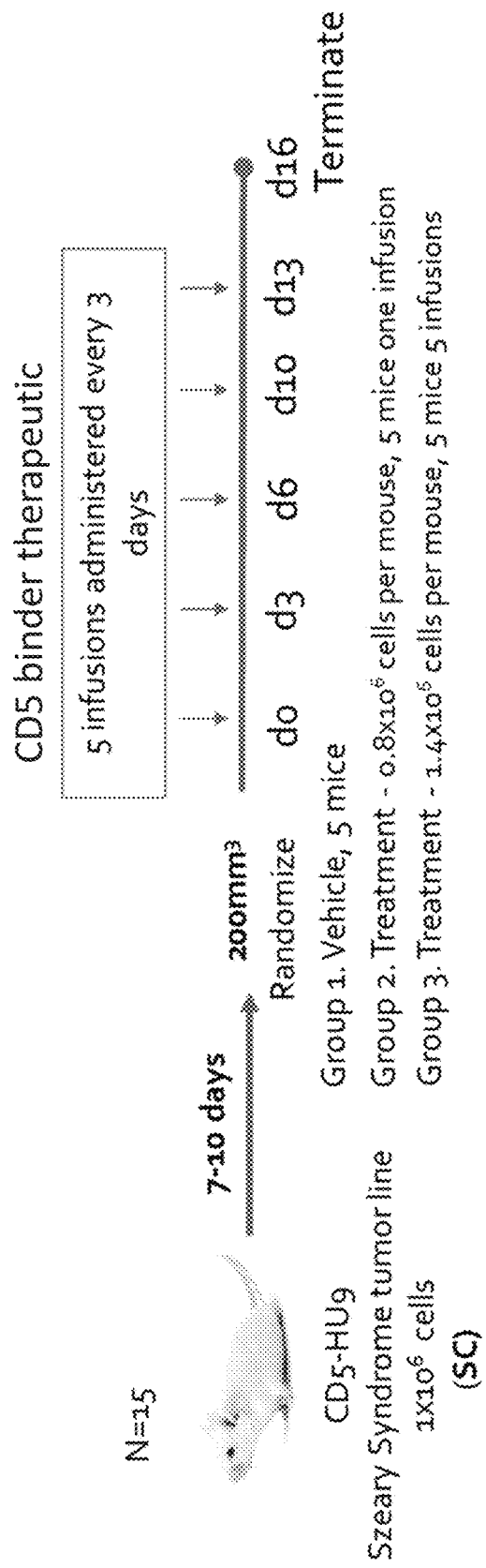
FIG. 7B depicts a schematic showing an exemplary experimental flow diagram of treatment of a peripheral T cell lymphoma animal model experiment. 1×10^6 CD5-HU9 Szeary Syndrome tumor line cells were injected subcutaneously into mice. Treatment with the indicated amounts of human primary monocytes expressing an anti-CD5 CFP was initiated at day 11 post injection of the tumor line cells. 5 total infusions were administered, one infusion every 3 days. The same approach can be used to test in vitro efficacy of any of the binders described herein in a suitable experimental tumor model in vivo.
Figure 7C:
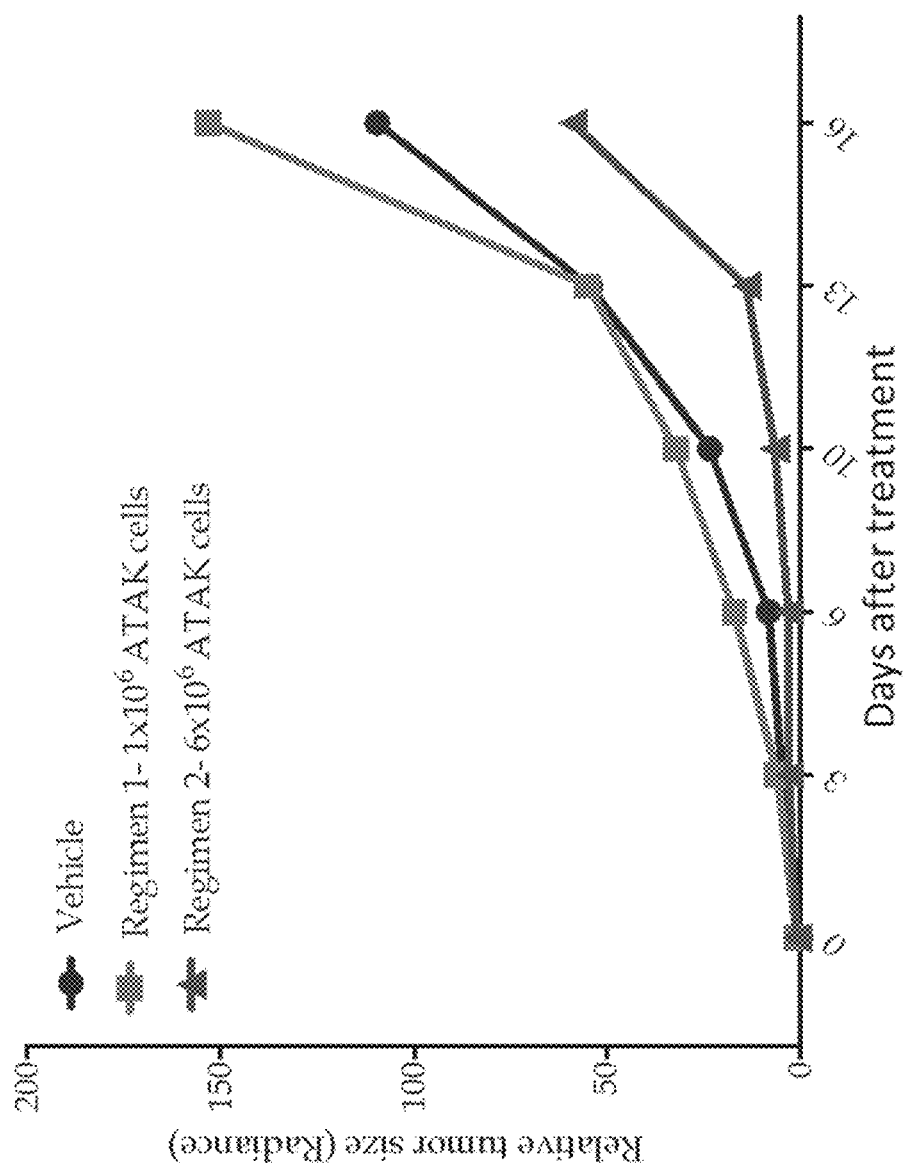
FIG. 7C depicts a graph of relative tumor size (radiance) at the indicated time points according to the experimental regimen described in FIG. 7B.

An in vivo model for a CD137 expressing tumor can be utilized to investigate the tumor penetration and activation of the cells expressing a CD137-CFP. A schematic diagram of the experimental design is shown in FIG. 7B. Migration and penetration of the CD137-targeted CFP expressing cells can be determined at 24 hours after a single infusion of the CFP expressing cells that have been labeled with cytoplasmic dye CSFE. Tumors can be removed and processed for histology. As shown in the prophetic data in FIG. 7C, CD137-CFP expressing myeloid cells can migrate into the tumor and accumulate around tumor cells. Twenty four hours after CFSE labelled CD137-targeted CFP expressing cell administration in MSTO tumor bearing NSG mice, spleens can be removed and processed for histology.

Example 3. Chimeric Antigen Receptors for Myeloid Specific Expression

Figure 8:
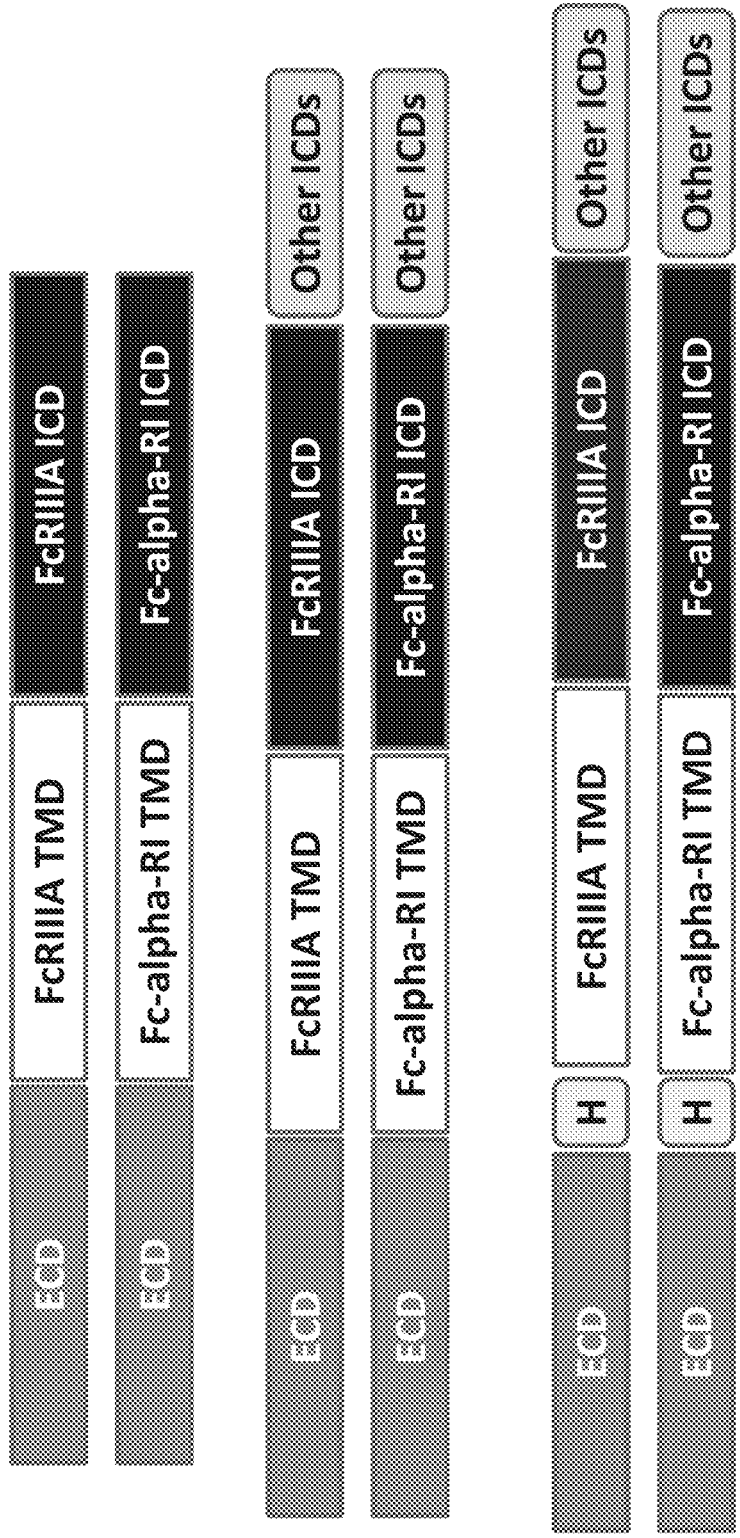
FIG. 8 shows exemplary modular designs of CFP constructs for monocyte-specific expression (ECD=extracellular domain; H=hinge; TMD=transmembrane domain; ICD=intracellular domain).

This example shows a chimeric antigenic receptor design for myeloid specific expression. A chimeric fusion protein of the design has a transmembrane domain consisting of an FcR TDM the expression of which in the cell membrane is dependent on it multimerizes with an Fcgamma receptor that is endogenously expressed in monocytes. In this example, CFP constructs for monocyte-specific expression are designed with a transmembrane domain (TMD) of CD16 or CD89. Specific CFP can be designed based on the general schematics outlined in FIG. 8. Exemplary designs include one that has an extracellular cancer antigen binding domain, operably linked with a CD16 (FcRIIIA) TMD and a CD16 intracellular domain; or one that has an extracellular cancer antigen binding domain, operably linked with a CD89 (FcRI alpha) TMD and a CD89 intracellular domain. There can be a hinge (H) in between the extracellular antigen binding domain. In certain constructs the CD16 or CD89 TMD extends for about 10 amino acids in the extracellular region for flexibility, and a separate hinge domain may or may not be included. The ECD cancer antigen binding domain can be an scFv, or an antibody or fragment thereof that binds to any one of the various antigens that are contemplated herein.

Example 4. TROP2-Antigen Specific CFP Constructs

Figure 9:
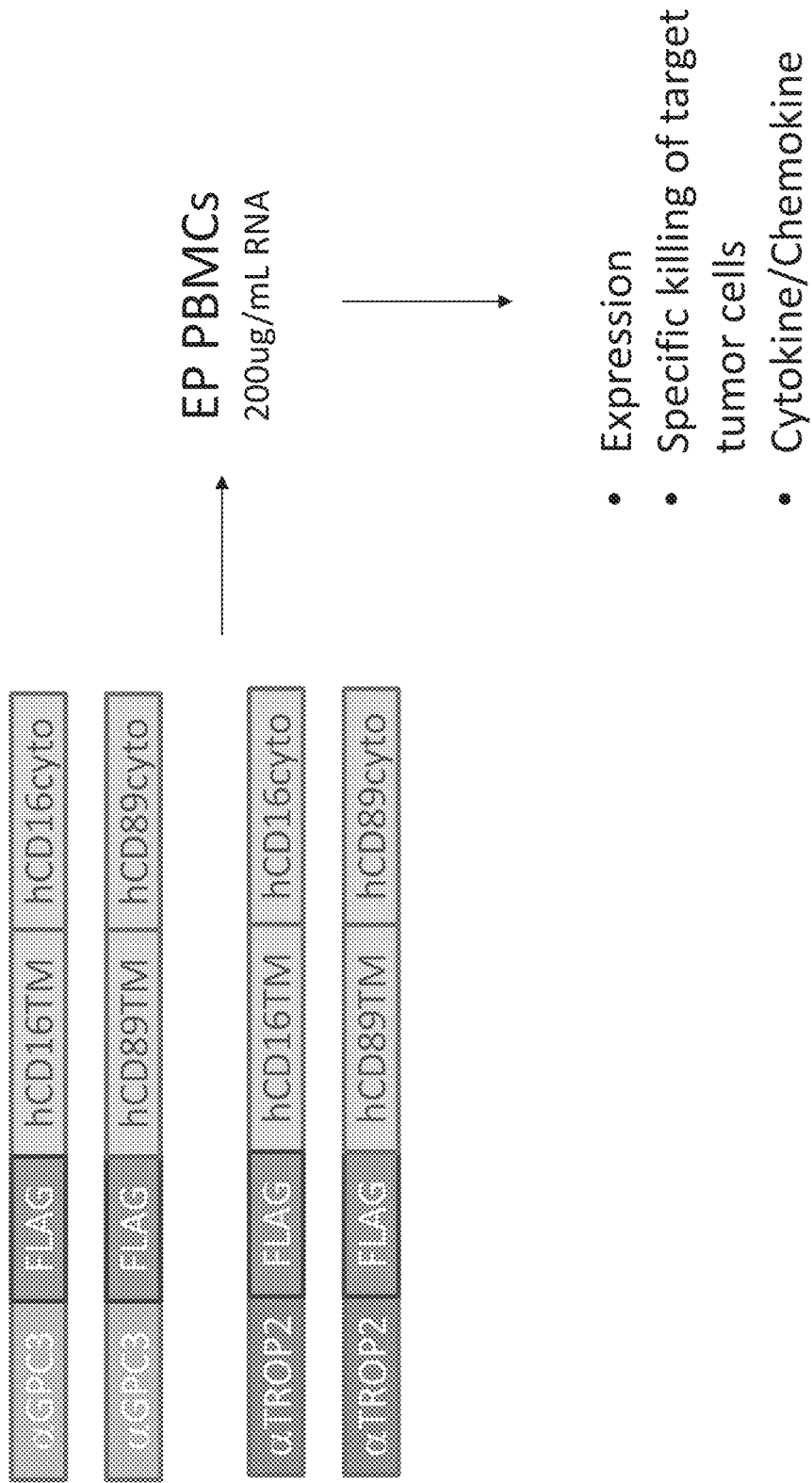
FIG. 9 shows a representative workflow for expression and functional analysis of exemplary CFP constructs, including anti-GPC3 CFP constructs and anti-TROP2 CFP constructs with an anti-GPC3 or anti-TROP2 antibody domain, a FLAG extracellular domain, human CD16 or human CD89 transmembrane (TM) domains and human CD16 or human CD89 intracellular (cyto) domains. As depicted, 200 ug/mL RNA encoding the constructs can be electroporated (EP) into PBMCs and expression, killing of target tumor cells and production of cytokines/chemokines can be analyzed.

This example demonstrates designs of a CFP that targets TROP2 on a cancer cell, and is expressed on a myeloid cell. Shown in FIG. 9 is an exemplary version, which has an extracellular FLAG-tag for in vitro testing purposes. Briefly, one construct consists of an extracellular anti-TROP2 scFv, in this case fused to a FLAG tag, followed by a transmembrane domain of a FcRIIIA (CD16) protein, and a cytoplasmic domain from the same protein. Another construct consists of an extracellular anti-TROP2 scFv, in this case fused to a FLAG tag, followed by a transmembrane domain of a Fc-alpha R (CD89) protein, and a CD89 cytoplasmic domain.

Figure 16:
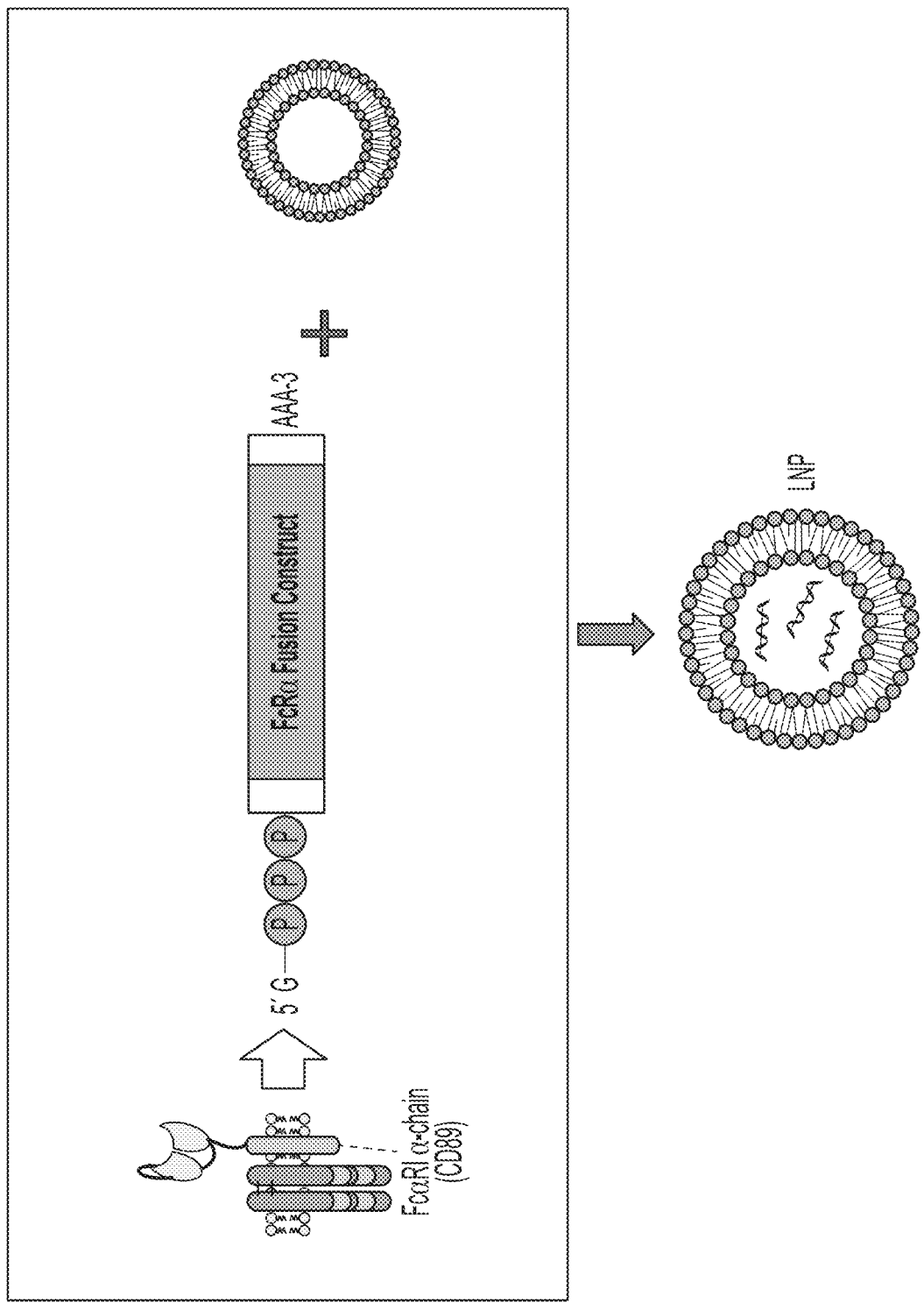
FIG. 16 depicts an exemplary schematic for preparing LNPs containing mRNA encoding various CFP constructs for in vivo delivery.

Also demonstrated in the figure is a simplified experimental plan for electroporation of recombinant mRNA encoding each of the constructs in PBMC and in vitro testing of phagocytosis and cytokine generation. FIG. 16 graphically demonstrates a generalized LNP formulation for in vivo delivery.

Figure 10A:
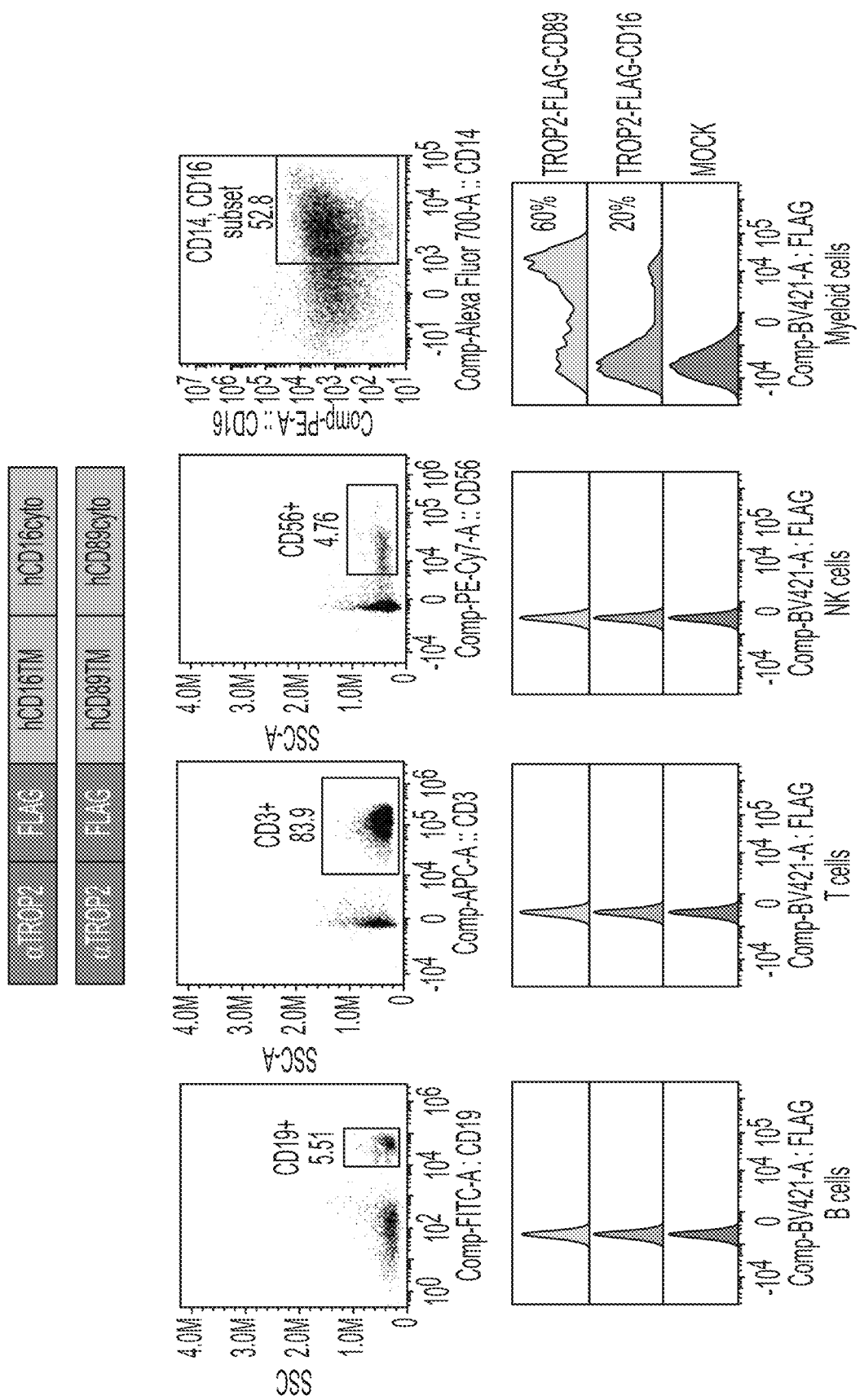
FIG. 10A depicts flow cytometry data analyzing expression of the indicated anti-TROP2 CFP constructs in various cell types. As shown in the bottom panel, expression of the indicated anti-TROP2 CFP constructs was observed in CD14+ myeloid cells, but not in CD19+B cells, CD3+ T cells or CD56+NK cells.
Figure 10B:
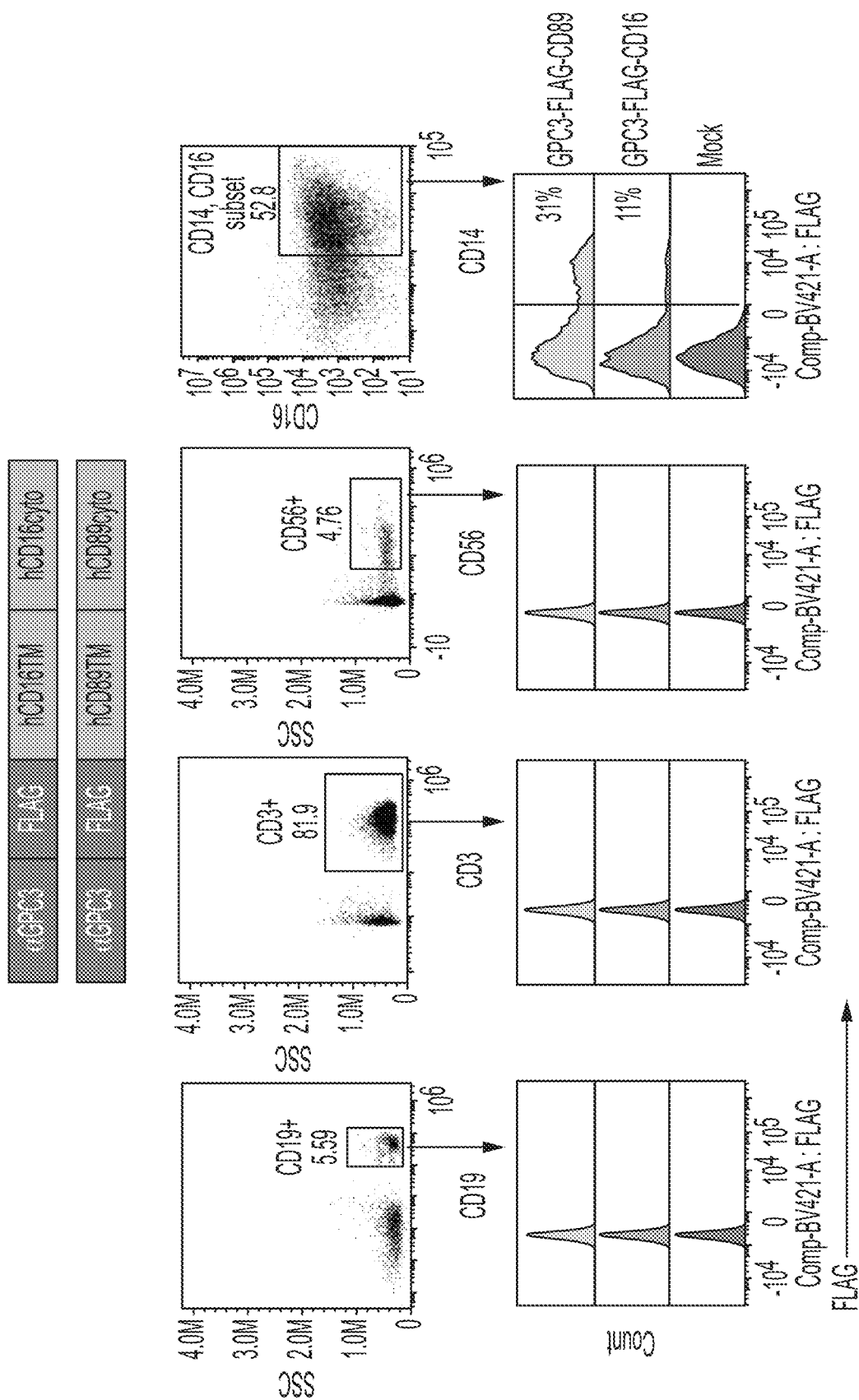
FIG. 10B depicts flow cytometry data analyzing expression of the indicated anti-GPC3 CFP constructs in various cell types. As shown in the bottom panel, expression of the indicated anti-GPC3 CFP constructs was observed in CD14+ myeloid cells, but not in CD19+B cells, CD3+ T cells or CD56+NK cells.

Example 5. TROP2-CD16 and TROP2-CD89 Constructs have Preferential Expression in Myeloid Cells/Monocytes The constructs having the CD16 and CD89 TMDs and TROP2 binder were tested for expression in different cell types, using the FLAG tag for flow cytometry assay. The TROP2 binder, as disclosed also elsewhere is an anti-TROP2 scFV. PBMCs, which is the source for B cells, T cells, NK cells and monocytes were electroporated with TROP2-FLAG-CD16 and TROP2-FLAG-CD89 mRNA and flow cytometry was performed at 24 hours. The data is shown in FIG. 10, which shows that the constructs successfully express preferentially in the monocytes (extreme right) and expression was not detected in CD19+(B cells), CD3+ (lymphocytes), or CD56+(NK cells). CD89 based constructs show higher expression than CD16 based constructs, with over 60% gated cells showing TROP2-FLAG-CD89 constructs.

Example 6. TROP2-CD16 and TROP2-CD89 Cells Showed Target Cell Phagocytosis

Figure 11A:
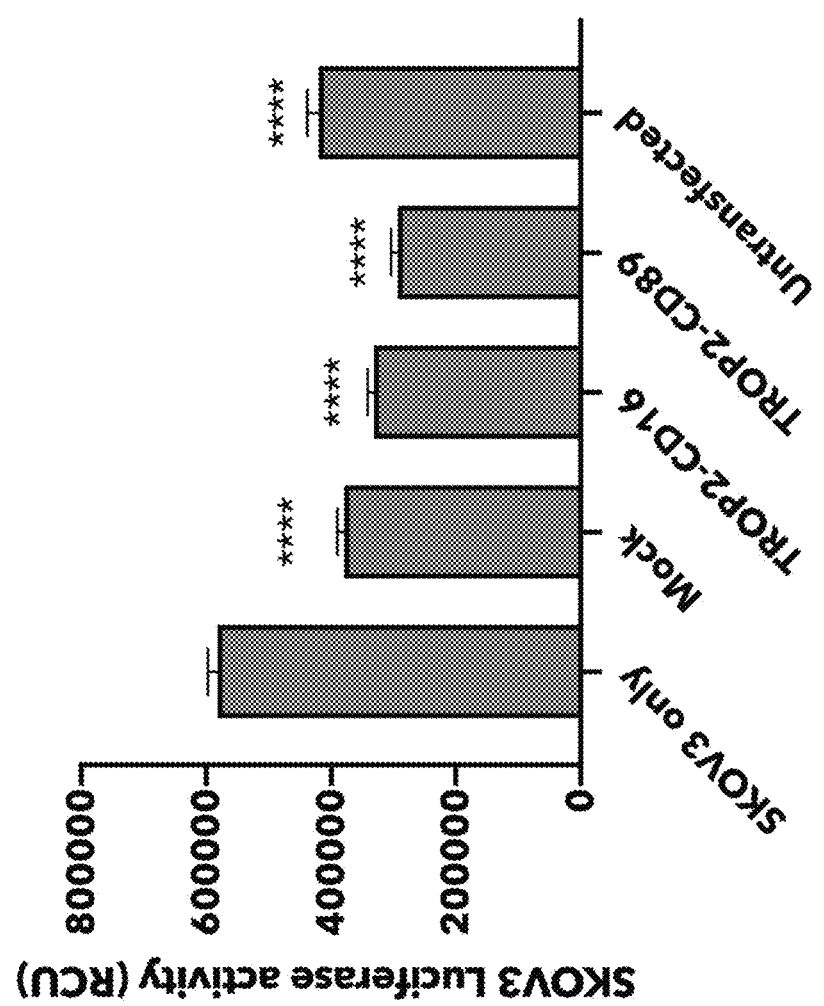
FIG. 11A depicts data from a luciferase assay to measure killing of SKOV3 cells by PBMCs transfected with the indicated anti-TROP2 CFP constructs. PBMCs transfected with the indicated anti-TROP2 CFP constructs were cocultured with SKOV3-Luc cells at an effector cell:target cell ratio of 5:1 for 3 days. PBMCs transfected with the indicated anti-TROP2 CFP constructs demonstrated specific killing of SKOV3 cells compared to controls.
Figure 11B:
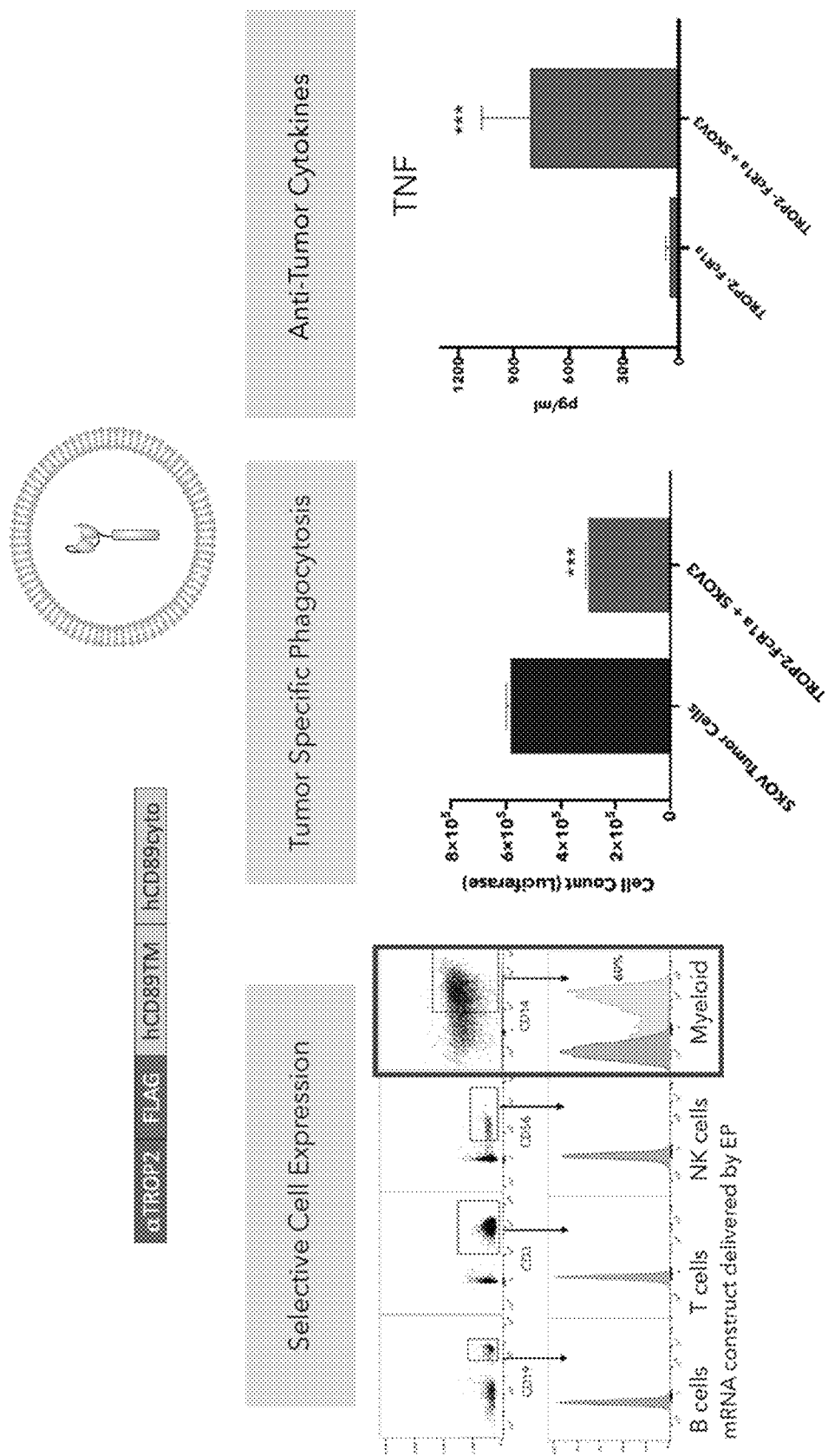
FIG. 11B depicts data analyzing expression, tumor specific phagocytosis and anti-tumor cytokine production using myeloid cells contacted with an LNP containing an mRNA encoding the indicated anti-TROP2 CFP construct. The left panel depicts flow cytometry data analyzing expression of the indicated anti-TROP2 CFP construct in various cell types contacted with an LNP containing an mRNA encoding the indicated anti-TROP2 CFP construct. Expression of the indicated anti-TROP2 CFP constructs was observed in CD14+ myeloid cells, but not in CD19+B cells, CD3+ T cells or CD56+NK cells. The middle panel depicts a graph of data from a luciferase assay to measure killing of SKOV3 cells by PBMCs contacted with an LNP containing an mRNA encoding the indicated anti-TROP2 CFP construct. PBMCs contacted with an LNP containing an mRNA encoding the indicated anti-TROP2 CFP construct and cocultured with SKOV3-Luc cells demonstrated specific killing of SKOV3 cells compared to control. The right panel depicts a graph of TNF-alpha production of the samples from the middle panel.

PBMCs electroporated with TROP2 constructs were tested for effect on phagocytosis of tumor cells in vitro. Target tumor cells used were SKOV3 cell line expressing a luciferase. Mock transfected monocytes and untransfected monocytes showed a basal level of phagocytosis, determined by the reduction in luciferase activity. Cells expressing the two TROP2 CFPs showed statistically significant reduction in luciferase activity compared to these controls, which shows that expression of the constructs increase phagocytosis capability of the cells (FIG. 11).

Figure 12A:
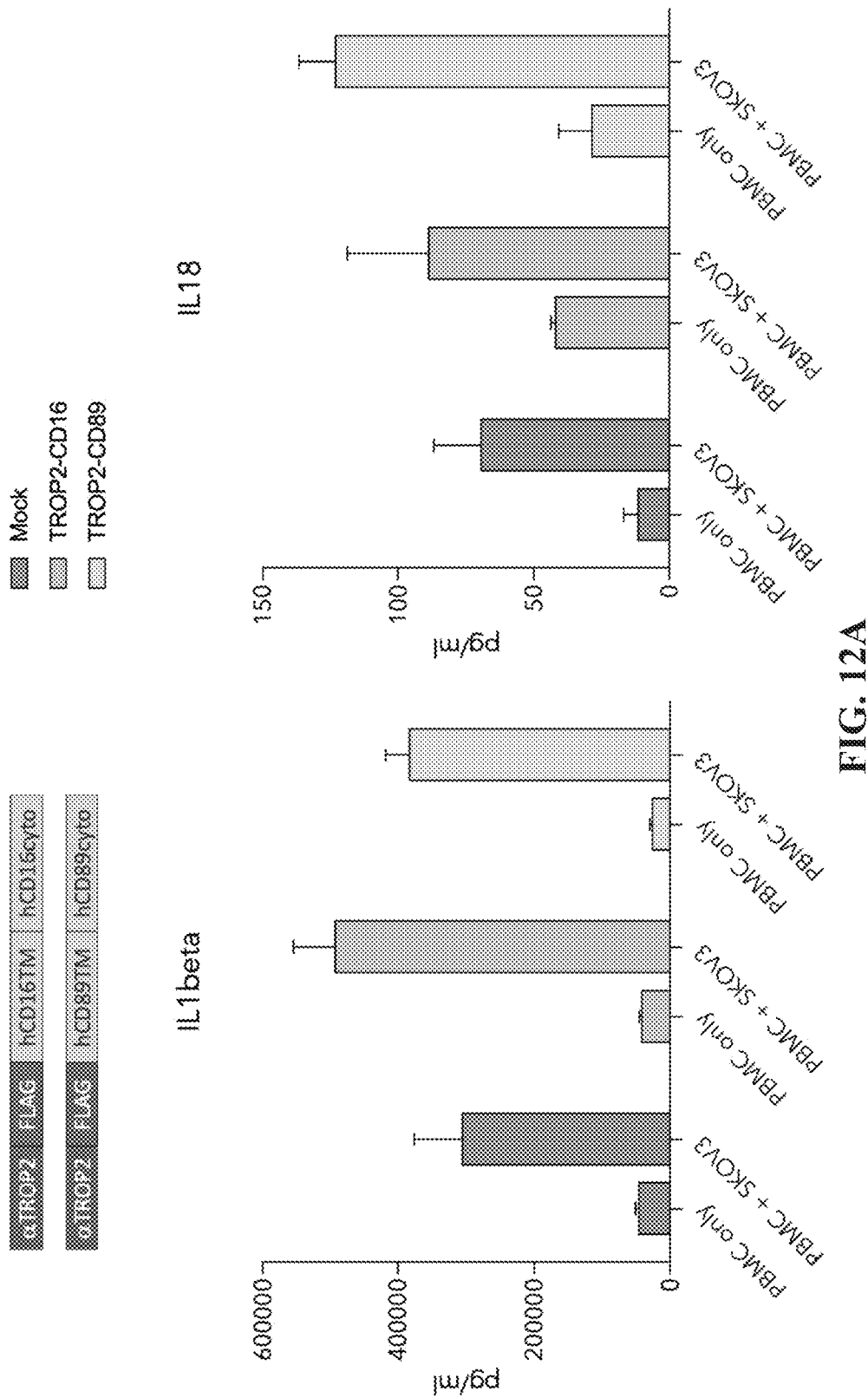
FIG. 12A depicts data of cytokine production using myeloid cells contacted with an LNP containing an mRNA encoding the indicated anti-TROP2 CFP constructs. Graphs of IL-1beta and IL-18 production from samples in which PBMCs contacted with an LNP containing an mRNA encoding the indicated anti-TROP2 CFP construct were cultured alone or cocultured with SKOV3 cells are shown.
Figure 12B:
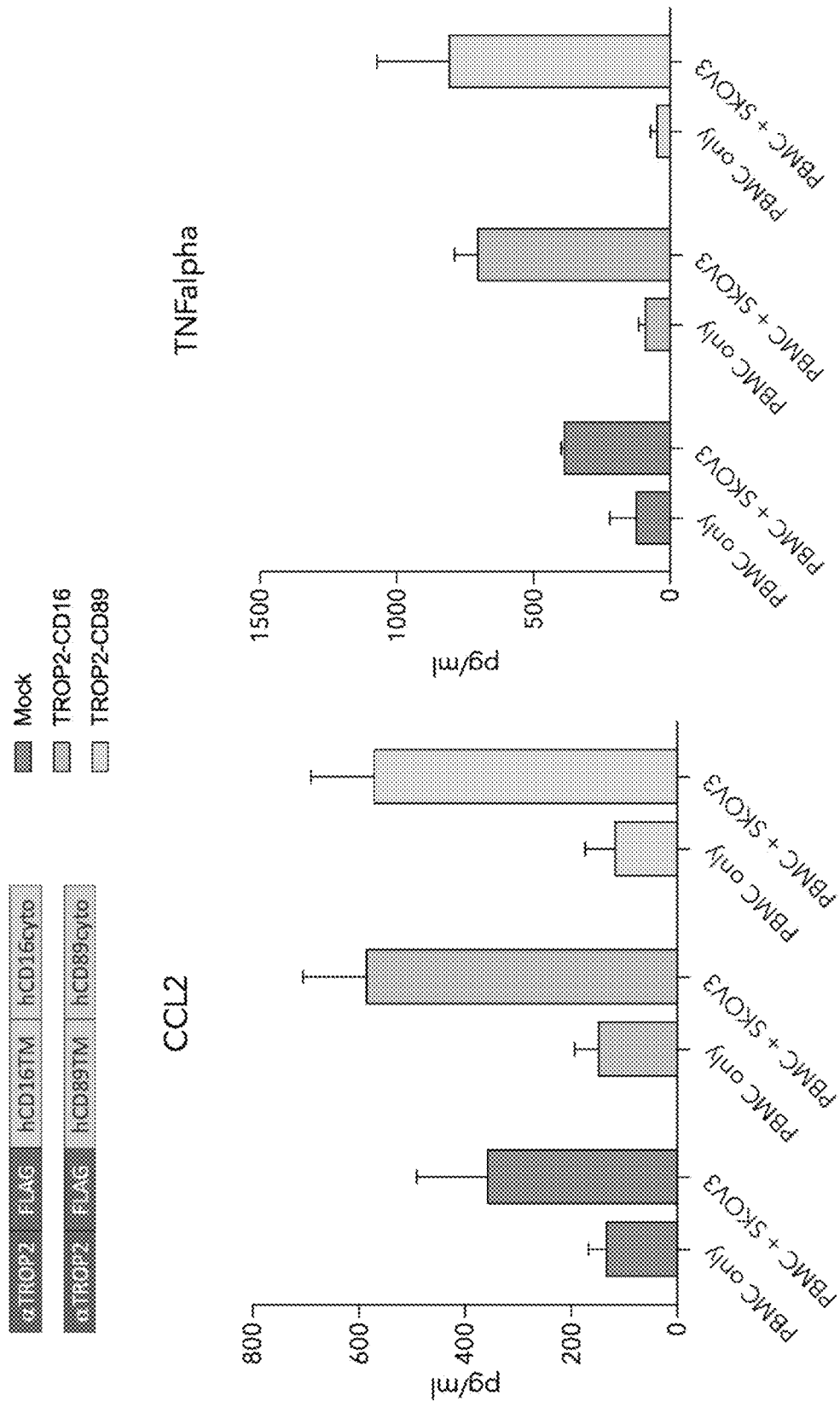
FIG. 12B depicts data of cytokine production using myeloid cells contacted with an LNP containing an mRNA encoding the indicated anti-TROP2 CFP constructs. Graphs of CCL2 and TNF-alpha production from samples in which PBMCs contacted with an LNP containing an mRNA encoding the indicated anti-TROP2 CFP construct were cultured alone or cocultured with SKOV3 cells are shown.
Figure 12C:
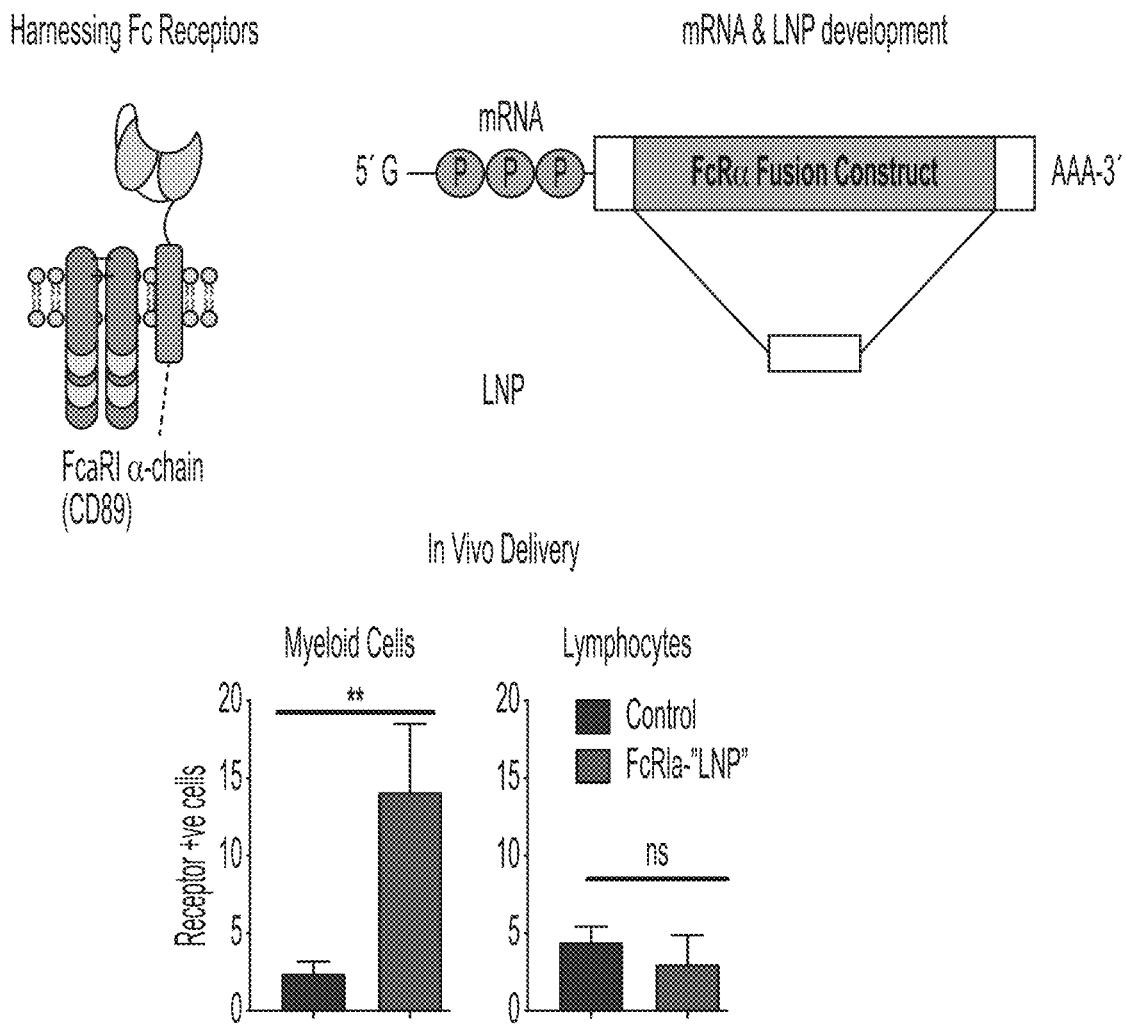
FIG. 12C shows a schematic of successful harnessing of CD89 (FcR alpha chain) to drive myeloid cell specific in vivo programming. An mRNA encoding a CFP with an scFv attached to CD89 was formulated in an LNP and injected into mice. A graph of the percentage of myeloid cells and lymphocytes expressing the CFP is shown. Expression of the CFP was observed in CD14+ myeloid cells, but not in lymphocytes compared to control.

Cytokine expression was examined in the results shown in the TROP2-FLAG-CD16 and TROP2-FLAG-CD89-expressing cells both in presence and absence the target SKOV3 cells. Data depicted in FIGS. 12A and 12B show that expression of the TROP2-CD16 and TROP2-CD89 constructs do not exhibit tonic signaling in monocytes. This is demonstrated by the fact that cytokine or chemokine expression (IL-1b, IL-18, or TNF-alpha, or chemokine CCL2), were induced in presence of the target cells (SKOV3), that is upon engagement of ECD of the CFP with its target. In absence of the target cells, no induction or negligible induction of the cytokines were evident. These results suggest specific, myeloid targeted CFPs have been generated that can bind to TROP2 on cancer cells, and activate the myeloid cells for targeted destruction of the targeted cancer cells, and that further development towards a therapeutic composition can be carried out with these constructs.

Figure 13A:
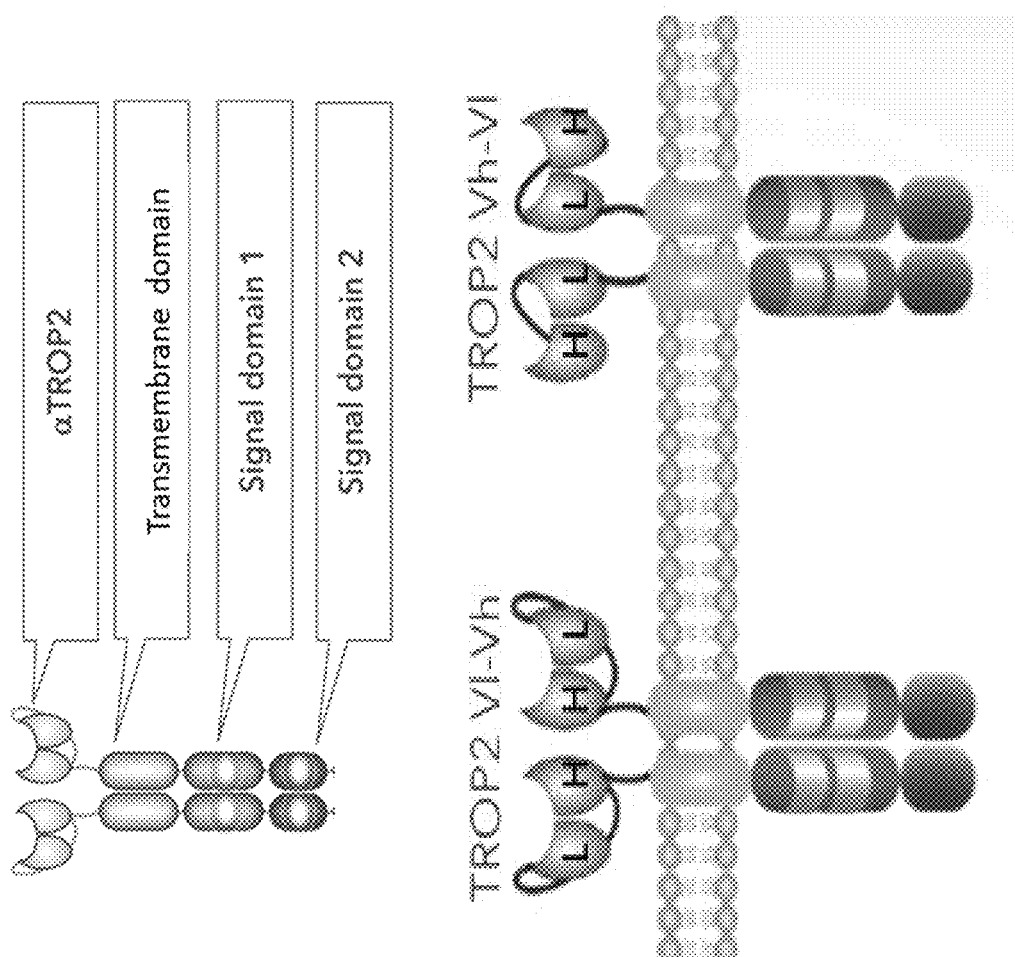
FIG. 13A depicts exemplary schematics of different VH and VL domain configurations for two exemplary anti-TROP2 CFP constructs with an scFv.
Figure 13B:
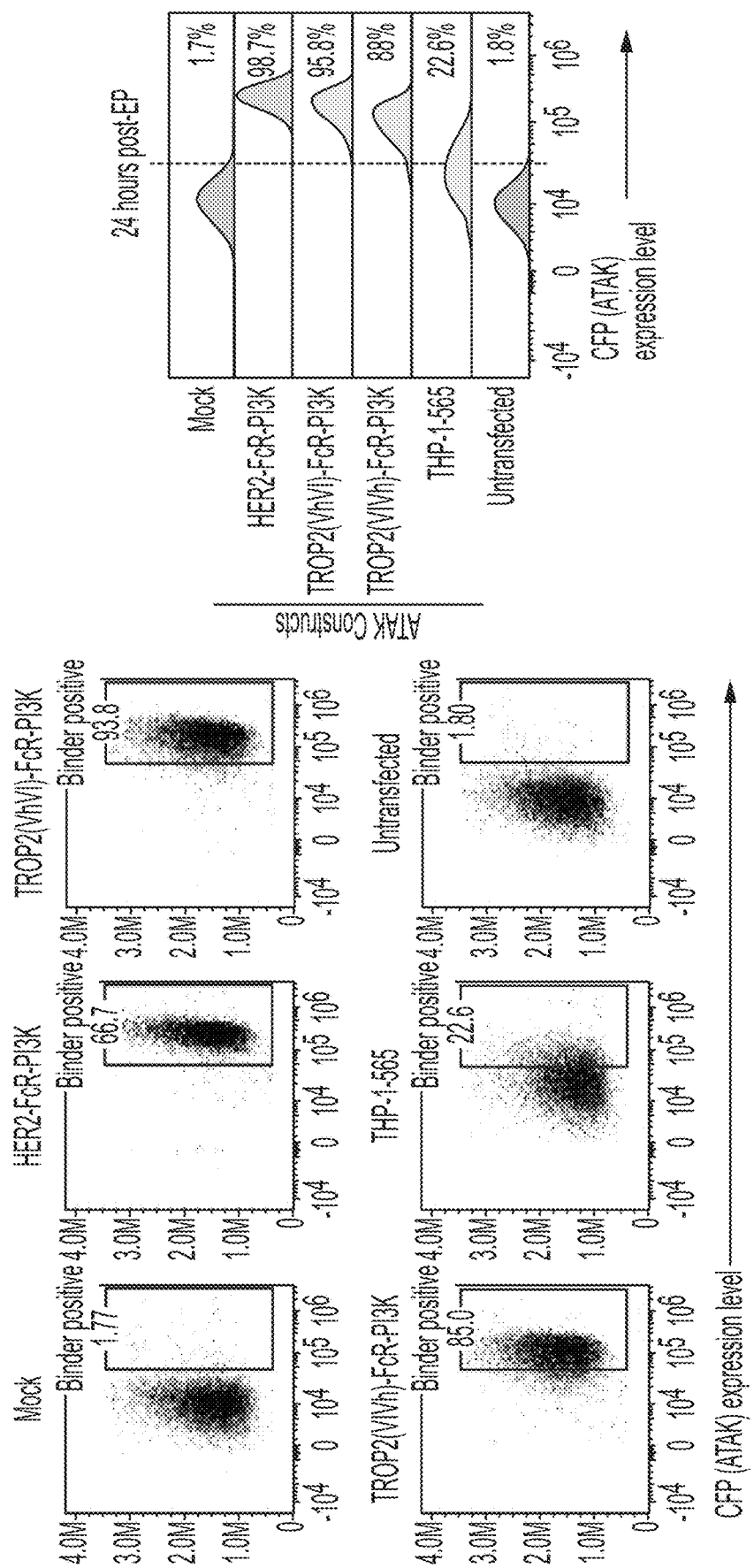
FIG. 13B depicts exemplary flow cytometry data showing the effects of the different VH and VL domain configurations for the two exemplary anti-TROP2 CFP constructs with an scFv shown in FIG. 13A on expression in THP-1 cells electroporated with RNA encoding the indicated CFP constructs.
Figure 13C:
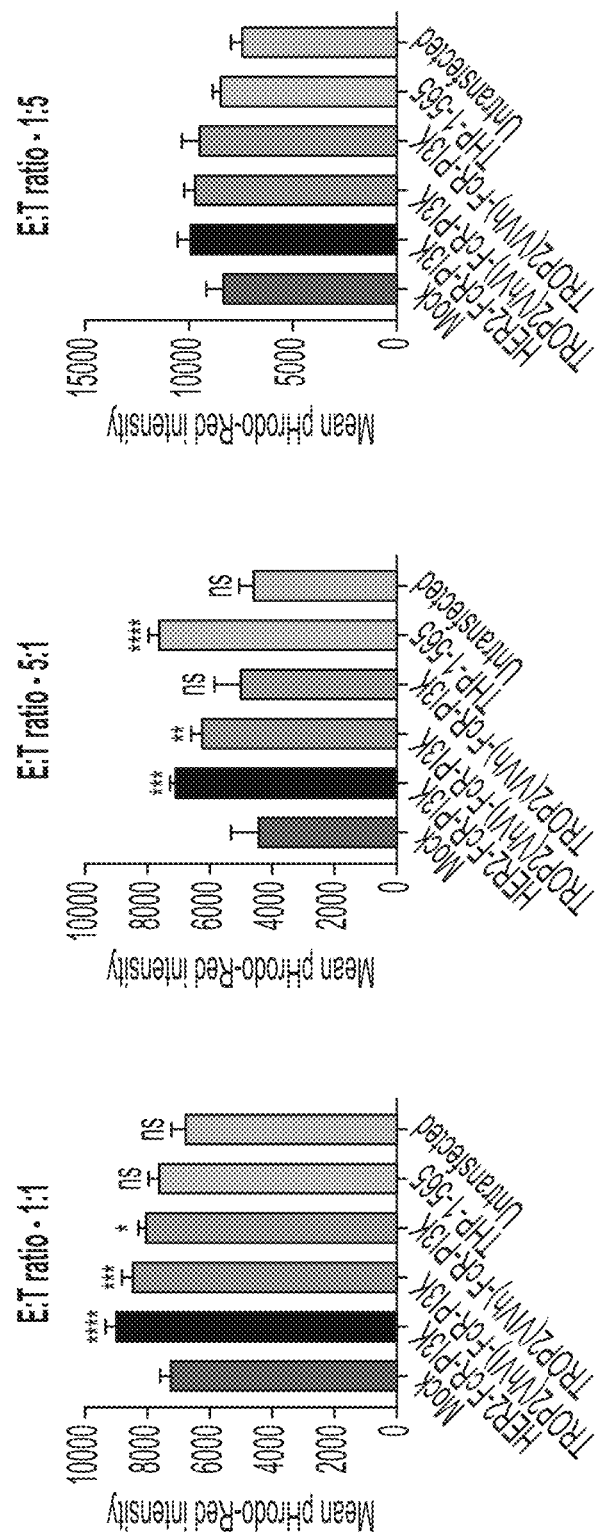
FIG. 13C depicts exemplary graphs showing phagocytosis of SKOV3 cells by THP-1 cells expressing the indicated constructs indicated in the X-axis, quantified by pHrhodo Red signal increase, at the indicated effector:target cell (E:T) ratios.

It was then tested whether orientation of the VH and the VL of the scFv that binds to TROP2 makes a difference in the expression levels. FIG. 13A illustrates the constructs having VL-VH (left) and VH-VL (right) orientations. Exemplary VL-VH scFv has a sequence of SEQ ID NO: 34. Exemplary VH-VL scFv has a sequence of SEQ ID NO: 35. Expression of VH-VL constructs show higher expression in both THP-1 cells (FIG. 13B) and primary monocytes (data not shown). Also, THP-1 cells expressing the VH-VL constructs showed a slightly higher phagocytic ability than the VL-VH constructs (FIG. 13C). TROP2 binding CFP constructs comprising a combination of transmembrane and intracellular domains were constructed. TROP2-CD8hinge-CD8TM-FcRγ-PI3K construct was generated such that the transmembrane domain (TMD) is a TM domain comprising a CD8 hinge and TM domain, and a intracellular domain comprising a Fc receptor γ-chain and PI3Kinase recruitment domain. Likewise, TROP2-FcR-41BB construct was generated as having a CD8 hinge and TM domain, and a CD137 (4-1BB) intracellular domain; TROP2-41BB-FcR construct was generated as having a CD8 hinge and TM domain, and an FcRγ intracellular domain a CD137 (4-1BB) intracellular domain. TROP2-CD40-FcR was constructed using a CD8 hinge and TM domain, CD40 intracellular domain, and an FcR intracellular domain. TROP2-FcR-MDA5 was constructed a CD8 hinge and TM domain, and an FcRγ intracellular domain a MDA5 tandem CARD domains. TROP2-CD64 and TROP2 CD89 constructs were generated as having CD64 or CD89 TM domain and intracellular domains, and require dimerization or multimerization with endogenous FcR γ-chain to transmits intracellular signaling. THP-1-565 cell line that stably express HER2-CD8hinge-CD8TM-FcRγ-PI3K and other constructs for testing phagocytosis potential in vitro.

Figure 13D:
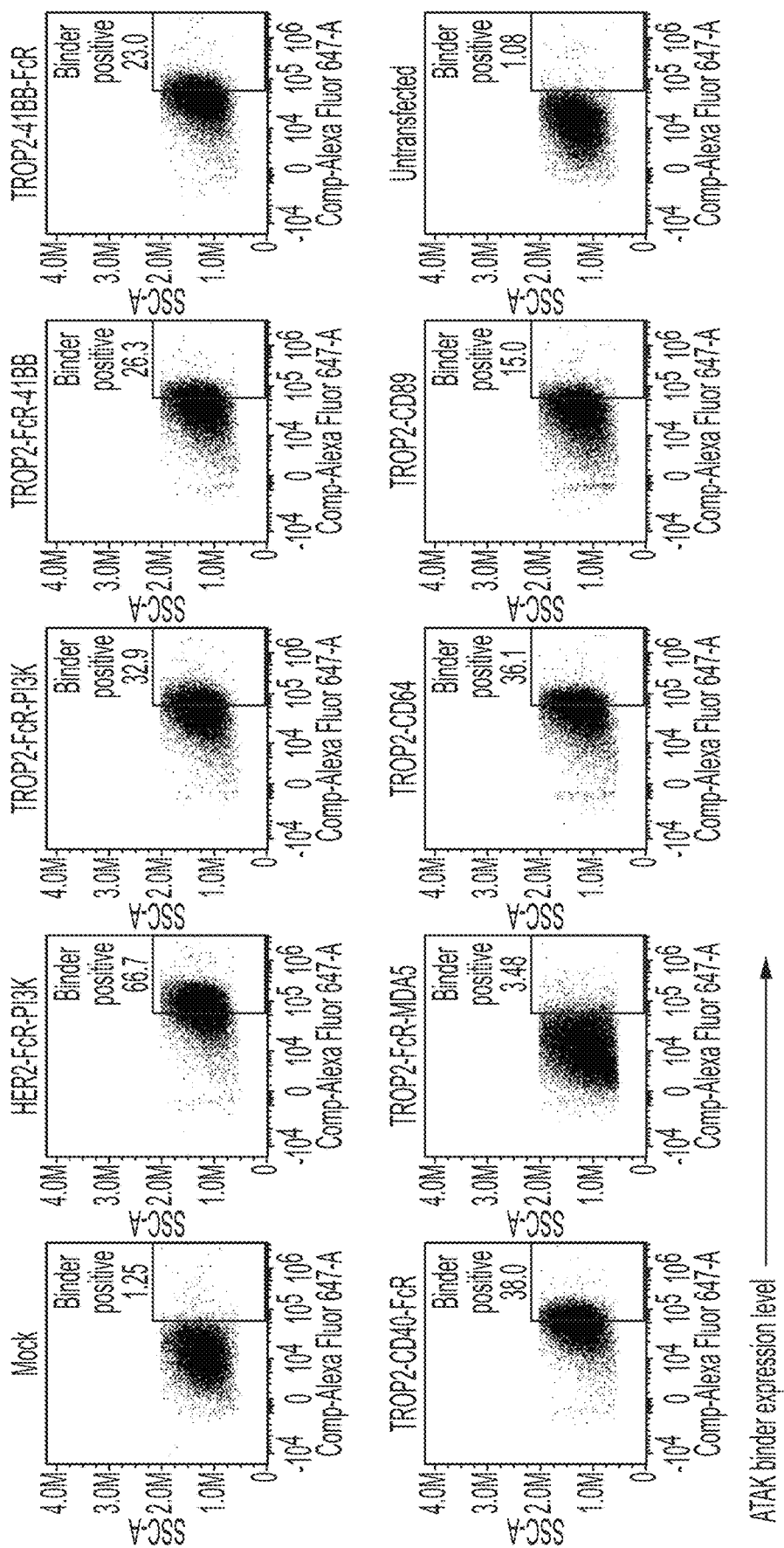
FIG. 13D depicts exemplary flow cytometry data showing expression of the indicated anti-TROP2 CFP constructs with the indicated transmembrane and intracellular domain combinations. Mock-transfected and an anti-HER2 CFP construct transfected set serve as a negative and positive control, respectively.
Figure 13E:
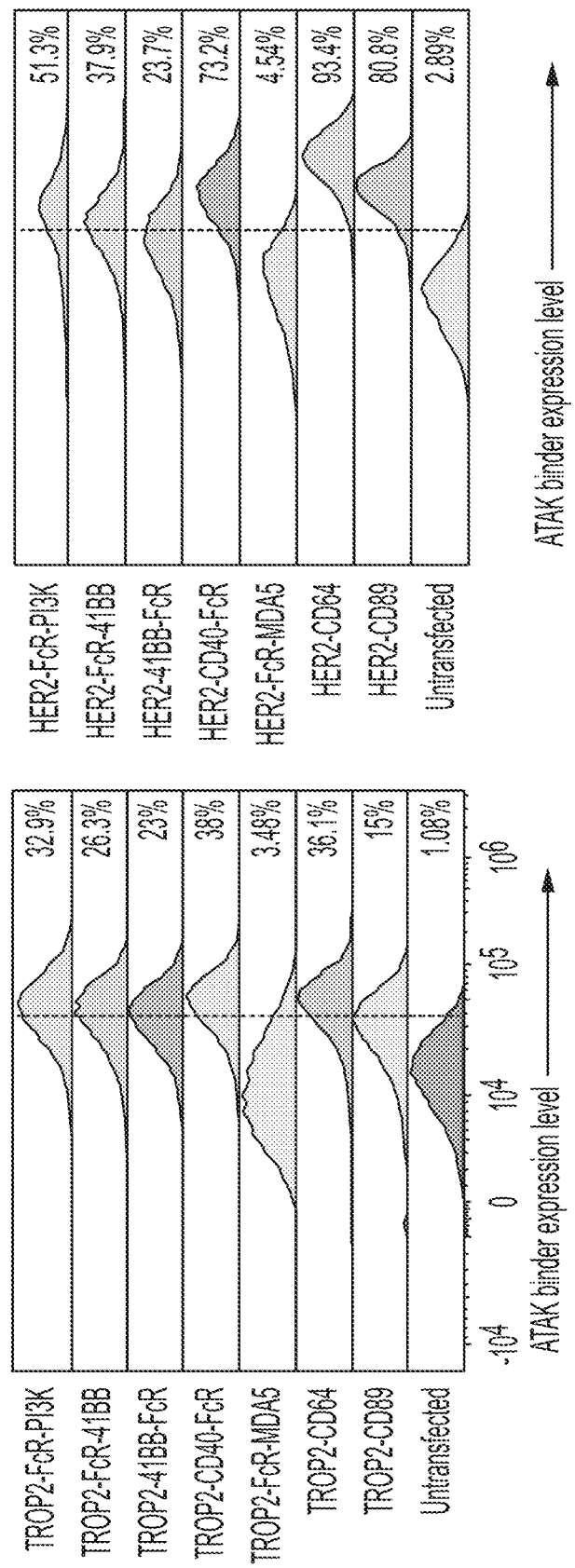
FIG. 13E depicts exemplary data showing expression of the indicated anti-HER2 (right) and anti-TROP2 (left) CFP constructs with the indicated transmembrane and intracellular domain combinations.

FIG. 13D shows flow cytometry data indicating expression of the constructs. Each of the TROP2-binder constructs have lower expression level compared to a HER2-binder CFP construct. FIG. 13E shows a direct comparison by flow cytometry detection of expression levels of each TROP2 binder and HER2 binder constructs.

Example 7. GP75 Targeted CAR-P Constructs and Expression

Figure 14A:
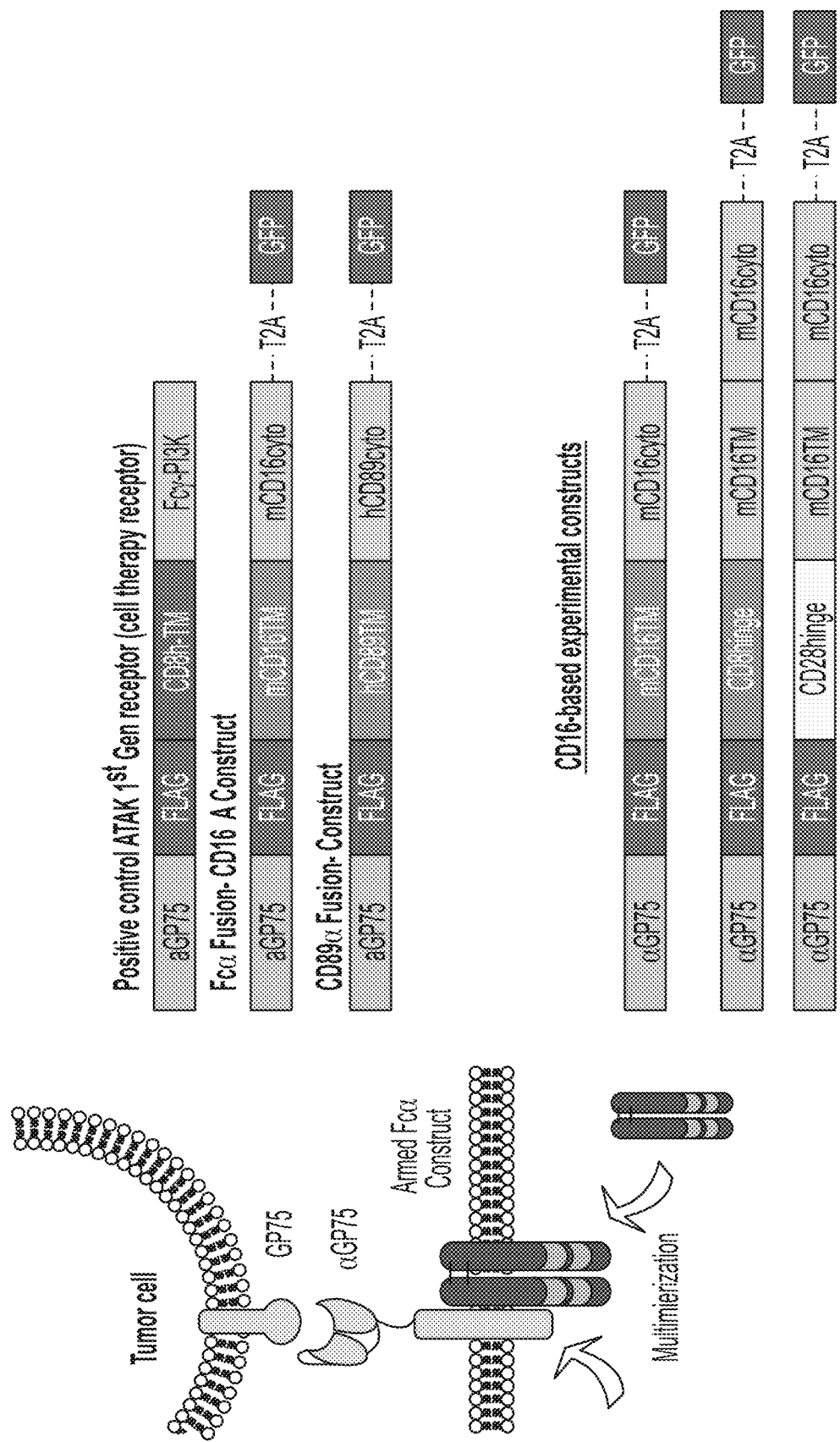
FIG. 14A depicts schematics of exemplary anti-GP75 (αGP75) CFP constructs. An exemplary anti-GP75-FLAG-hCD8-Fcg-PI3K construct ($1^{st}$ gen ATAK receptor) is shown on top. Each of the other anti-GP75 CFP constructs depicted contain sequences encoding the indicated domains and a sequence encoding GFP separated from the sequence encoding the intracellular domain by a T2A peptide encoding sequence are depicted. The graphic on the left depicts multimerization of the CD16 transmembrane domain or the CD89 transmembrane domain of the anti-GP75 CFP constructs with endogenous Fcγ receptor proteins and binding of the anti-GP75 CFP constructs to GP75 antigen on a tumor cell.

GP75 is a melanosomal glycoprotein expressed in both melanomas and normal melanocytes. GP75 can be expressed on the cell surface as well as intracellularly in human and mouse melanomas. Chimeric fusion proteins having GP75-binding domains were constructed for testing in cells and animal models. Experimental constructs were designed for testing expression, having an extracellular FLAG domain that does not interfere with anti-GP75 binding extracellular domain of a chimeric receptor, as shown in FIG. 14A. In one construct, a CD8 hinge and transmembrane domain is fused to the extracellular anti-GP75-ScFv-FLAG sequence. An Fcγ domain is included as an ICD. A PI3Kinase recruitment domain is incorporated in the ICD. An exemplary set of CFP constructs were generated having anti-GP75 extracellular binding domain, with CD16 or CD89 transmembrane regions as shown in FIG. 14A. In some constructs, CD16 and CD89 domains have their entire cytoplasmic portion. A GFP encoding sequence is tagged at the cytosolic end separated from the cytosolic domain of the chimeric fusion protein (CFP) by a sequence encoding a self-cleavable peptide, T2A. For mouse specific expression and mouse in vivo experiments, sequence encoding mouse CD16 or CD89 transmembrane domains were incorporated instead of human sequences. Constructs comprising the corresponding human CD89 were also designed and prepared.

Some exemplary CD16 based anti-GP75-FLAG constructs with varying hinge/TM and ICD for experimentation were generated to test the effect of the hinge domains on the expression levels, as specifically shown in the lower panel of FIG. 14A. Constructs ranged from lacking a hinge domain (MYL157), to having a CD8 hinge domain (MYL184), to having a CD28 hinge domain (MYL185). Other constructs not shown here include anti-GP75-FLAG-hCD89 TM-hCD89 ICD (MYL158).

Figure 14B:
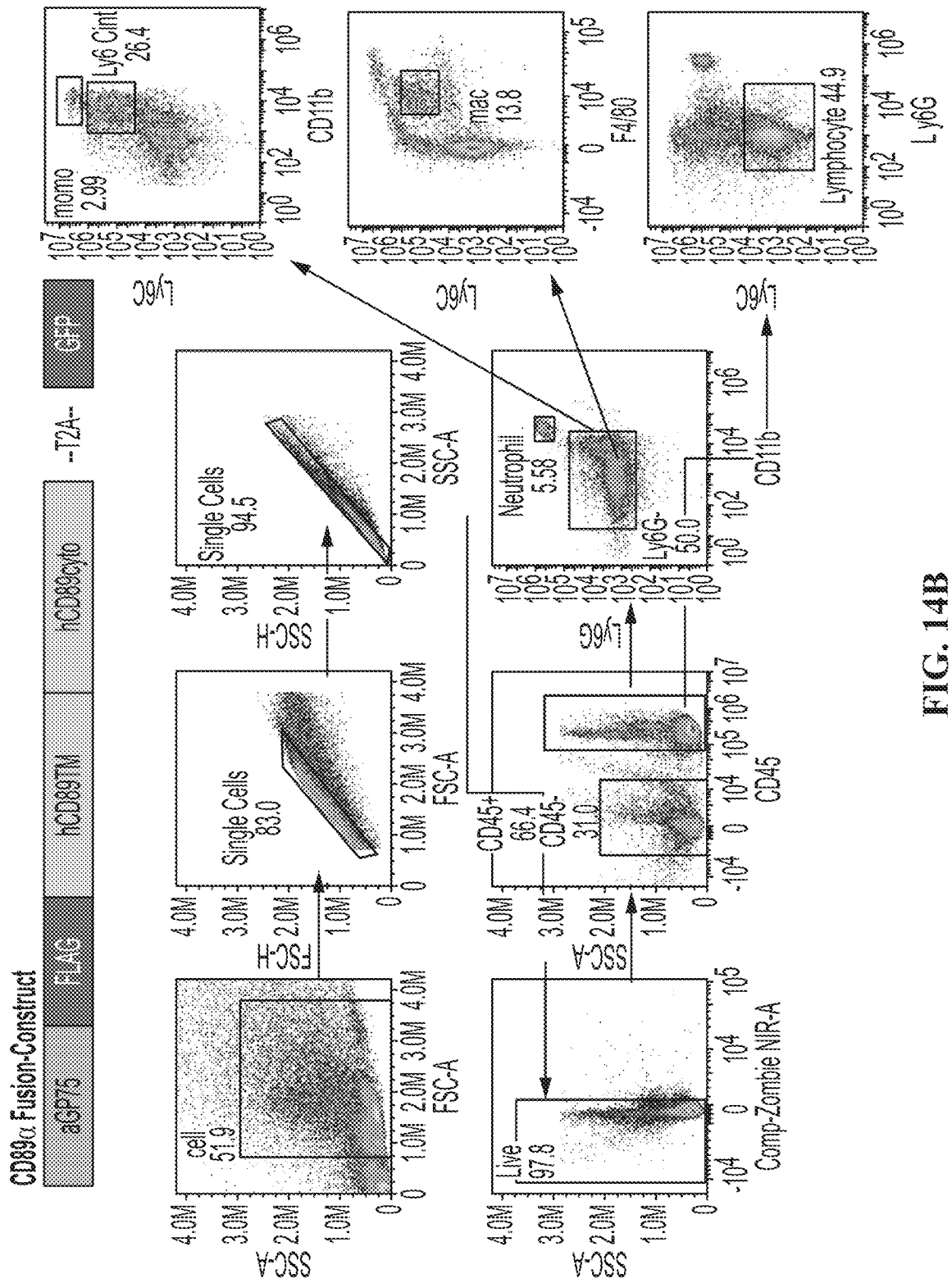
FIG. 14B depicts an exemplary flow cytometry gating strategy used to analyze expression of the indicated CFP construct in various types of mouse lung cells in vivo after injection of LNPs containing RNA encoding the indicated CFP construct into mice.
Figure 14C:
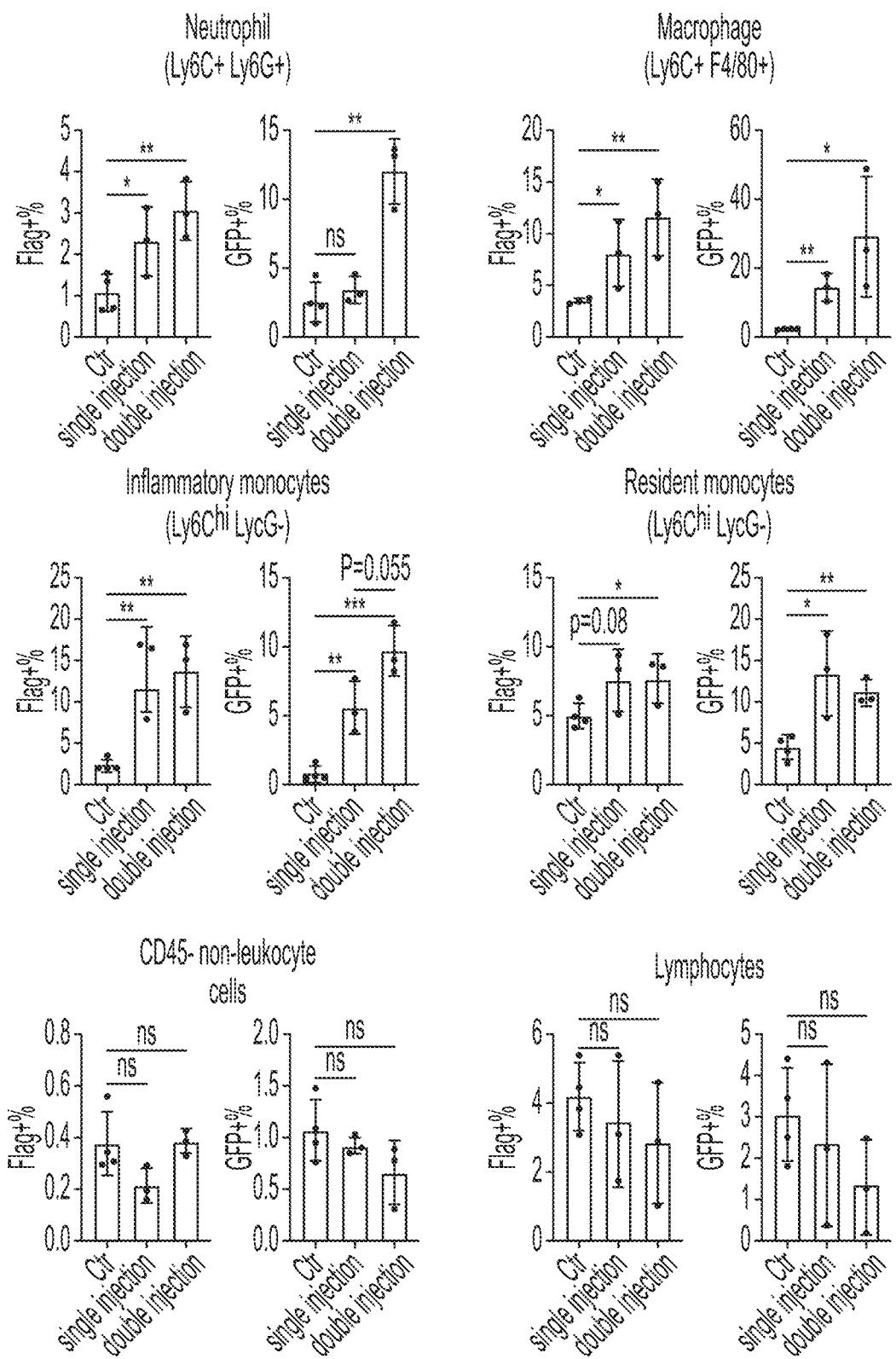
FIG. 14C depicts graphs of expression of a CFP construct as measured by percent cells positive for GFP fluorescence or flag expression as measured by immunoassay in the indicated types of mouse lung cells in vivo after a single or double injection of LNPs containing RNA encoding the CFP construct into mice and flow cytometry analysis according to the gating strategy depicted in FIG. 14B. Expression was observed in myeloid cells of the lung, but not in lymphocytes or CD45– cells.
Figure 14D:
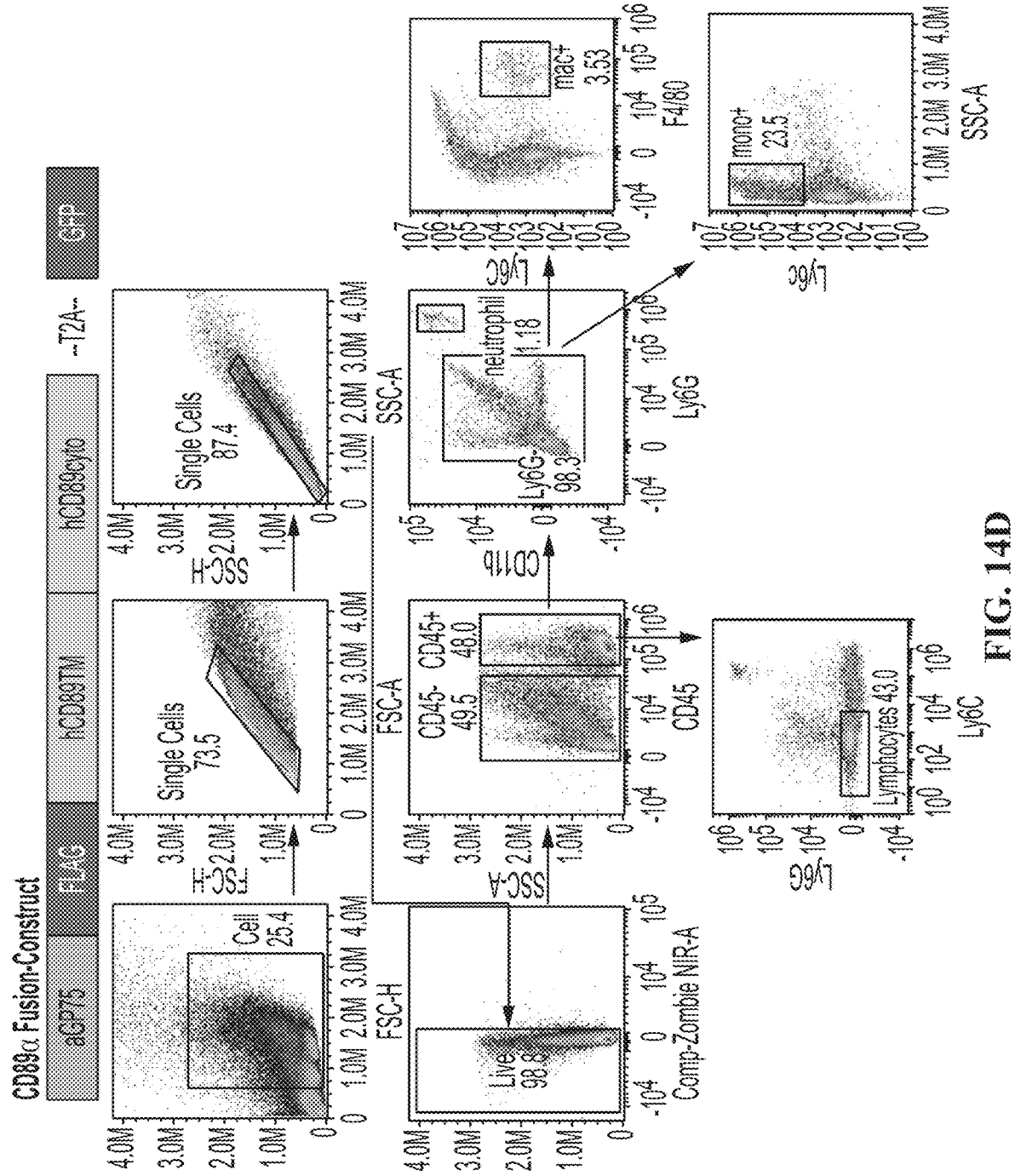
FIG. 14D depicts an exemplary flow cytometry gating strategy used to analyze expression of the indicated CFP construct in various types of mouse liver cells in vivo after injection of LNPs containing RNA encoding the indicated CFP construct into mice.
Figure 14E:
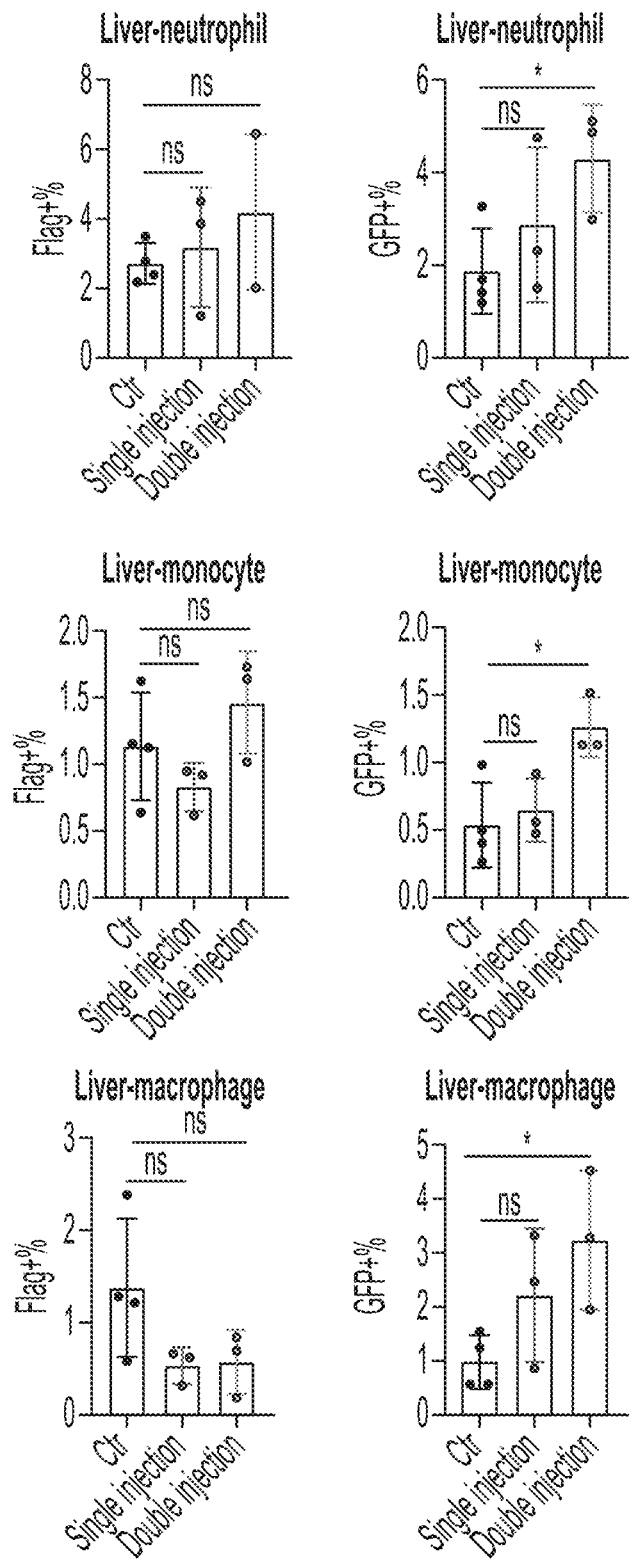
FIG. 14E depicts graphs of expression of a CFP construct as measured by percent cells positive for GFP fluorescence or flag expression as measured by immunoassay in the indicated types of mouse liver cells in vivo after a single or double injection of LNPs containing RNA encoding the CFP construct into mice and flow cytometry analysis according to the gating strategy depicted in FIG. 14D. Expression was observed in myeloid cells of the liver.
Figure 14F:
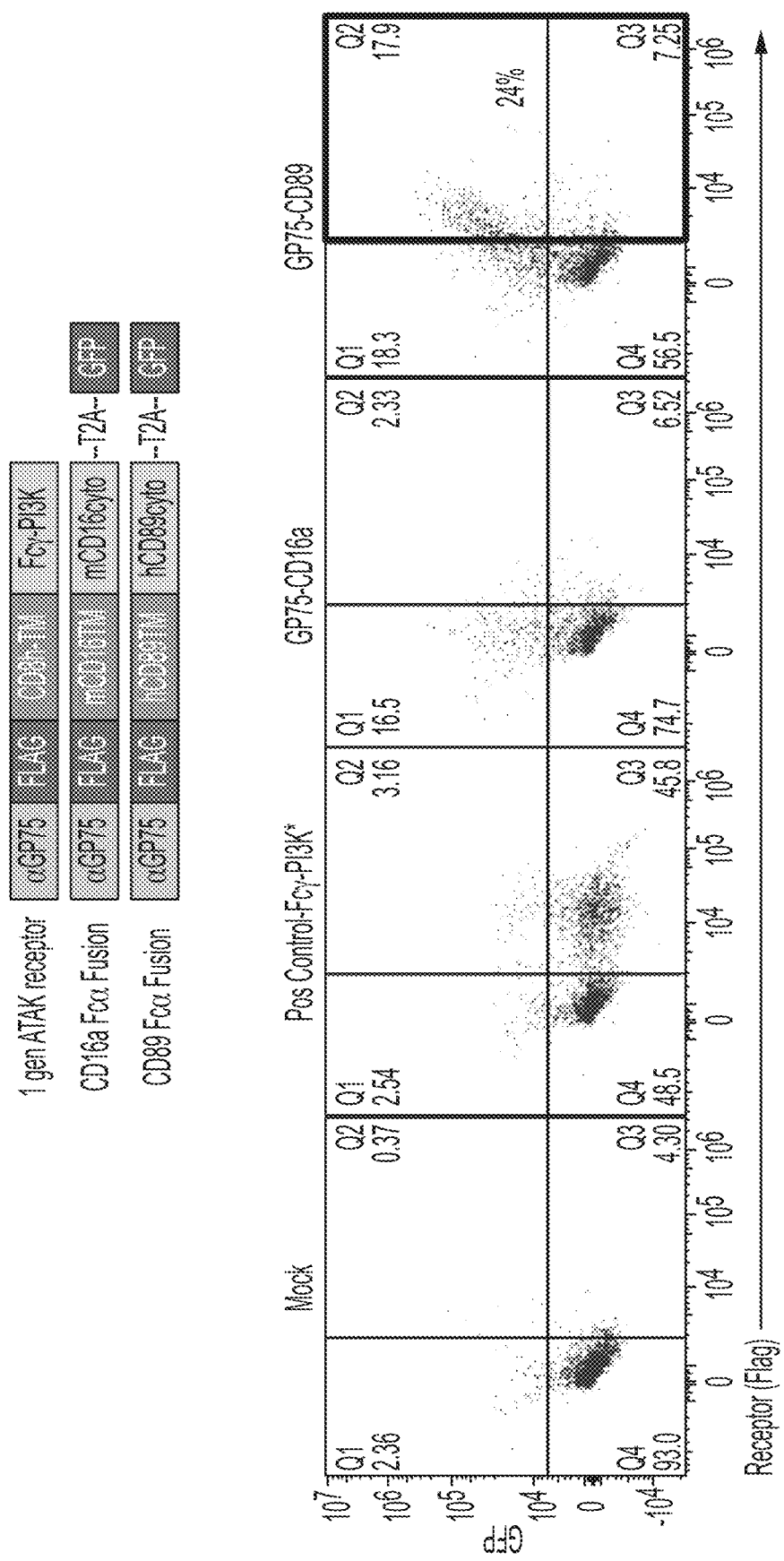
FIG. 14F depicts exemplary flow cytometry data showing expression of the indicated anti-GP75 CFP constructs in mouse monocytes contacted in vitro with an LNP containing an mRNA encoding the CFP constructs.
Figure 15A:
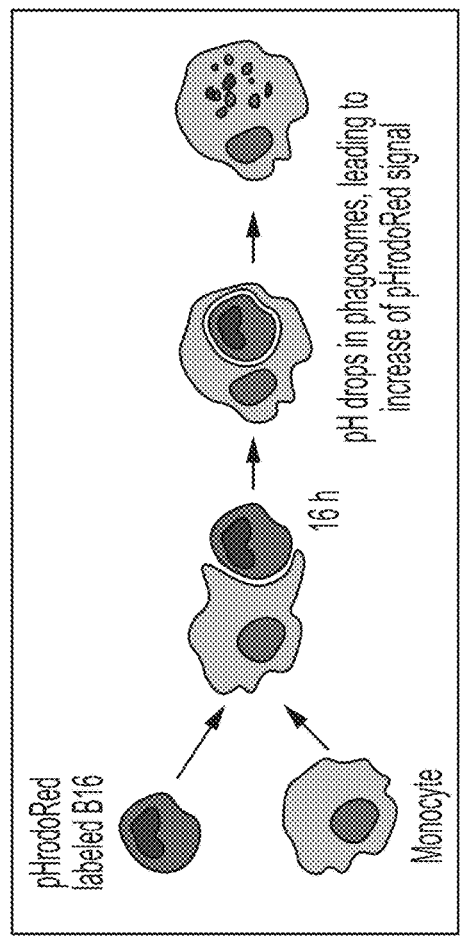
FIG. 15A depicts an exemplary in vitro assay to measure phagocytosis of pHrhodoRed labeled B16 cells by myeloid cells expressing anti-GP75 CFP constructs. The myeloid cells had been contacted with (e.g., electroporated with) LNPs containing mRNA encoding the CFP construct. The depicted flow cytometry data shows CD11b positive monocyte phagocytosis the pHrhodoRed labeled B16 cells.
Figure 15A:
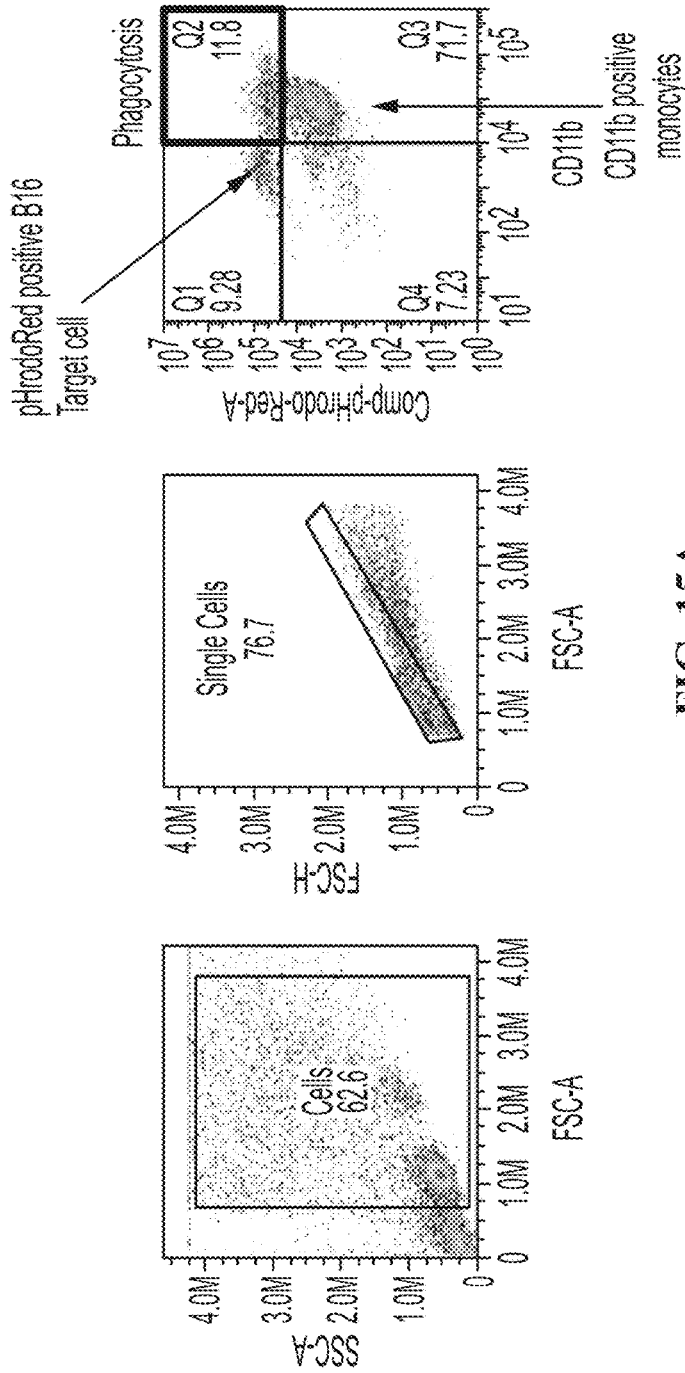
Figure 15B:
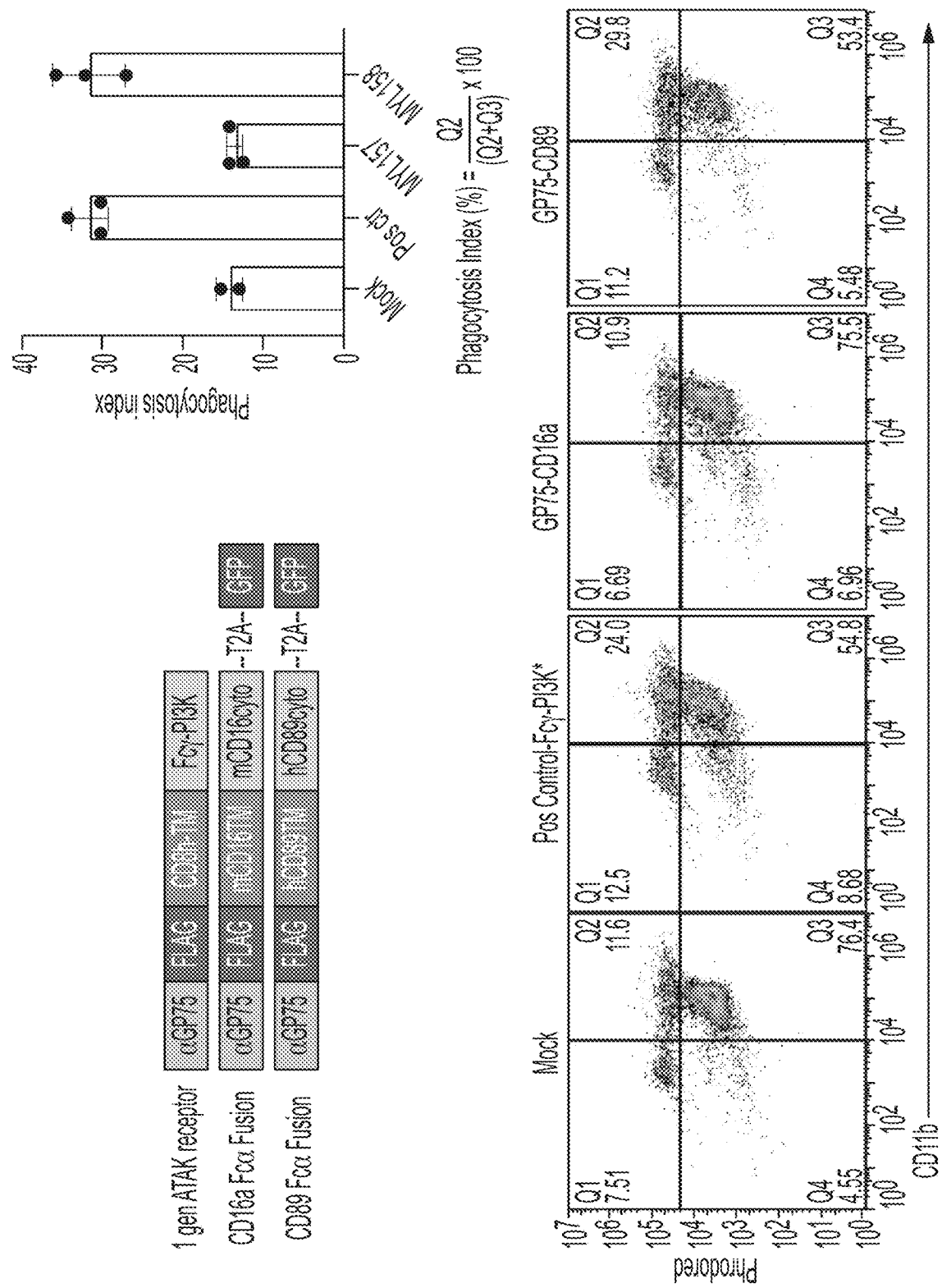
FIG. 15B depicts exemplary data using monocytes expressing the indicated anti-GP75 CFP constructs after being electroporated with LNPs containing mRNA encoding the CFP construct using the assay described in FIG. 15A. A graph of phagocytosis index and flow cytometry data is shown. MYL157 construct=αGP75-FLAG-mouse CD16 TMD-mouse CD16 ICD-T2A-GFP (also depicted as GP75-CD16a). MYL158 construct=αGP75-FLAG-mouse CD89 TMD-mouse CD89 ICD-T2A-GFP (also depicted as GP75-CD89).
Figure 15C:
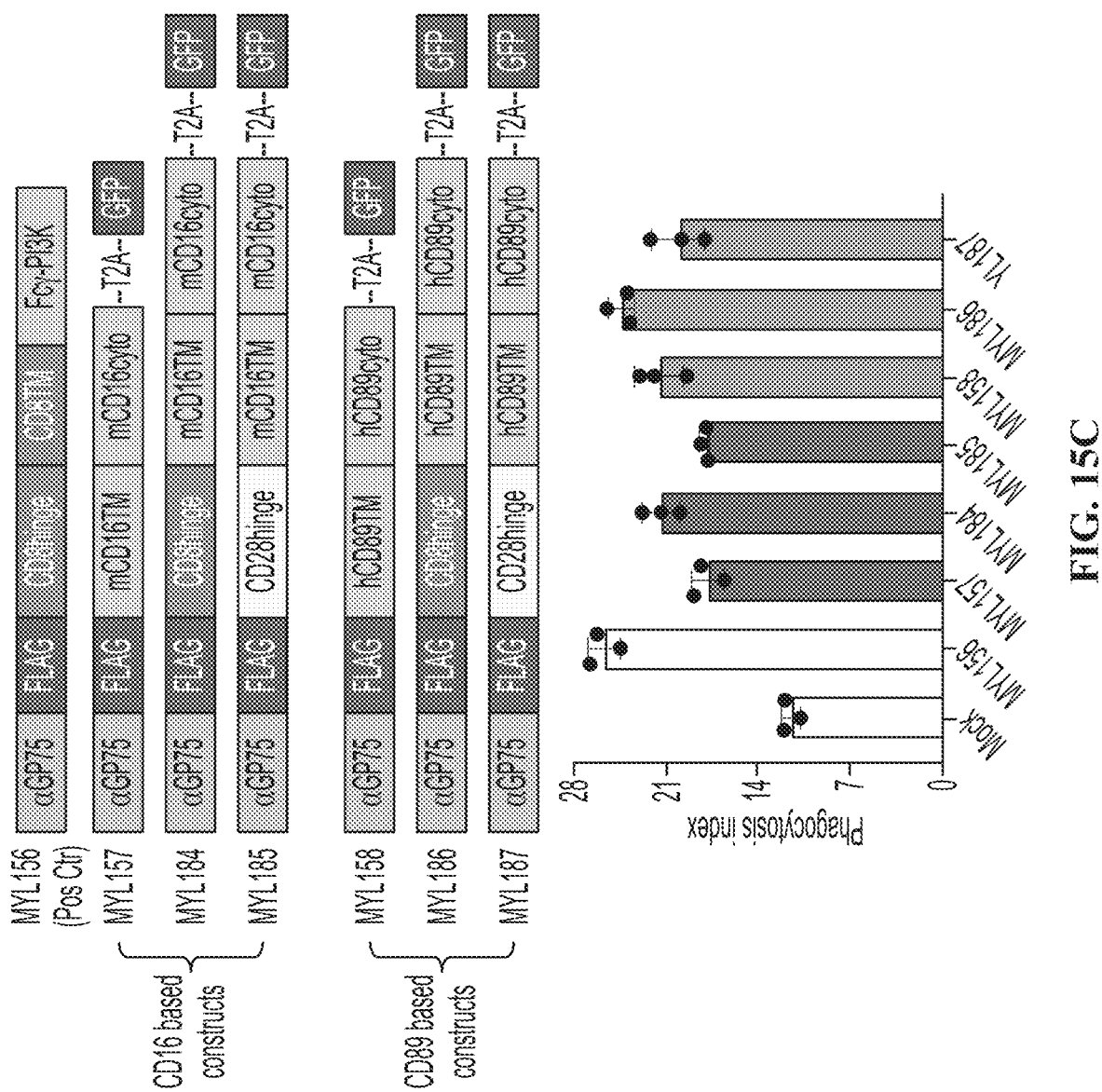
FIG. 15C depicts exemplary data using monocytes expressing the indicated anti-GP75 CFP constructs after being electroporated with LNPs containing RNA encoding the CFP construct using the assay described in FIG. 15A. The constructs are graphically represented in the top panel. Data depicting phagocytosis index based on flow cytometry analysis is shown in the graph. Constructs that included a CD8 hinge showed slightly better expression.
Figure 15D:
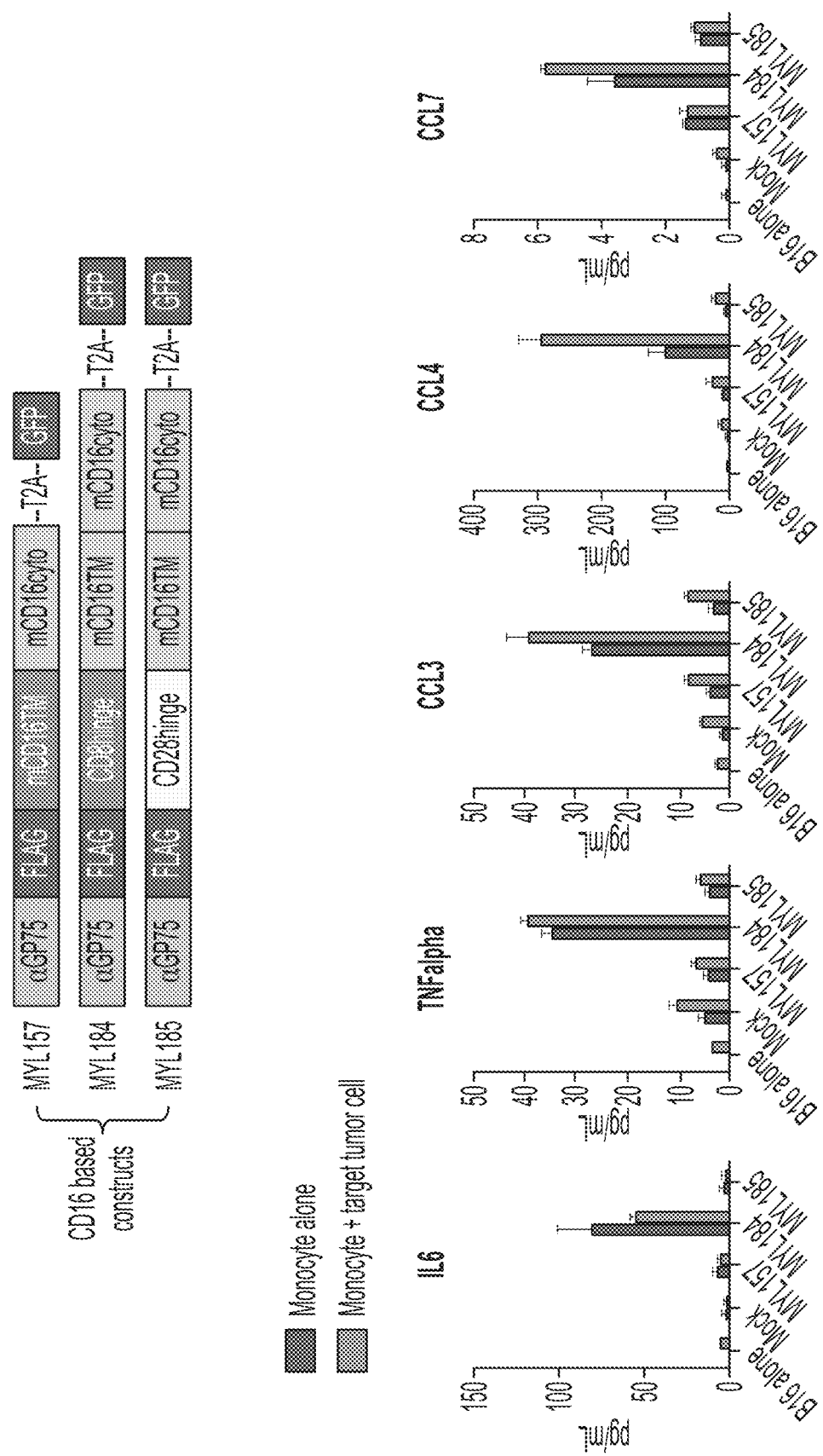
FIG. 15D depicts data of cytokine production by myeloid cells electroporated with an LNP containing an mRNA encoding the indicated anti-GP75 CFP constructs using the assay described in FIG. 15A. Graphs of TNF-alpha, CCL3, CCL4 and CCL7 production from B16 cells alone or monocytes contacted with an LNP containing an mRNA encoding the indicated anti-GP75 CFP constructs were cocultured with B16 cells are shown.

Monocytes were isolated from mouse femurs by negative selection, and were electroporated with the mRNA constructs, cultured overnight and them incubated with GP75 expressing B16 tumor cells. Successful expression of the constructs was observed in the murine cells (FIG. 14B). Incorporation of CD8 hinge domain showed slight advantage of the constructs in expression levels (not shown). Robust tumor cell specific phagocytosis was observed as shown in FIGS. 15A-15C. As specifically shown in FIG. 15B, the construct MYL158, having anti-GP75 ECD and CD89 TM domains showed increased phagocytosis. Similarly, as shown in FIG. 15C, both MYL158 and MYL 186 constructs having GP75 extracellular antigen binding domain and CD89 TM domains, showed increased phagocytosis. The positive control in the figure is a first generation myeloid cell CFP construct from the inventors that had FcR-PI3K recruitment ICD and showed high phagocytic index. FIG. 15D shows cytokine release data by monocyte cells expressing the indicated constructs.

Example 8. Syngeneic Mouse Tumor Model and CAR-P Therapy

In this example, a HER2 syngeneic mouse model was used to test the effect of the CFP on an endogenous tumor. Human Erb B2-driven by a whey protein promoter construct was used to express human HER2 in the syngeneic mouse brain and mammary glands, allowing the establishment of the hHER2 tumors without rejection. HER2+ tumor was established in a fully immunocompetent host. Effect of the anti-HER2 CFP expressing hHER2 was then examined in the mouse model. CRISPR-edited HER2-CFP expressing monocytes were used to treat HER2 tumors in this model. Tumor growth, trafficking of CAR cells, persistence and infiltration of CAR cells into the tumor and immune analyses were performed.

Example 9. In Vivo Delivery and Myeloid Specific Expression of CFP

Figure 17A:
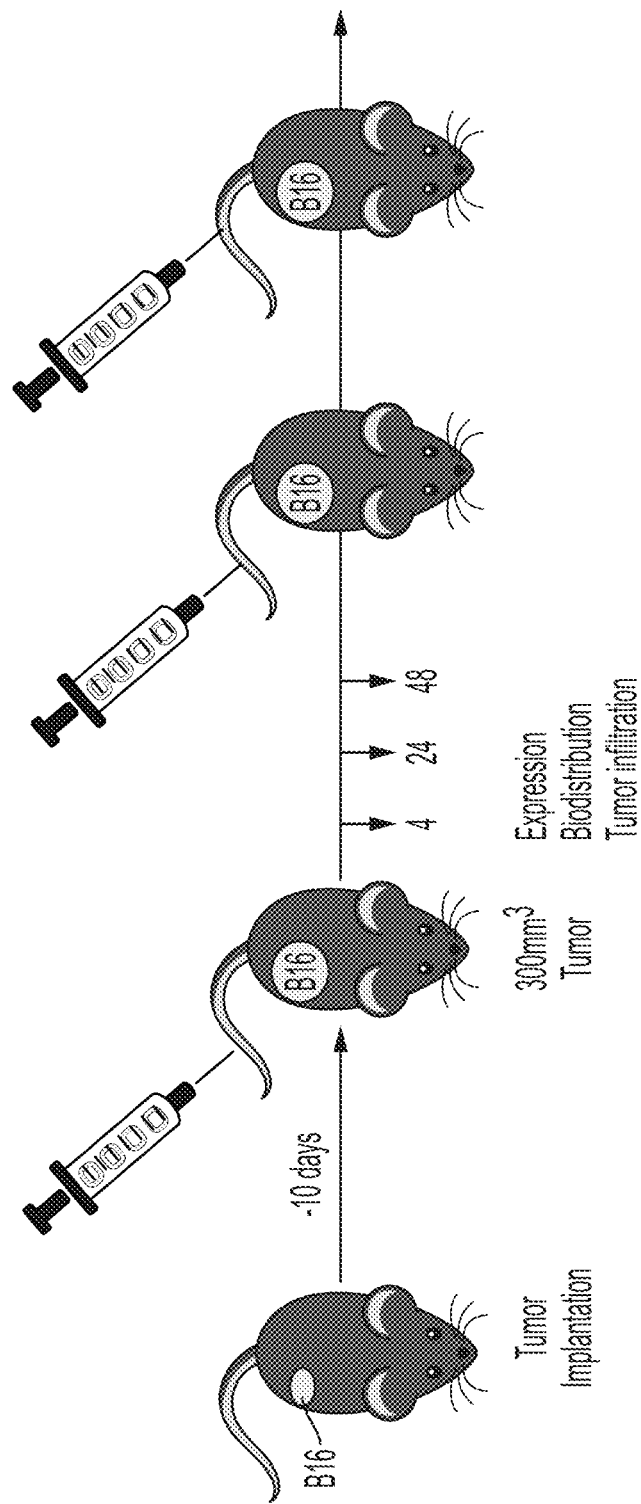
FIG. 17A depicts an exemplary LNP dosing schedule for establishing and monitoring tumor growth in a B16 syngeneic mouse model. Tumor cells are injected at day 0 and establishment of the tumor in the mouse is allowed to occur over 10 days post injection. Following establishment of the tumor, the mice are injected with an LNP formulation containing an mRNA encoding the CFP constructs multiple times and tumor size is monitored.

FIG. 16 shows a graphical representation of a recombinant mRNA encoding an engineered CFP with a GFP tag and/or FLAG tag, encapsulated in an LNP, which was introduced into mouse melanoma model by injection (FIG. 17A) for testing myeloid cell specific expression and anti-tumor activity in vivo.

Figure 17B:
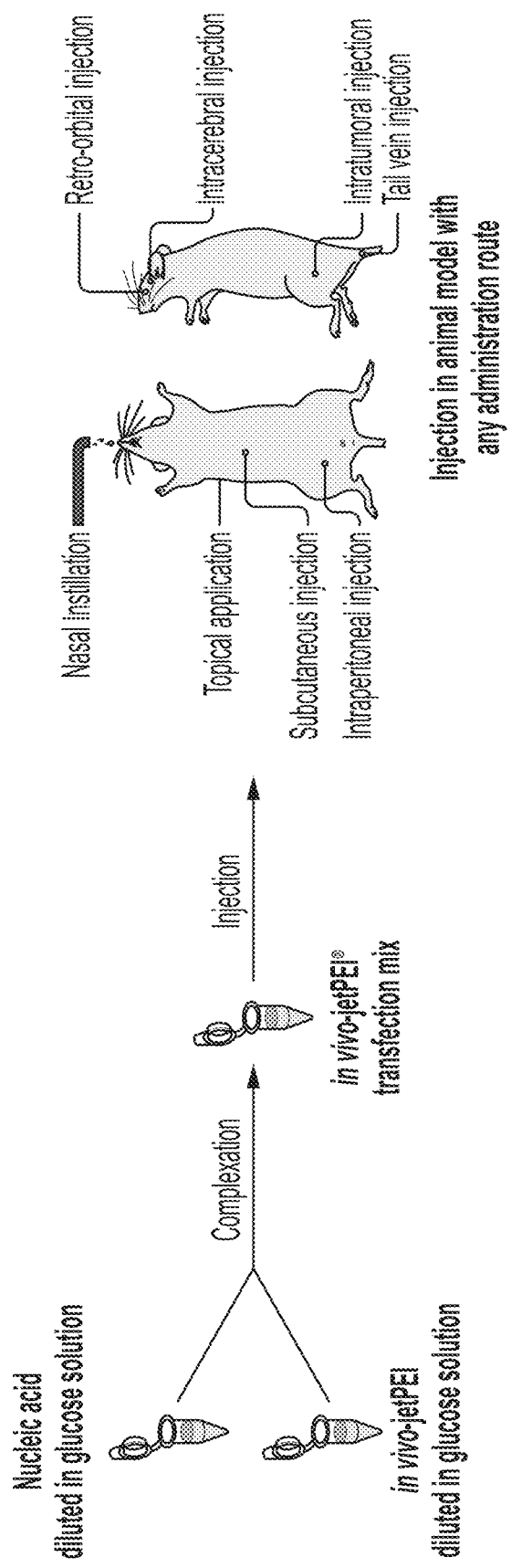
FIG. 17B depicts an exemplary schematic for preparing jet PEI mediate transfection complex containing mRNA encoding various CFP constructs and for delivering of the complex in vivo via injection.

FIG. 17B shows a PEI formulation for in vivo delivery of the mRNA encoding the CFPs in vivo.

Figure 18A:
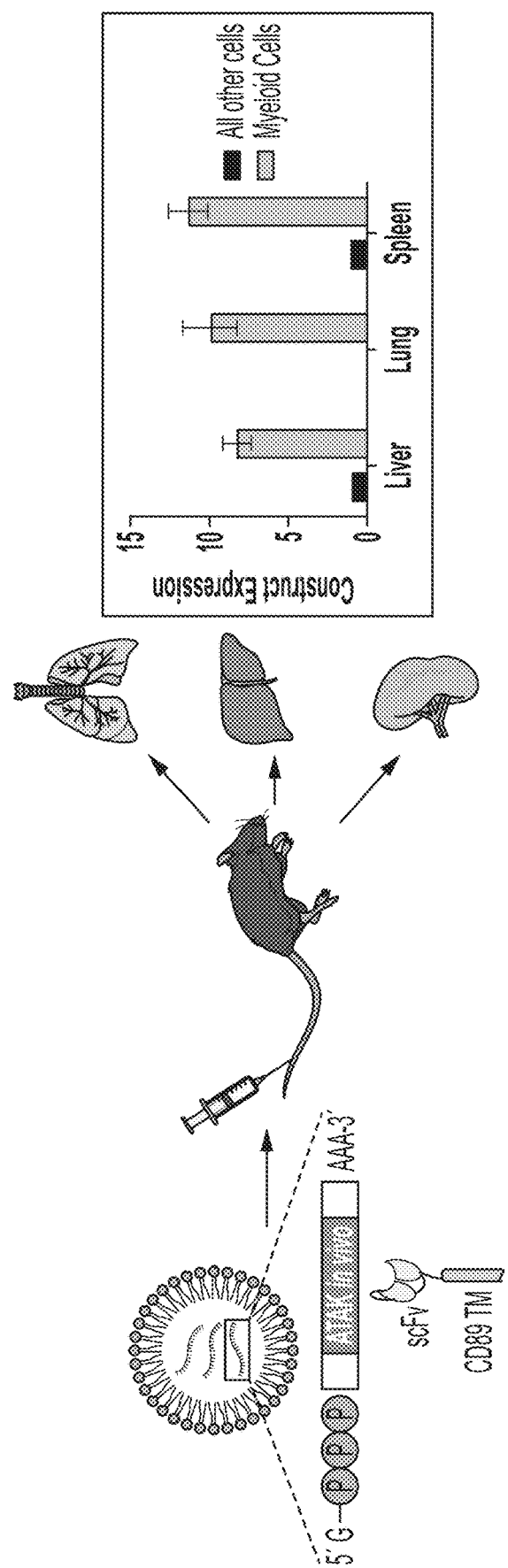
FIG. 18A depicts expression data of the indicated CFP construct demonstrating positive expression of the indicated CFP construct in myeloid cells of the lung, liver and spleen in vivo after tail vein injection of the LNPs containing mRNA encoding the CFP construct. Expression was not observed in non-myeloid cell types of the lung, liver and spleen.
Figure 18B:
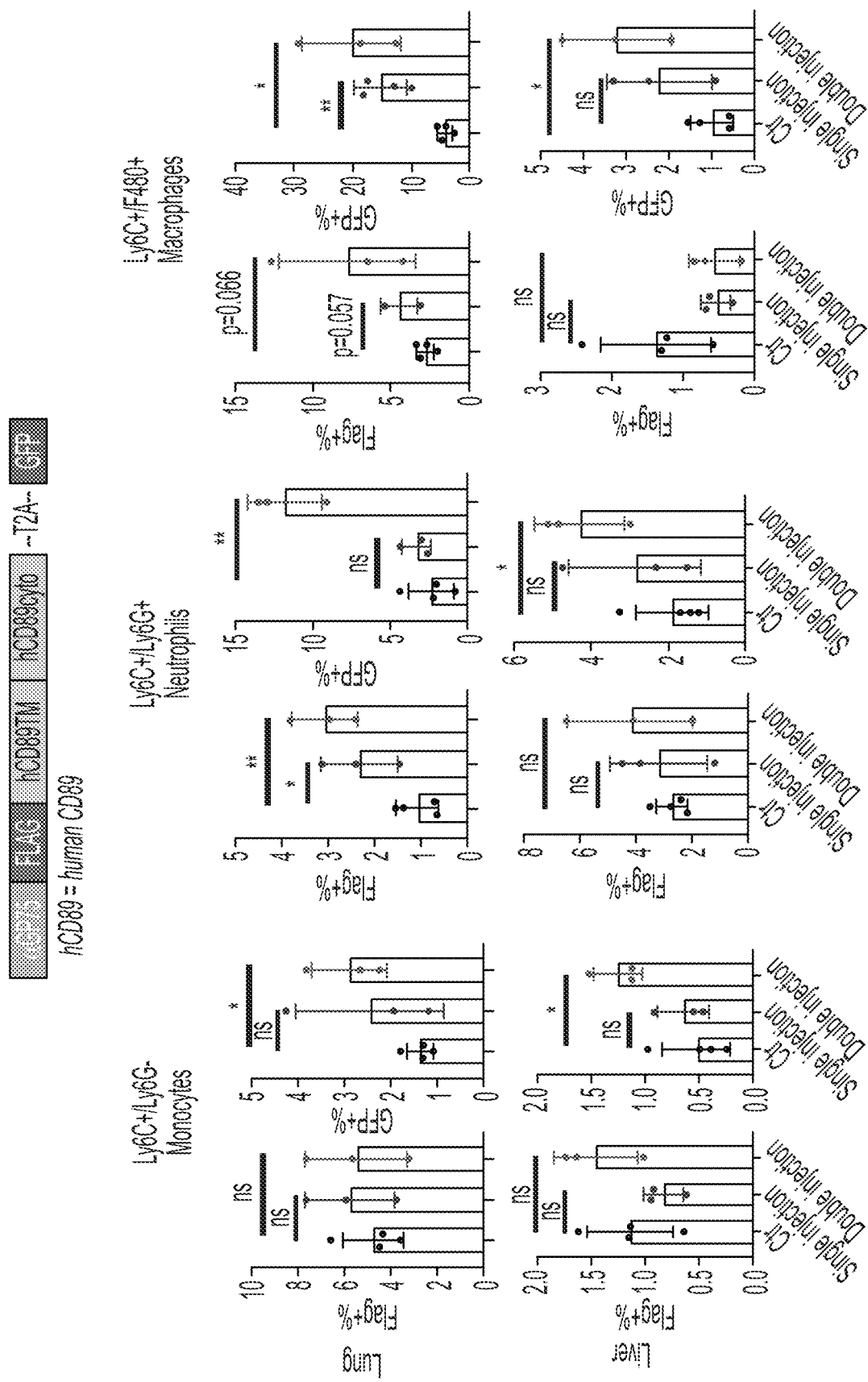
FIG. 18B depicts graphs of expression of an exemplary CFP construct (graphically represented at the top), as measured by percent cells positive for GFP fluorescence or FLAG expression as measured by immunoassay in the indicated types of mouse lung and liver cells in vivo after a single or double injection of LNPs containing RNA encoding the CFP construct into mice and flow cytometry analysis according to the gating strategy depicted in FIG. 14B or FIG. 14D.
Figure 18C:
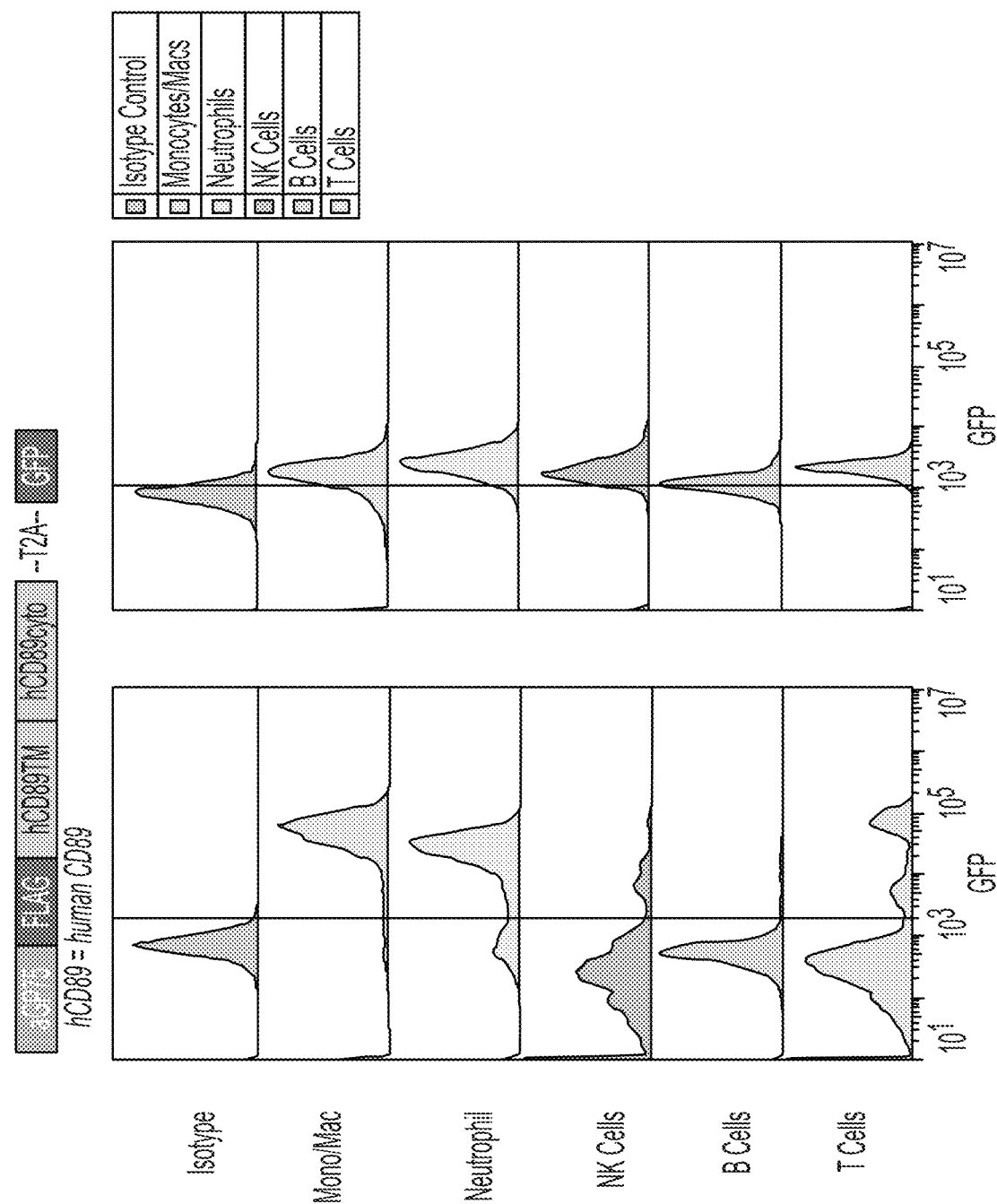
FIG. 18C depicts GFP and FLAG offset histograms showing clear GFP expression in monocytes and neutrophils.
Figure 18D:
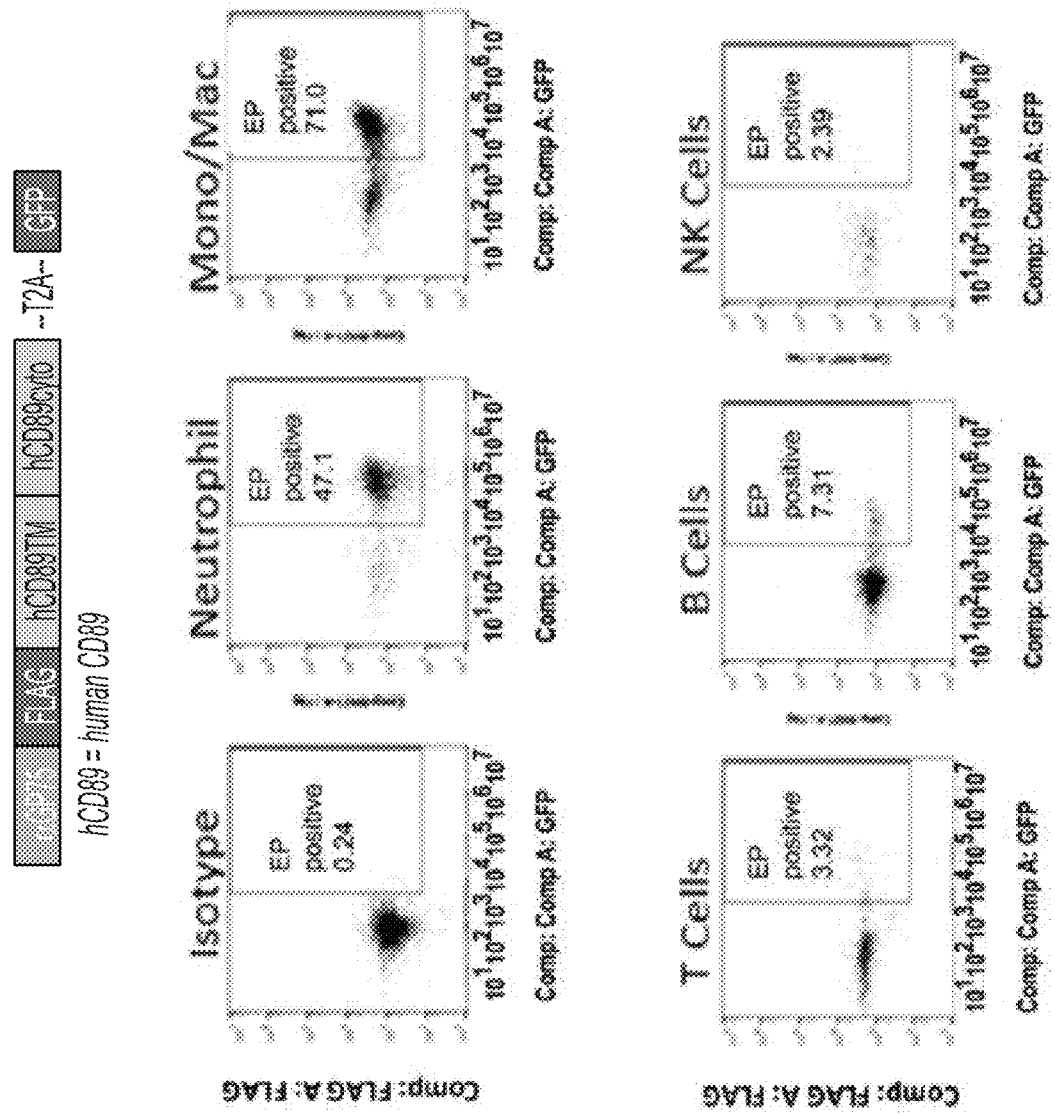
FIG. 18D depicts flow cytometry data of expression of a CFP construct as measured by percent cells positive for GFP fluorescence or FLAG expression as measured by flow cytometry immunoassay in the indicated types of mouse lung and liver cells in vivo after injection of LNPs containing RNA encoding the CFP construct into mice and flow cytometry analysis according to the gating strategy depicted in FIG. 14B or FIG. 14D.

The CFP has a CD89 transmembrane domain. Organs were periodically harvested as indicated in FIG. 18A and organ specific expression of the mRNA encoded CFP was assayed. Non-myeloid cells (such as lymphocytes) did not express the CFP. Expression was positively verified in the myeloid cells of lung, liver and spleen. FIG. 18B further analyses the cell type specific expression. Cells isolated after first or second injections of the CFP showed that there was a statistically significant increase in the expression of the tag in Ly6C+/F4/80+ macrophages and LY6C+Ly6G− monocytes in both the organs. Neutrophils also showed expression of the constructs. Non-myeloid cells such as T cells did not show expression. FIGS. 18C-18J further exemplify the cell specific and tissue specific expressions of the construct having the specific transmembrane domains as indicated in the figures, allowing myeloid cell specific expression both in vitro and in vivo.

Figure 19:
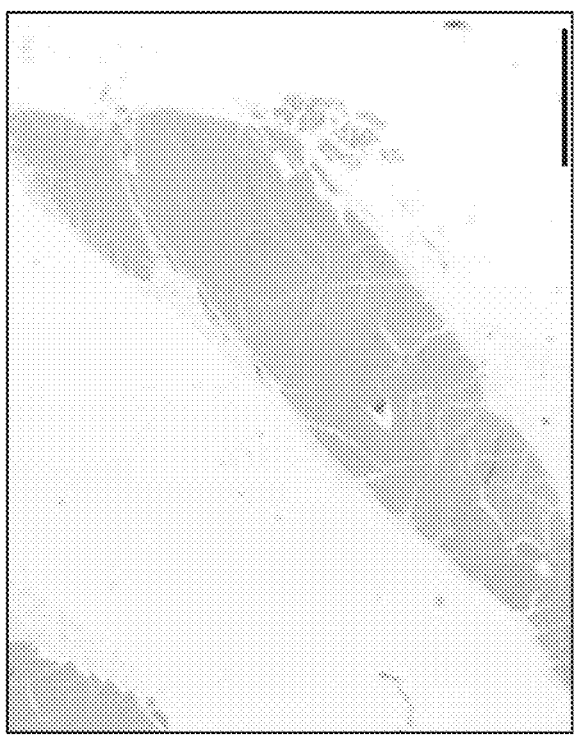
FIG. 19 depicts histopathological analysis of tumor in B16 mice treated with LNPs containing RNA encoding an anti-GP75 construct. 2 of 4 mice show complete anti-tumor response and no tumor was detected.
Figure 19:
Figure 20B:
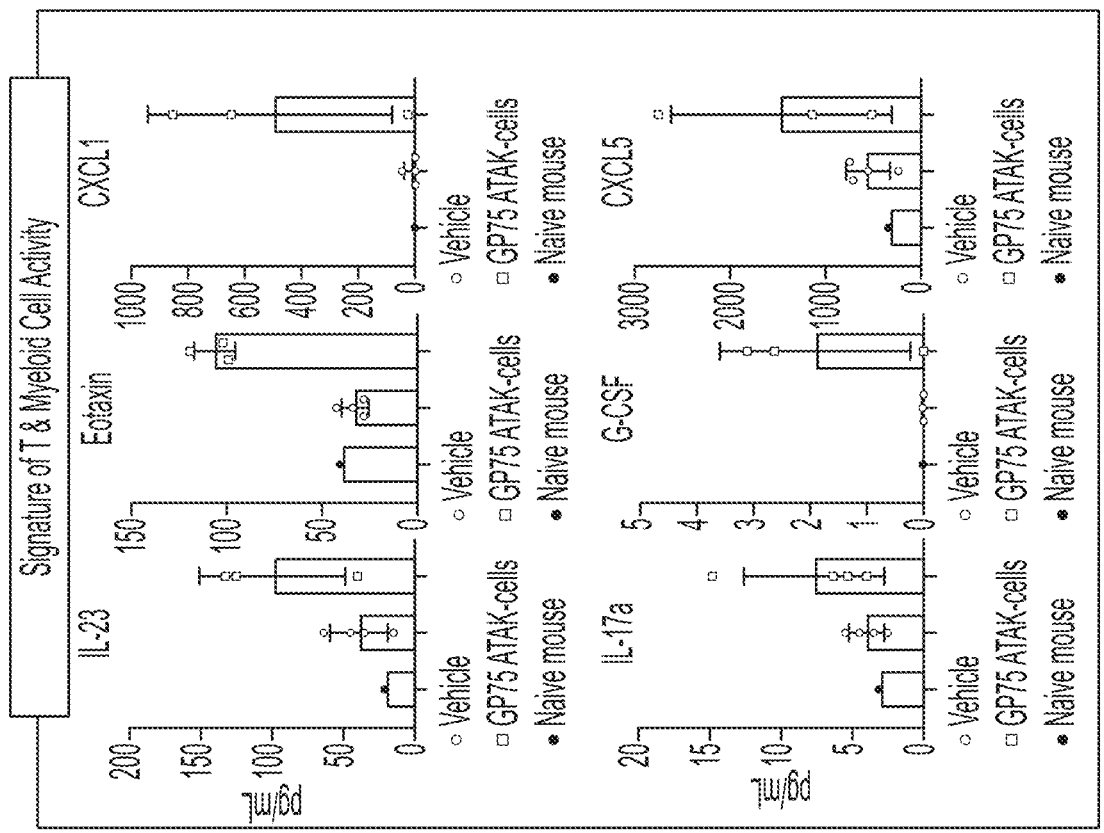
FIG. 20B depicts data of cytokine production of cells from naive mice or a mouse tumor model treated with vehicle or myeloid cells expressing an anti-GP75 CFP construct. Graphs of IL23, Eotaxin, CXCL1, IL17a, G-CSF, and CXCL5 production from mice are shown and indicate increased T cell and myeloid cell activation.
Figure 20A:
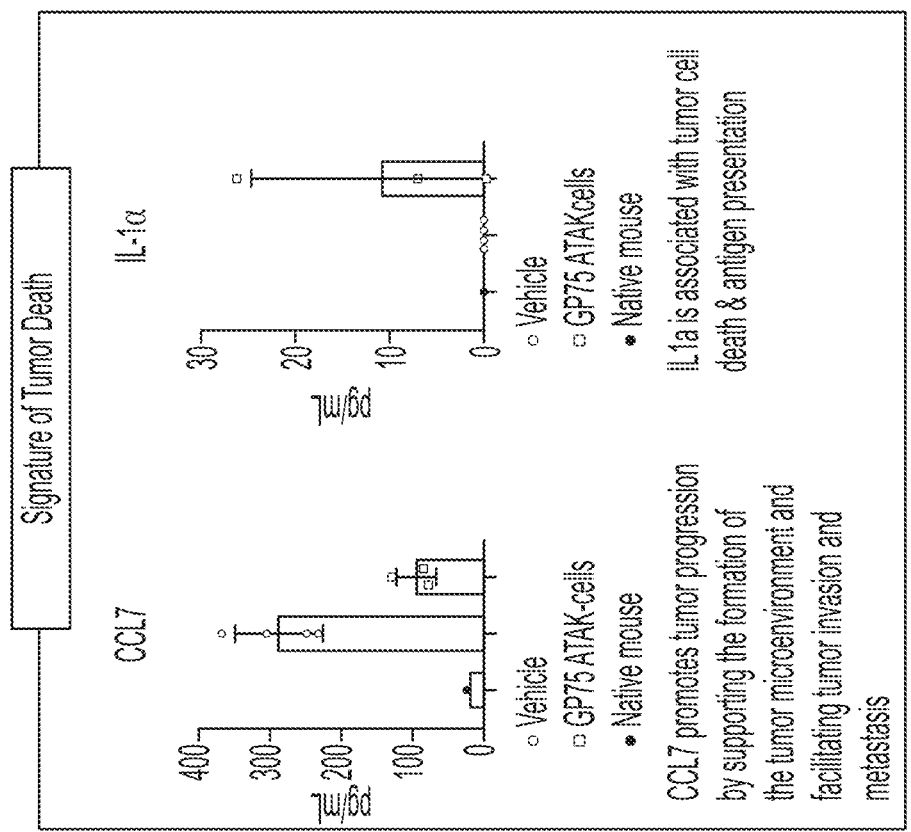
FIG. 20A depicts data of cytokine production of cells from naive mice or a mouse tumor model treated with vehicle or myeloid cells expressing an anti-GP75-ATAK CFP construct. Graphs of CCL2 and IL-1alpha production from mice are shown. CCL7, which promotes tumor progression is reduced in treated mice, whereas IL-1alpha, which is associated with tumor cell death is increased. ATAK, acronym for antigen targeting and killing.
Figure 20C:
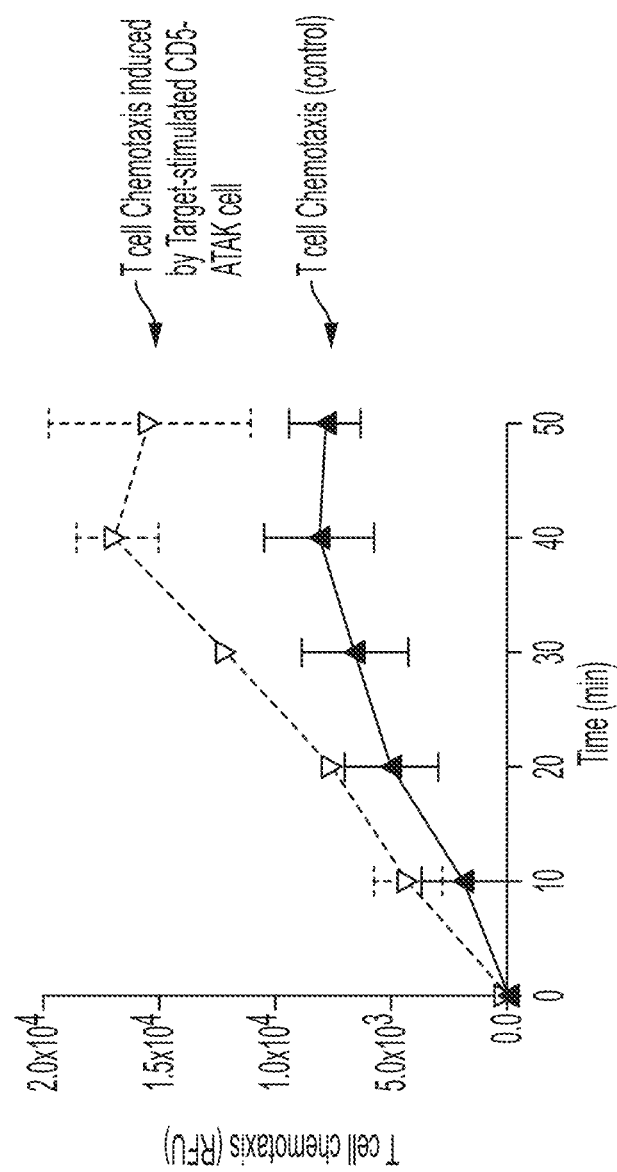
FIG. 20C shows that CAR-expressing monocytes upon stimulation recruit T cells. In an in vitro assay, CD5-ATAK cells induce T cell chemotaxis.
Figure 21:
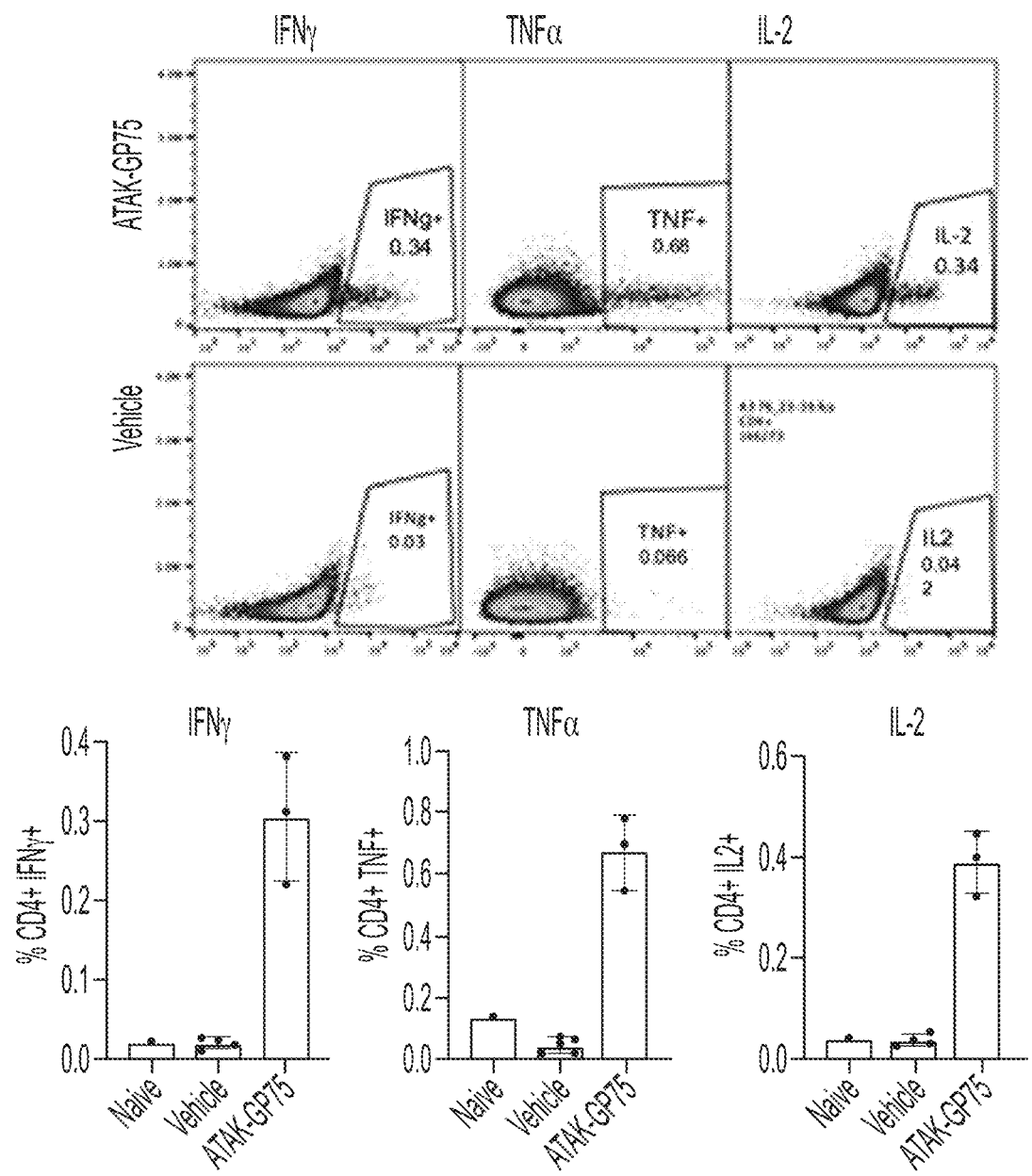
FIG. 21 depicts data of cytokine production of cells from naive mice or a mouse tumor model treated with vehicle or myeloid cells expressing an anti-GP75 CFP construct. Flow cytometry data of IFN gamma, TNF-alpha and IL-2 production from cells isolated from respective mice is shown. Graphs of the percentage of CD4+ T cells producing IFN gamma, TNF-alpha and IL-2 production are also shown.
Figure 41:
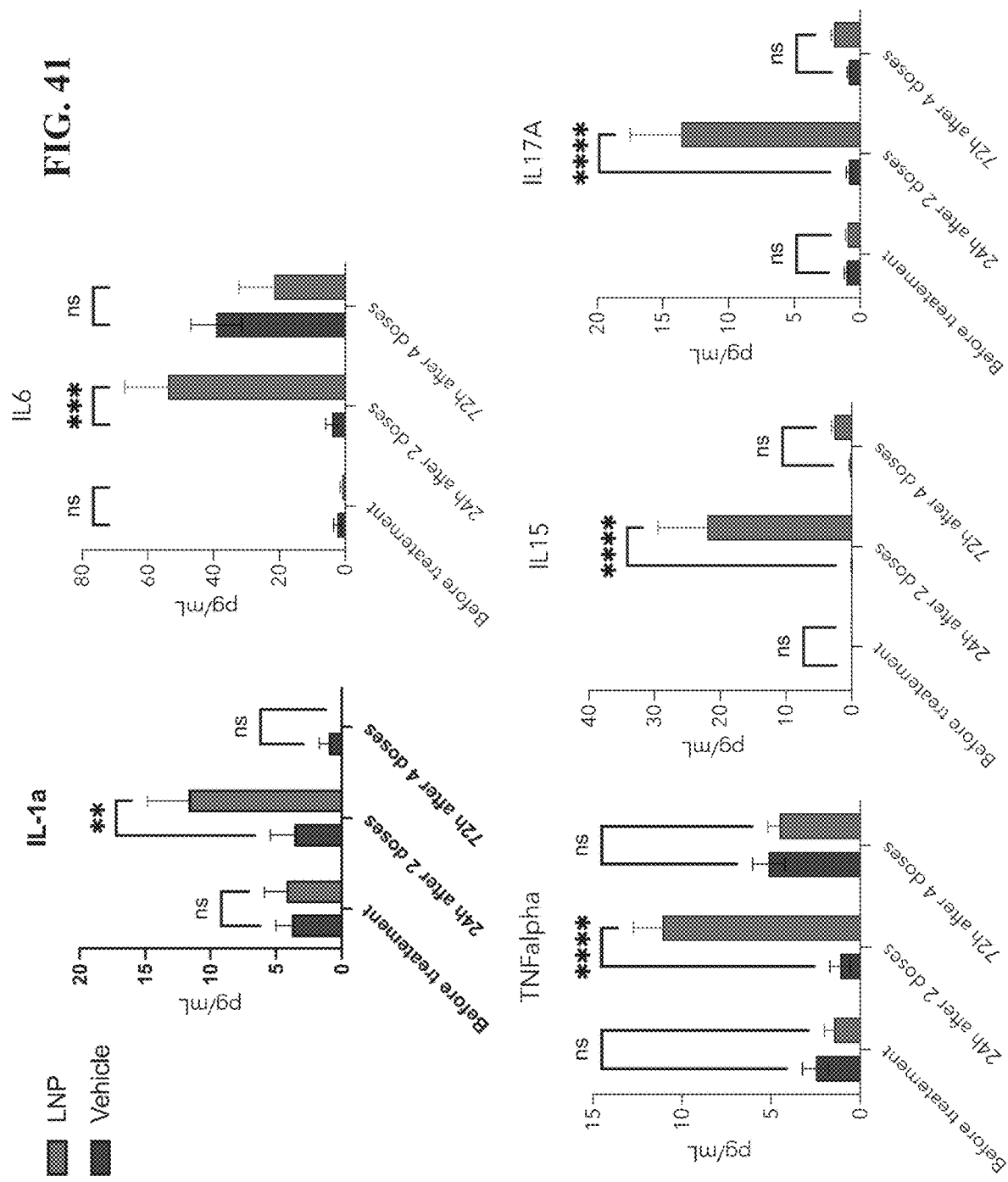
FIG. 41 depicts data of production of the indicated proinflammatory serum cytokines before and 24 hours after 2 injections and 72 hours after 4 injections of an LNP containing RNA encoding an anti-GP75 CFP with a CD89 (FcRalpha) chain into mice.
Figure 42:
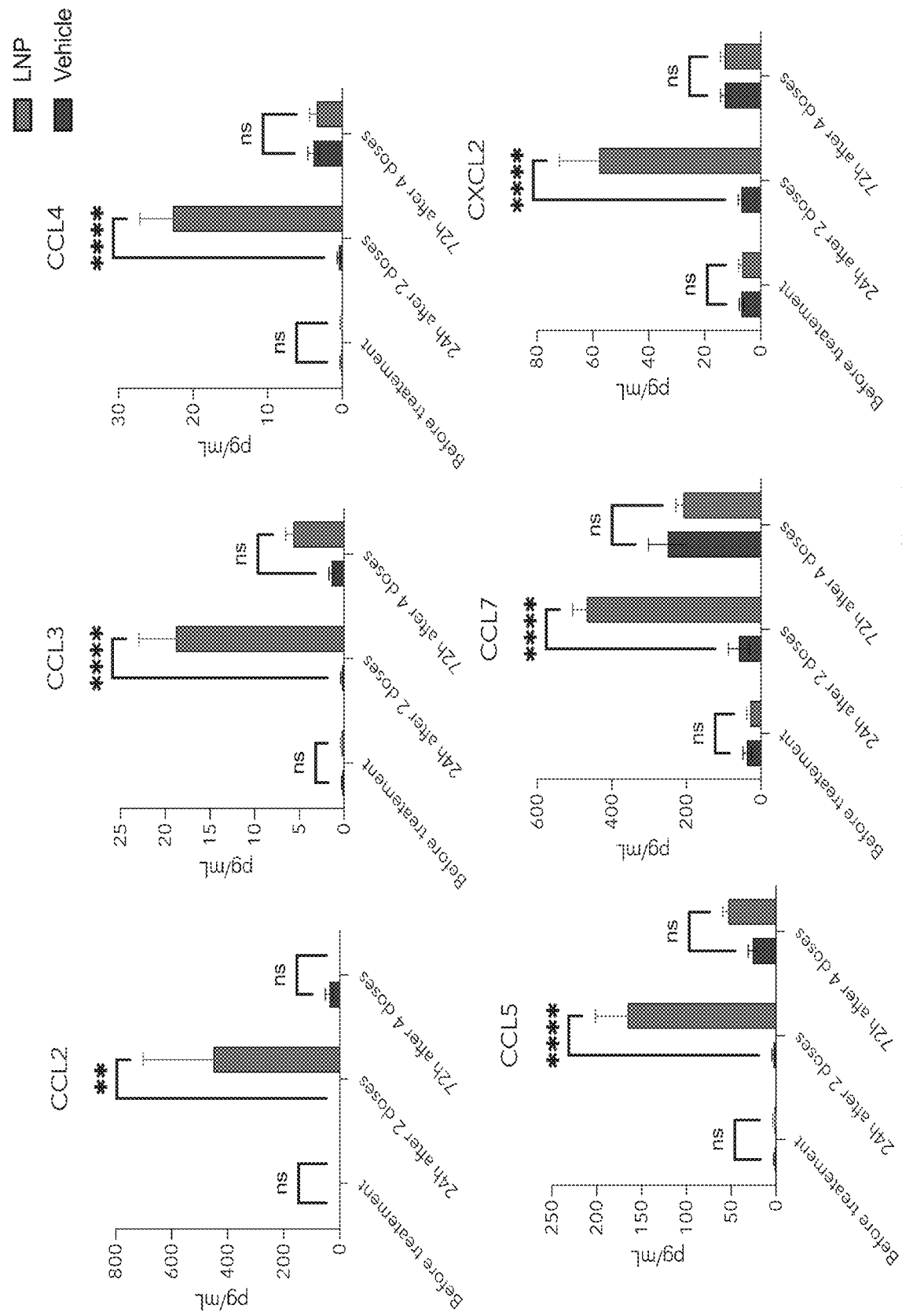
FIG. 42 depicts data of production of the indicated serum chemokines before and 24 hours after 2 injections and 72 hours after 4 injections of an LNP containing RNA encoding an anti-GP75 CFP with a CD89 (FcRalpha) chain into mice.

Example 10. Immunological Impact of the CAR-Expressing Macrophage Treatment in Mice Tumor histopathology results indicate considerable reduction and obliteration of tumor in 2 out of 4 treated mice, and no reduction in the untreated group. Representative results shown in FIG. 19. Additionally, FIGS. 20A and 20B show cytokine and chemokine signature in the tissues that indicate high myeloid cell activity necessary for tumor killing. FIG. 20C demonstrates that the engineered monocytes recruit T cells in an in vitro assay. FIG. 21 and FIGS. 41 and 42 show increased inflammatory cytokine secretion by cells isolated from mice with tumor, those of which were administered the CFP constructs. Such inflammatory cytokines turn potentially turn a cold tumor into a hot TME.

Figure 22:
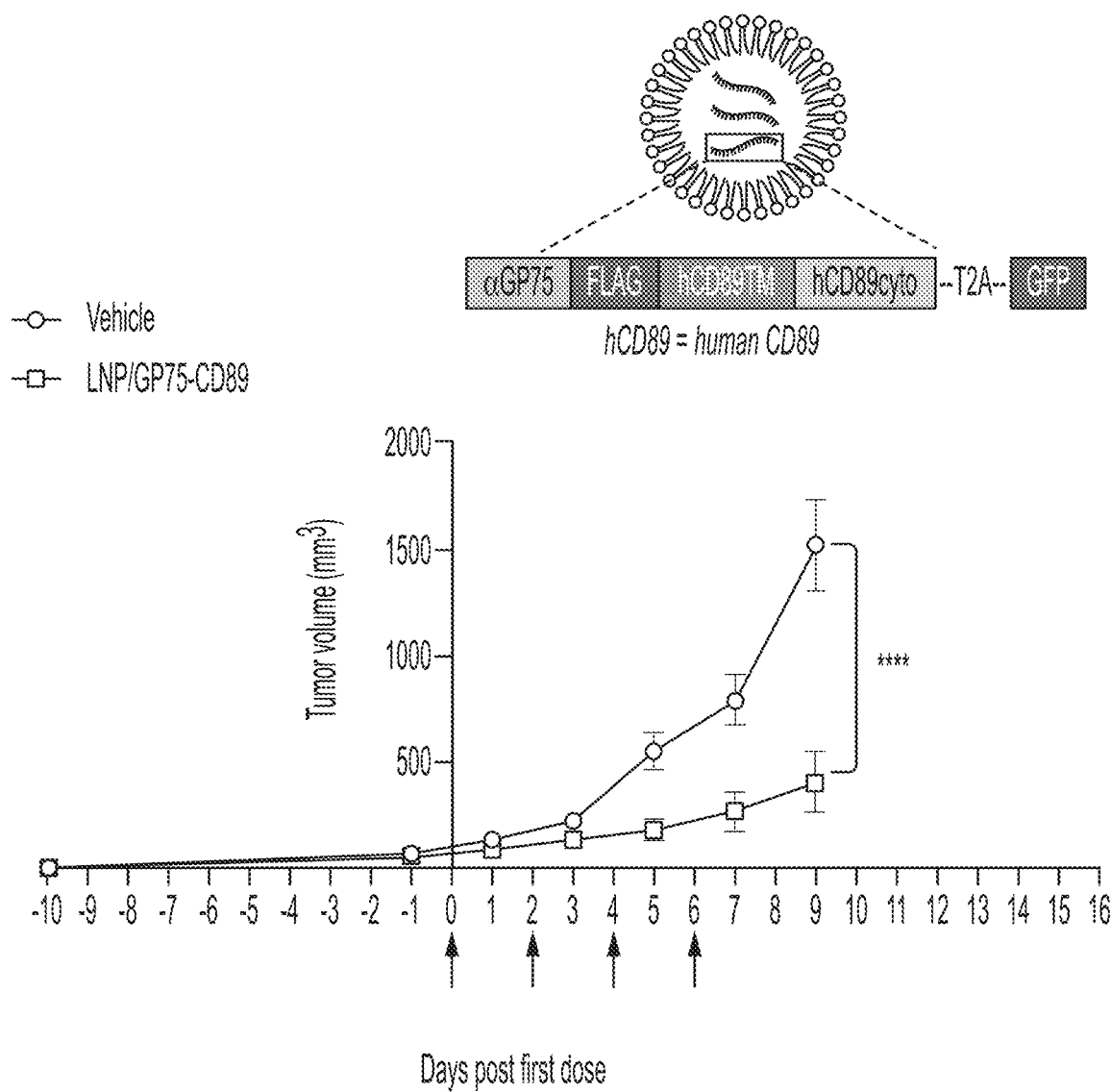
FIG. 22 depicts a graph of tumor volume over time in mice treated with an LNP containing an mRNA encoding the indicated anti-GP75 CFP construct at the indicated time points (shown by arrows below the X-axis). 5 mice from each group were taken down on day 9 post treatment. Organs were harvested for flow analysis: of the tumor, lung, liver and spleen. RNA samples from tumor samples were saved for NanoString gene expression analysis. A T cell restimulation assay with Ova peptide was also performed.
Figure 29:
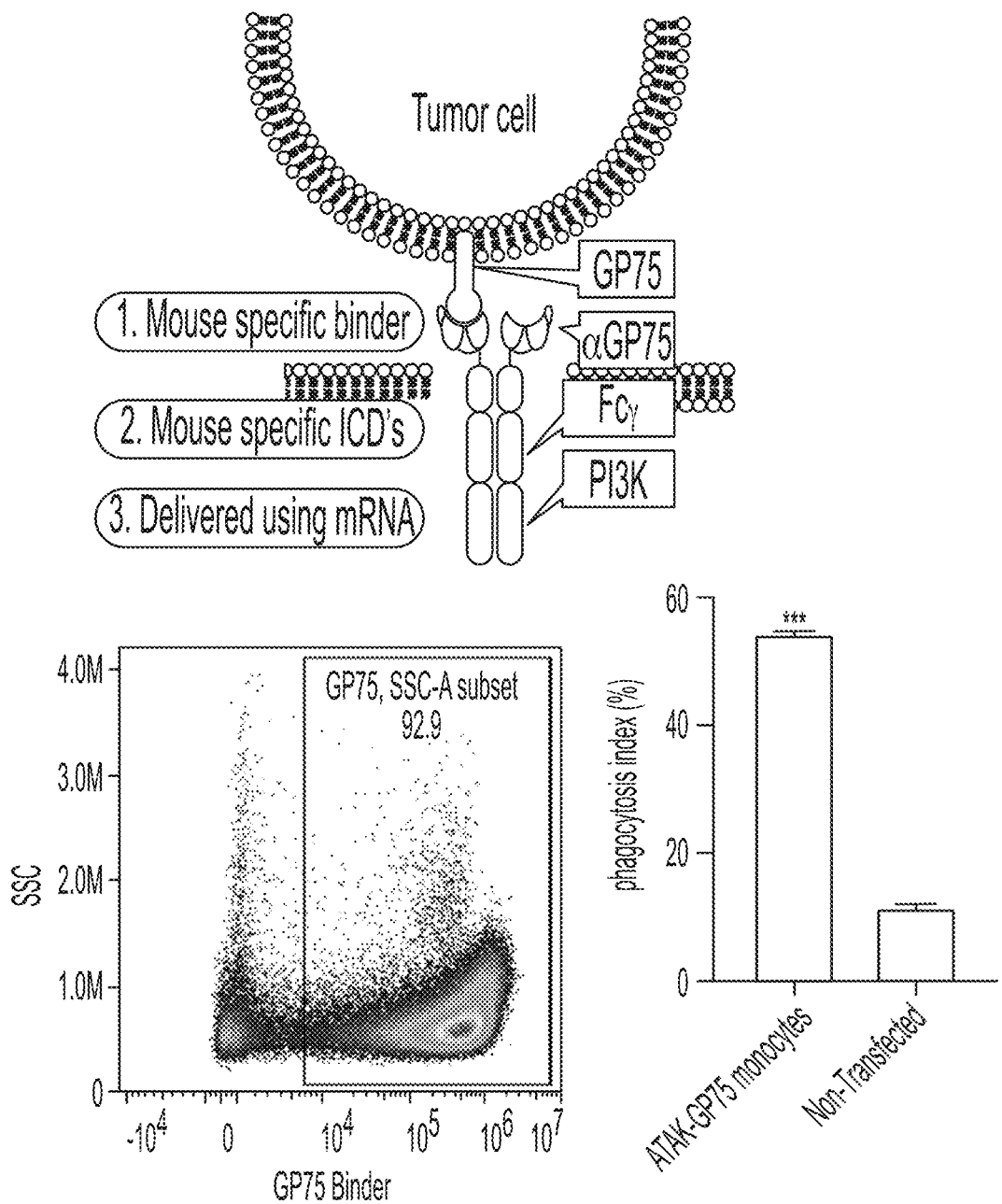
FIG. 29 shows a schematic demonstrating generation of mouse anti-GP75 (Trp-1) CFP ATAK cells. The anti-GP75 CFP is efficiently expressed in the mouse monocytes via electroporation of mRNA encoding the anti-GP75 CFP and cells expressing the anti-GP75 CFP have phagocytic activity.
Figure 30:
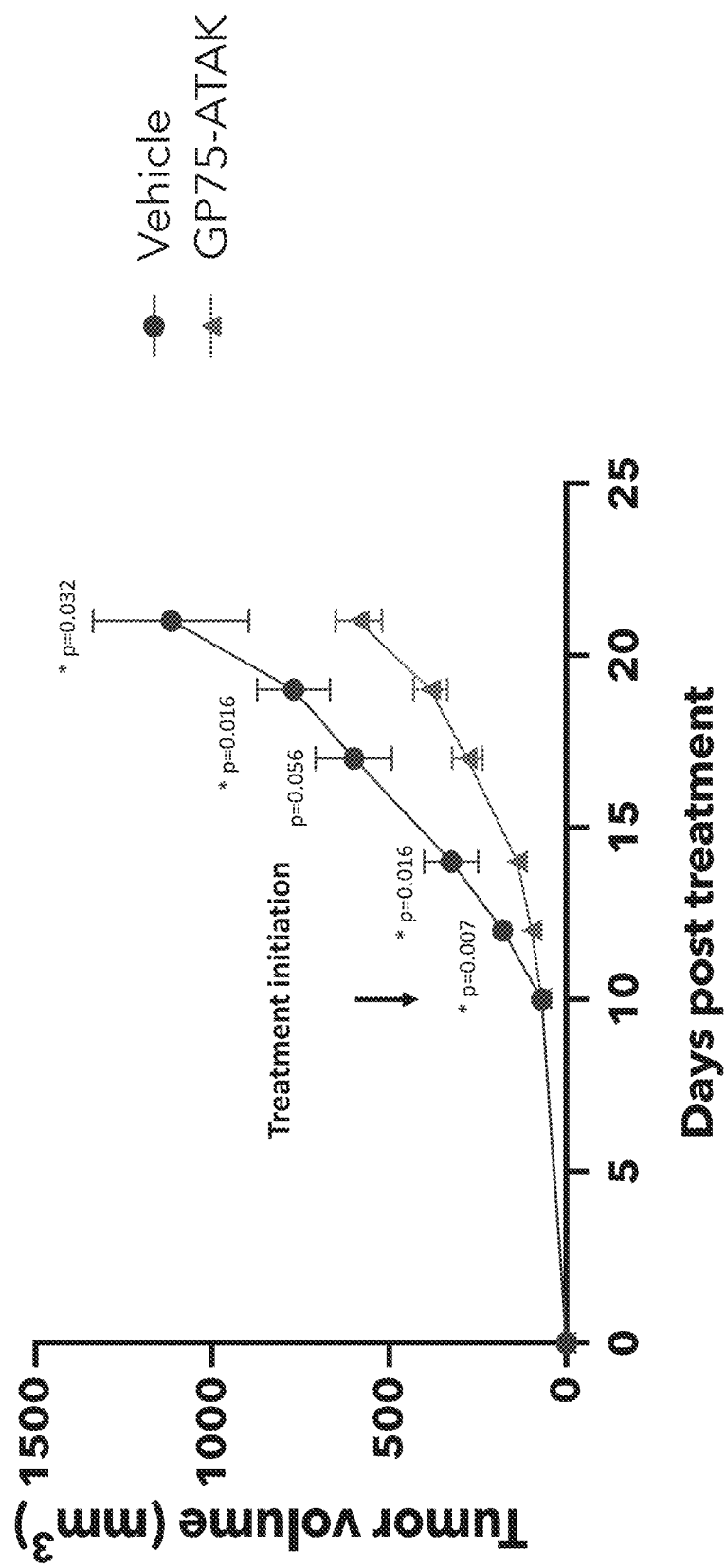
FIG. 30 shows data demonstrating anti-GP75 ATAK monocytes suppress tumors in syngeneic B16 murine model. The data shows a graph of tumor volume in a mouse tumor model refractory to CAR-T and checkpoint inhibitors over time post treatment with mouse monocytes expressing an anti-GP75 CFP. Mice were administered 8 infusions of $2 \times 10^{\wedge}6$ cells vs vehicle. Infusions daily ×4, 3 days rest, daily ×4+/−SD (Mann-Whitney test).
Figure 36:
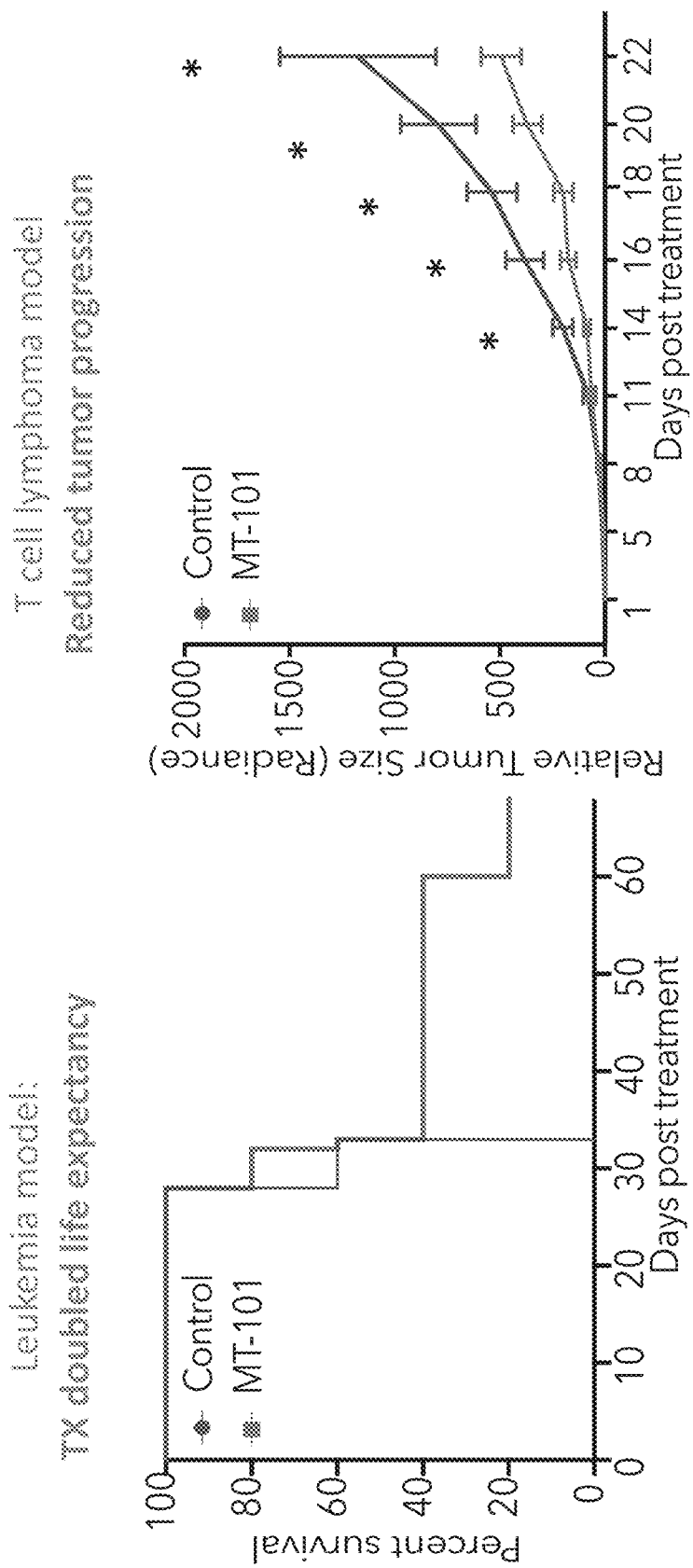
FIG. 36 depicts data showing that human monocytes expressing an anti-CD5 CFP inhibit growth and prolong survival in CD5+ CTCL xenograft models despite having no adaptive immune system.
Figure 37:
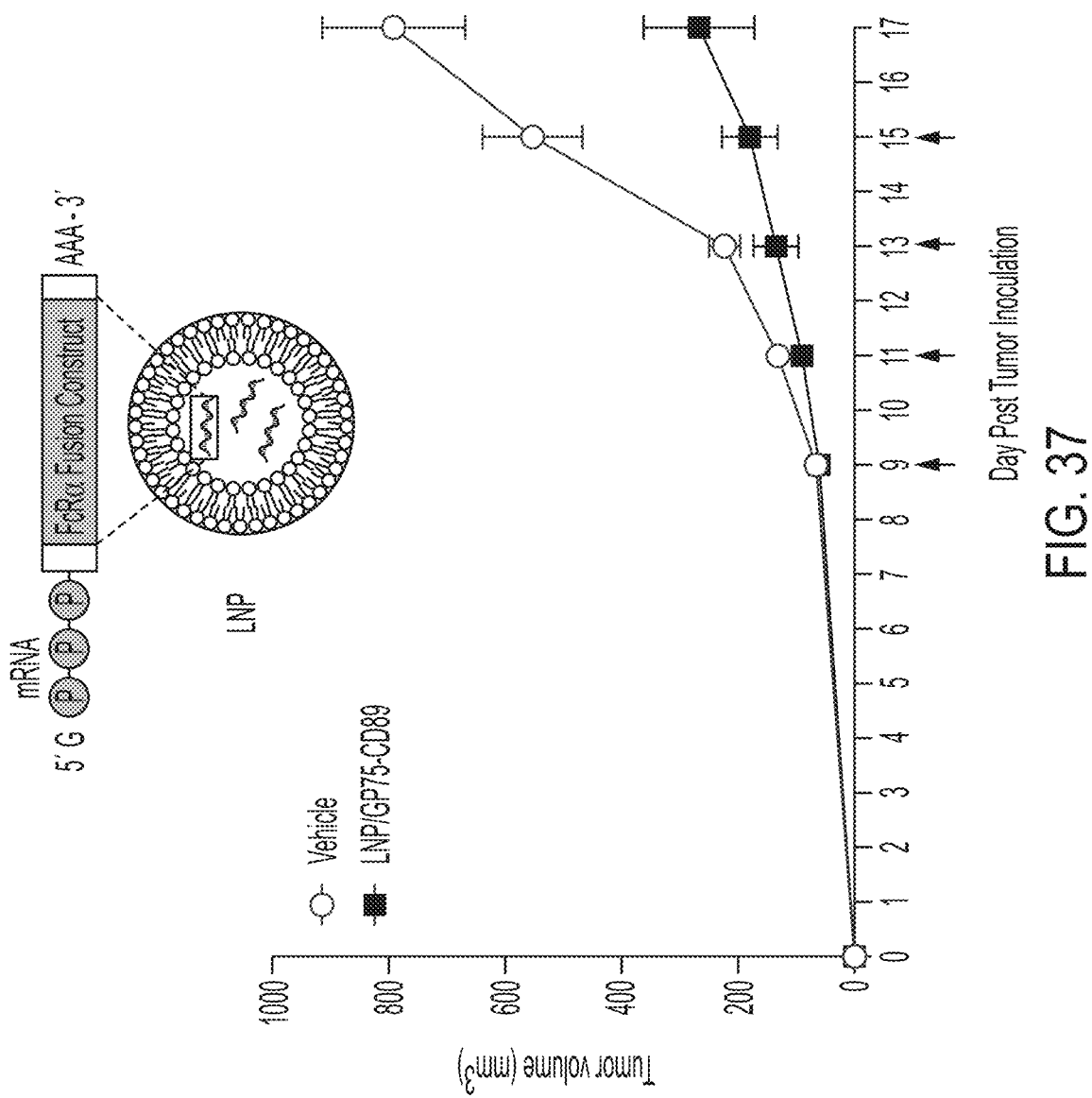
FIG. 37 depicts data showing that injection of an LNP containing RNA encoding an anti-GP75 CFP with a CD89 (FcRalpha) chain into mice selectively programs myeloid cells in vivo resulting in potent anti-tumor activity. A 75% reduction in tumor mass (volume, measure in mm$^3$) in an established cold tumor model was observed.

FIG. 22 shows data to confirm tumor reduction in mice that received the LNP comprising CFP injection. A syngeneic mouse model was generated with myeloid cells expressing GP75 binding CFP. Generation of Mouse anti-GP75 (Trp-1) ATAK Cells is shown in FIG. 29. The ATAK-GP75 receptor is efficiently expressed in the mouse monocytes via electroporation of mRNA as demonstrated in the flow cytometry plot at the lower left panel. These cells were able to efficiently phagocytose GP75 expressing tumor cells (FIG. 29 lower, right graph). Similar data is corroborated by the data in FIGS. 30, and 36 and 37 depicting tumor reduction and survival advantage in mice expressing the respective CFP. FIG. 30 represents the first in vivo illustration of the power of ATAK myeloid cells to contain tumor growth in a tumor model that is refractory to CAR T & Checkpoint inhibitors. 8 infusions of 2×10$^6$ ATAK cells vs Vehicle. Infusions daily ×4, 3 days rest, daily ×4+/−SD (Mann-Whitney test). When GP-75 ATAK monocytes are injected i.v. into immunocompetent C57Bl/6 mice bearing s.c. implanted GP75+B16 melanoma tumors (these mice are tolerant to the B16 syngeneic tumor), the mice were then able to control the growth of the tumors and experience significantly improved survival compared with mice administered vehicle or control monocytes. In addition, when tumors were removed from animals and examined for immune cell content, the animals treated with the GP75-ATAK monocytes showed significantly higher levels of infiltration of the tumor by inflammatory monocyte/macrophages and neutrophils as well as increases in dendritic cells vs. MDSC's. This proved that ATAK monocytes traffic to tumor sites, suppress tumor growth, and recruit other immune cell populations to the TME.

FIG. 21 specifically shows that the treatment of mice with myeloid cells expressing the CFP was associated with broad T cell activity in spleen re-stimulated cultures, including spread of CD4 epitopes. In this experiment splenocyte recall cultures were undertaken, in which spleen cells were stimulated for 6 hours with OVA$_{323*329}$SINFECKEL ("SINFECKEL" disclosed as SEQ ID NO: 86) or PMA/ionomycin. The cytokines were detected by flow cytometry. GP75-ATAK cell treatment was associated with increased non-antigen specific activity, which is indicative of cross-presentation.

Figure 23:
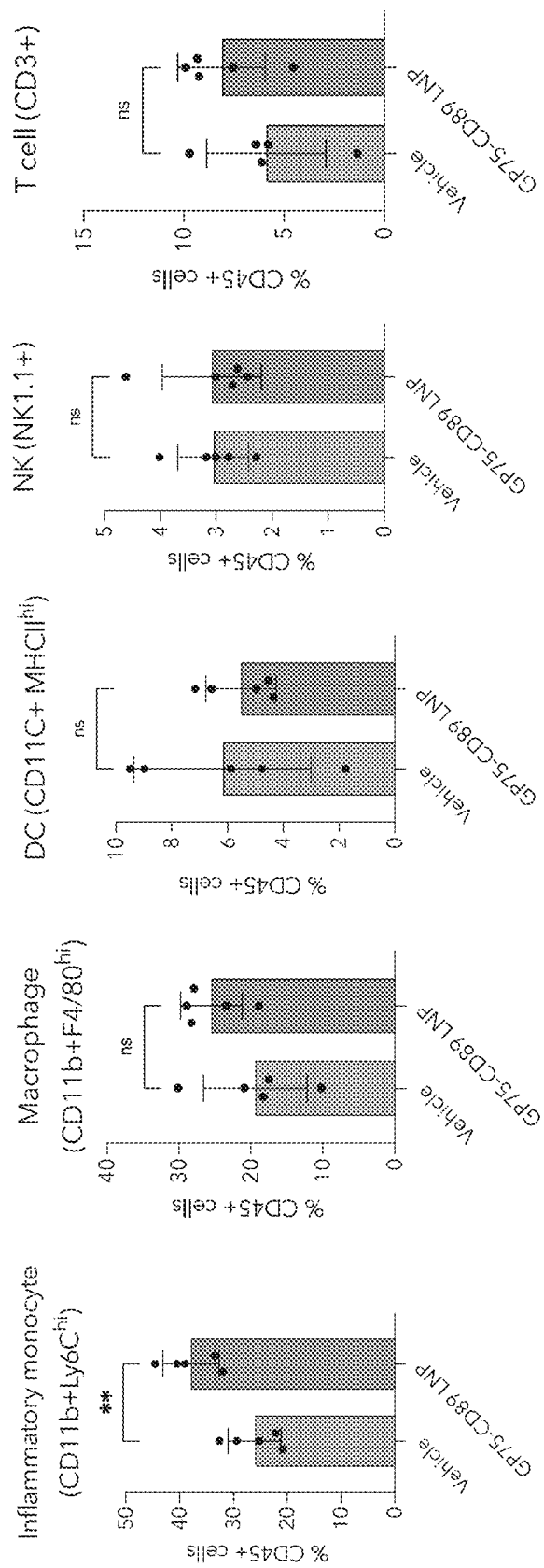
FIG. 23 shows that LNP treatment changed immune cell tumor infiltration. Graphs of the percentage of the indicated cell types among all CD45+ immune cells in the tumor microenvironment of mice treated with an LNP containing an mRNA encoding the indicated anti-GP75 CFP construct are depicted. Treatment resulted in clear increase of inflammatory monocytes in the tumor, and a slight increase of macrophages and T cells.
Figure 24:
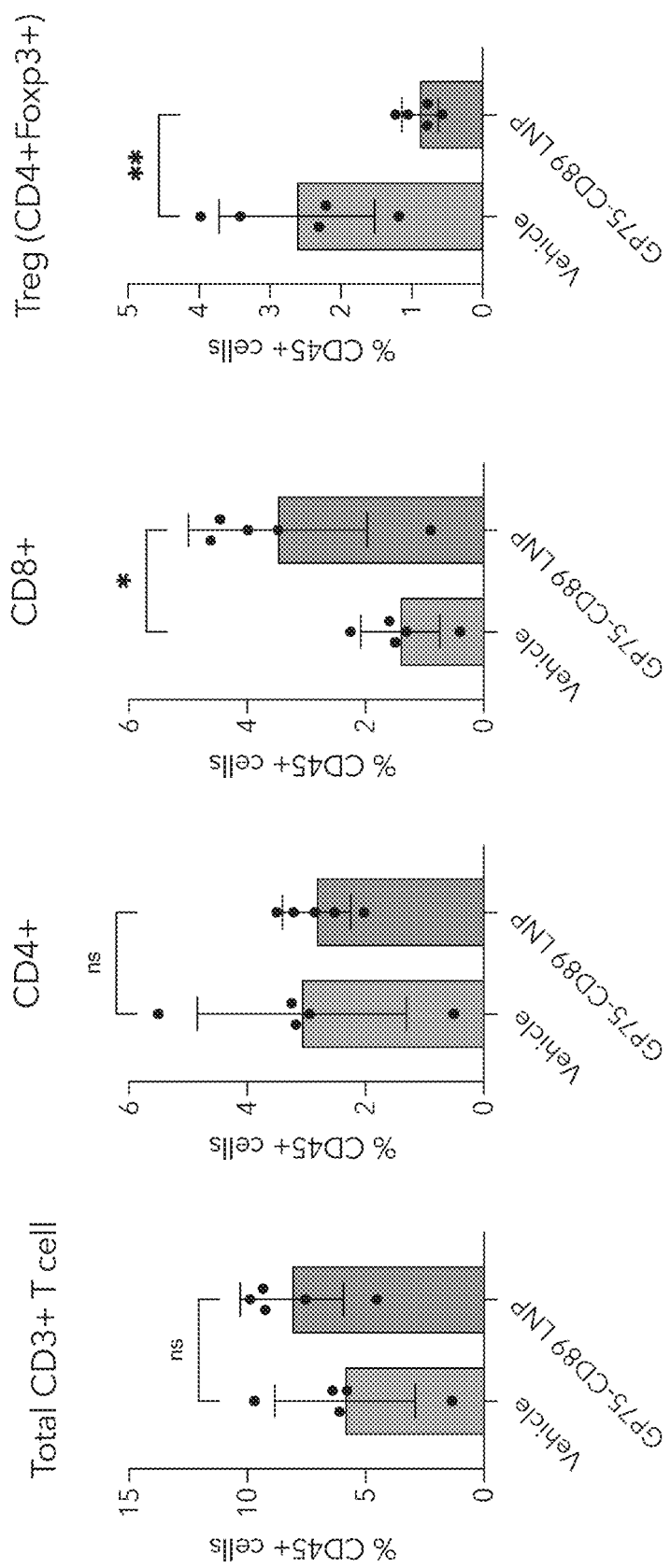
FIG. 24 shows that LNP treatment resulted in a significant increase of CD8 cytotoxic T cells and a reduction of Treg cells. Graphs of the percentage of the indicated cell types among all CD45+ immune cells of mice treated with an LNP containing an mRNA encoding the indicated anti-GP75 CFP construct are depicted. Treatment increased the presence of CD8+ cytotoxic T cells while reducing immunosuppressive Tregs.
Figure 25:
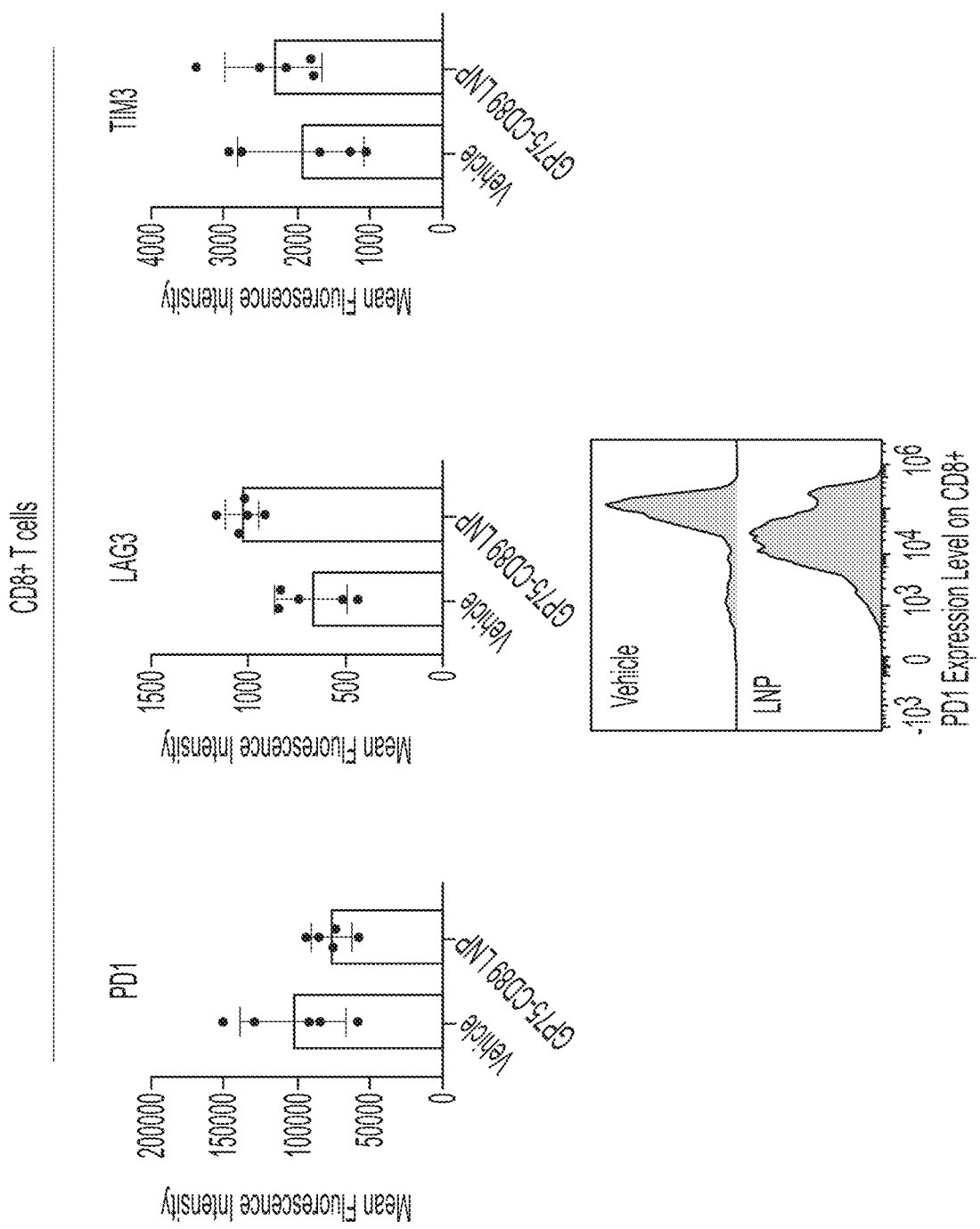
FIG. 25 shows that LNP treatment resulted in reduced CD8 T cell immune checkpoint expression. Graphs of the expression level of the indicated immune checkpoint molecules by CD8+ T cells from the tumor microenvironment of mice treated with an LNP containing an mRNA encoding the indicated anti-GP75 CFP construct are depicted. Treatment resulted in a reduction of PD1 expression level and slight increase of LAG3 expression.
Figure 31:
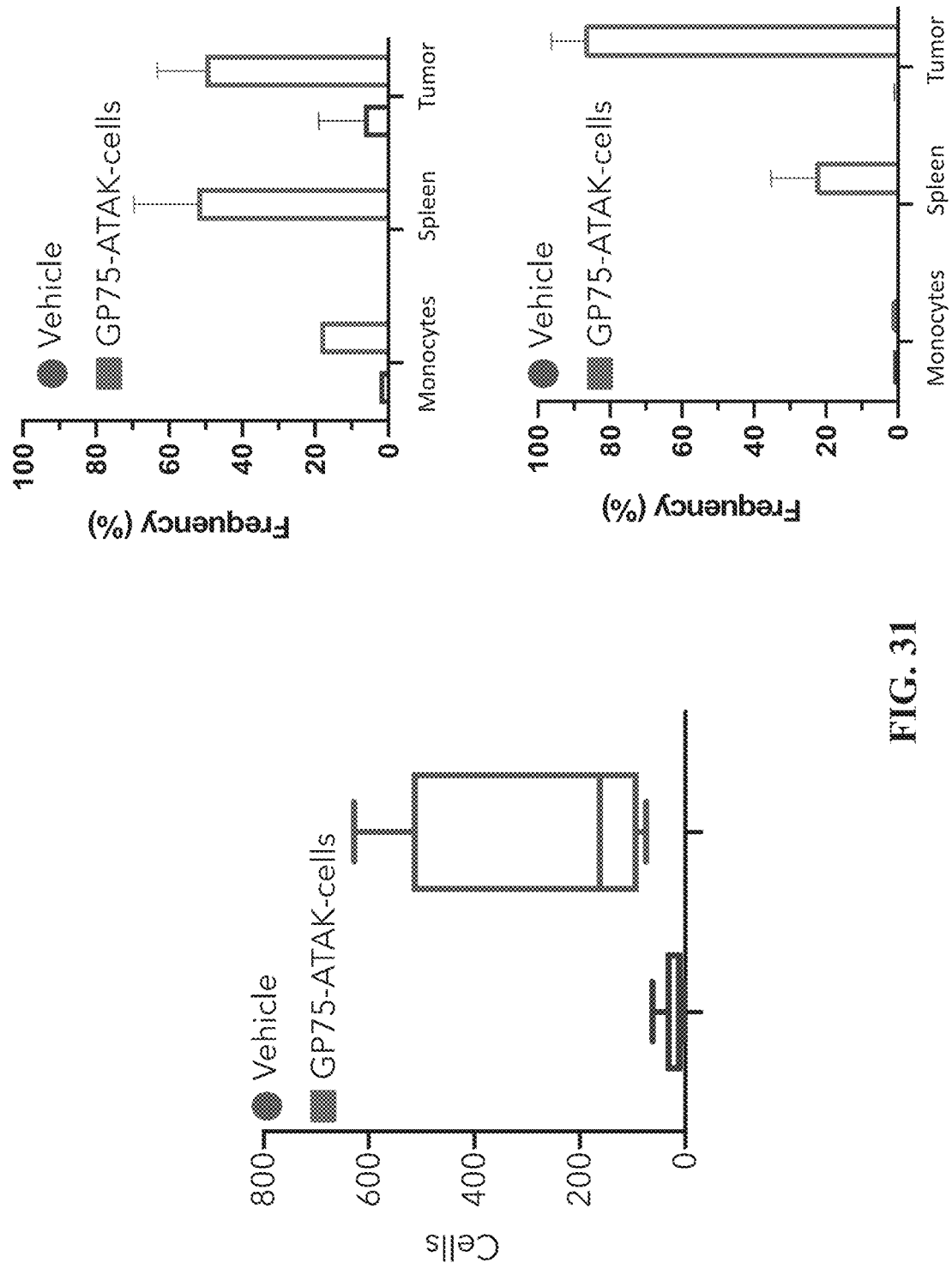
FIG. 31 shows graphs demonstrating that after infusion into a mouse tumor model, mouse monocytes expressing an anti-GP75 CFP penetrate into tumors, sustain expression of the CFP and differentiate into effector cells, such as inflammatory cell, dendritic cells and macrophages. Left graph shows that about ~40% of the mouse monocytes expressing the anti-GP75 CFP maintained expression of the CFP 5 days after infusion. Top right graph shows ATAK Cells (CFP expressing cells) penetrate tumor and spleen and become dendritic cells. Bottom right graph shows ATAK Cells penetrate tumor and spleen and become macrophage cells.
Figure 32:
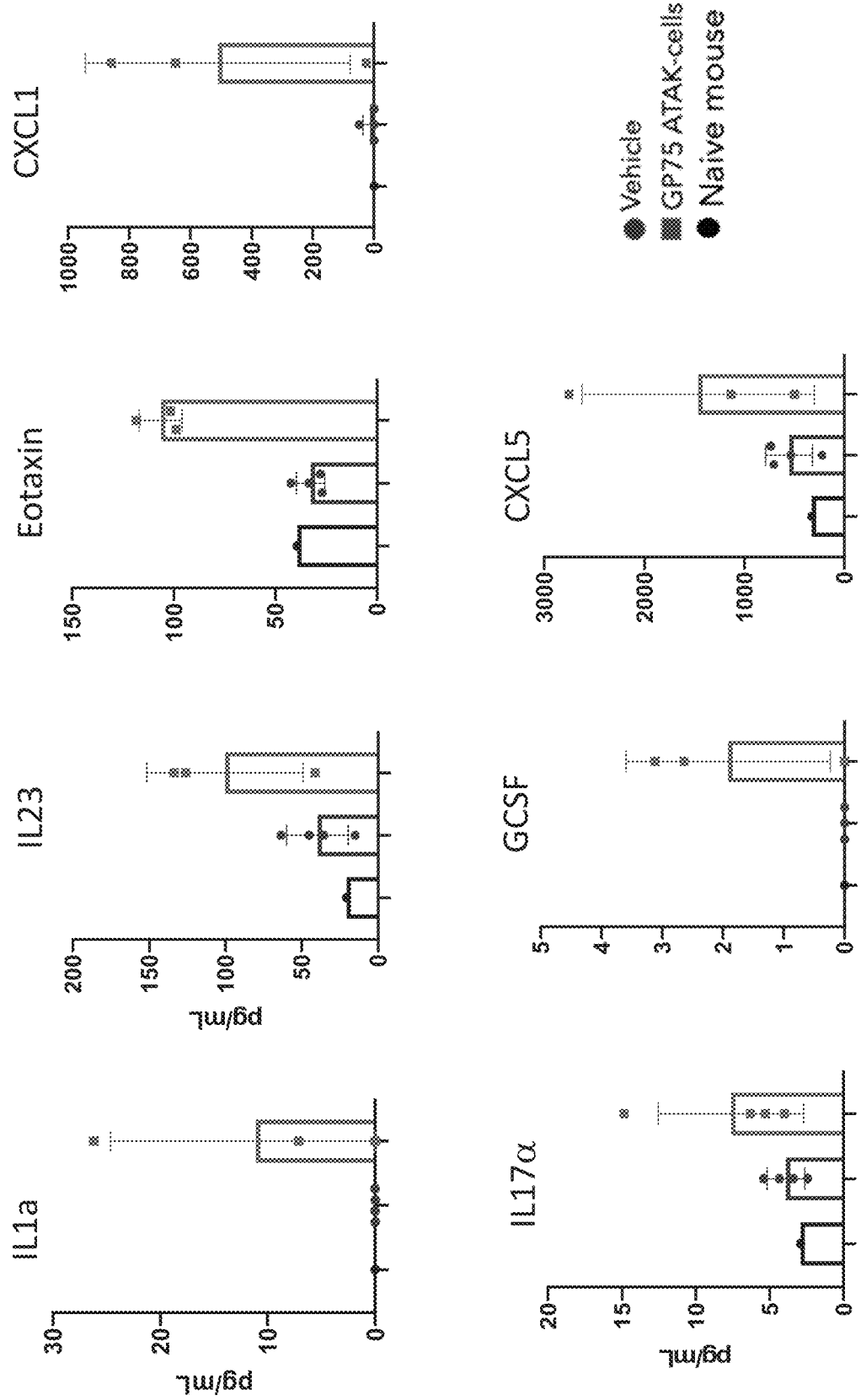
FIG. 32 depicts data of cytokine production of cells from naive mice or a mouse tumor model treated with vehicle or myeloid cells expressing an anti-GP75 CFP construct. Graphs of production of the indicated cytokines/chemokines are shown. Treatment responses correlated with anti-tumor serum cytokine profile. Analysis includes responder animals in treatment group at study termination.
Figure 33:
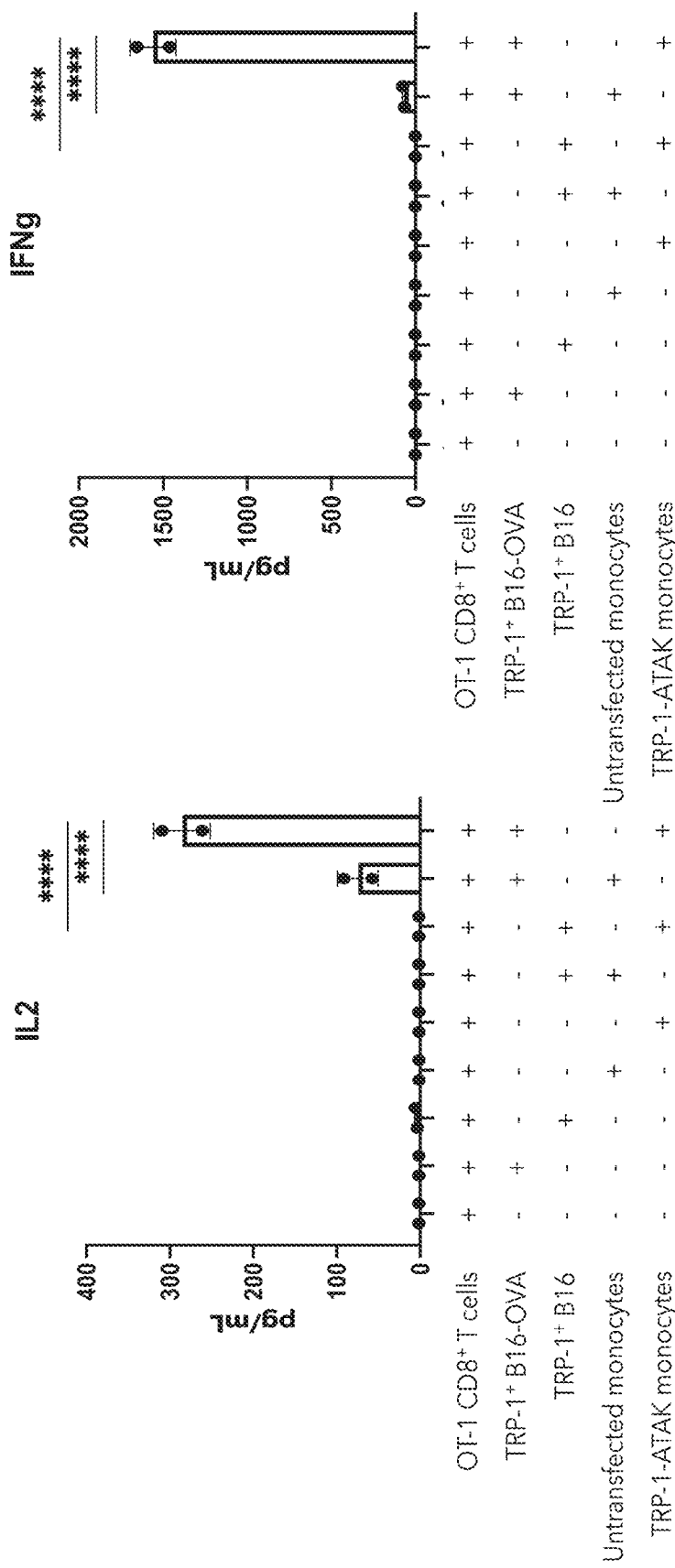
FIG. 33 depicts data showing cross-presentation of tumor antigen by mouse monocytes expressing an anti-GP75 CFP. The mouse monocytes expressing an anti-GP75 CFP are able to phagocytize, process and present a surrogate tumor neoantigen, in this case derived from the OVA protein, to T cells that bear a cognate TCR for a class I restricted peptide derived from OVA (SIINFEKL (SEQ ID NO: 87)), and T cell activation is determined by IL2 (left) or Interferon (right) generation; while monocytes from the same mouse that do not express the ATAK receptor cannot. This proves that mouse monocytes expressing an anti-GP75 CFP can process and cross-present antigen to adaptive immune cells such as CD8 T cells. ATAK-GP75 (aka TRP-1 ATAK) construct.

Positive CFP expression was identified in myeloid cells and some CD3+ cells (FIG. 23 and FIG. 24). Increased phagocytosis, and cytokine secretion is also evident in data shown in FIGS. 31, 32, 33 and 35. As shown in FIG. 31, the monocytes further became DCs and mature monocytes inside the tumor and spleen. Serum cytokine levels shown in FIG. 32 illustrate broad myeloid activity in the responders. Treatment Responses Correlated With Anti-Tumor Serum Cytokine Profile. The other significant observation was the Cross-Presentation of Tumor Antigen by ATAK monocytes (FIG. 33). ATAK myeloid cells can phagocytose, liberate & present neoantigen to T cells, resulting in adaptive T cell immune response. The ATAK-GP75 (aka TRP-1 ATAK) monocytes are able to phagocytize, process and present a surrogate tumor neoantigen, in this case derived from the OVA protein, to T cells that bear a cognate TCR for a class I restricted peptide derived from OVA (SIINFEKL (SEQ ID NO: 87)) while monocytes from the same mouse that do not express the ATAK receptor cannot. This proves that ATAK monocytes can process and cross-present antigen to adaptive immune cells such as CD8 T cells. This further indicates that potential novel subsets of T cells could be stimulated via function of these myeloid cells in vivo, thereby demonstrating wider immunological coverage as opposed to treatment by other immune cell types, such as T cells.

Figure 38:
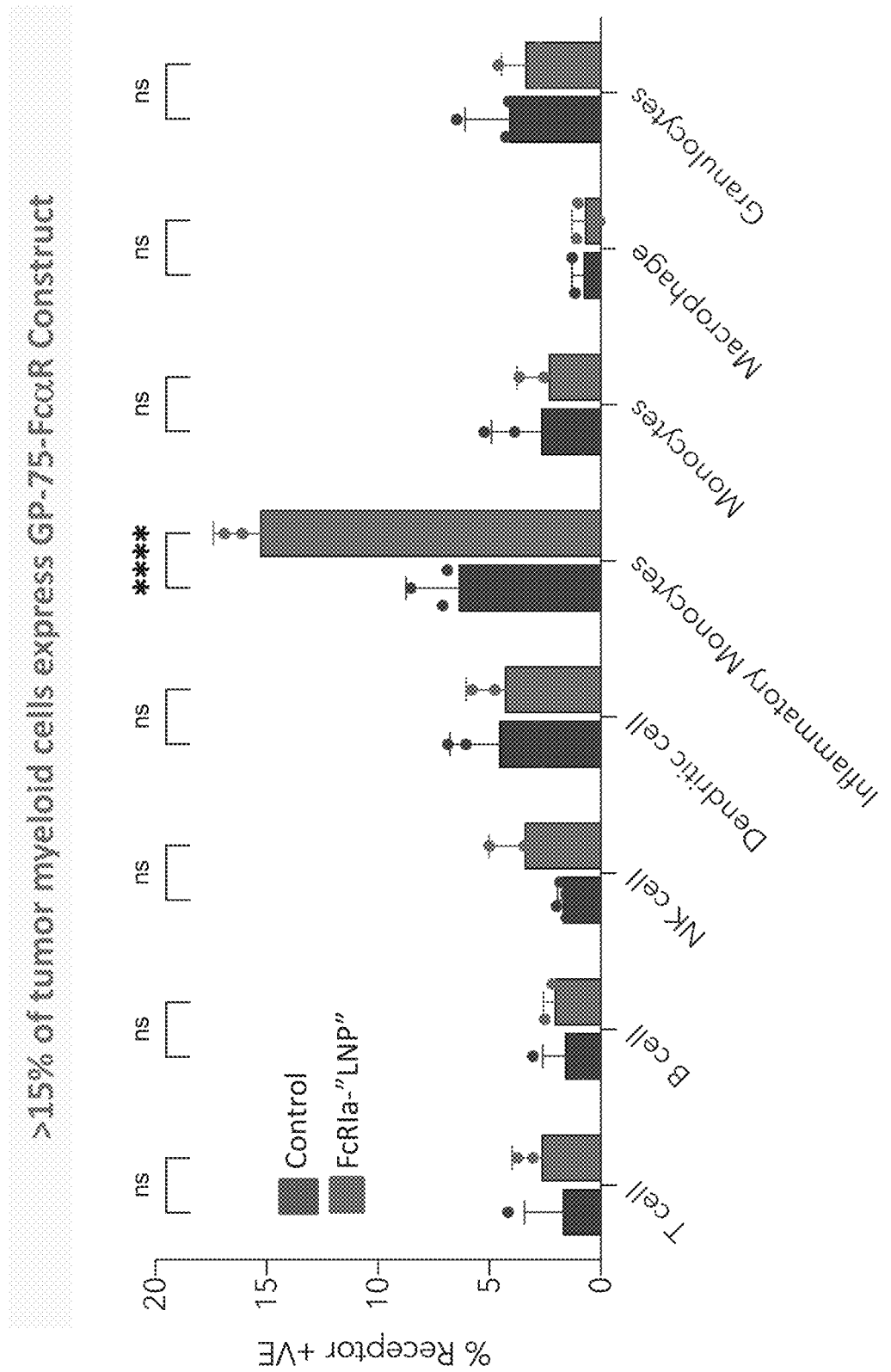
FIG. 38 depicts data showing that injection of an LNP containing RNA encoding an anti-GP75 CFP with a CD89 (FcRalpha) chain into mice results in expression of the CFP by inflammatory monocytes within the TME.>15% of tumor myeloid cells were observed to express the anti-GP75 CFP.

Preferential expression of the constructs in myeloid cells in vivo was corroborated in the data depicted in FIG. 38. LNP-FcRα chain receptor was expressed by inflammatory monocytes within the TME, and greater than 15% of tumor myeloid cells express GP-75-FcαR construct.

Figure 26:
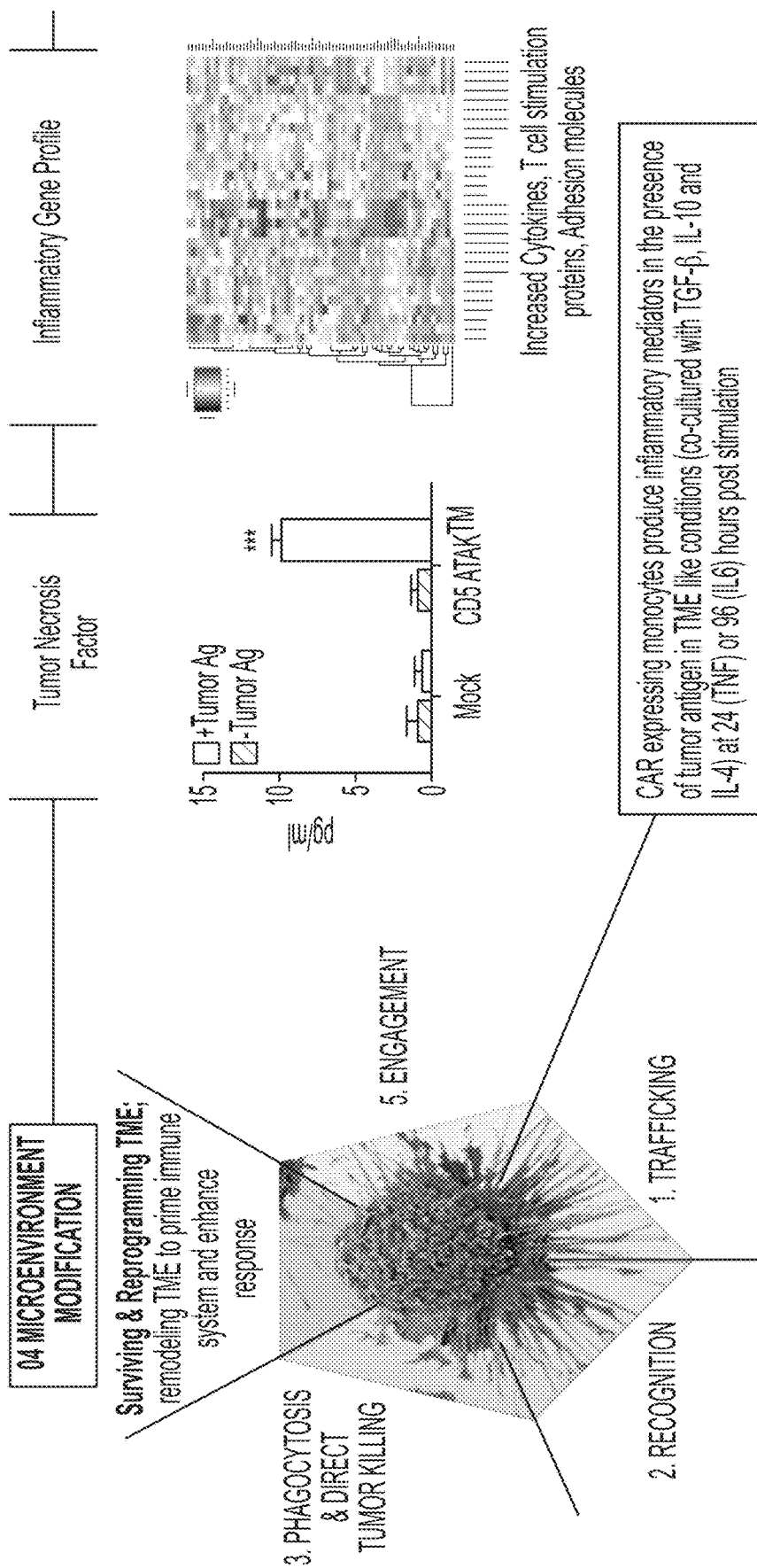
FIG. 26 shows conversion of tumor microenvironment into inflammatory phenotype upon in vivo administration of nucleic acid encoding CFP in an LNP composition.
Figure 27:
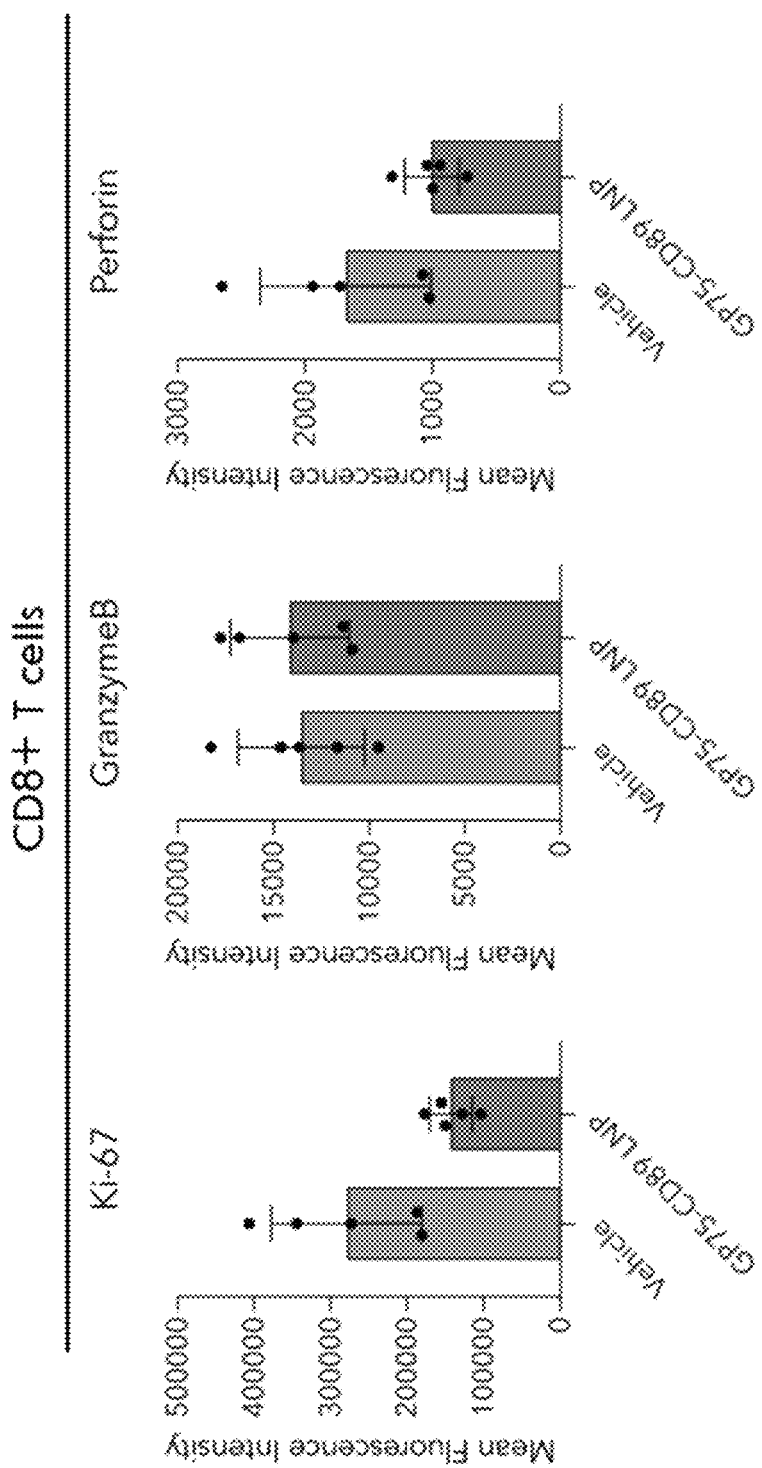
FIG. 27 shows that LNP treatment resulted in a reduction of expression of Ki-67 and Perforin in CD8+ T cells. Graphs of the expression level of the indicated molecules by CD8+ T cells from the tumor microenvironment of mice treated with an LNP containing an mRNA encoding the indicated anti-GP75 CFP construct are depicted.
Figure 28:
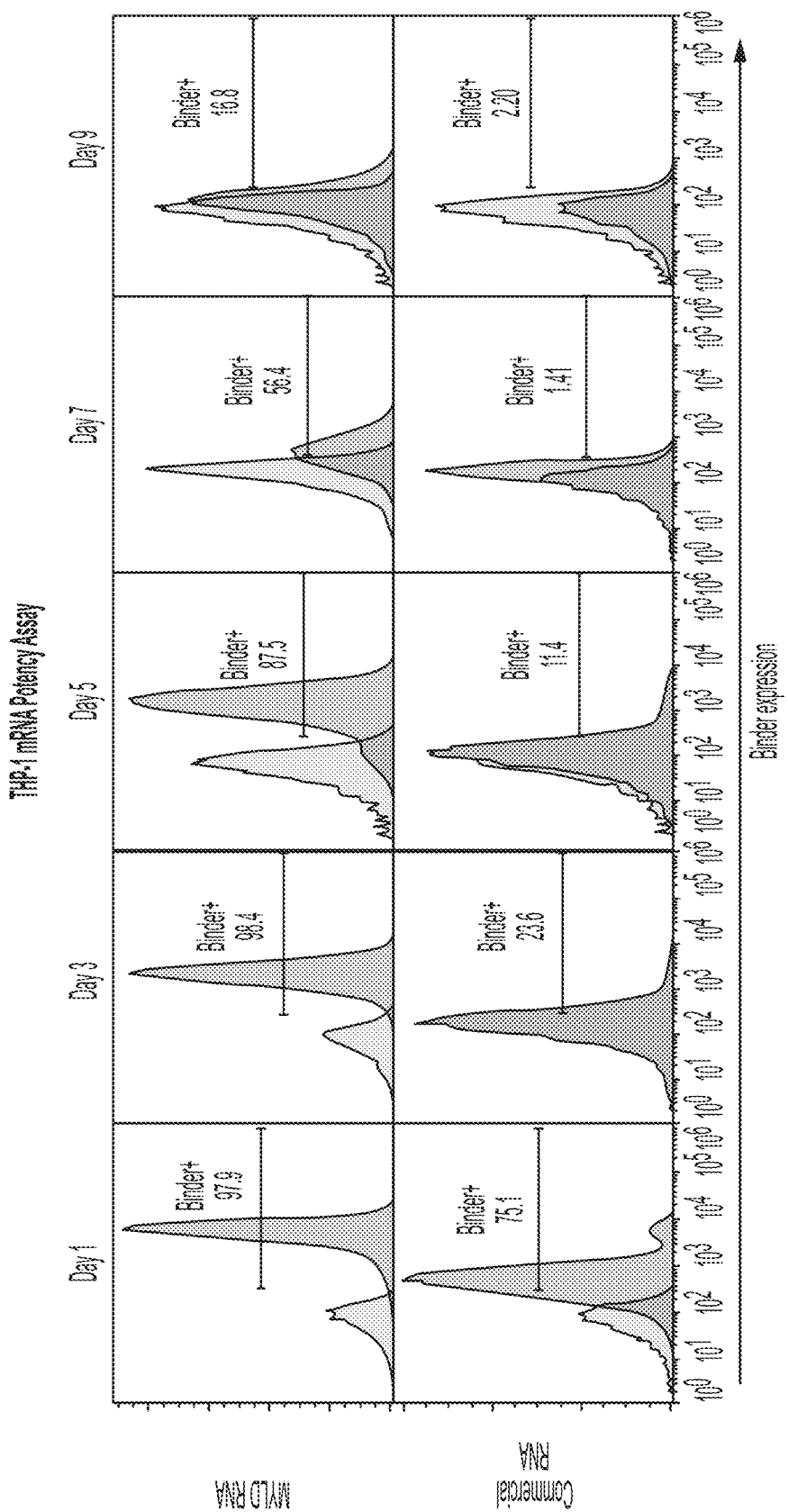
FIG. 28 shows flow cytometry data showing expression of a CFP construct in THP-1 cells electroporated with mRNA encoding the CFP.
Figure 34:
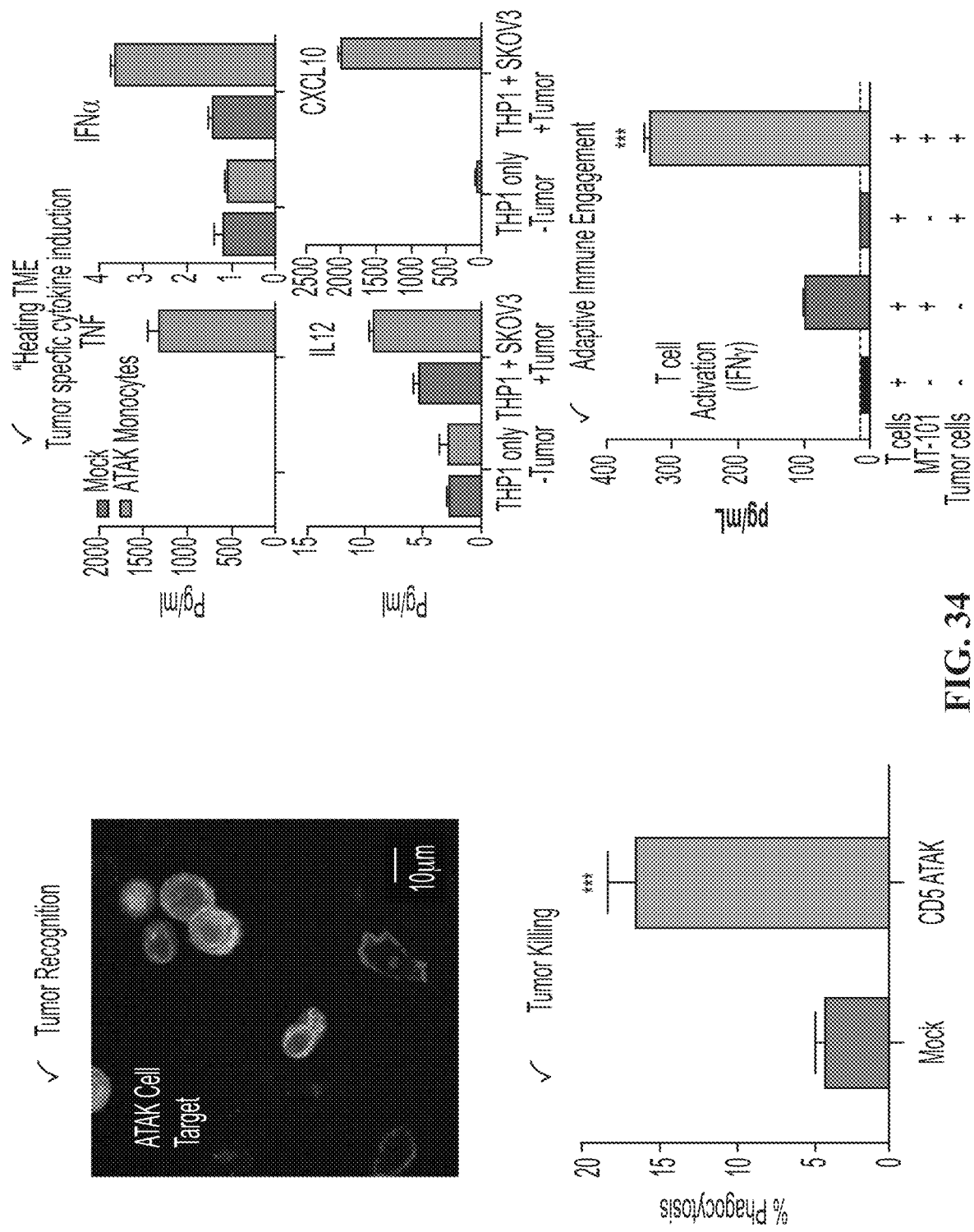
FIG. 34 depicts data showing that human monocytes expressing a CFP harness innate immunity and stimulate adaptive anti-tumor immune responses. The data demonstrates that human monocytes expressing a CFP penetrate tumors, accumulate in tumors and recognize tumors (upper left). The data demonstrates that human monocytes expressing a CFP result in myeloid cell activation, cytokine production, chemokine production and inflammatory polarization (upper right graphs). The data demonstrates that human monocytes expressing a CFP directly kill tumor cells via phagocytosis (lower left), cytokines and death receptors (CD95L). The data demonstrates that human monocytes expressing a CFP demonstrate long-term control of tumors via antigen presentation, epitope spreading and T cell engagement (lower right graphs), thereby ensuring complete activation of the immune repertoire.
Figure 35:
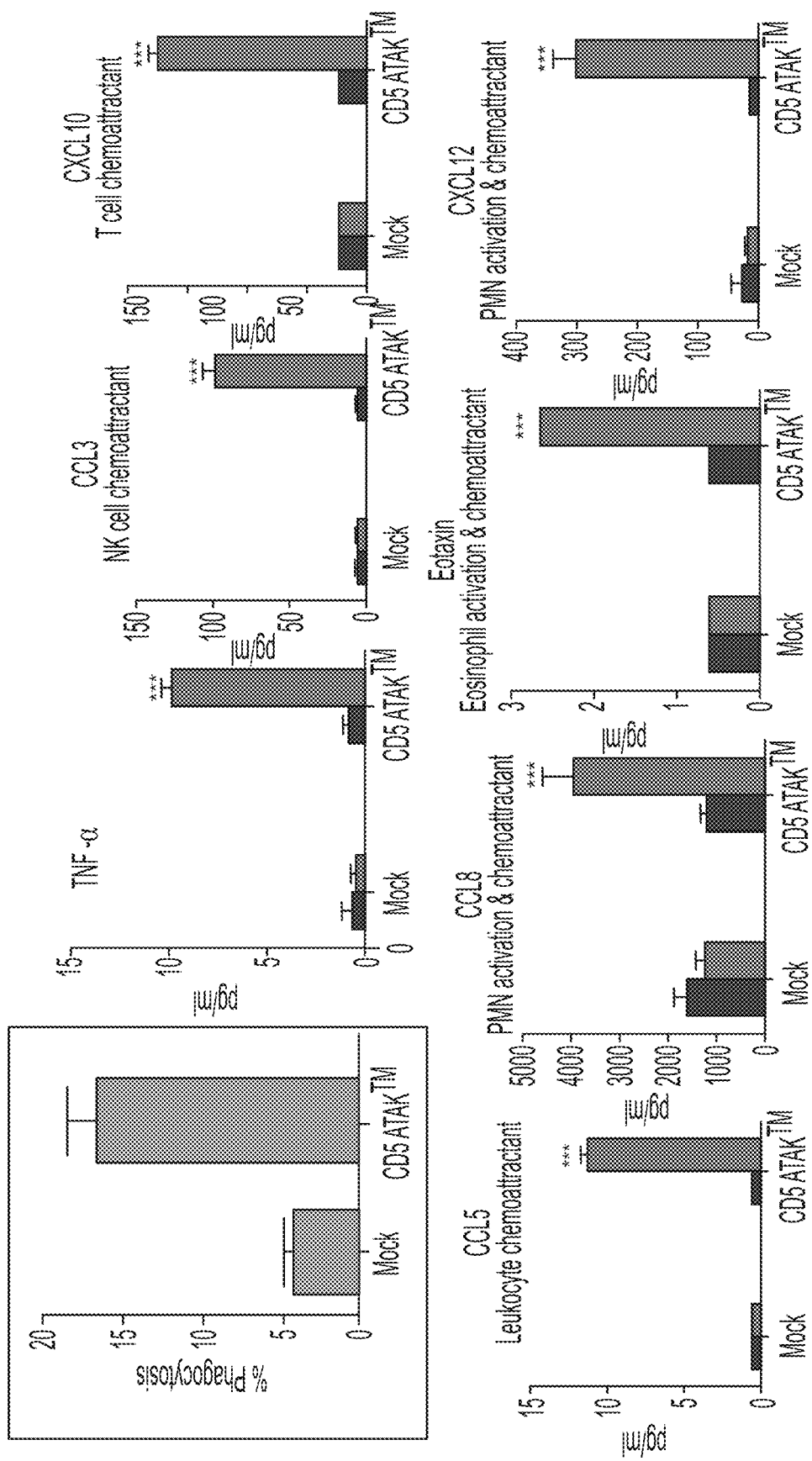
FIG. 35 depicts data showing that human monocytes expressing an anti-CD5 CFP show potent activity in suppressive tumor microenvironment (TME) conditions in vitro. Human monocytes expressing an anti-CD5 CFP were incubated overnight in the absence or presence of cognate antigen in media containing IL10, IL4 & TGF-β. Phagocytic activity of the cells are demonstrated in the graph on extreme left on top. Cytokines/chemokines as indicated were measured in culture supernatant.
Figure 39:
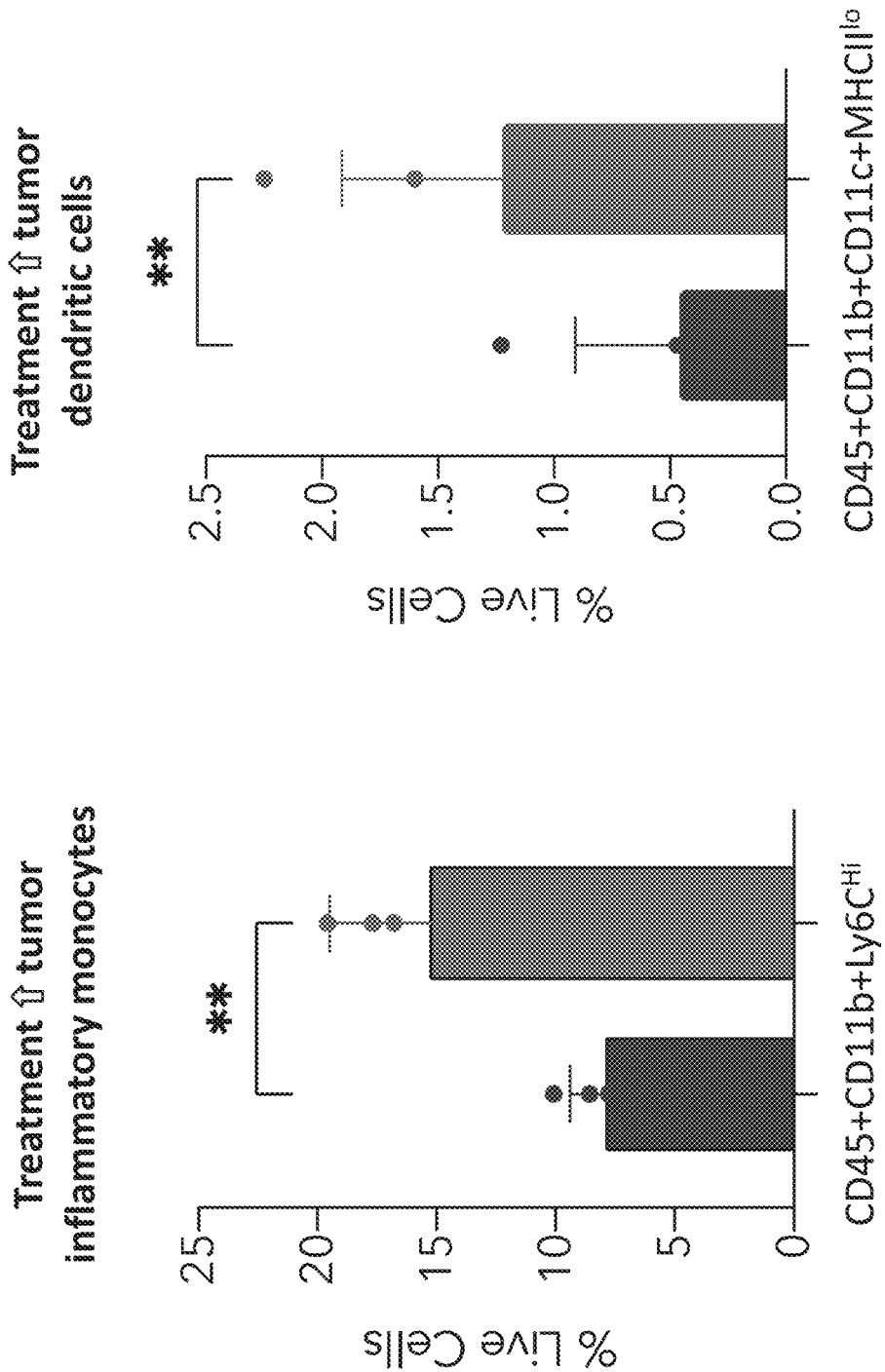
FIG. 39 depicts data showing that injection of an LNP containing RNA encoding an anti-GP75 CFP with a CD89 (FcRalpha) chain into mice results in modification of the TME, characterized by accumulation of inflammatory cells. Treatment induces tumor inflammatory monocytes (left), and dendritic cells (right) in vivo as measured post mortem of the treated animals. Treatment increased immune cells associated with bridging innate & adaptive immunity.

Example 11. Microenvironment Modification by CFP Expressing Modification In Vivo In this example, inflammatory gene expression was profiled from in vivo tumor samples which indicate that the CFP constructs turn the tumor microenvironment into an active inflammatory site, with expression of proinflammatory cytokines and chemokines (FIG. 26), (heating of the TME) and FIG. 34 (top right). FIG. 27 and FIG. 34 show data indicating that the CFP injection in vivo was capable of T cell induction. FIG. 34 demonstrates that the human ATAK monocytes as disclosed herein were able to harness innate immunity and stimulate adaptive anti-tumor immune response. The key summary points indicating that the engineered human cell products were confirmed to have key functional mechanism are enumerated below:

Tumor Penetration & Recognition
Penetration
Accumulation
Tumor recognition
Signaling Dynamics
Myeloid cell activation
Cytokine production
Chemokine production
Inflammatory polarization
Direct Tumor Kill
Phagocytosis
Cytokines
Death receptors (CD95L)
Long-term Tumor Control
Antigen presentation
Epitope spreading
T cell engagement From the data shown, it is apparent that the myeloid cells have the capability to alter the tumor microenvironment with increase in inflammatory monocytes and DCs are shown in data in FIG. 39. The data in FIG. 39 shows upregulation of inflammatory monocytes (left) and dendritic cells (right). In addition, these cells influence the T cell functioning. Taken together, such dramatic effects of therapeutic potential and relevance have not been achieved ad/or demonstrated before, to the best of the applicant's knowledge.

Example 12. Characterization of T Cells In Vivo Following Treatment in Mice

Figure 40:
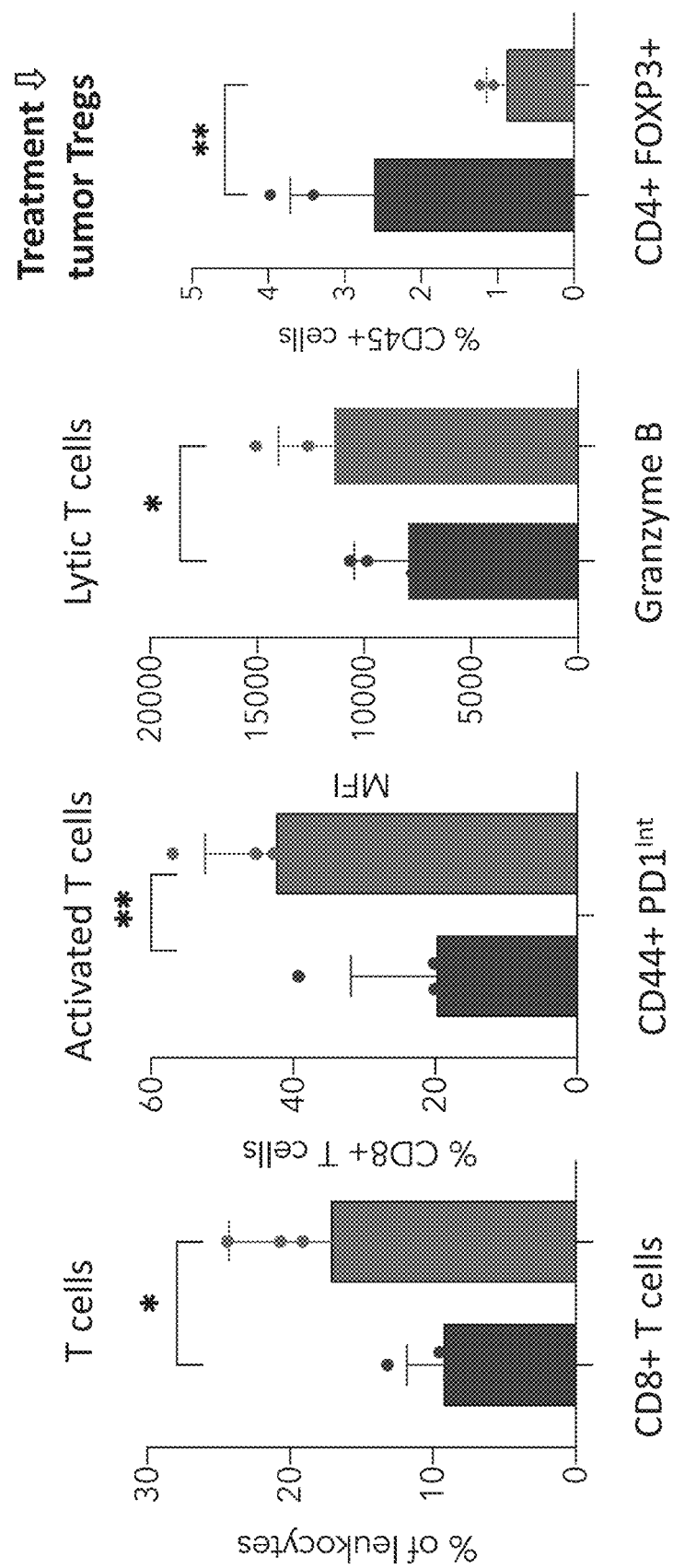
FIG. 40 depicts data showing that injection of an LNP containing RNA encoding an anti-GP75 CFP with a CD89 (FcRalpha) chain into mice results in modification of the TME, characterized by increasing CTLs and decreasing Tregs. Treatment promoted anti-tumor CD8 T cells and reduced tumor associated Tregs.
Figure 43:
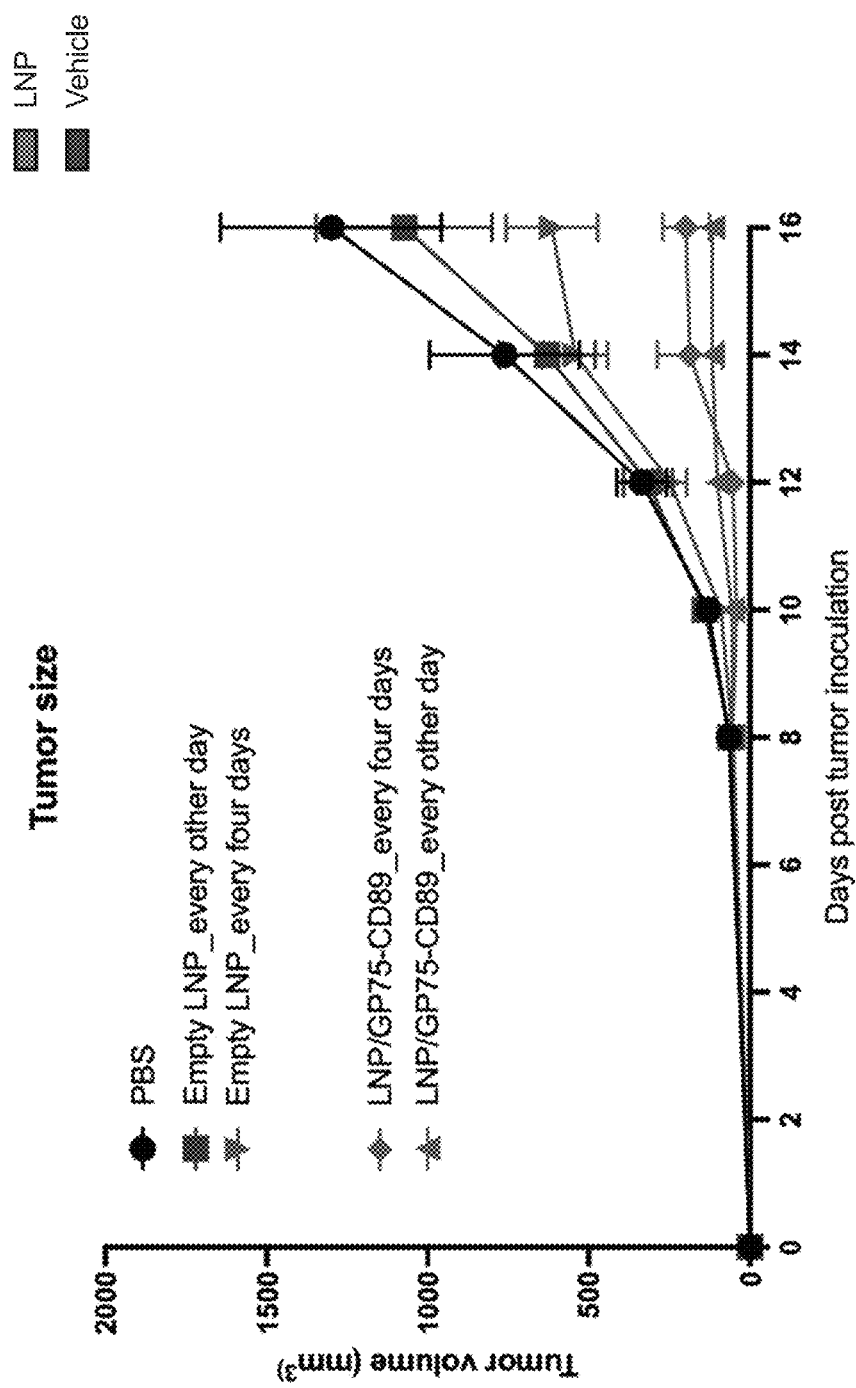
FIG. 43 depicts experimental design and tumor growth. Tumor was inoculated on day 0 and allow to grow to 75 mm$^3$. LNP-mRNA was dosed at 2 mg/kg.
Figure 44:
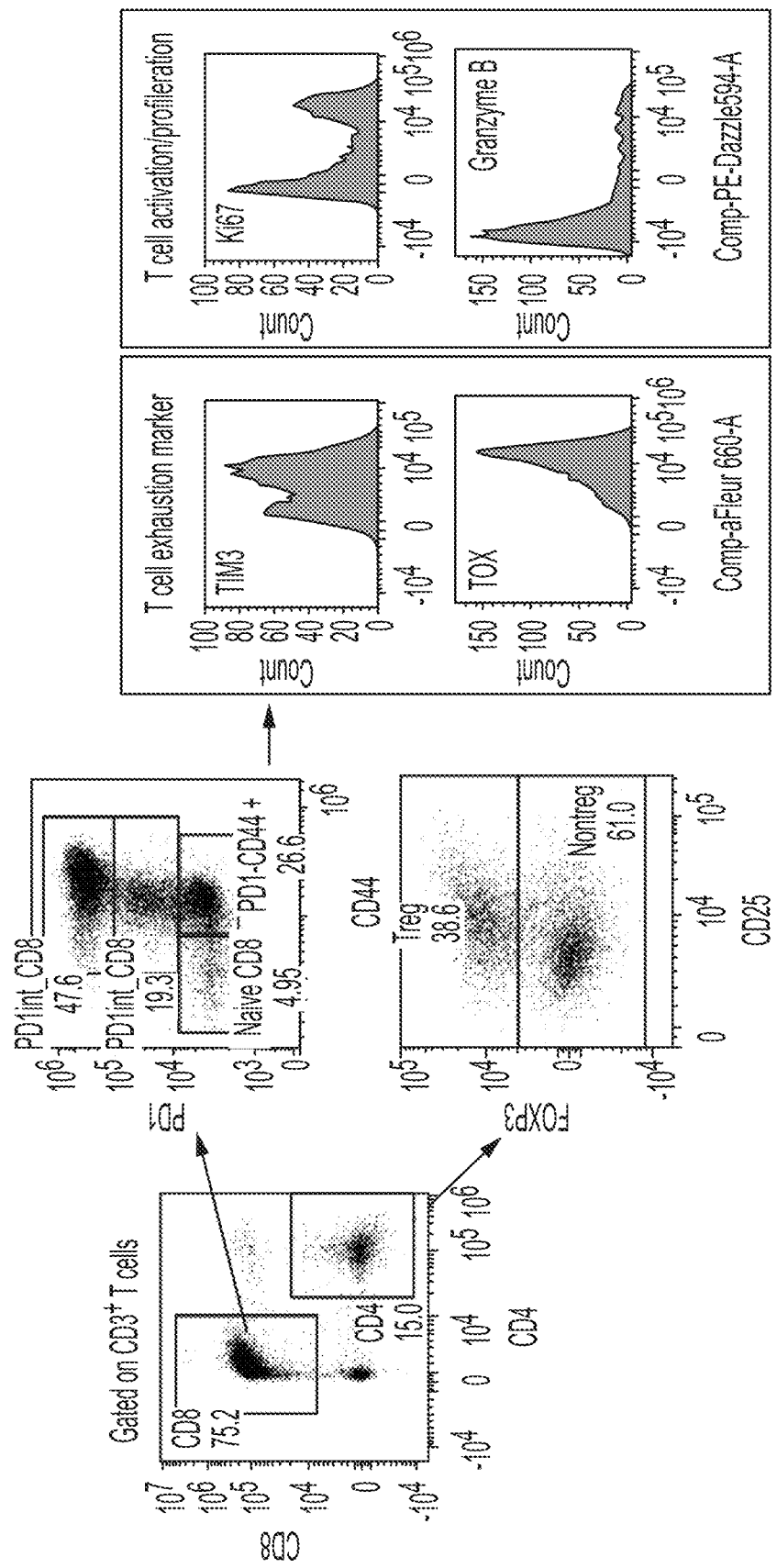
FIG. 44 depicts investigation of T cell subsets and phenotype in tumor.

The data shown in FIG. 40-FIG. 60 involve use of an LNP composition for delivery. FIG. 40 demonstrates upregulation of CD8+ T cells by the treatment of CFP in mice via tail yin injection. An investigation of the T cell subset phenotypes is shown in FIG. 41, with the cytokine profile. An investigation of the T cell subset phenotypes is shown in FIG. 42, with the chemokine profile. In the study discussed herein, GP75 tumor bearing syngeneic mice were dosed either once every four days or once every other day, and the tumor progression was determined by measuring tumor size. As shown in FIG. 43, both the treatment groups showed efficient inhibition of tumor progression compared to controls. FIG. 44 showed the gating strategy for studying T cell subtypes.

Figure 45:
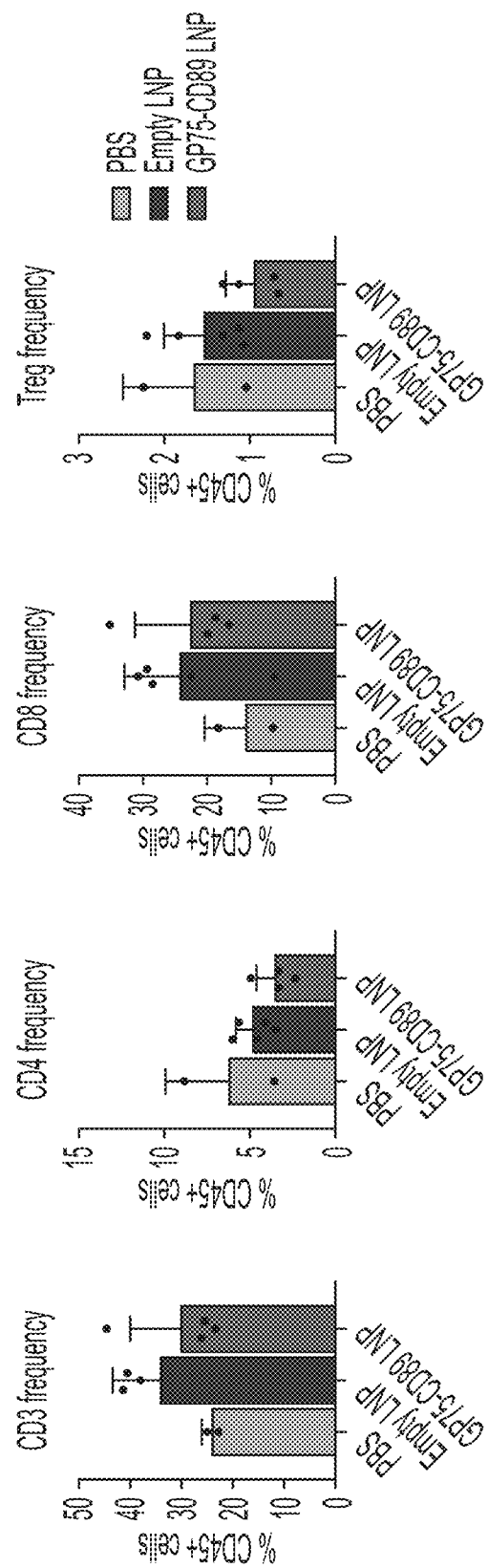
FIG. 45 depicts data that mRNA-LNP treatment induces changes in T cell subset frequency inside tumor. The treatment caused reduction in % Treg in tumor.
Figure 46A:
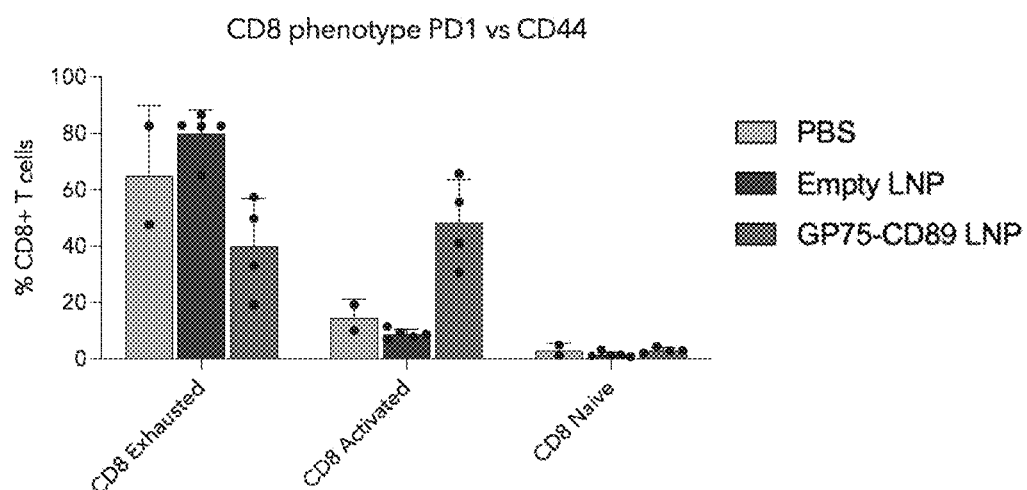
FIG. 46A depicts graph showing flow cytometry analysis of CD8 exhaustion marker (PD1) and an CD8 maturation/effector T cell marker (CD44) of the % CD8+ T cells in mice injected with GP75-CD89-LNP.
Figure 46B:
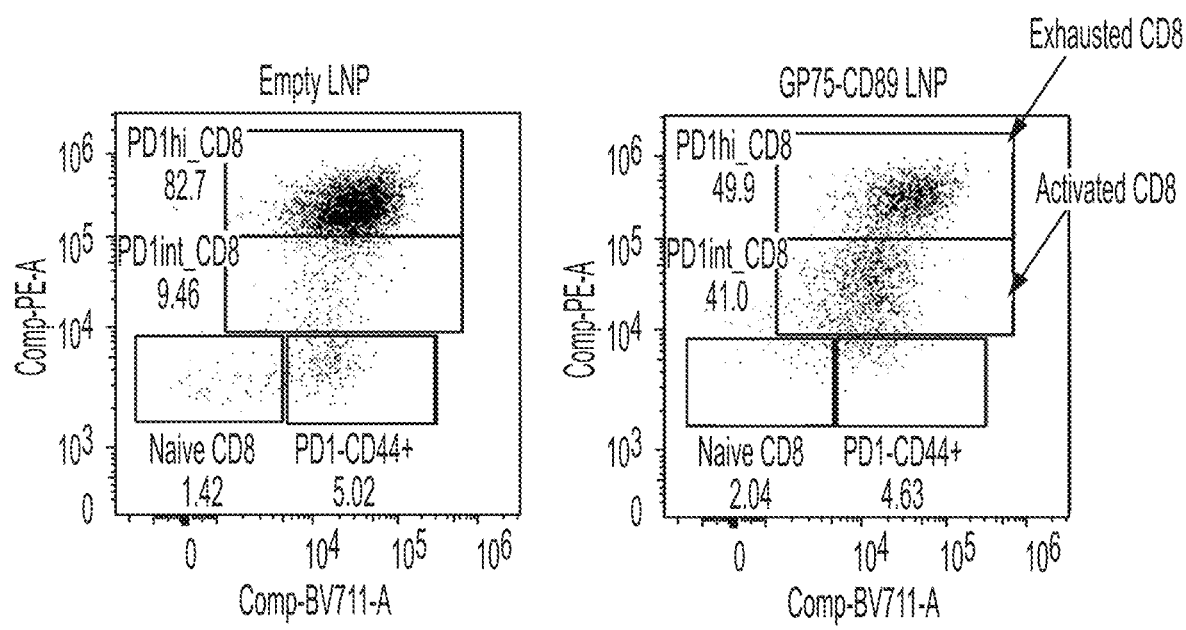
FIG. 46B depicts flow cytometry data of PD1 and CD44 expression in T cells.
Figure 47A:
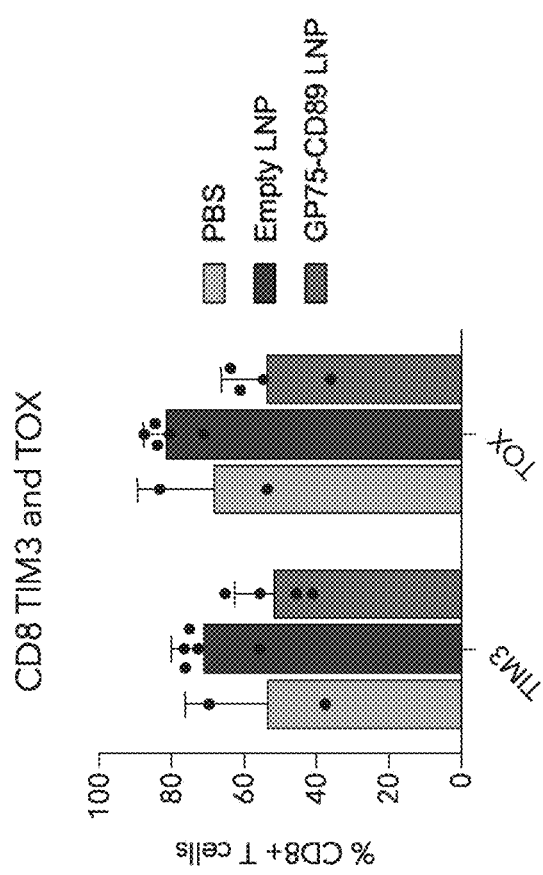
FIG. 47A depicts graph showing flow cytometry analysis of CD8 exhaustion marker (TIM3 and TOX) of the % CD8+ T cells in mice injected with GP75-CD89-LNP.
Figure 47B:
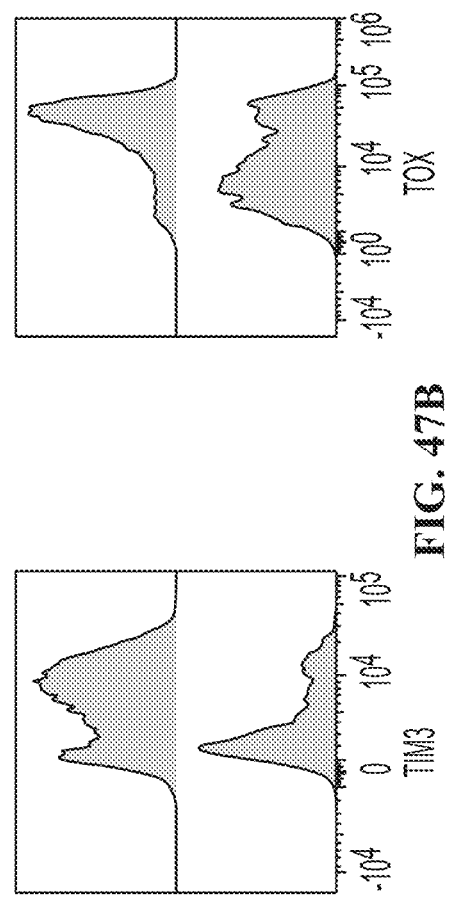
FIG. 47B depicts flow cytometry data of TIM3 and TOX expression in T cells.
Figures 48A, 48B:
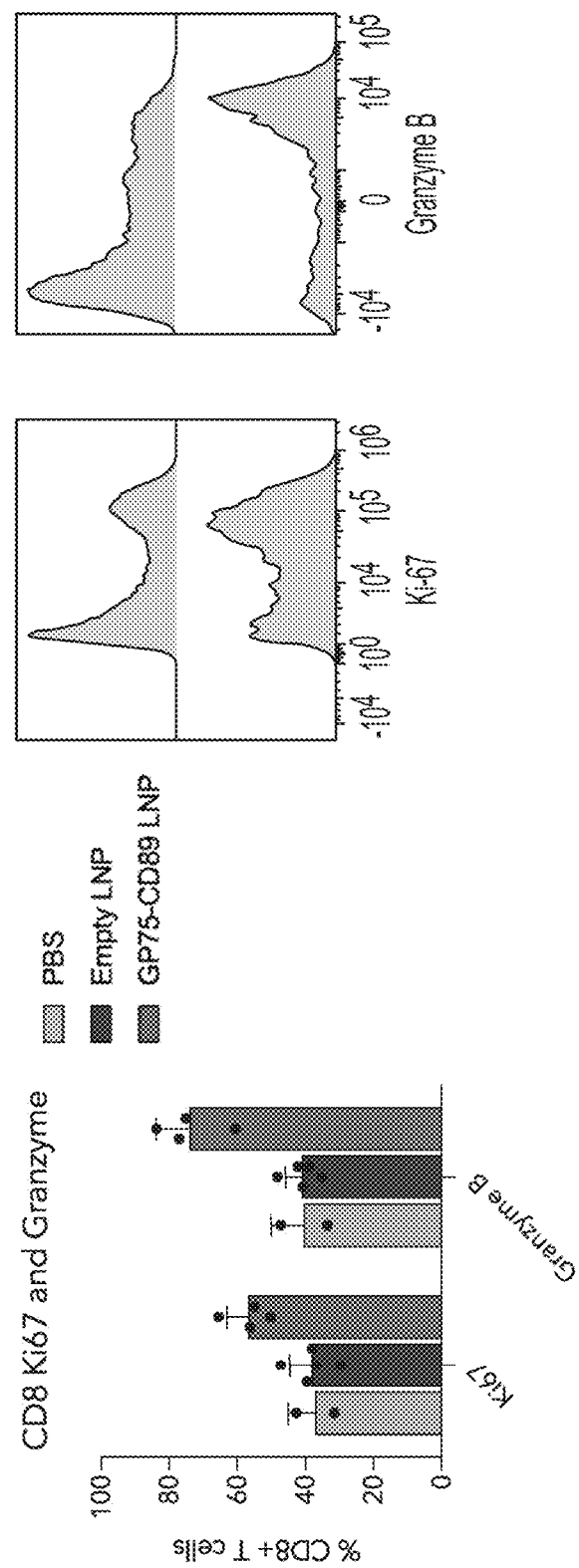
FIG. 48A depicts graph showing flow cytometry analysis of cell proliferation marker Ki67, and T cell activation marker Granzyme B mice injected with GP75-CD89-LNP.
FIG. 48B depicts flow cytometry data of Ki67 and Granzyme B in the CD8T cells from mice injected with GP75-CD89-LNP.
Figure 49:
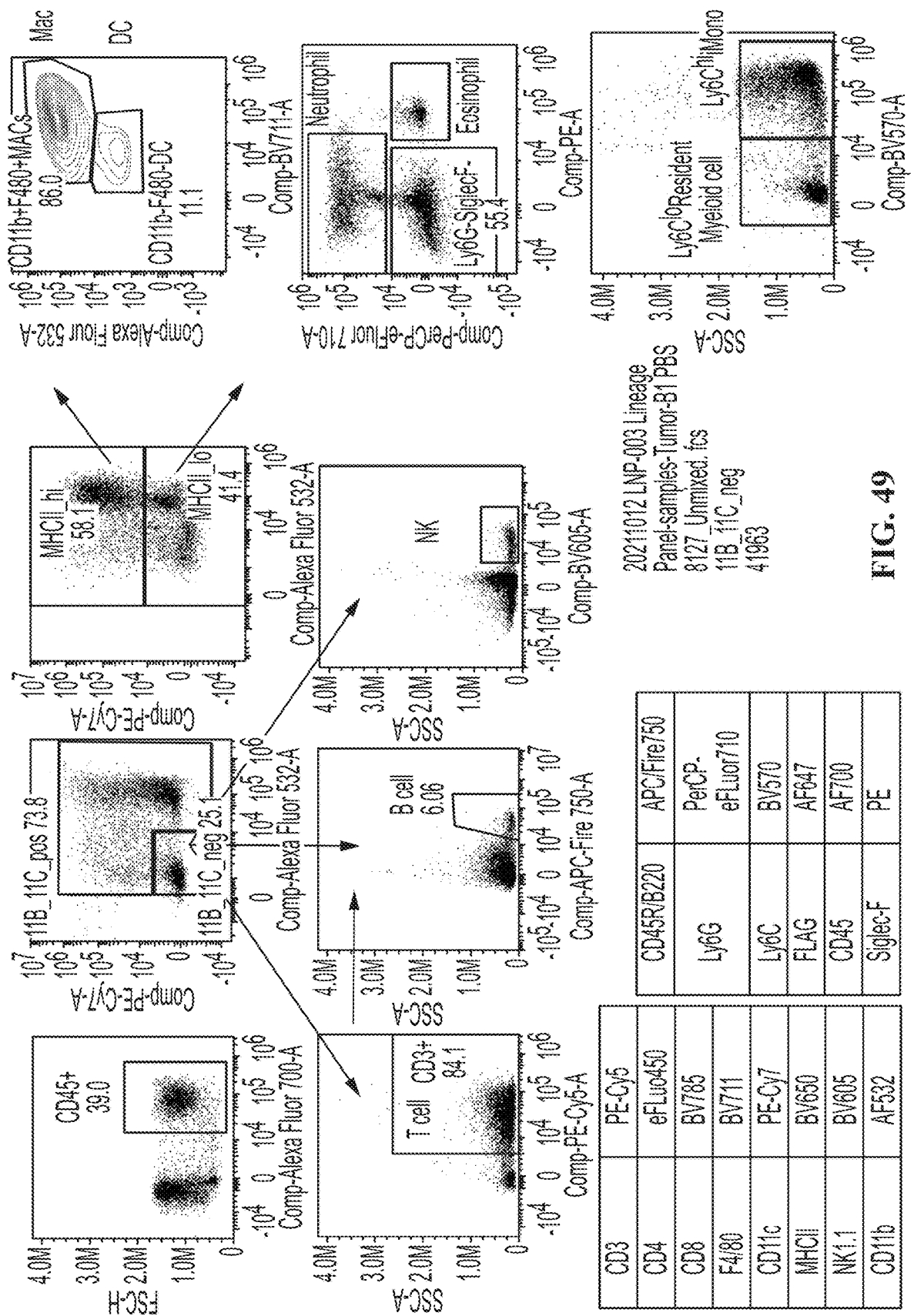
FIG. 49 shows data from investigation of cell lineages; the panel of markers and fluorophores are indicated on the left.

Analysis of the T cell subtypes revealed high induction of CD8+ cells and reduction of Tregs in tumor (FIG. 45). A rise in T cell activation markers with a lowering of T cell exhaustion marker (PD1) was noted in the T cells (FIGS. 46A and 46B, FIGS. 47A and 47B, FIGS. 48A and 48B).

Figure 50:
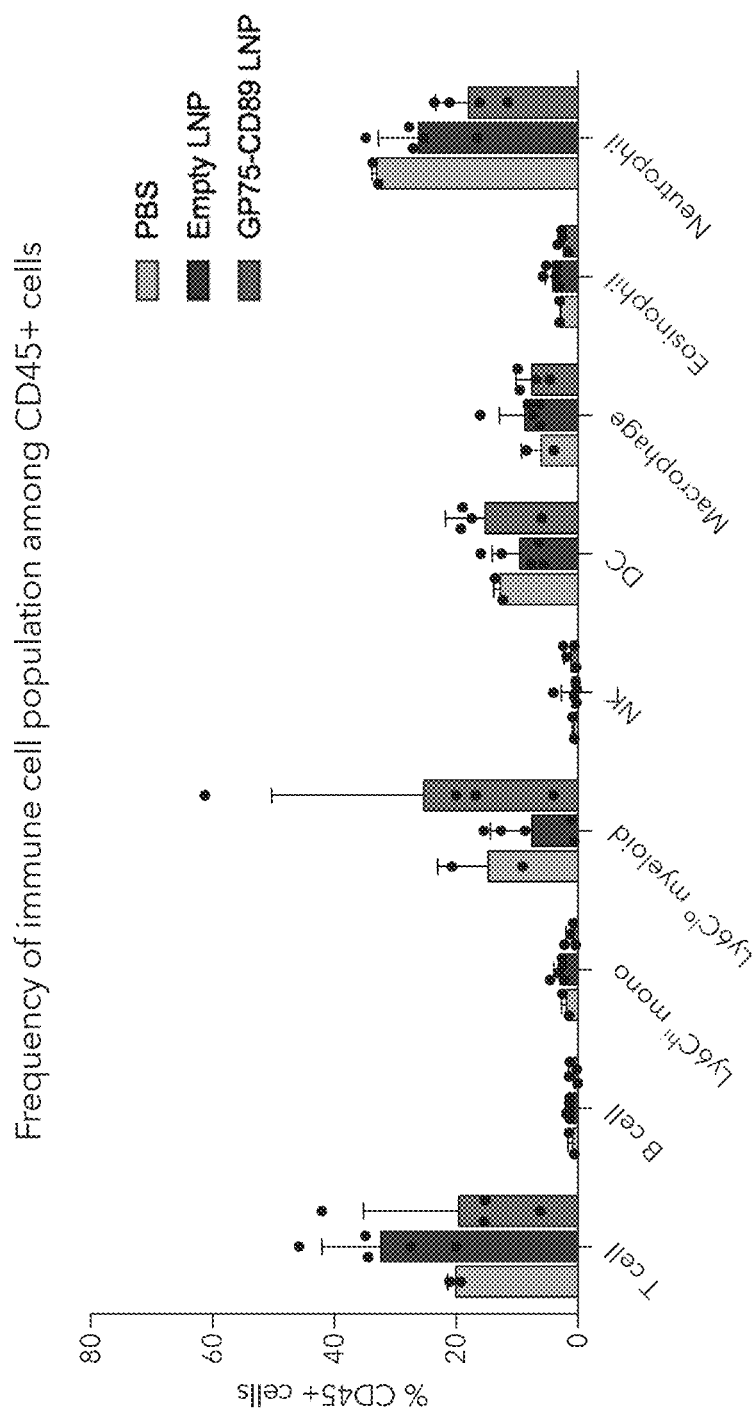
FIG. 50 depicts data indicating mRNA/LNP treatment did not induce significant shift in immune cell population.
Figure 51:
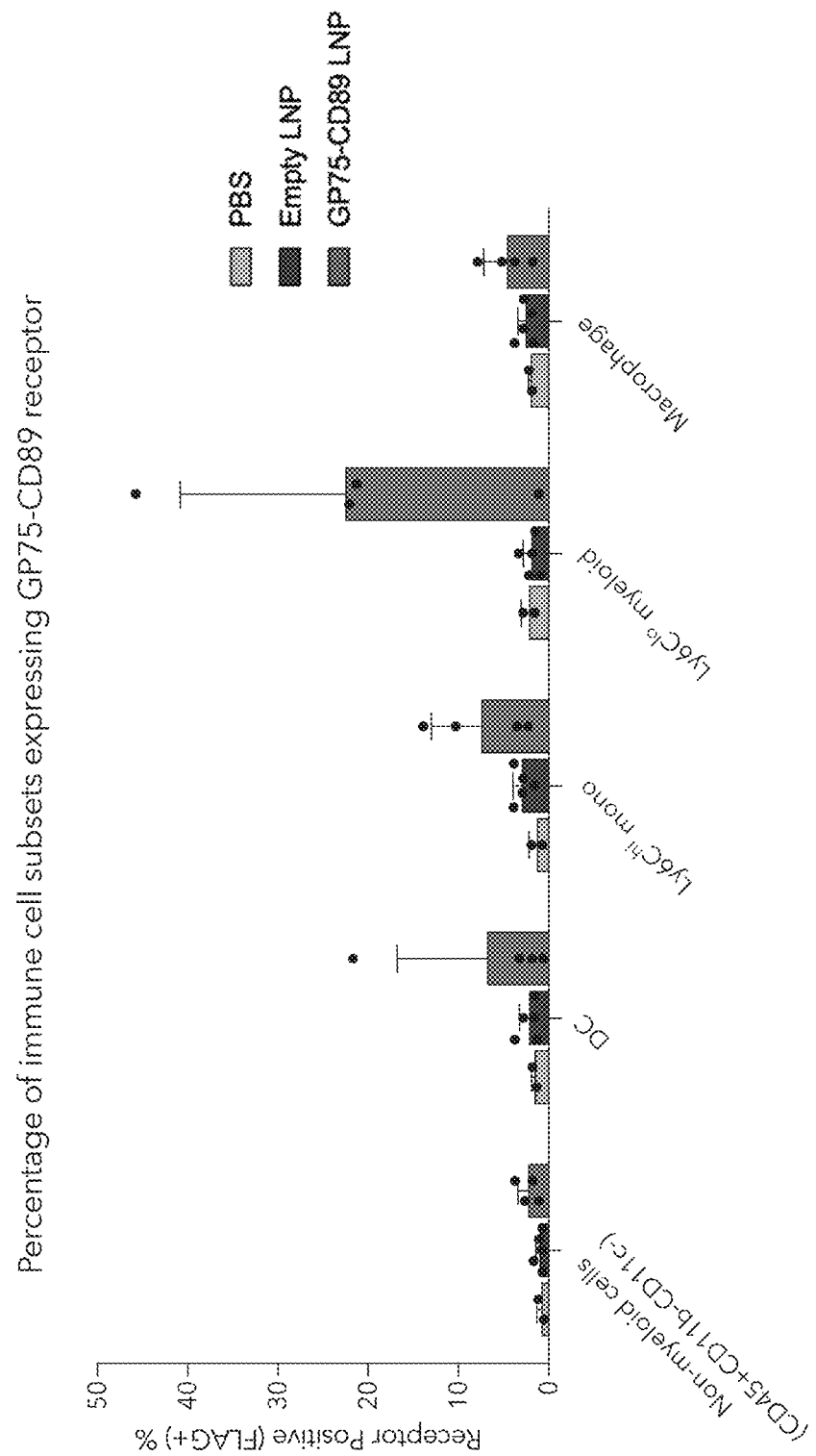
FIG. 51 shows data on receptor expression.
Figure 52:
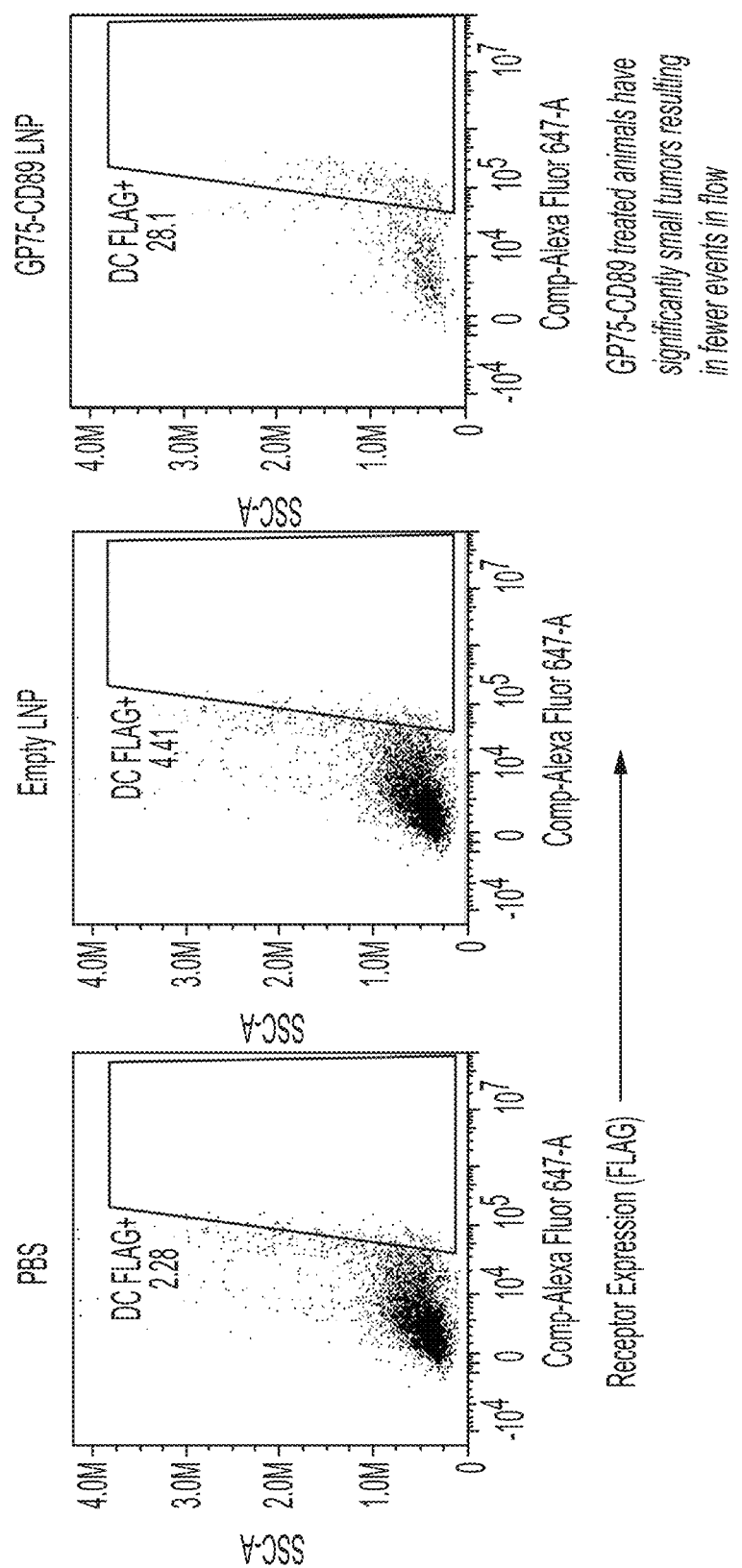
FIG. 52 shows dot plot showing FLAG (i.e., receptor) expression in dendritic cells.
Figure 53:
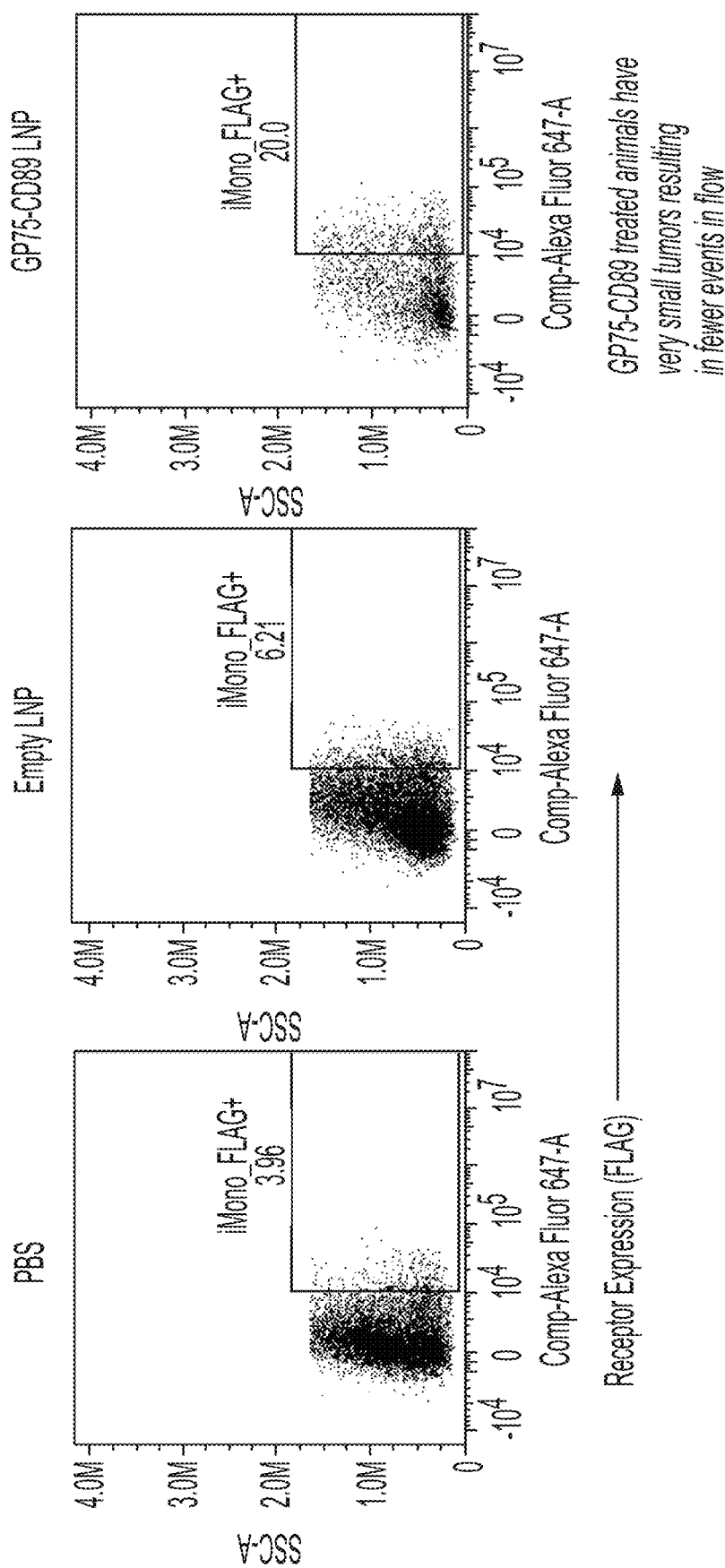
FIG. 53 shows dot plot showing FLAG expression in Ly6C$^{hi}$ inflammatory monocytes.
Figure 54:
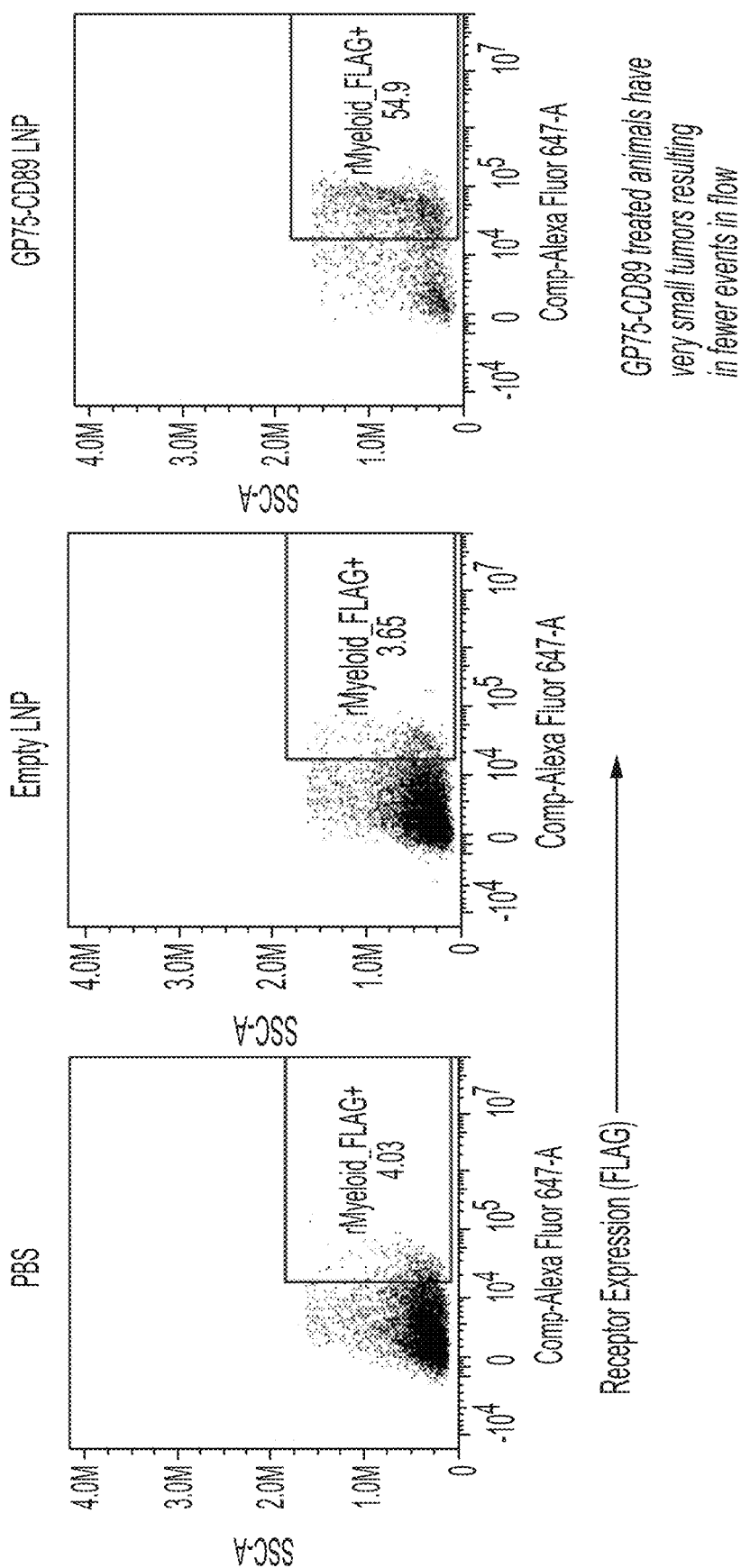
FIG. 54 shows dot plot showing FLAG expression in Ly6C$^{lo}$ resident myeloid cells.
Figure 55:
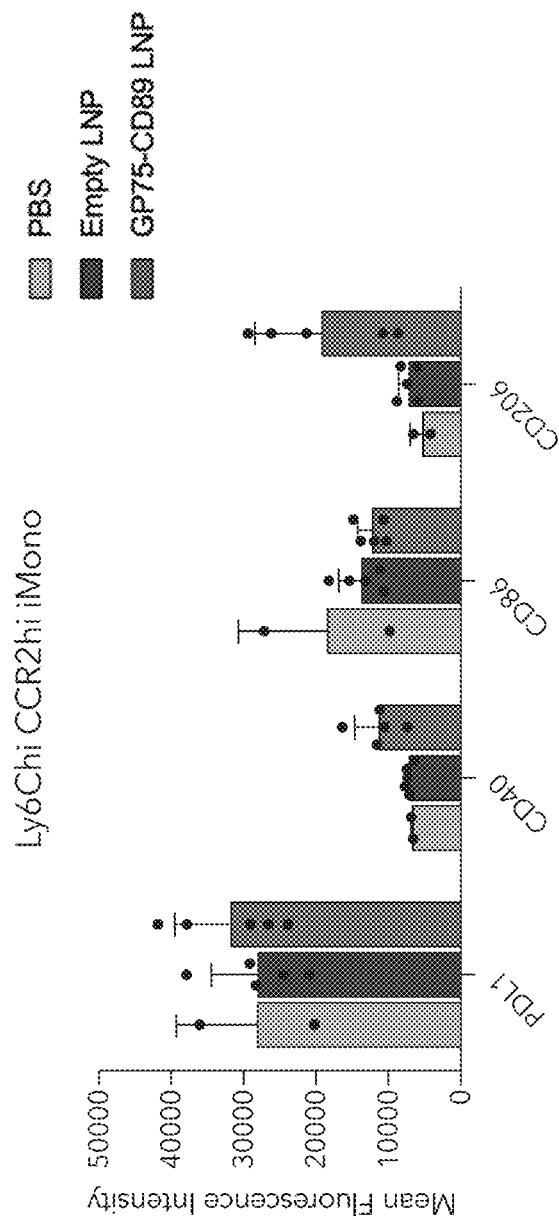
FIG. 55 depicts data indicating that the treatment in mice significantly increased CD40 and CD206 levels in Ly6C$^{hi}$ and CCR2$^{hi}$ inflammatory monocytes.

Example 13. Characterization of Myeloid Cells In Vivo Following Treatment in Mice Further, all cell types including lymphocytes, DCs etc were profiled following isolated from treated vs untreated GP75 mice, using the gating strategy shown in FIG. 49. Overall the immune cell frequency did not show remarkable change (FIG. 50). Myeloid and dendritic cells show high expression of the receptor construct. Expression is characterized in the various cell types as shown in FIGS. 51-53, indicating myeloid cells show marked expression of the constructs delivered via the LNP preparations. FIG. 54 shows receptor expression in greater than 50% resident myeloid)(Ly6C$^{lo}$) cells. FIG. 55 depicts data indicating that the treatment in mice significantly increased CD40 and CD206 levels in Ly6C$^{hi}$ and CCR2$^{hi}$ inflammatory monocytes.

Figure 56:
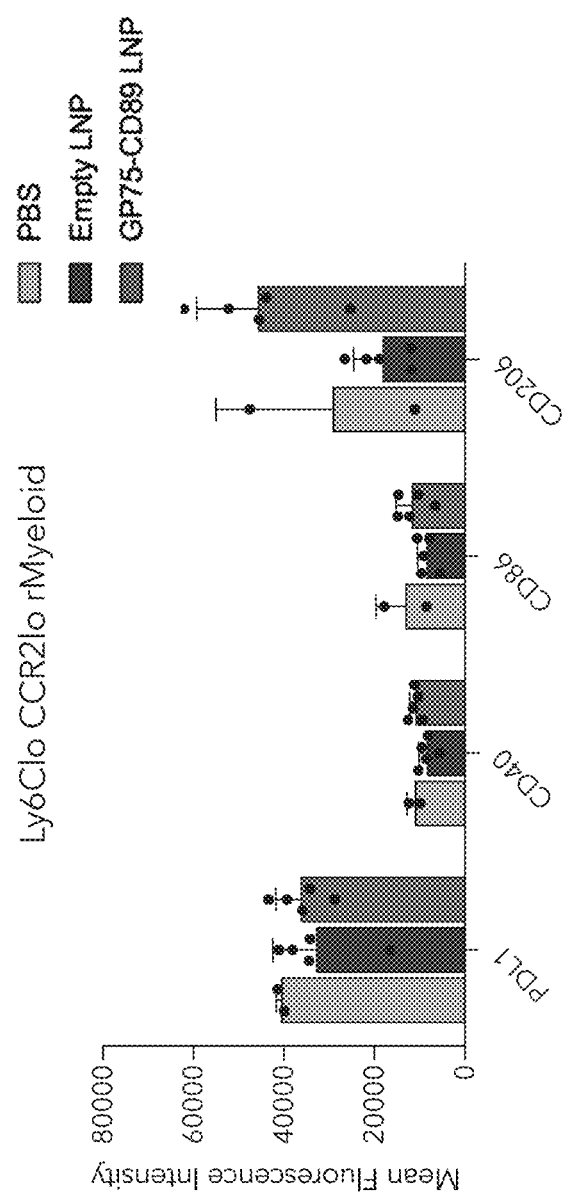
FIG. 56 depicts PDL1, CD40, CD86, and CD206 levels in Ly6C$^{lo}$ and CCR2$^{lo}$ resident myeloid cells. The data indicating that the treatment in mice significantly increased CD40 and CD206 levels.
Figure 57:
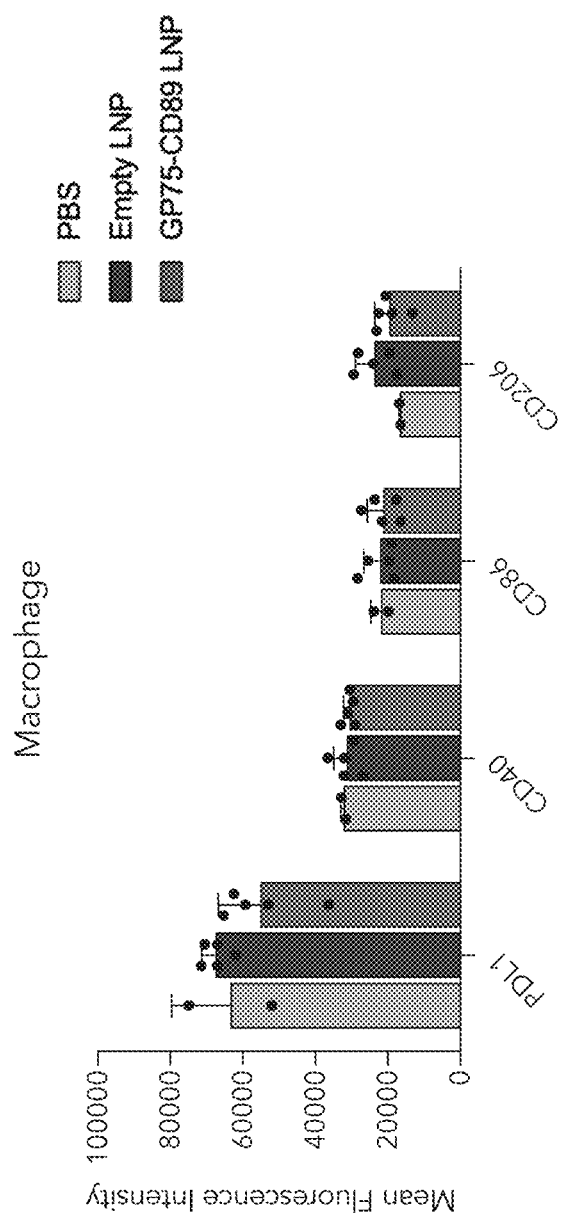
FIG. 57 shows PDL1, CD40, CD86, and CD206 levels; results indicate that the treatment slightly reduced PDL1 level in tumor resident macrophages.
Figure 58:
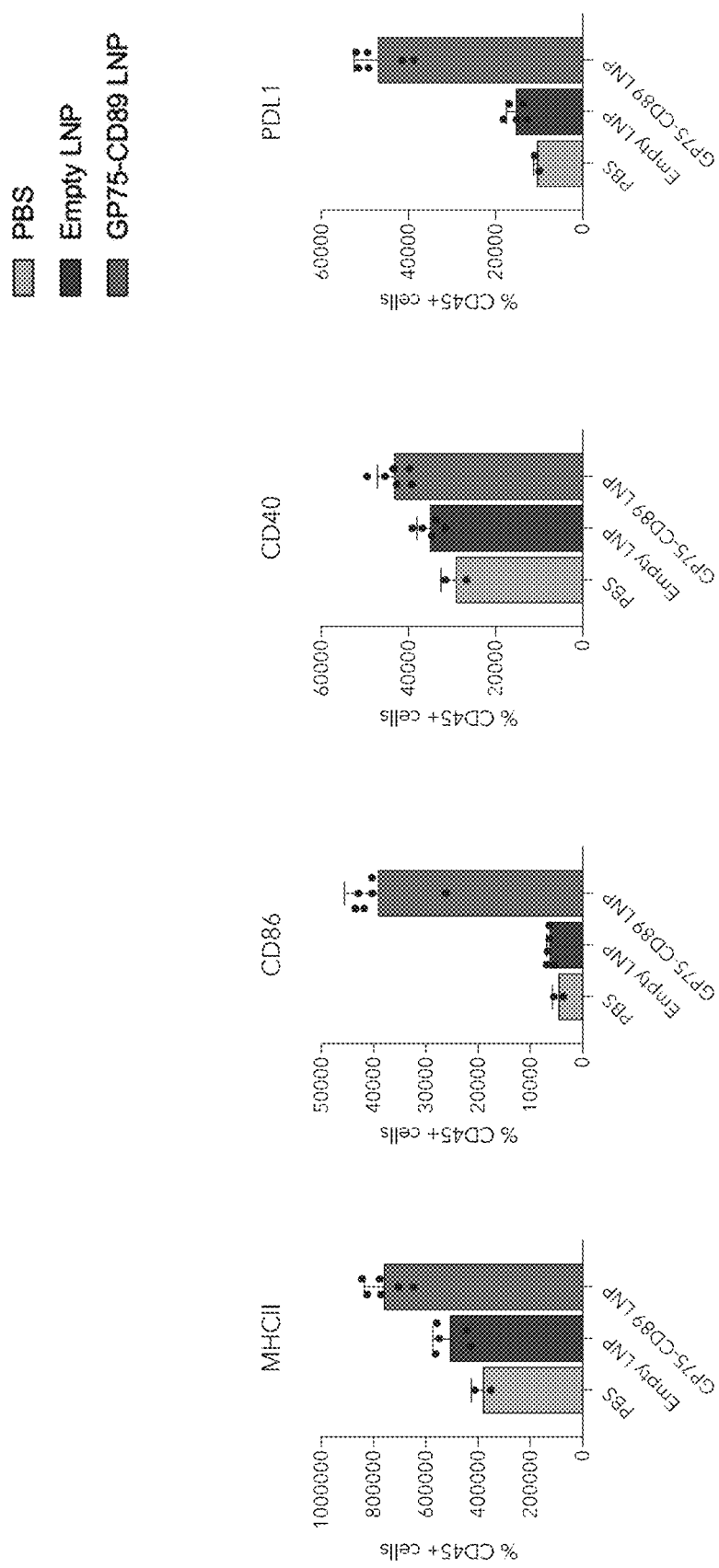
FIG. 58 shows that the treatment significantly increased DC activation marker including MHCII, CD86 and CD40, but also increased PD-L1 level in CD103+CD11b− dendritic cell phenotype in spleen.
Figure 59:
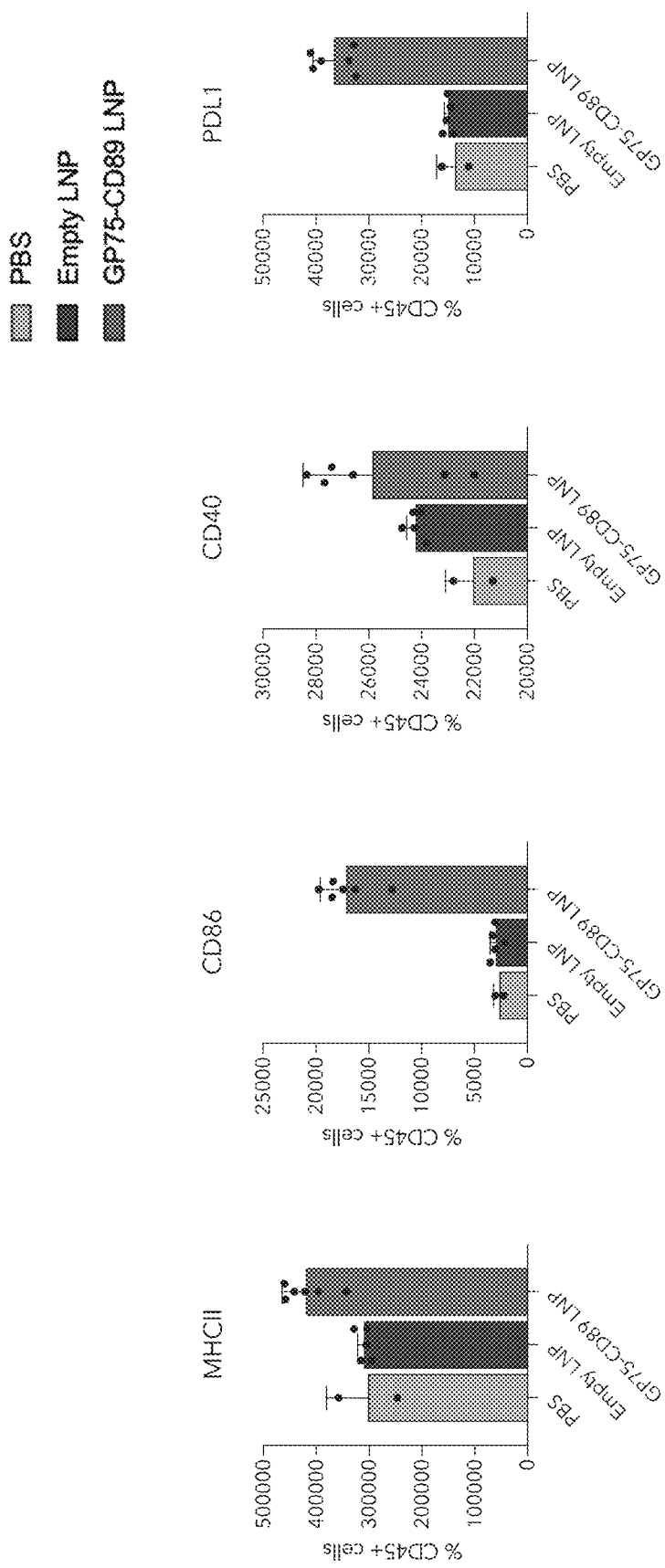
FIG. 59 shows that the treatment significantly increased DC activation marker including MHCII, CD86 and CD40, but also increased PD-L1 level in CD103-CD11b+ dendritic cell phenotype in spleen.
Figure 60:
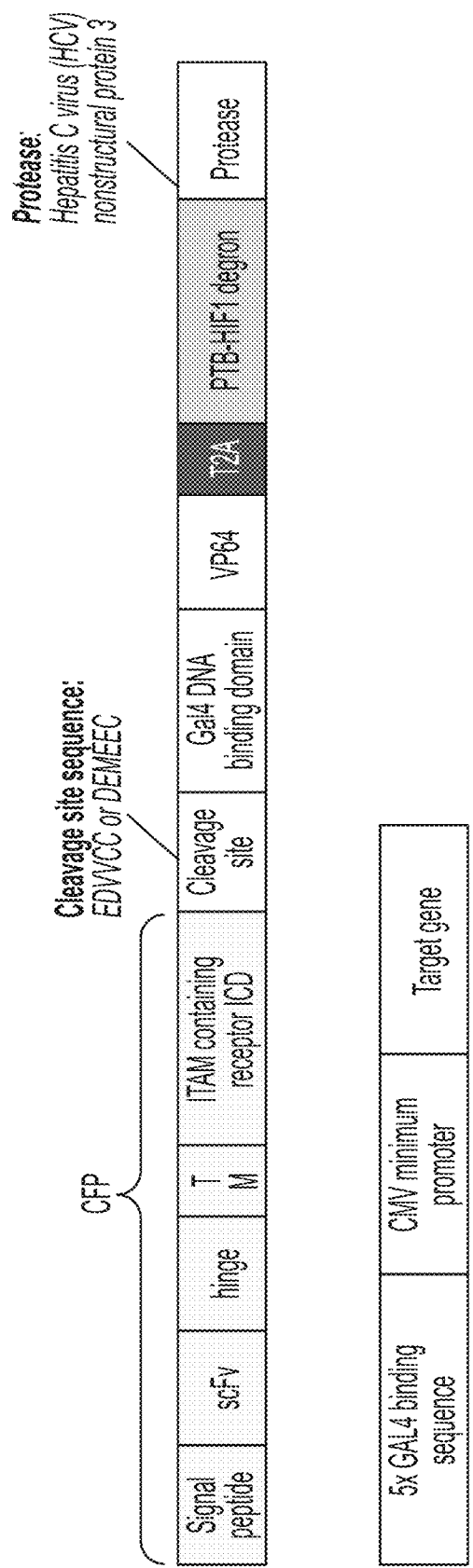
FIG. 60 shows a graphical representation of an exemplary expression vector design for expressing in a myeloid cell a first vector encoding a chimeric receptor protein comprising a protease cleavable, inducible gene transcription activator protein that is activated specifically when the myeloid cell is in contact with a cancer cell; and a second vector expressing a target gene inducible by the gene transcription activator encoded by the first vector.

CD40 and CD206 levels are significantly increased in Ly6C$^{lo}$ and CCR2$^{lo}$ resident myeloid cells, as shown in FIG. 56; and PDL1 level were slightly reduced in tumor resident macrophages (FIG. 57). FIG. 58 shows that the treatment significantly increased DC activation marker including MHCII, CD86 and CD40, but also increased PD-L1 level in CD103+CD11b-dendritic cell phenotype in spleen. FIG. 59 shows that the treatment significantly increased DC activation marker including MHCII, CD86 and CD40, but also increased PD-L1 level in CD103-CD11b+ dendritic cell phenotype in spleen.

Example 14. Generation of a Chimeric Fusion Protein Library with a Protease Recruiting Tyrosine Phosphorylation Domain, and a Protease Inducible Transcription Activator In this example, a target specific, programmable expression vector is designed, which when expressed in a macrophage or a myeloid cell, allows target cell specific activation of the myeloid cell, and the myeloid cell then performs its expected function leading to immunogenic response against the target cell and target cell destruction. The vector can be a lentiviral or an adenoviral expression vector. The target cell is a cancer cell. In this example, composition and methods for making an exemplary myeloid cell expression vector is demonstrated, where the expression vector encodes a membrane protein having cancer specific extracellular binding domain, a transmembrane domain and intracellular domain having tyrosine phosphorylation and activation moiety (ITAM domain) that recruits phosphotyrosine binding proteins (PTB), whereas the intracellular domain is linked via phosphotyrosine binding protease cleavable sequence to a transcription activator domain and a protease (such as a T2A cleaving protease) fused to an HIF-degron sequence (HIF-degron-protease). An expression vector encodes a target gene sequence that can be activated by the transcription activator. The target gene or a fragment thereof is a proinflammatory or pro-phagocytic protein or protein fragment. The vector may be designed so as to retain flexibility of using any target gene of choice for transcriptional activation. The exemplary macrophage expression vector is designed as shown in indicated in FIG. 60.

The vector comprises from 5' to 3': a nucleic acid sequence encoding each of the following: (a) an extracellular cancer cell binding domain having an N-terminal signal sequence that allows for transmembrane localization, (b) a transmembrane domain, (c) an intracellular domain comprising a phosphotyrosine activation/recruitment domain (e.g. ITAM); (d) a DNA binding domain and a transcription activation factor comprising a GAL4 DNA binding sequence and VP64 transcription activator, linked to the intracellular domain encoding sequence by a cleavable sequence that is a substrate of a phosphotyrosine binding protein (PTB) dependent protease, (e) sequence encoding a phosphotyrosine PTB dependent protease, which, in the exemplary construct is an HCV non-structural protease (NS3) fused to a PTB-HIF degron; the PTB-HIF-NS3 sequence is T2A cleavable. The cleavable sequence that is the substrate of a phosphotyrosine binding protein (PTB) dependent protease is EDVVCC (SEQ ID NO: 36) or DEMEEC (SEQ ID NO: 37). A second vector construct is used to co-express a sequence encoding a target gene, the transcription of which is activated by the transcription activation factor encoded upstream. The target gene is driven by CMV minipromoter, with an upstream GAL4 binding and activation domain. The nucleic acid sequence encoding an extracellular cancer cell binding moiety, encodes an scfv antibody, which in the exemplary construct, is a CD19-binding scfv, but could be an scfv specific for another protein that is specifically expressed on a cancer cell, or a target cell. The transcription binding and activation factor comprises a 5×GAL4 sequence fused to a VP64 sequence, which can bind via the GAL-4 DNA binding region upstream of a CMV promoter, thereby activating transcription of the target gene. The PTB-HIF and the adjoining protease sequences are flanked by T2A cleavable sequence and are auto-cleavable by T2A protease, thereby releasing the protease following translation.

The vector design encoding the various parts shown in the example can be variously designed otherwise. For example, a polycistronic design or multiple vector design is equally contemplated herein.

The modular vector design with the co-expression of the components described above makes way for a flexible incorporation of a target gene downstream of CMV promoter that can lead to activation and potentiation of macrophage mediated phagocytosis and killing of the target cell. Exemplary target genes are inflammatory genes, inflammasome activation genes, cytokines, chemokines, REDOX genes.

Figures 61A, 61B:
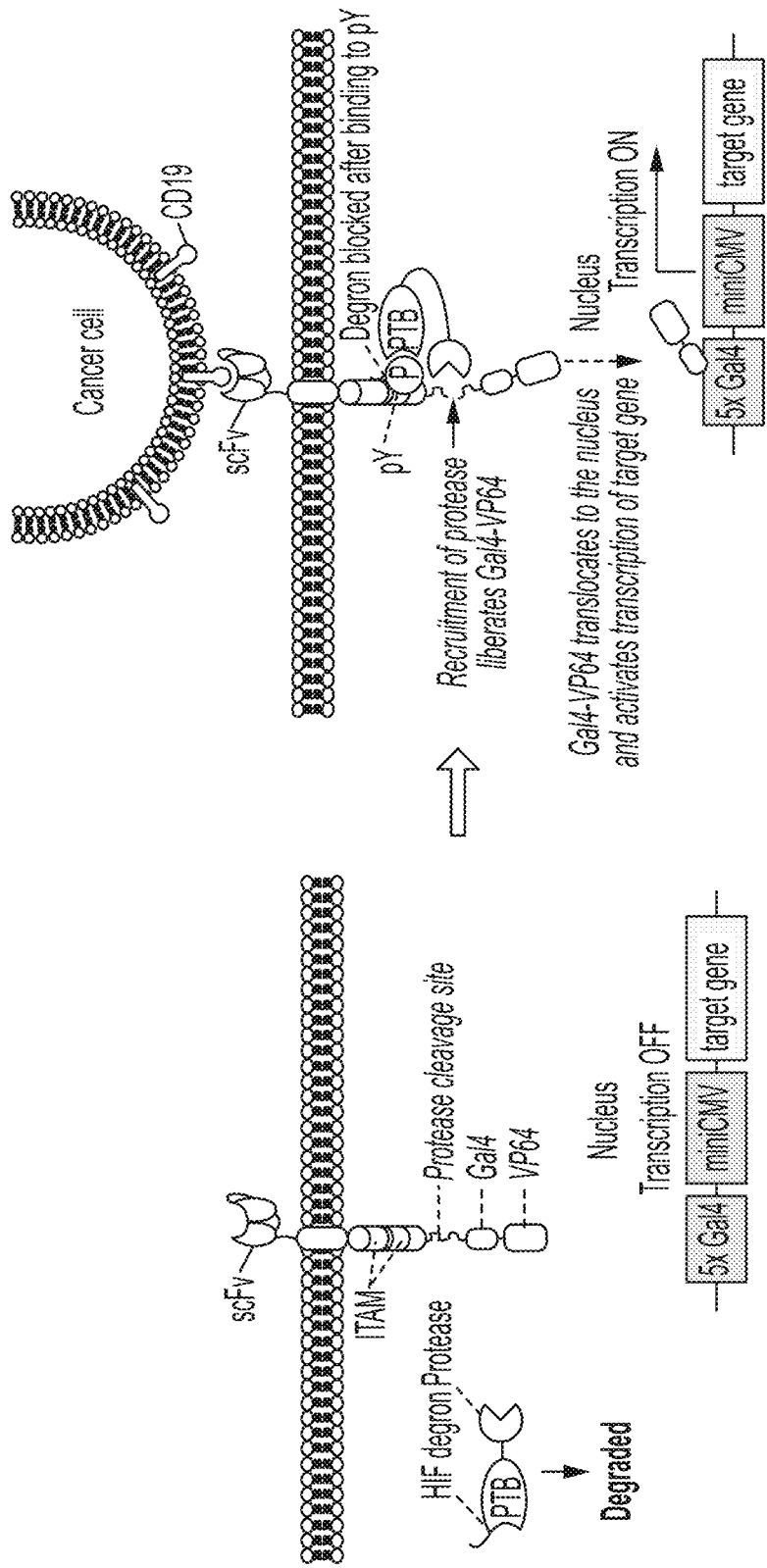
FIG. 61A shows a graphical representation of an exemplary chimeric protein generated by the expression of vectors of FIG. 60.
FIG. 61B illustrates the expected mode of action of the chimeric proteins of FIG. 61A leading to target gene expression. Upon binding of the HIF-degron protease to the phosphorylated ITAM motif of the receptor, the protease is activated and cleaves the transcription activator GAL-VP64.

The basic structural layout of the extracellular and intracellular domains and the cleavable units are demonstrated in FIG. 61A. The construct as described above is expressed in a macrophage cell. Following expression, the expected mode of action after translation and release of the mature proteins is shown in FIG. 61B. The HIF-degron, when binds to a phosphotyrosine binding element on the intracellular domain via a PTB and ITAM interaction is deactivated, and allows proper function of the protease, thereby allowing cleavage and release of the transcription factor. In absence of the association with the ITAM, the degron is responsible for the degradation of the HIF-protease element, as shown in FIG. 61B. Therefore this function allows for a cancer cell-specific activation of the transcription factor and in turn the specific target gene transcription driven by the CMV promoter, since the ITAM is activated and recruits PTB only when it receives signal from the extracellular domain, e.g. the scfv—bound to its CD19 target on a cancer cell.

Example 15. Generation of a Tumor Activated Eosinophil Lytic Protein

In this example, the eosinophil lytic protein is utilized for preparing an engineered macrophage or a myeloid cell capable of lysis of a target cell, such as a cancer cell. As was indicated in the previous example, an exemplary expression vector is constructed and expressed in a macrophage; whereas the expression vector allows target specificity, and is programmable for executing a cell-lytic function.

Figure 62A:
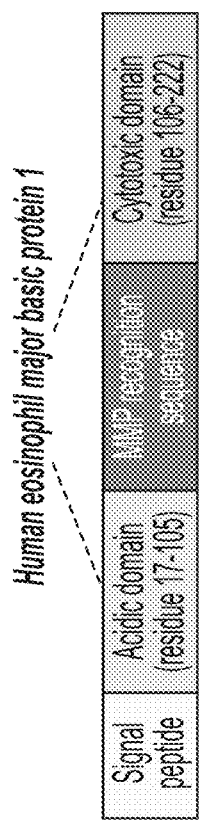
FIG. 62A shows a graphical illustration of a nucleic acid construct that encodes an inducible cytotoxic protein. The construct is designed for expression and secretion by a myeloid (e.g., macrophage) cell. The construct comprises an acidic domain and a cytotoxic domain of a human eosinophil major basic protein. The two domains are interspersed with a sequence encoding MMP recognition peptide; the MMP recognition peptide is cleavable by MMP, which is abundantly present in the tumor microenvironment. In absence of MMP, the secreted cytotoxic protein is retained in inactive form by association with the acidic domain, held together by the MMP recognition peptide.
Figure 62B:
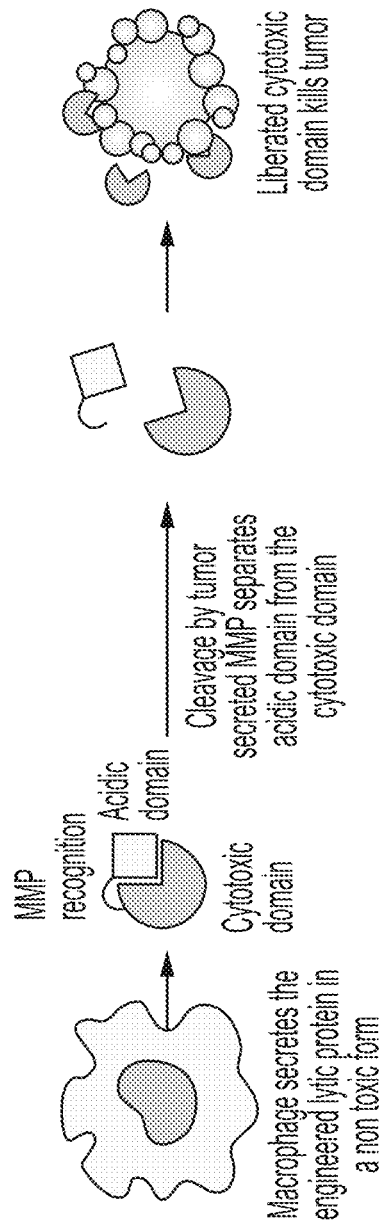
FIG. 62B shows a graphical representation of the cytotoxic domain protein activation upon cleavage of the MMP recognition sequence by MMP in a tumor microenvironment, leading to lysis of tumor cell by the cytotoxic domain protein.

The construct design is demonstrated in FIG. 62A. Essentially, the vector encodes a recombinant chimeric protein, comprising a sequence encoding the acidic domain (amino acid residues 17-105) of a human eosinophil major binding protein 1; a sequence encoding the cytotoxic domain (amino acid residues 106-222) of a human eosinophil major binding protein 1; interspersed in frame between the two domains of the eosinophil major binding protein is a sequence encoding matrix metalloprotease protein (MMP) recognition sequence which is cleavable by the cognate MMP. The chimeric protein encoding sequence is preceded by a sequence encoding a signal peptide that allows for secretion of the chimeric protein outside the macrophage cell. The mature chimeric protein as is secreted from the macrophage is shown in the exemplary FIG. 62B. The acidic domain and the cytotoxic domain form a compact pair configuration, held together by the MMP, whereas the acidic domain bound form keeps the cytotoxic domain inactive.

Since the tumor microenvironment is rich in MMP, the secreted chimeric protein having the MMP recognition cleavable domain is readily cleaved, thereby releasing the acidic domain from the cytotoxic domain, and thus freeing the cytotoxic domain to perform lytic activity. The tumor cells are in abundance in the milieu, and are thereupon attacked, lysed and damaged by the released eosinophil major basic protein cytotoxic domain protein, whereas the macrophage in the vicinity phagocytose and scavenge the lysed and/or damaged cells more readily. On the other hand, the macrophage may further express additional proteins, chimeric receptors and or target cell tethering moieties to potentiate the effect of the secreted eosinophil major basic protein on the cancer cell.

---

The invention claimed is:

1. A method of treating a TROP2-expressing cancer in a subject in need thereof, comprising: administering to the subject a therapeutically effective amount of a composition comprising a recombinant polynucleic acid encapsulated by a nanoparticle delivery vehicle, wherein the recombinant polynucleic acid comprises a sequence encoding a chimeric fusion protein (CFP), the CFP comprising:
(a) an extracellular domain comprising an anti-TROP2 binding domain, and
(b) a transmembrane domain operatively linked to the extracellular domain;
wherein the transmembrane domain is a transmembrane domain from a protein that dimerizes with endogenous FcR-gamma receptors expressed in myeloid cells, monocytes or macrophages of the subject;
wherein the CFP is expressed on the surface of myeloid cells of the subject that express endogenous FcR-gamma receptors;
wherein the anti-TROP2 binding domain comprises a Fab fragment or an scFv domain comprising a heavy chain variable domain and a light chain variable domain on a single polypeptide chain linked via a linker; and
wherein the anti-TROP2 binding domain comprises (a) a heavy chain complementarity determining region 1 (HC CDR1), a HC CDR2 and a HC CDR3 of SEQ ID NO: 34 and a light chain complementarity determining region 1 (LC CDR1), a LC CDR2 and a LC CDR3 of SEQ ID NO: 34; or (b) a HC CDR1, a HC CDR2 and a HC CDR3 of SEQ ID NO: 35 and a LC CDR1, a LC CDR2 and a LC CDR3 of SEQ ID NO: 35.

2. The method of claim 1, wherein the extracellular domain further comprises an extracellular domain from CD16a, CD64, CD68 or CD89 or a fragment thereof.

3. The method of claim 1, wherein after administration of the composition to a human subject the CFP is preferentially or specifically expressed in myeloid cells, monocytes or macrophages of the human subject.

4. The method of claim 1, wherein the transmembrane domain is a transmembrane domain from CD16a, CD64, CD68 or CD89.

5. The method of claim 1, wherein the CFP further comprises an intracellular domain comprising one or more intracellular signaling domains, wherein the one or more intracellular signaling domains comprises an intracellular signaling domain from CD16a, CD64, CD68, CD89, FCERIG, CD40 or CD3 zeta.

6. The method of claim 1, wherein the recombinant polynucleic acid is an mRNA.

7. The method of claim 1, wherein the anti-TROP2 binding domain comprises a sequence selected from the group consisting of SEQ ID NO: 34 and 35.

8. The method of claim 1, wherein the CFP is not substantially expressed on the surface of T cells of the subject.

9. The method of claim 1, wherein the nanoparticle delivery vehicle comprises a lipid nanoparticle.

10. The method of claim 9, wherein the lipid nanoparticle comprises a polar lipid and a non-polar lipid.

11. The method of claim 9, wherein the lipid nanoparticle comprises a cationic lipid, a non-cationic lipid, a neutral lipid, or a PEGylated lipid.

12. The method of claim 9, wherein the lipid nanoparticle is from 100 to 300 nm in diameter.

13. A method of treating a TROP2-expressing cancer in a subject in need thereof, comprising: administering to the subject a therapeutically effective amount of a composition comprising a recombinant polynucleic acid encapsulated by a nanoparticle delivery vehicle, wherein the recombinant polynucleic acid comprises a sequence encoding a chimeric fusion protein (CFP), the CFP comprising:
  (a) an extracellular domain comprising an anti-TROP2 binding domain, and
  (b) a transmembrane domain operatively linked to the extracellular domain;
  wherein the transmembrane domain is a transmembrane domain from a protein that dimerizes with endogenous FcR-gamma receptors expressed in myeloid cells, monocytes or macrophages of the subject;
  wherein the CFP is expressed on the surface of myeloid cells of the subject that express endogenous FcR-gamma receptors;
  wherein the extracellular domain further comprises an extracellular domain from CD16a, CD64, CD68 or CD89; wherein the extracellular domain from CD16a, CD64, CD68 or CD89 comprises an amino acid sequence of IHQDYTTQN (SEQ ID NO: 82).

14. A method of treating a TROP2-expressing cancer in a subject in need thereof, comprising: administering to the subject a therapeutically effective amount of a composition comprising a recombinant polynucleic acid encapsulated by a nanoparticle delivery vehicle, wherein the recombinant polynucleic acid comprises a sequence encoding a chimeric fusion protein (CFP), the CFP comprising:
  (a) an extracellular domain comprising an anti-TROP2 binding domain, and
  (b) a transmembrane domain operatively linked to the extracellular domain;
  wherein the transmembrane domain is a transmembrane domain from a protein that dimerizes with endogenous FcR-gamma receptors expressed in myeloid cells, monocytes or macrophages of the subject;
  wherein the CFP is expressed on the surface of myeloid cells of the subject that express endogenous FcR-gamma receptors;
  wherein the transmembrane domain is a transmembrane domain from CD16a, CD64, CD68 or CD89; and
  wherein the transmembrane domain from CD16a, CD64, CD68 or CD89 comprises an amino acid sequence of LIRMAVAGLVLVALLAILV (SEQ ID NO: 83).

15. The method of claim 14, wherein the CFP further comprises a signal peptide sequence.

16. The method of claim 15, wherein the signal peptide sequence is MWLQSLLLLGTVACSIS (SEQ ID NO: 7).

17. The method of claim 14, wherein the anti-TROP2 binding domain comprises a Fab fragment, or an scFv domain or an sdAb domain.

18. The method of claim 17, wherein the anti-TROP2 binding domain comprises a heavy chain variable domain and a light chain variable domain on a single polypeptide chain and linked via a linker, comprising (a) a heavy chain complementarity determining region 1 (HC CDR1), a HC CDR2 and a HC CDR3 of SEQ ID NO: 34 and a light chain complementarity determining region 1 (LC CDR1), a LC CDR2 and a LC CDR3 of SEQ ID NO: 34; or (b) a HC CDR1, a HC CDR2 and a HC CDR3 of SEQ ID NO: 35 and a LC CDR1, a LC CDR2 and a LC CDR3 of SEQ ID NO: 35.

19. The method of claim 14, wherein the extracellular domain further comprises an extracellular domain from CD16a, CD64, CD68 or CD89.

20. A method of treating a TROP2-expressing cancer in a subject in need thereof, comprising: administering to the subject a therapeutically effective amount of a composition comprising a recombinant polynucleic acid encapsulated by a nanoparticle delivery vehicle, wherein the recombinant polynucleic acid comprises a sequence encoding a chimeric fusion protein (CFP), the CFP comprising:
  (a) an extracellular domain comprising an anti-TROP2 binding domain, and
  (b) a transmembrane domain operatively linked to the extracellular domain;
  wherein the transmembrane domain is a transmembrane domain from a protein that dimerizes with endogenous FcR-gamma receptors expressed in myeloid cells, monocytes or macrophages of the subject;
  wherein the CFP is expressed on the surface of myeloid cells of the subject that express endogenous FcR-gamma receptors;
  wherein the transmembrane domain is a transmembrane domain from CD16a, CD64, CD68 or CD89; and
  wherein the intracellular domain comprises an amino acid sequence of ENWHSHTALNKEASADVAEPSWSQQMCQPGLTFARTPSVCK (SEQ ID NO: 84).

21. A method of treating a TROP2-expressing cancer in a subject in need thereof, comprising: administering to the subject a therapeutically effective amount of a composition comprising a recombinant polynucleic acid encapsulated by a nanoparticle delivery vehicle, wherein the recombinant polynucleic acid comprises a sequence encoding a chimeric fusion protein (CFP), the CFP comprising:
  (a) an extracellular domain comprising an anti-TROP2 binding domain, and
  (b) a transmembrane domain operatively linked to the extracellular domain;
  wherein the transmembrane domain is a transmembrane domain from a protein that dimerizes with endogenous FcR-gamma receptors expressed in myeloid cells, monocytes or macrophages of the subject;
  wherein the CFP is expressed on the surface of myeloid cells of the subject that express endogenous FcR-gamma receptors; and
  wherein the signal peptide sequence is a GMCSF signal peptide sequence.

22. A method of treating a TROP2-expressing cancer in a subject in need thereof, comprising: administering to the subject a therapeutically effective amount of a composition comprising a recombinant polynucleic acid encapsulated by a nanoparticle delivery vehicle, wherein the recombinant polynucleic acid comprises a sequence encoding a chimeric fusion protein (CFP), wherein the CFP comprises:
 (i) an extracellular domain comprising:
  (I) an anti-TROP2 binding domain comprising: an scFv having a heavy chain variable domain and a light chain variable domains on a single polypeptide chain linked via a linker, wherein the scFv comprises a sequence selected from the group consisting of SEQ ID NO: 34 and 35; and
  (II) a hinge domain comprising an amino acid sequence of IHQDYTTQN (SEQ ID NO: 82);
 (ii) a transmembrane domain having an amino acid sequence of LIRMAVAGLVLVALLAILV (SEQ ID NO: 83); and
 (iii) an intracellular domain comprising an amino acid sequence of ENWHSHTALNKEASADVAEPSWSQQMCQPGLTFARTPSVCK (SEQ ID NO: 84).

* * * * *

SEQUENCE LISTING

```
<160> NUMBER OF SEQ ID NOS: 87

<210> SEQ ID NO 1
<211> LENGTH: 432
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Met Trp Leu Gln Ser Leu Leu Leu Gly Thr Val Ala Cys Ser Ile
1               5                   10                  15

Ser Glu Ile Gln Leu Val Gln Ser Gly Gly Leu Val Lys Pro Gly
                20                  25                  30

Gly Ser Val Arg Ile Ser Cys Ala Ala Ser Gly Tyr Thr Phe Thr Asn
            35                  40                  45

Tyr Gly Met Asn Trp Val Arg Gln Ala Pro Gly Lys Gly Leu Glu Trp
        50                  55                  60

Met Gly Trp Ile Asn Thr His Thr Gly Glu Pro Thr Tyr Ala Asp Ser
65                  70                  75                  80

Phe Lys Gly Arg Phe Thr Phe Ser Leu Asp Asp Ser Lys Asn Thr Ala
                85                  90                  95

Tyr Leu Gln Ile Asn Ser Leu Arg Ala Glu Asp Thr Ala Val Tyr Phe
            100                 105                 110

Cys Thr Arg Arg Gly Tyr Asp Trp Tyr Phe Asp Val Trp Gly Gln Gly
        115                 120                 125

Thr Thr Val Thr Val Ser Ser Gly Gly Gly Gly Ser Gly Gly Gly Gly
130                 135                 140

Ser Gly Gly Gly Gly Ser Asp Ile Gln Met Thr Gln Ser Pro Ser Ser
145                 150                 155                 160

Leu Ser Ala Ser Val Gly Asp Arg Val Thr Ile Thr Cys Arg Ala Ser
                165                 170                 175

Gln Asp Ile Asn Ser Tyr Leu Ser Trp Phe Gln Gln Lys Pro Gly Lys
            180                 185                 190

Ala Pro Lys Thr Leu Ile Tyr Arg Ala Asn Arg Leu Glu Ser Gly Val
        195                 200                 205

Pro Ser Arg Phe Ser Gly Ser Gly Ser Gly Thr Asp Tyr Thr Leu Thr
    210                 215                 220

Ile Ser Ser Leu Gln Tyr Glu Asp Phe Gly Ile Tyr Tyr Cys Gln Gln
225                 230                 235                 240

Tyr Asp Glu Ser Pro Trp Thr Phe Gly Gly Gly Thr Lys Leu Glu Ile
                245                 250                 255
```

```
Lys Ser Gly Gly Gly Ser Gly Ala Leu Ser Asn Ser Ile Met Tyr
            260                 265                 270

Phe Ser His Phe Val Pro Val Phe Leu Pro Ala Lys Pro Thr Thr Thr
        275                 280                 285

Pro Ala Pro Arg Pro Pro Thr Pro Ala Pro Thr Ile Ala Ser Gln Pro
    290                 295                 300

Leu Ser Leu Arg Pro Glu Ala Cys Arg Pro Ala Ala Gly Gly Ala Val
305                 310                 315                 320

His Thr Arg Gly Leu Asp Ile Tyr Ile Trp Ala Pro Leu Ala Gly Thr
                325                 330                 335

Cys Gly Val Leu Leu Leu Ser Leu Val Ile Thr Leu Tyr Cys Arg Arg
            340                 345                 350

Leu Lys Ile Gln Val Arg Lys Ala Ala Ile Thr Ser Tyr Glu Lys Ser
            355                 360                 365

Asp Gly Val Tyr Thr Gly Leu Ser Thr Arg Asn Gln Glu Thr Tyr Glu
    370                 375                 380

Thr Leu Lys His Glu Lys Pro Pro Gln Gly Ser Gly Ser Tyr Glu Asp
385                 390                 395                 400

Met Arg Gly Ile Leu Tyr Ala Ala Pro Gln Leu Arg Ser Ile Arg Gly
                405                 410                 415

Gln Pro Gly Pro Asn His Glu Glu Asp Ala Asp Ser Tyr Glu Asn Met
                420                 425                 430

<210> SEQ ID NO 2
<211> LENGTH: 436
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Met Trp Leu Gln Ser Leu Leu Leu Leu Gly Thr Val Ala Cys Ser Ile
1               5                   10                  15

Ser Asp Ile Gln Met Thr Gln Ser Pro Ser Ser Leu Ser Ala Ser Val
            20                  25                  30

Gly Asp Arg Val Thr Ile Thr Cys Arg Ala Ser Gln Asp Val Asn Thr
        35                  40                  45

Ala Val Ala Trp Tyr Gln Gln Lys Pro Gly Lys Ala Pro Lys Leu Leu
    50                  55                  60

Ile Tyr Ser Ala Ser Phe Leu Tyr Ser Gly Val Pro Ser Arg Phe Ser
65                  70                  75                  80

Gly Ser Arg Ser Gly Thr Asp Phe Thr Leu Thr Ile Ser Ser Leu Gln
                85                  90                  95

Pro Glu Asp Phe Ala Thr Tyr Tyr Cys Gln Gln His Tyr Thr Thr Pro
            100                 105                 110

Pro Thr Phe Gly Gln Gly Thr Lys Val Glu Ile Lys Arg Thr Gly Ser
        115                 120                 125

Thr Ser Gly Ser Gly Lys Pro Gly Ser Gly Glu Gly Ser Glu Val Gln
    130                 135                 140

Leu Val Glu Ser Gly Gly Gly Leu Val Gln Pro Gly Gly Ser Leu Arg
145                 150                 155                 160

Leu Ser Cys Ala Ala Ser Gly Phe Asn Ile Lys Asp Thr Tyr Ile His
                165                 170                 175
```

```
Trp Val Arg Gln Ala Pro Gly Lys Gly Leu Glu Trp Val Ala Arg Ile
            180                 185                 190

Tyr Pro Thr Asn Gly Tyr Thr Arg Tyr Ala Asp Ser Val Lys Gly Arg
            195                 200                 205

Phe Thr Ile Ser Ala Asp Thr Ser Lys Asn Thr Ala Tyr Leu Gln Met
210                 215                 220

Asn Ser Leu Arg Ala Glu Asp Thr Ala Val Tyr Tyr Cys Ser Arg Trp
225                 230                 235                 240

Gly Gly Asp Gly Phe Tyr Ala Met Asp Val Trp Gly Gln Gly Thr Leu
                245                 250                 255

Val Thr Val Ser Ser Gly Gly Gly Ser Gly Ala Leu Ser Asn
            260                 265                 270

Ser Ile Met Tyr Phe Ser His Phe Val Pro Val Phe Leu Pro Ala Lys
            275                 280                 285

Pro Thr Thr Thr Pro Ala Pro Arg Pro Pro Thr Pro Ala Pro Thr Ile
            290                 295                 300

Ala Ser Gln Pro Leu Ser Leu Arg Pro Glu Ala Cys Arg Pro Ala Ala
305                 310                 315                 320

Gly Gly Ala Val His Thr Arg Gly Leu Asp Ile Tyr Ile Trp Ala Pro
                325                 330                 335

Leu Ala Gly Thr Cys Gly Val Leu Leu Leu Ser Leu Val Ile Thr Leu
            340                 345                 350

Tyr Cys Arg Arg Leu Lys Ile Gln Val Arg Lys Ala Ala Ile Thr Ser
            355                 360                 365

Tyr Glu Lys Ser Asp Gly Val Tyr Thr Gly Leu Ser Thr Arg Asn Gln
370                 375                 380

Glu Thr Tyr Glu Thr Leu Lys His Glu Lys Pro Pro Gln Gly Ser Gly
385                 390                 395                 400

Ser Tyr Glu Asp Met Arg Gly Ile Leu Tyr Ala Ala Pro Gln Leu Arg
                405                 410                 415

Ser Ile Arg Gly Gln Pro Gly Pro Asn His Glu Glu Asp Ala Asp Ser
            420                 425                 430

Tyr Glu Asn Met
            435

<210> SEQ ID NO 3
<211> LENGTH: 454
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Met Trp Leu Gln Ser Leu Leu Leu Leu Gly Thr Val Ala Cys Ser Ile
1               5                   10                  15

Ser Glu Ile Gln Leu Val Gln Ser Gly Gly Gly Leu Val Lys Pro Gly
            20                  25                  30

Gly Ser Val Arg Ile Ser Cys Ala Ala Ser Gly Tyr Thr Phe Thr Asn
        35                  40                  45

Tyr Gly Met Asn Trp Val Arg Gln Ala Pro Gly Lys Gly Leu Glu Trp
    50                  55                  60

Met Gly Trp Ile Asn Thr His Thr Gly Glu Pro Thr Tyr Ala Asp Ser
65                  70                  75                  80
```

```
Phe Lys Gly Arg Phe Thr Phe Ser Leu Asp Asp Ser Lys Asn Thr Ala
                85                  90                  95

Tyr Leu Gln Ile Asn Ser Leu Arg Ala Glu Asp Thr Ala Val Tyr Phe
            100                 105                 110

Cys Thr Arg Arg Gly Tyr Asp Trp Tyr Phe Asp Val Trp Gly Gln Gly
        115                 120                 125

Thr Thr Val Thr Val Ser Ser Gly Gly Gly Ser Gly Gly Gly Gly
130                 135                 140

Ser Gly Gly Gly Gly Ser Asp Ile Gln Met Thr Gln Ser Pro Ser Ser
145                 150                 155                 160

Leu Ser Ala Ser Val Gly Asp Arg Val Thr Ile Thr Cys Arg Ala Ser
                165                 170                 175

Gln Asp Ile Asn Ser Tyr Leu Ser Trp Phe Gln Gln Lys Pro Gly Lys
            180                 185                 190

Ala Pro Lys Thr Leu Ile Tyr Arg Ala Asn Arg Leu Glu Ser Gly Val
        195                 200                 205

Pro Ser Arg Phe Ser Gly Ser Gly Ser Gly Thr Asp Tyr Thr Leu Thr
210                 215                 220

Ile Ser Ser Leu Gln Tyr Glu Asp Phe Gly Ile Tyr Tyr Cys Gln Gln
225                 230                 235                 240

Tyr Asp Glu Ser Pro Trp Thr Phe Gly Gly Gly Thr Lys Leu Glu Ile
                245                 250                 255

Lys Ser Gly Gly Gly Gly Ser Gly Ala Leu Ser Asn Ser Ile Met Tyr
            260                 265                 270

Phe Ser His Phe Val Pro Val Phe Leu Pro Ala Lys Pro Thr Thr Thr
        275                 280                 285

Pro Ala Pro Arg Pro Pro Thr Pro Ala Pro Thr Ile Ala Ser Gln Pro
290                 295                 300

Leu Ser Leu Arg Pro Glu Ala Cys Arg Pro Ala Ala Gly Gly Ala Val
305                 310                 315                 320

His Thr Arg Gly Leu Asp Ile Tyr Ile Trp Ala Pro Leu Ala Gly Thr
                325                 330                 335

Cys Gly Val Leu Leu Leu Ser Leu Val Ile Thr Leu Tyr Cys Arg Leu
            340                 345                 350

Lys Ile Gln Val Arg Lys Ala Ala Ile Thr Ser Tyr Glu Lys Ser Asp
        355                 360                 365

Gly Val Tyr Thr Gly Leu Ser Thr Arg Asn Gln Glu Thr Tyr Glu Thr
370                 375                 380

Leu Lys His Glu Lys Pro Pro Gln Lys Lys Val Ala Lys Lys Pro Thr
385                 390                 395                 400

Asn Lys Ala Pro His Pro Lys Gln Glu Pro Gln Glu Ile Asn Phe Pro
                405                 410                 415

Asp Asp Leu Pro Gly Ser Asn Thr Ala Ala Pro Val Gln Glu Thr Leu
            420                 425                 430

His Gly Cys Gln Pro Val Thr Gln Glu Asp Gly Lys Glu Ser Arg Ile
        435                 440                 445

Ser Val Gln Glu Arg Gln
    450

<210> SEQ ID NO 4
<211> LENGTH: 607
<212> TYPE: PRT
<213> ORGANISM: Artificial Sequence
<220> FEATURE:
```

<223> OTHER INFORMATION: Description of Artificial Sequence: Synthetic
       polypeptide

<400> SEQUENCE: 4

Met Trp Leu Gln Ser Leu Leu Leu Gly Thr Val Ala Cys Ser Ile
1               5                   10                  15

Ser Glu Ile Gln Leu Val Gln Ser Gly Gly Leu Val Lys Pro Gly
            20                  25                  30

Gly Ser Val Arg Ile Ser Cys Ala Ala Ser Gly Tyr Thr Phe Thr Asn
        35                  40                  45

Tyr Gly Met Asn Trp Val Arg Gln Ala Pro Gly Lys Gly Leu Glu Trp
    50                  55                  60

Met Gly Trp Ile Asn Thr His Thr Gly Glu Pro Thr Tyr Ala Asp Ser
65                  70                  75                  80

Phe Lys Gly Arg Phe Thr Phe Ser Leu Asp Asp Ser Lys Asn Thr Ala
                85                  90                  95

Tyr Leu Gln Ile Asn Ser Leu Arg Ala Glu Asp Thr Ala Val Tyr Phe
            100                 105                 110

Cys Thr Arg Arg Gly Tyr Asp Trp Tyr Phe Asp Val Trp Gly Gln Gly
        115                 120                 125

Thr Thr Val Thr Val Ser Ser Gly Gly Gly Ser Gly Gly Gly Gly
    130                 135                 140

Ser Gly Gly Gly Ser Asp Ile Gln Met Thr Gln Ser Pro Ser Ser
145                 150                 155                 160

Leu Ser Ala Ser Val Gly Asp Arg Val Thr Ile Thr Cys Arg Ala Ser
                165                 170                 175

Gln Asp Ile Asn Ser Tyr Leu Ser Trp Phe Gln Gln Lys Pro Gly Lys
            180                 185                 190

Ala Pro Lys Thr Leu Ile Tyr Arg Ala Asn Arg Leu Glu Ser Gly Val
        195                 200                 205

Pro Ser Arg Phe Ser Gly Ser Gly Ser Gly Thr Asp Tyr Thr Leu Thr
    210                 215                 220

Ile Ser Ser Leu Gln Tyr Glu Asp Phe Gly Ile Tyr Tyr Cys Gln Gln
225                 230                 235                 240

Tyr Asp Glu Ser Pro Trp Thr Phe Gly Gly Gly Thr Lys Leu Glu Ile
                245                 250                 255

Lys Ser Gly Gly Gly Gly Ser Gly Ala Leu Ser Asn Ser Ile Met Tyr
            260                 265                 270

Phe Ser His Phe Val Pro Val Phe Leu Pro Ala Lys Pro Thr Thr Thr
        275                 280                 285

Pro Ala Pro Arg Pro Pro Thr Pro Ala Pro Thr Ile Ala Ser Gln Pro
    290                 295                 300

Leu Ser Leu Arg Pro Glu Ala Cys Arg Pro Ala Ala Gly Gly Ala Val
305                 310                 315                 320

His Thr Arg Gly Leu Asp Ile Tyr Ile Trp Ala Pro Leu Ala Gly Thr
                325                 330                 335

Cys Gly Val Leu Leu Leu Ser Leu Val Ile Thr Leu Tyr Cys Arg Leu
            340                 345                 350

Lys Ile Gln Val Arg Lys Ala Ala Ile Thr Ser Tyr Glu Lys Ser Asp
        355                 360                 365

Gly Val Tyr Thr Gly Leu Ser Thr Arg Asn Gln Glu Thr Tyr Glu Thr
    370                 375                 380

Leu Lys His Glu Lys Pro Pro Gln Gly Ser Gly Ser Met Ser Asn Gly
385                 390                 395                 400

```
Tyr Ser Thr Asp Glu Asn Phe Arg Tyr Leu Ile Ser Cys Phe Arg Ala
            405                 410                 415

Arg Val Lys Met Tyr Ile Gln Val Glu Pro Val Leu Asp Tyr Leu Thr
        420                 425                 430

Phe Leu Pro Ala Glu Val Lys Glu Gln Ile Gln Arg Thr Val Ala Thr
    435                 440                 445

Ser Gly Asn Met Gln Ala Val Glu Leu Leu Ser Thr Leu Glu Lys
450                 455                 460

Gly Val Trp His Leu Gly Trp Thr Arg Glu Phe Val Glu Ala Leu Arg
465                 470                 475                 480

Arg Thr Gly Ser Pro Leu Ala Ala Arg Tyr Met Asn Pro Glu Leu Thr
                485                 490                 495

Asp Leu Pro Ser Pro Ser Phe Glu Asn Ala His Asp Glu Tyr Leu Gln
            500                 505                 510

Leu Leu Asn Leu Leu Gln Pro Thr Leu Val Asp Lys Leu Leu Val Arg
        515                 520                 525

Asp Val Leu Asp Lys Cys Met Glu Glu Leu Leu Thr Ile Glu Asp
    530                 535                 540

Arg Asn Arg Ile Ala Ala Ala Glu Asn Gly Asn Glu Ser Gly Val
545                 550                 555                 560

Arg Glu Leu Leu Lys Arg Ile Val Gln Lys Glu Asn Trp Phe Ser Ala
                565                 570                 575

Phe Leu Asn Val Leu Arg Gln Thr Gly Asn Asn Glu Leu Val Gln Glu
            580                 585                 590

Leu Thr Gly Ser Asp Cys Ser Glu Ser Asn Ala Glu Ile Glu Asn
        595                 600                 605

<210> SEQ ID NO 5
<211> LENGTH: 615
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Met Trp Leu Gln Ser Leu Leu Leu Gly Thr Val Ala Cys Ser Ile
1               5                   10                  15

Ser Glu Ile Gln Leu Val Gln Ser Gly Gly Leu Val Lys Pro Gly
            20                  25                  30

Gly Ser Val Arg Ile Ser Cys Ala Ala Ser Gly Tyr Thr Phe Thr Asn
        35                  40                  45

Tyr Gly Met Asn Trp Val Arg Gln Ala Pro Gly Lys Gly Leu Glu Trp
    50                  55                  60

Met Gly Trp Ile Asn Thr His Thr Gly Glu Pro Thr Tyr Ala Asp Ser
65                  70                  75                  80

Phe Lys Gly Arg Phe Thr Phe Ser Leu Asp Asp Ser Lys Asn Thr Ala
                85                  90                  95

Tyr Leu Gln Ile Asn Ser Leu Arg Ala Glu Asp Thr Ala Val Tyr Phe
            100                 105                 110

Cys Thr Arg Arg Gly Tyr Asp Trp Tyr Phe Asp Val Trp Gly Gln Gly
        115                 120                 125

Thr Thr Val Thr Val Ser Ser Gly Gly Gly Gly Ser Gly Gly Gly Gly
    130                 135                 140
```

```
Ser Gly Gly Gly Gly Ser Asp Ile Gln Met Thr Gln Ser Pro Ser Ser
145                 150                 155                 160

Leu Ser Ala Ser Val Gly Asp Arg Val Thr Ile Thr Cys Arg Ala Ser
                165                 170                 175

Gln Asp Ile Asn Ser Tyr Leu Ser Trp Phe Gln Gln Lys Pro Gly Lys
            180                 185                 190

Ala Pro Lys Thr Leu Ile Tyr Arg Ala Asn Arg Leu Glu Ser Gly Val
        195                 200                 205

Pro Ser Arg Phe Ser Gly Ser Gly Ser Gly Thr Asp Tyr Thr Leu Thr
    210                 215                 220

Ile Ser Ser Leu Gln Tyr Glu Asp Phe Gly Ile Tyr Tyr Cys Gln Gln
225                 230                 235                 240

Tyr Asp Glu Ser Pro Trp Thr Phe Gly Gly Gly Thr Lys Leu Glu Ile
                245                 250                 255

Lys Ser Gly Gly Gly Gly Ser Gly Ala Leu Ser Asn Ser Ile Met Tyr
            260                 265                 270

Phe Ser His Phe Val Pro Val Phe Leu Pro Ala Lys Pro Thr Thr Thr
        275                 280                 285

Pro Ala Pro Arg Pro Pro Thr Pro Ala Pro Thr Ile Ala Ser Gln Pro
    290                 295                 300

Leu Ser Leu Arg Pro Glu Ala Cys Arg Pro Ala Ala Gly Gly Ala Val
305                 310                 315                 320

His Thr Arg Gly Leu Asp Ile Tyr Ile Trp Ala Pro Leu Ala Gly Thr
                325                 330                 335

Cys Gly Val Leu Leu Leu Ser Leu Val Ile Thr Leu Tyr Cys Arg Leu
            340                 345                 350

Lys Ile Gln Val Arg Lys Ala Ala Ile Thr Ser Tyr Glu Lys Ser Asp
        355                 360                 365

Gly Val Tyr Thr Gly Leu Ser Thr Arg Asn Gln Glu Thr Tyr Glu Thr
    370                 375                 380

Leu Lys His Glu Lys Pro Pro Gln Gly Ser Gly Ser Gln Arg Trp Lys
385                 390                 395                 400

Ser Lys Leu Tyr Ser Ile Val Cys Gly Lys Ser Thr Pro Glu Lys Glu
                405                 410                 415

Gly Glu Leu Glu Gly Thr Thr Thr Lys Pro Leu Ala Pro Asn Pro Ser
            420                 425                 430

Phe Ser Pro Thr Pro Gly Phe Thr Pro Thr Leu Gly Phe Ser Pro Val
        435                 440                 445

Pro Ser Ser Thr Phe Thr Ser Ser Ser Thr Tyr Thr Pro Gly Asp Cys
    450                 455                 460

Pro Asn Phe Ala Ala Pro Arg Arg Glu Val Ala Pro Pro Tyr Gln Gly
465                 470                 475                 480

Ala Asp Pro Ile Leu Ala Thr Ala Leu Ala Ser Asp Pro Ile Pro Asn
                485                 490                 495

Pro Leu Gln Lys Trp Glu Asp Ser Ala His Lys Pro Gln Ser Leu Asp
            500                 505                 510

Thr Asp Asp Pro Ala Thr Leu Tyr Ala Val Val Glu Asn Val Pro Pro
        515                 520                 525

Leu Arg Trp Lys Glu Phe Val Arg Arg Leu Gly Leu Ser Asp His Glu
530                 535                 540

Ile Asp Arg Leu Glu Leu Gln Asn Gly Arg Cys Leu Arg Glu Ala Gln
545                 550                 555                 560
```

```
Tyr Ser Met Leu Ala Thr Trp Arg Arg Thr Pro Arg Arg Glu Ala
                565                 570                 575

Thr Leu Glu Leu Leu Gly Arg Val Leu Arg Asp Met Asp Leu Leu Gly
        580                 585                 590

Cys Leu Glu Asp Ile Glu Glu Ala Leu Cys Gly Pro Ala Ala Leu Pro
        595                 600                 605

Pro Ala Pro Ser Leu Leu Arg
        610                 615

<210> SEQ ID NO 6
<211> LENGTH: 567
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Met Trp Leu Gln Ser Leu Leu Leu Gly Thr Val Ala Cys Ser Ile
 1               5                  10                  15

Ser Glu Ile Gln Leu Val Gln Ser Gly Gly Gly Leu Val Lys Pro Gly
            20                  25                  30

Gly Ser Val Arg Ile Ser Cys Ala Ala Ser Gly Tyr Thr Phe Thr Asn
        35                  40                  45

Tyr Gly Met Asn Trp Val Arg Gln Ala Pro Gly Lys Gly Leu Glu Trp
    50                  55                  60

Met Gly Trp Ile Asn Thr His Thr Gly Glu Pro Thr Tyr Ala Asp Ser
65                  70                  75                  80

Phe Lys Gly Arg Phe Thr Phe Ser Leu Asp Asp Ser Lys Asn Thr Ala
                85                  90                  95

Tyr Leu Gln Ile Asn Ser Leu Arg Ala Glu Asp Thr Ala Val Tyr Phe
            100                 105                 110

Cys Thr Arg Arg Gly Tyr Asp Trp Tyr Phe Asp Val Trp Gly Gln Gly
        115                 120                 125

Thr Thr Val Thr Val Ser Ser Gly Gly Gly Ser Gly Gly Gly Gly
    130                 135                 140

Ser Gly Gly Gly Gly Ser Asp Ile Gln Met Thr Gln Ser Pro Ser Ser
145                 150                 155                 160

Leu Ser Ala Ser Val Gly Asp Arg Val Thr Ile Thr Cys Arg Ala Ser
                165                 170                 175

Gln Asp Ile Asn Ser Tyr Leu Ser Trp Phe Gln Gln Lys Pro Gly Lys
            180                 185                 190

Ala Pro Lys Thr Leu Ile Tyr Arg Ala Asn Arg Leu Glu Ser Gly Val
        195                 200                 205

Pro Ser Arg Phe Ser Gly Ser Gly Ser Gly Thr Asp Tyr Thr Leu Thr
    210                 215                 220

Ile Ser Ser Leu Gln Tyr Glu Asp Phe Gly Ile Tyr Tyr Cys Gln Gln
225                 230                 235                 240

Tyr Asp Glu Ser Pro Trp Thr Phe Gly Gly Gly Thr Lys Leu Glu Ile
                245                 250                 255

Lys Ser Gly Gly Gly Gly Ser Gly Ala Leu Ser Asn Ser Ile Met Tyr
            260                 265                 270

Phe Ser His Phe Val Pro Val Phe Leu Pro Ala Lys Pro Thr Thr Thr
        275                 280                 285

Pro Ala Pro Arg Pro Pro Thr Pro Ala Pro Thr Ile Ala Ser Gln Pro
    290                 295                 300
```

```
Leu Ser Leu Arg Pro Glu Ala Cys Arg Pro Ala Ala Gly Gly Ala Val
305                 310                 315                 320

His Thr Arg Gly Leu Asp Ile Tyr Ile Trp Ala Pro Leu Ala Gly Thr
            325                 330                 335

Cys Gly Val Leu Leu Leu Ser Leu Val Ile Thr Leu Tyr Cys Arg Leu
        340                 345                 350

Lys Ile Gln Val Arg Lys Ala Ala Ile Thr Ser Tyr Glu Lys Ser Asp
    355                 360                 365

Gly Val Tyr Thr Gly Leu Ser Thr Arg Asn Gln Glu Thr Tyr Glu Thr
370                 375                 380

Leu Lys His Glu Lys Pro Pro Gln Gly Ser Gly Ser Pro Leu Cys Leu
385                 390                 395                 400

Gln Arg Glu Ala Lys Val Pro His Leu Pro Ala Asp Lys Ala Arg Gly
            405                 410                 415

Thr Gln Gly Pro Glu Gln Gln His Leu Leu Ile Thr Ala Pro Ser Ser
        420                 425                 430

Ser Ser Ser Ser Leu Glu Ser Ala Ser Ala Leu Asp Arg Arg Ala
    435                 440                 445

Pro Thr Arg Asn Gln Pro Gln Ala Pro Gly Val Glu Ala Ser Gly Ala
450                 455                 460

Gly Glu Ala Arg Ala Ser Thr Gly Ser Ser Asp Ser Ser Pro Gly Gly
465                 470                 475                 480

His Gly Thr Gln Val Asn Val Thr Cys Ile Val Asn Val Cys Ser Ser
            485                 490                 495

Ser Asp His Ser Ser Gln Cys Ser Ser Gln Ala Ser Ser Thr Met Gly
        500                 505                 510

Asp Thr Asp Ser Ser Pro Ser Glu Ser Pro Lys Asp Glu Gln Val Pro
    515                 520                 525

Phe Ser Lys Glu Glu Cys Ala Phe Arg Ser Gln Leu Glu Thr Pro Glu
530                 535                 540

Thr Leu Leu Gly Ser Thr Glu Glu Lys Pro Leu Pro Leu Gly Val Pro
545                 550                 555                 560

Asp Ala Gly Met Lys Pro Ser
                565

<210> SEQ ID NO 7
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Met Trp Leu Gln Ser Leu Leu Leu Leu Gly Thr Val Ala Cys Ser Ile
1               5                   10                  15

Ser

<210> SEQ ID NO 8
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 8

Glu Ile Gln Leu Val Gln Ser Gly Gly Gly Leu Val Lys Pro Gly Gly
1               5                   10                  15

Ser Val Arg Ile Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Met
        35                  40                  45

Gly Trp Ile Asn Thr His Thr Gly Glu Pro Thr Tyr Ala Asp Ser Phe
    50                  55                  60

Lys Gly Arg Phe Thr Phe Ser Leu Asp Asp Ser Lys Asn Thr Ala Tyr
65                  70                  75                  80

Leu Gln Ile Asn Ser Leu Arg Ala Glu Asp Thr Ala Val Tyr Phe Cys
                85                  90                  95

Thr Arg Arg Gly Tyr Asp Trp Tyr Phe Asp Val Trp Gly Gln Gly Thr
            100                 105                 110

Thr Val Thr Val
            115

<210> SEQ ID NO 9
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Asn Ser Tyr
            20                  25                  30

Leu Ser Trp Phe Gln Gln Lys Pro Gly Lys Ala Pro Lys Thr Leu Ile
        35                  40                  45

Tyr Arg Ala Asn Arg Leu Glu Ser Gly Val Pro Ser Arg Phe Ser Gly
    50                  55                  60

Ser Gly Ser Gly Thr Asp Tyr Thr Leu Thr Ile Ser Ser Leu Gln Tyr
65                  70                  75                  80

Glu Asp Phe Gly Ile Tyr Tyr Cys Gln Gln Tyr Asp Glu Ser Pro Trp
                85                  90                  95

Thr Phe Gly Gly Gly Thr Lys Leu Glu Ile Lys
            100                 105

<210> SEQ ID NO 10
<211> LENGTH: 240
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Glu Ile Gln Leu Val Gln Ser Gly Gly Gly Leu Val Lys Pro Gly Gly
1               5                   10                  15

Ser Val Arg Ile Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Met
        35                  40                  45

Gly Trp Ile Asn Thr His Thr Gly Glu Pro Thr Tyr Ala Asp Ser Phe
 50                  55                  60

Lys Gly Arg Phe Thr Phe Ser Leu Asp Asp Ser Lys Asn Thr Ala Tyr
 65                  70                  75                  80

Leu Gln Ile Asn Ser Leu Arg Ala Glu Asp Thr Ala Val Tyr Phe Cys
                 85                  90                  95

Thr Arg Arg Gly Tyr Asp Trp Tyr Phe Asp Val Trp Gly Gln Gly Thr
                100                 105                 110

Thr Val Thr Val Ser Ser Gly Gly Gly Ser Gly Gly Gly Gly Ser
                115                 120                 125

Gly Gly Gly Gly Ser Asp Ile Gln Met Thr Gln Ser Pro Ser Ser Leu
130                 135                 140

Ser Ala Ser Val Gly Asp Arg Val Thr Ile Thr Cys Arg Ala Ser Gln
145                 150                 155                 160

Asp Ile Asn Ser Tyr Leu Ser Trp Phe Gln Gln Lys Pro Gly Lys Ala
                165                 170                 175

Pro Lys Thr Leu Ile Tyr Arg Ala Asn Arg Leu Glu Ser Gly Val Pro
                180                 185                 190

Ser Arg Phe Ser Gly Ser Gly Ser Gly Thr Asp Tyr Thr Leu Thr Ile
                195                 200                 205

Ser Ser Leu Gln Tyr Glu Asp Phe Gly Ile Tyr Tyr Cys Gln Gln Tyr
210                 215                 220

Asp Glu Ser Pro Trp Thr Phe Gly Gly Gly Thr Lys Leu Glu Ile Lys
225                 230                 235                 240

<210> SEQ ID NO 11
<211> LENGTH: 257
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Met Trp Leu Gln Ser Leu Leu Leu Leu Gly Thr Val Ala Cys Ser Ile
 1               5                  10                  15

Ser Glu Ile Gln Leu Val Gln Ser Gly Gly Leu Val Lys Pro Gly
                 20                  25                  30

Gly Ser Val Arg Ile Ser Cys Ala Ala Ser Gly Tyr Thr Phe Thr Asn
                 35                  40                  45

Tyr Gly Met Asn Trp Val Arg Gln Ala Pro Gly Lys Gly Leu Glu Trp
 50                  55                  60

Met Gly Trp Ile Asn Thr His Thr Gly Glu Pro Thr Tyr Ala Asp Ser
 65                  70                  75                  80

Phe Lys Gly Arg Phe Thr Phe Ser Leu Asp Asp Ser Lys Asn Thr Ala
                 85                  90                  95

Tyr Leu Gln Ile Asn Ser Leu Arg Ala Glu Asp Thr Ala Val Tyr Phe
                100                 105                 110

Cys Thr Arg Arg Gly Tyr Asp Trp Tyr Phe Asp Val Trp Gly Gln Gly
                115                 120                 125

Thr Thr Val Thr Val Ser Ser Gly Gly Gly Gly Ser Gly Gly Gly Gly
                130                 135                 140

Ser Gly Gly Gly Gly Ser Asp Ile Gln Met Thr Gln Ser Pro Ser Ser
145                 150                 155                 160

Leu Ser Ala Ser Val Gly Asp Arg Val Thr Ile Thr Cys Arg Ala Ser
                165                 170                 175

```
Gln Asp Ile Asn Ser Tyr Leu Ser Trp Phe Gln Gln Lys Pro Gly Lys
            180                 185                 190

Ala Pro Lys Thr Leu Ile Tyr Arg Ala Asn Arg Leu Glu Ser Gly Val
        195                 200                 205

Pro Ser Arg Phe Ser Gly Ser Gly Ser Gly Thr Asp Tyr Thr Leu Thr
    210                 215                 220

Ile Ser Ser Leu Gln Tyr Glu Asp Phe Gly Ile Tyr Tyr Cys Gln Gln
225                 230                 235                 240

Tyr Asp Glu Ser Pro Trp Thr Phe Gly Gly Gly Thr Lys Leu Glu Ile
                245                 250                 255

Lys

<210> SEQ ID NO 12
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Gly Ser Thr
            100                 105                 110

Ser Gly Ser Gly Lys Pro Gly Ser Gly Glu Gly Ser Glu Val Gln Leu
        115                 120                 125

Val Glu
    130

<210> SEQ ID NO 13
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Leu Val Gln Pro Gly Gly Ser Leu Arg Leu Ser Cys Ala Ala Ser Gly
1               5                   10                  15

Phe Asn Ile Lys Asp Thr Tyr Ile His Trp Val Arg Gln Ala Pro Gly
            20                  25                  30

Lys Gly Leu Glu Trp Val Ala Arg Ile Tyr Pro Thr Asn Gly Tyr Thr
        35                  40                  45

Arg Tyr Ala Asp Ser Val Lys Gly Arg Phe Thr Ile Ser Ala Asp Thr
    50                  55                  60
```

```
Ser Lys Asn Thr Ala Tyr Leu Gln Met Asn Ser Leu Arg Ala Glu Asp
 65                  70                  75                  80

Thr Ala Val Tyr Tyr Cys Ser Arg Trp Gly Gly Asp Gly Phe Tyr Ala
                 85                  90                  95

Met Asp Val Trp Gly Gln Gly Thr Leu Val Thr Val
            100                 105

<210> SEQ ID NO 14
<211> LENGTH: 255
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Val Asn Thr Ala
                 20                  25                  30

Val Ala Trp Tyr Gln Gln Lys Pro Gly Lys Ala Pro Lys Leu Leu Ile
             35                  40                  45

Tyr Ser Ala Ser Phe Leu Tyr Ser Gly Val Pro Ser Arg Phe Ser Gly
 50                  55                  60

Ser Arg Ser Gly Thr Asp Phe Thr Leu Thr Ile Ser Ser Leu Gln Pro
 65                  70                  75                  80

Glu Asp Phe Ala Thr Tyr Tyr Cys Gln Gln His Tyr Thr Thr Pro Pro
                 85                  90                  95

Thr Phe Gly Gln Gly Thr Lys Val Glu Ile Lys Arg Thr Gly Ser Thr
            100                 105                 110

Ser Gly Ser Gly Lys Pro Gly Ser Gly Glu Gly Ser Glu Val Gln Leu
            115                 120                 125

Val Glu Ser Gly Gly Gly Gly Ser Gly Gly Gly Ser Gly Gly
130                 135                 140

Gly Gly Ser Leu Val Gln Pro Gly Gly Ser Leu Arg Leu Ser Cys Ala
145                 150                 155                 160

Ala Ser Gly Phe Asn Ile Lys Asp Thr Tyr Ile His Trp Val Arg Gln
                165                 170                 175

Ala Pro Gly Lys Gly Leu Glu Trp Val Ala Arg Ile Tyr Pro Thr Asn
            180                 185                 190

Gly Tyr Thr Arg Tyr Ala Asp Ser Val Lys Gly Arg Phe Thr Ile Ser
        195                 200                 205

Ala Asp Thr Ser Lys Asn Thr Ala Tyr Leu Gln Met Asn Ser Leu Arg
    210                 215                 220

Ala Glu Asp Thr Ala Val Tyr Tyr Cys Ser Arg Trp Gly Gly Asp Gly
225                 230                 235                 240

Phe Tyr Ala Met Asp Val Trp Gly Gln Gly Thr Leu Val Thr Val
                245                 250                 255

<210> SEQ ID NO 15
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 15

Ile Tyr Ile Trp Ala Pro Leu Ala Gly Thr Cys Gly Val Leu Leu Leu
1               5                   10                  15

Ser Leu Val Ile Thr
            20

<210> SEQ ID NO 16
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Ile Tyr Ile Trp Ala Pro Leu Ala Gly Thr Cys Gly Val Leu Leu Leu
1               5                   10                  15

Ser Leu Val Ile Thr Leu Tyr Cys
            20

<210> SEQ ID NO 17
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Ile Tyr Leu Ile Ile Gly Ile Cys Gly Gly Gly Ser Leu Leu Met Val
1               5                   10                  15

Phe Val Ala Leu Leu Val Phe Tyr Ile Thr
            20                  25

<210> SEQ ID NO 18
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Phe Trp Val Leu Val Val Val Gly Gly Val Leu Ala Cys Tyr Ser Leu
1               5                   10                  15

Leu Val Thr Val Ala Phe Ile Ile Phe Trp Val
            20                  25

<210> SEQ ID NO 19
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Ile Leu Leu Pro Leu Ile Ile Gly Leu Ile Leu Leu Gly Leu Leu Ala
1               5                   10                  15

Leu Val Leu Ile Ala Phe Cys Ile Ile
            20                  25

<210> SEQ ID NO 20
```

<211> LENGTH: 86
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Ala Leu Ser Asn Ser Ile Met Tyr Phe Ser His Phe Val Pro Val Phe
1               5                   10                  15

Leu Pro Ala Lys Pro Thr Thr Thr Pro Ala Pro Arg Pro Pro Thr Pro
            20                  25                  30

Ala Pro Thr Ile Ala Ser Gln Pro Leu Ser Leu Arg Pro Glu Ala Cys
        35                  40                  45

Arg Pro Ala Ala Gly Gly Ala Val His Thr Arg Gly Leu Asp Ile Tyr
    50                  55                  60

Ile Trp Ala Pro Leu Ala Gly Thr Cys Gly Val Leu Leu Leu Ser Leu
65                  70                  75                  80

Val Ile Thr Leu Tyr Cys
                85

<210> SEQ ID NO 21
<211> LENGTH: 83
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Ala Leu Ser Asn Ser Ile Met Tyr Phe Ser His Phe Val Pro Val Phe
1               5                   10                  15

Leu Pro Ala Lys Pro Thr Thr Thr Pro Ala Pro Arg Pro Pro Thr Pro
            20                  25                  30

Ala Pro Thr Ile Ala Ser Gln Pro Leu Ser Leu Arg Pro Glu Ala Cys
        35                  40                  45

Arg Pro Ala Ala Gly Gly Ala Val His Thr Arg Gly Leu Asp Ile Tyr
    50                  55                  60

Ile Trp Ala Pro Leu Ala Gly Thr Cys Gly Val Leu Leu Leu Ser Leu
65                  70                  75                  80

Val Ile Thr

<210> SEQ ID NO 22
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Leu Tyr Cys Arg Arg Leu Lys Ile Gln Val Arg Lys Ala Ala Ile Thr
1               5                   10                  15

Ser Tyr Glu Lys Ser Asp Gly Val Tyr Thr Gly Leu Ser Thr Arg Asn
            20                  25                  30

Gln Glu Thr Tyr Glu Thr Leu Lys His Glu Lys Pro Pro Gln
                35                  40                  45

<210> SEQ ID NO 23
<211> LENGTH: 45
<212> TYPE: PRT

<213> ORGANISM: Artificial Sequence
<220> FEATURE:
<223> OTHER INFORMATION: Description of Artificial Sequence: Synthetic
      polypeptide

<400> SEQUENCE: 23

Leu Tyr Cys Arg Leu Lys Ile Gln Val Arg Lys Ala Ala Ile Thr Ser
1               5                   10                  15

Tyr Glu Lys Ser Asp Gly Val Tyr Thr Gly Leu Ser Thr Arg Asn Gln
                20                  25                  30

Glu Thr Tyr Glu Thr Leu Lys His Glu Lys Pro Pro Gln
            35                  40                  45

<210> SEQ ID NO 24
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Arg Leu Lys Ile Gln Val Arg Lys Ala Ala Ile Thr Ser Tyr Glu Lys
1               5                   10                  15

Ser Asp Gly Val Tyr Thr Gly Leu Ser Thr Arg Asn Gln Glu Thr Tyr
                20                  25                  30

Glu Thr Leu Lys His Glu Lys Pro Pro Gln
            35                  40

<210> SEQ ID NO 25
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Arg Leu Lys Ile Gln Val Arg Lys Ala Ala Ile Thr Ser Tyr Glu Lys
1               5                   10                  15

Ser Asp Gly Val Tyr Thr Gly Leu Ser Thr Arg Asn Gln Glu Thr Tyr
                20                  25                  30

Glu Thr Leu Lys His Glu Lys Pro Pro Gln
            35                  40

<210> SEQ ID NO 26
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Tyr Glu Asp Met Arg Gly Ile Leu Tyr Ala Ala Pro Gln Leu Arg Ser
1               5                   10                  15

Ile Arg Gly Gln Pro Gly Pro Asn His Glu Glu Asp Ala Asp Ser Tyr
                20                  25                  30

Glu Asn Met
        35

<210> SEQ ID NO 27
<211> LENGTH: 62

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Lys Lys Val Ala Lys Lys Pro Thr Asn Lys Ala Pro His Pro Lys Gln
1               5                   10                  15

Glu Pro Gln Glu Ile Asn Phe Pro Asp Asp Leu Pro Gly Ser Asn Thr
            20                  25                  30

Ala Ala Pro Val Gln Glu Thr Leu His Gly Cys Gln Pro Val Thr Gln
        35                  40                  45

Glu Asp Gly Lys Glu Ser Arg Ile Ser Val Gln Glu Arg Gln
    50                  55                  60

<210> SEQ ID NO 28
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Gln Arg Trp Lys Ser Lys Leu Tyr Ser Ile Val Cys Gly Lys Ser Thr
1               5                   10                  15

Pro Glu Lys Glu Gly Glu Leu Glu Gly Thr Thr Thr Lys Pro Leu Ala
            20                  25                  30

Pro Asn Pro Ser Phe Ser Pro Thr Pro Gly Phe Thr Pro Thr Leu Gly
        35                  40                  45

Phe Ser Pro Val Pro Ser Ser Thr Phe Thr Ser Ser Ser Thr Tyr Thr
    50                  55                  60

Pro Gly Asp Cys Pro Asn Phe Ala Ala Pro Arg Arg Glu Val Ala Pro
65                  70                  75                  80

Pro Tyr Gln Gly Ala Asp Pro Ile Leu Ala Thr Ala Leu Ala Ser Asp
                85                  90                  95

Pro Ile Pro Asn Pro Leu Gln Lys Trp Glu Asp Ser Ala His Lys Pro
            100                 105                 110

Gln Ser Leu Asp Thr Asp Asp Pro Ala Thr Leu Tyr Ala Val Val Glu
        115                 120                 125

Asn Val Pro Pro Leu Arg Trp Lys Glu Phe Val Arg Arg Leu Gly Leu
    130                 135                 140

Ser Asp His Glu Ile Asp Arg Leu Glu Leu Gln Asn Gly Arg Cys Leu
145                 150                 155                 160

Arg Glu Ala Gln Tyr Ser Met Leu Ala Thr Trp Arg Arg Arg Thr Pro
                165                 170                 175

Arg Arg Glu Ala Thr Leu Glu Leu Leu Gly Arg Val Leu Arg Asp Met
            180                 185                 190

Asp Leu Leu Gly Cys Leu Glu Asp Ile Glu Glu Ala Leu Cys Gly Pro
        195                 200                 205

Ala Ala Leu Pro Pro Ala Pro Ser Leu Leu Arg
    210                 215

<210> SEQ ID NO 29
<211> LENGTH: 171
<212> TYPE: PRT
<213> ORGANISM: Artificial Sequence
<220> FEATURE:

<223> OTHER INFORMATION: Description of Artificial Sequence: Synthetic
     polypeptide

<400> SEQUENCE: 29

```
Pro Leu Cys Leu Gln Arg Glu Ala Lys Val Pro His Leu Pro Ala Asp
1               5                   10                  15

Lys Ala Arg Gly Thr Gln Gly Pro Glu Gln Gln His Leu Leu Ile Thr
            20                  25                  30

Ala Pro Ser Ser Ser Ser Ser Leu Glu Ser Ser Ala Ser Ala Leu
        35                  40                  45

Asp Arg Arg Ala Pro Thr Arg Asn Gln Pro Gln Ala Pro Gly Val Glu
    50                  55                  60

Ala Ser Gly Ala Gly Glu Ala Arg Ala Ser Thr Gly Ser Ser Asp Ser
65                  70                  75                  80

Ser Pro Gly Gly His Gly Thr Gln Val Asn Val Thr Cys Ile Val Asn
                85                  90                  95

Val Cys Ser Ser Ser Asp His Ser Ser Gln Cys Ser Ser Gln Ala Ser
            100                 105                 110

Ser Thr Met Gly Asp Thr Asp Ser Ser Pro Ser Glu Ser Pro Lys Asp
        115                 120                 125

Glu Gln Val Pro Phe Ser Lys Glu Glu Cys Ala Phe Arg Ser Gln Leu
    130                 135                 140

Glu Thr Pro Glu Thr Leu Leu Gly Ser Thr Glu Glu Lys Pro Leu Pro
145                 150                 155                 160

Leu Gly Val Pro Asp Ala Gly Met Lys Pro Ser
                165                 170
```

<210> SEQ ID NO 30
<211> LENGTH: 211
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 30

```
Met Ser Asn Gly Tyr Ser Thr Asp Glu Asn Phe Arg Tyr Leu Ile Ser
1               5                   10                  15

Cys Phe Arg Ala Arg Val Lys Met Tyr Ile Gln Val Glu Pro Val Leu
            20                  25                  30

Asp Tyr Leu Thr Phe Leu Pro Ala Glu Val Lys Glu Gln Ile Gln Arg
        35                  40                  45

Thr Val Ala Thr Ser Gly Asn Met Gln Ala Val Glu Leu Leu Leu Ser
    50                  55                  60

Thr Leu Glu Lys Gly Val Trp His Leu Gly Trp Thr Arg Glu Phe Val
65                  70                  75                  80

Glu Ala Leu Arg Arg Thr Gly Ser Pro Leu Ala Ala Arg Tyr Met Asn
                85                  90                  95

Pro Glu Leu Thr Asp Leu Pro Ser Pro Ser Phe Glu Asn Ala His Asp
            100                 105                 110

Glu Tyr Leu Gln Leu Leu Asn Leu Leu Gln Pro Thr Leu Val Asp Lys
        115                 120                 125

Leu Leu Val Arg Asp Val Leu Asp Lys Cys Met Glu Glu Glu Leu Leu
    130                 135                 140

Thr Ile Glu Asp Arg Asn Arg Ile Ala Ala Ala Glu Asn Asn Gly Asn
145                 150                 155                 160
```

```
Glu Ser Gly Val Arg Glu Leu Leu Lys Arg Ile Val Gln Lys Glu Asn
                165                 170                 175

Trp Phe Ser Ala Phe Leu Asn Val Leu Arg Gln Thr Gly Asn Asn Glu
            180                 185                 190

Leu Val Gln Glu Leu Thr Gly Ser Asp Cys Ser Glu Ser Asn Ala Glu
        195                 200                 205

Ile Glu Asn
    210

<210> SEQ ID NO 31
<211> LENGTH: 191
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Met Glu Phe Gly Leu Ser Trp Leu Phe Leu Val Ala Ile Leu Lys Gly
1               5                   10                  15

Val Gln Cys Gly Leu Leu Asp Leu Arg Gln Gly Met Phe Ala Gln Leu
            20                  25                  30

Val Ala Gln Asn Val Leu Leu Ile Asp Gly Pro Leu Ser Trp Tyr Ser
        35                  40                  45

Asp Pro Gly Leu Ala Gly Val Ser Leu Thr Gly Gly Leu Ser Tyr Lys
    50                  55                  60

Glu Asp Thr Lys Glu Leu Val Val Ala Lys Ala Gly Val Tyr Tyr Val
65                  70                  75                  80

Phe Phe Gln Leu Glu Leu Arg Arg Val Val Ala Gly Glu Gly Ser Gly
                85                  90                  95

Ser Val Ser Leu Ala Leu His Leu Gln Pro Leu Arg Ser Ala Ala Gly
            100                 105                 110

Ala Ala Ala Leu Ala Leu Thr Val Asp Leu Pro Pro Ala Ser Ser Glu
        115                 120                 125

Ala Arg Asn Ser Ala Phe Gly Phe Gln Gly Arg Leu Leu His Leu Ser
    130                 135                 140

Ala Gly Gln Arg Leu Gly Val His Leu His Thr Glu Ala Arg Ala Arg
145                 150                 155                 160

His Ala Trp Gln Leu Thr Gln Gly Ala Thr Val Leu Gly Leu Phe Arg
                165                 170                 175

Val Thr Pro Glu Ile Pro Ala Gly Leu Pro Ser Pro Arg Ser Glu
            180                 185                 190

<210> SEQ ID NO 32
<211> LENGTH: 247
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
        35                  40                  45
```

```
Gly Trp Ile Asn Thr Tyr Thr Gly Glu Pro Thr Tyr Ala Asp Ala Phe
         50                  55                  60

Lys Gly Arg Val Thr Met Thr Thr Asp Thr Ser Thr Ser Thr Ala Tyr
 65                  70                  75                  80

Met Glu Leu Arg Ser Leu Arg Ser Asp Asp Thr Ala Val Tyr Tyr Cys
                 85                  90                  95

Ala Arg Asp Tyr Gly Asp Tyr Gly Met Asp Tyr Trp Gly Gln Gly Thr
            100                 105                 110

Thr Val Thr Val Ser Ser Gly Ser Thr Ser Gly Ser Gly Lys Pro Gly
        115                 120                 125

Ser Ser Glu Gly Ser Thr Lys Gly Asp Ile Val Met Thr Gln Ser Pro
130                 135                 140

Asp Ser Leu Ala Val Ser Leu Gly Glu Arg Ala Thr Ile Asn Cys Arg
145                 150                 155                 160

Ala Ser Lys Ser Val Ser Thr Ser Gly Tyr Ser Phe Met His Trp Tyr
                165                 170                 175

Gln Gln Lys Pro Gly Gln Pro Pro Lys Leu Leu Ile Tyr Leu Ala Ser
            180                 185                 190

Asn Leu Glu Ser Gly Val Pro Asp Arg Phe Ser Gly Ser Gly Ser Gly
        195                 200                 205

Thr Asp Phe Thr Leu Thr Ile Ser Ser Leu Gln Ala Glu Asp Val Ala
210                 215                 220

Val Tyr Tyr Cys Gln His Ser Arg Glu Val Pro Trp Thr Phe Gly Gln
225                 230                 235                 240

Gly Thr Lys Val Glu Ile Lys
                245

<210> SEQ ID NO 33
<211> LENGTH: 247
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Gln Val Gln Leu Gln Glu Ser Gly Pro Gly Leu Val Lys Pro Ser Gln
 1               5                  10                  15

Thr Leu Ser Leu Thr Cys Thr Val Ser Gly Gly Ser Ile Ser Ser Gly
             20                  25                  30

Tyr Asn Trp His Trp Ile Arg Gln Pro Pro Gly Lys Gly Leu Glu Trp
         35                  40                  45

Ile Gly Tyr Ile His Tyr Thr Gly Ser Thr Asn Tyr Asn Pro Ala Leu
 50                  55                  60

Arg Ser Arg Val Thr Ile Ser Val Asp Thr Ser Lys Asn Gln Phe Ser
 65                  70                  75                  80

Leu Lys Leu Ser Ser Val Thr Ala Ala Asp Thr Ala Val Tyr Tyr Cys
                 85                  90                  95

Ala Arg Ile Tyr Asn Gly Asn Ser Phe Pro Tyr Trp Gly Gln Gly Thr
            100                 105                 110

Thr Val Thr Val Ser Ser Gly Gly Gly Ser Gly Gly Gly Ser
        115                 120                 125

Gly Gly Gly Gly Ser Asp Ile Val Met Thr Gln Ser Pro Asp Ser Leu
        130                 135                 140

Ala Tyr Ser Leu Gly Glu Arg Ala Thr Ile Asn Cys Lys Ser Ser Gln
145                 150                 155                 160
```

```
Ser Leu Phe Asn Ser Gly Asn Gln Lys Asn Tyr Leu Thr Trp Tyr Gln
                165                 170                 175

Gln Lys Pro Gly Gln Pro Pro Lys Leu Leu Ile Tyr Trp Ala Ser Thr
            180                 185                 190

Arg Glu Ser Gly Val Pro Asp Arg Phe Ser Gly Ser Gly Ser Gly Thr
        195                 200                 205

Asp Ile Phe Ile Thr Ile Ser Ser Leu Gln Ala Glu Asp Val Ala Val
    210                 215                 220

Tyr Tyr Cys Gln Asn Ala Tyr Ser Phe Pro Tyr Thr Phe Gly Gly Gly
225                 230                 235                 240

Thr Lys Leu Glu Ile Lys Arg
                245

<210> SEQ ID NO 34
<211> LENGTH: 244
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Asp Ile Gln Leu Thr Gln Ser Pro Ser Ser Leu Ser Ala Ser Val Gly
1               5                   10                  15

Asp Arg Val Ser Ile Thr Cys Lys Ala Ser Gln Asp Val Ser Ile Ala
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Asp Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Val Tyr Tyr Cys Gln Gln His Tyr Ile Thr Pro Leu
                85                  90                  95

Thr Phe Gly Ala Gly Thr Lys Val Glu Ile Lys Arg Gly Gly Gly Gly
            100                 105                 110

Ser Gly Gly Gly Gly Ser Gly Gly Gly Ser Gln Val Gln Leu Gln
        115                 120                 125

Gln Ser Gly Ser Glu Leu Lys Lys Pro Gly Ala Ser Val Lys Val Ser
130                 135                 140

Cys Lys Ala Ser Gly Tyr Thr Phe Thr Asn Tyr Gly Met Asn Trp Val
145                 150                 155                 160

Lys Gln Ala Pro Gly Gln Gly Leu Lys Trp Met Gly Trp Ile Asn Thr
                165                 170                 175

Tyr Thr Gly Glu Pro Thr Tyr Thr Asp Asp Phe Lys Gly Arg Phe Ala
            180                 185                 190

Phe Ser Leu Asp Thr Ser Val Ser Thr Ala Tyr Leu Gln Ile Ser Ser
        195                 200                 205

Leu Lys Ala Asp Asp Thr Ala Val Tyr Phe Cys Ala Arg Gly Gly Phe
    210                 215                 220

Gly Ser Ser Tyr Trp Tyr Phe Asp Val Trp Gly Gln Gly Ser Leu Val
225                 230                 235                 240

Thr Val Ser Ser

<210> SEQ ID NO 35
```

```
<211> LENGTH: 244
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35
```

Gln Val Gln Leu Gln Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Lys Gln Ala Pro Gly Gln Gly Leu Lys Trp Met
        35                  40                  45

Gly Trp Ile Asn Thr Tyr Thr Gly Glu Pro Thr Tyr Thr Asp Asp Phe
    50                  55                  60

Lys Gly Arg Phe Ala Phe Ser Leu Asp Thr Ser Val Ser Thr Ala Tyr
65                  70                  75                  80

Leu Gln Ile Ser Ser Leu Lys Ala Asp Asp Thr Ala Val Tyr Phe Cys
                85                  90                  95

Ala Arg Gly Gly Phe Gly Ser Ser Tyr Trp Tyr Phe Asp Val Trp Gly
            100                 105                 110

Gln Gly Ser Leu Val Thr Val Ser Ser Gly Gly Gly Ser Gly Gly
        115                 120                 125

Gly Gly Ser Gly Gly Gly Ser Asp Ile Gln Leu Thr Gln Ser Pro
    130                 135                 140

Ser Ser Leu Ser Ala Ser Val Gly Asp Arg Val Ser Ile Thr Cys Lys
145                 150                 155                 160

Ala Ser Gln Asp Val Ser Ile Ala Val Ala Trp Tyr Gln Gln Lys Pro
                165                 170                 175

Gly Lys Ala Pro Lys Leu Leu Ile Tyr Ser Ala Ser Tyr Arg Tyr Thr
            180                 185                 190

Gly Val Pro Asp Arg Phe Ser Gly Ser Gly Ser Gly Thr Asp Phe Thr
        195                 200                 205

Leu Thr Ile Ser Ser Leu Gln Pro Glu Asp Phe Ala Val Tyr Tyr Cys
    210                 215                 220

Gln Gln His Tyr Ile Thr Pro Leu Thr Phe Gly Ala Gly Thr Lys Val
225                 230                 235                 240

Glu Ile Lys Arg

```
<210> SEQ ID NO 36
<211> LENGTH: 6
<212> TYPE: PRT
<213> ORGANISM: Hepacirivirus C

<400> SEQUENCE: 36
```

Glu Asp Val Val Cys Cys
1               5

```
<210> SEQ ID NO 37
<211> LENGTH: 6
<212> TYPE: PRT
<213> ORGANISM: Hepacirivirus C

<400> SEQUENCE: 37
```

Asp Glu Met Glu Glu Cys
1               5

```
<210> SEQ ID NO 38
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Gly Tyr Thr Met Asn
1               5

<210> SEQ ID NO 39
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Leu Ile Asn Pro Tyr Asn Gly Gly Thr Ser Tyr Asn Gln Lys Phe Lys
1               5                   10                  15

Asp

<210> SEQ ID NO 40
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Gly Ser Tyr Gly Ser Ser Tyr Phe Asp Tyr
1               5                   10

<210> SEQ ID NO 41
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Glu Leu Val Lys Pro Gly Ala Ser Met Lys Ile Ser Cys Lys Ala Ser
1               5                   10                  15

Gly Tyr Ser Phe Thr Gly Tyr Thr Met Asn Trp Met Lys Gln Gly His
                20                  25                  30

Gly Lys Asn Leu Glu Trp Ile Gly Leu Ile Asn Pro Tyr Asn Gly Gly
            35                  40                  45

Thr Ser Tyr Asn Gln Lys Phe Lys Asp Lys Ala Thr Leu Thr Leu Asp
        50                  55                  60

Lys Ser Ser Ser Ser Ala Tyr Met Glu Leu Leu Ser Leu Thr Ser Glu
65                  70                  75                  80

Asp Ser Ala Val Tyr Tyr Cys Ala Arg Gly Ser Tyr Gly Ser Ser Tyr
                85                  90                  95

Phe Asp Tyr Trp Gly Gln Gly Thr Thr Leu Thr Val Ser Ser
            100                 105                 110

<210> SEQ ID NO 42
<211> LENGTH: 5
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 42

Asp Tyr Tyr Met Asn
1               5

<210> SEQ ID NO 43
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Arg Val Asn Pro Ser Asn Gly Gly Thr Ser Tyr Asn Gln Lys Phe Lys
1               5                   10                  15

<210> SEQ ID NO 44
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Gly Leu Ala Tyr Tyr Ser Asn Ser Phe Val Tyr
1               5                   10

<210> SEQ ID NO 45
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Asp Tyr
            20                  25                  30

Tyr Met Asn Trp Val Lys Gln Ser His Gly Lys Ser Leu Glu Trp Ile
        35                  40                  45

Gly Arg Val Asn Pro Ser Asn Gly Gly Thr Ser Tyr Asn Gln Lys Phe
    50                  55                  60

Lys Gly Lys Ala Thr Leu Thr Val Asp Lys Ser Leu Ser Thr Ala Tyr
65                  70                  75                  80

Met Gln Leu Asn Ser Leu Thr Ser Glu Asp Ser Ala Val Tyr Tyr Cys
                85                  90                  95

Ala Arg Gly Leu Ala Tyr Tyr Ser Asn Ser Phe Val Tyr Trp Gly Gln
            100                 105                 110

Gly Thr Leu Val Thr Val Ser Ala
        115                 120

<210> SEQ ID NO 46
<211> LENGTH: 5
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 46

Gly Tyr Phe Met Asn
1               5

<210> SEQ ID NO 47
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Arg Ile Asn Pro Tyr Asn Gly Asp Thr Phe Tyr Asn Gln Lys Phe Lys
1               5                   10                  15

Gly

<210> SEQ ID NO 48
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Ser Gly Asp Trp Tyr Phe Asp Val
1               5

<210> SEQ ID NO 49
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Ser Phe Thr Gly Tyr
                20                  25                  30

Phe Met Asn Trp Val Lys Gln Ser His Gly Lys Ser Leu Glu Trp Ile
            35                  40                  45

Gly Arg Ile Asn Pro Tyr Asn Gly Asp Thr Phe Tyr Asn Gln Lys Phe
        50                  55                  60

Lys Gly Lys Ala Thr Leu Thr Val Asp Lys Ser Ser Ser Thr Ala His
65                  70                  75                  80

Met Glu Leu Arg Ser Leu Thr Ser Glu Asp Ser Ala Val Tyr Tyr Cys
                85                  90                  95

Ala Arg Ser Gly Asp Trp Tyr Phe Asp Val Trp Gly Ala Gly Thr Thr
            100                 105                 110

Val Thr Val Ser Ser
        115

<210> SEQ ID NO 50
<211> LENGTH: 11
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 50

Gly Asp Gly Tyr Tyr Val Thr Ser Leu Ala Tyr
1               5                   10

<210> SEQ ID NO 51
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Ser Phe Thr Gly Tyr
            20                  25                  30

Phe Met Asn Trp Val Lys Gln Ser His Gly Lys Ser Leu Glu Trp Leu
        35                  40                  45

Gly Arg Ile Asn Pro Tyr Asn Gly Asp Thr Phe Tyr Asn Gln Lys Phe
    50                  55                  60

Lys Gly Lys Ala Thr Leu Thr Val Asp Lys Ser Ser Asn Thr Ala His
65                  70                  75                  80

Met Glu Leu Arg Ser Leu Thr Ser Glu Asp Ser Ala Val Tyr Tyr Cys
                85                  90                  95

Ala Arg Gly Asp Gly Tyr Tyr Val Thr Ser Leu Ala Tyr Trp Gly Gln
            100                 105                 110

Gly Thr Leu Val Thr Val Ser Ala
        115                 120

<210> SEQ ID NO 52
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Arg Val Asn Pro Ser Asn Gly Gly Thr Ser Tyr Asn Gln Lys Phe Lys
1               5                   10                  15

Gly

<210> SEQ ID NO 53
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Gly Leu Ala Tyr Tyr Ser Asn Ser Phe Thr Tyr
1               5                   10

<210> SEQ ID NO 54
<211> LENGTH: 120
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 54

```
Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Asp Tyr
            20                  25                  30

Tyr Met Asn Trp Val Lys Gln Ser His Gly Lys Ser Leu Glu Trp Ile
        35                  40                  45

Gly Arg Val Asn Pro Ser Asn Gly Gly Thr Ser Tyr Asn Gln Lys Phe
    50                  55                  60

Lys Gly Lys Ala Thr Leu Thr Val Asp Lys Ser Leu Ser Thr Ala Tyr
65                  70                  75                  80

Met Gln Leu Asn Ser Leu Thr Ser Glu Asp Ser Ala Val Tyr Tyr Cys
                85                  90                  95

Ala Arg Gly Leu Ala Tyr Tyr Ser Asn Ser Phe Thr Tyr Trp Gly Gln
            100                 105                 110

Gly Thr Leu Val Thr Val Ser Ala
        115                 120
```

<210> SEQ ID NO 55
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

```
Ser Gly Asn Tyr Val Met Asp Tyr
1               5
```

<210> SEQ ID NO 56
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

```
Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Ser Phe Thr Gly Tyr
            20                  25                  30

Phe Met Asn Trp Val Lys Gln Ser His Gly Lys Ser Leu Glu Trp Ile
        35                  40                  45

Gly Arg Ile Asn Pro Tyr Asn Gly Asp Thr Phe Tyr Asn Gln Lys Phe
    50                  55                  60

Lys Gly Lys Ala Thr Leu Thr Val Asp Lys Ser Ser Ser Thr Ala His
65                  70                  75                  80

Met Glu Leu Arg Ser Leu Thr Ser Glu Asp Ser Ala Leu Tyr Tyr Cys
                85                  90                  95

Ala Arg Ser Gly Asn Tyr Val Met Asp Tyr Trp Gly Gln Gly Thr Ser
            100                 105                 110

Val Thr Val Ser Ser
        115
```

```
<210> SEQ ID NO 57
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Lys Ser Ser Gln Ser Leu Leu Tyr Gly Ser Asn Gln Lys Asn Tyr Leu
1               5                   10                  15

<210> SEQ ID NO 58
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Trp Ala Ser Thr Arg Glu Ser
1               5

<210> SEQ ID NO 59
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Gln Gln Tyr Tyr Asn Phe Pro Tyr Thr
1               5

<210> SEQ ID NO 60
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Asp Ile Val Met Ser Gln Ser Pro Ser Ser Leu Ala Val Ser Val Gly
1               5                   10                  15

Glu Lys Val Thr Met Ser Cys Lys Ser Ser Gln Ser Leu Leu Tyr Gly
                20                  25                  30

Ser Asn Gln Lys Asn Tyr Leu Ala Trp Tyr Gln Gln Lys Pro Gly Gln
            35                  40                  45

Ser Pro Lys Leu Leu Ile Tyr Trp Ala Ser Thr Arg Glu Ser Gly Val
        50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys Gln Gln
                85                  90                  95

Tyr Tyr Asn Phe Pro Tyr Thr Phe Gly Gly Gly Thr Lys Leu Glu Ile
            100                 105                 110

Lys Arg

<210> SEQ ID NO 61
<211> LENGTH: 15
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 61

Arg Ala Ser Glu Ser Val Asp Ser Tyr Gly Asn Ser Phe Met His
1               5                   10                  15

<210> SEQ ID NO 62
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Arg Ala Ser Asn Leu Glu Ser
1               5

<210> SEQ ID NO 63
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Gln Gln Asn Asn Glu Asp Pro Trp Thr
1               5

<210> SEQ ID NO 64
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Lys Ile Val Leu Thr Gln Ser Pro Ala Ser Leu Ala Val Ser Leu Arg
1               5                   10                  15

Gln Arg Ala Thr Ile Ser Cys Arg Ala Ser Glu Ser Val Asp Ser Tyr
            20                  25                  30

Gly Asn Ser Phe Met His Trp Tyr Gln Gln Lys Pro Gly Gln Pro Pro
        35                  40                  45

Lys Leu Leu Ile Tyr Arg Ala Ser Asn Leu Glu Ser Gly Val Pro Ala
    50                  55                  60

Arg Phe Ser Gly Ser Gly Ser Arg Thr Asp Phe Thr Leu Thr Ile Asp
65                  70                  75                  80

Pro Val Glu Ala Asp Asp Ala Ala Thr Tyr Tyr Cys Gln Gln Asn Asn
                85                  90                  95

Glu Asp Pro Trp Thr Phe Gly Gly Gly Thr Lys Leu Glu Ile Lys Arg
                100                 105                 110

<210> SEQ ID NO 65
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 65

Arg Ala Ser Lys Ser Val Ser Thr Ser Ser Tyr Ser Tyr Met His
1               5                   10                  15

<210> SEQ ID NO 66
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Phe Ala Ser Tyr Leu Glu Ser
1               5

<210> SEQ ID NO 67
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Pro Val Glu Glu Glu Phe Pro Arg Thr
1               5

<210> SEQ ID NO 68
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

Asp Ile Val Leu Thr Gln Ser Pro Ala Ser Leu Ala Val Ser Leu Gly
1               5                   10                  15

Gln Arg Ala Thr Ile Ser Cys Arg Ala Ser Lys Ser Val Ser Thr Ser
                20                  25                  30

Ser Tyr Ser Tyr Met His Trp Tyr Gln Gln Lys Pro Gly Gln Pro Pro
            35                  40                  45

Lys Leu Leu Ile Lys Phe Ala Ser Tyr Leu Glu Ser Gly Val Pro Ala
        50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ser Arg
                85                  90                  95

Glu Phe Pro Arg Thr Phe Gly Gly Gly Thr Lys Leu Glu Ile Lys Arg
            100                 105                 110

<210> SEQ ID NO 69
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Lys Ala Ser Glu Asn Val Val Ser Tyr Val Ser
1               5                   10
```

<210> SEQ ID NO 70
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Gly Ala Ser Asn Arg Tyr Thr
1               5

<210> SEQ ID NO 71
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Gly Gln Ser Tyr Ser Tyr Pro Leu Thr
1               5

<210> SEQ ID NO 72
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

Asn Ile Val Met Thr Gln Ser Pro Lys Ser Met Ser Met Ser Val Gly
1               5                   10                  15

Glu Arg Val Thr Leu Ser Cys Lys Ala Ser Glu Asn Val Val Ser Tyr
            20                  25                  30

Val Ser Trp Phe Gln Gln Lys Pro Glu Gln Ser Pro Lys Leu Leu Ile
        35                  40                  45

Tyr Gly Ala Ser Asn Arg Tyr Thr Gly Val Pro Asp Arg Phe Thr Gly
    50                  55                  60

Ser Gly Ser Ala Thr Asp Phe Thr Leu Thr Ile Ser Ser Val Gln Ala
65                  70                  75                  80

Glu Asp Leu Ala Asp Tyr Tyr Cys Gly Gln Ser Tyr Ser Tyr Pro Leu
                85                  90                  95

Thr Phe Gly Ala Gly Thr Lys Leu Glu Leu Lys Arg
            100                 105

<210> SEQ ID NO 73
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Arg Ala Ser Glu Ser Val Glu Tyr Tyr Gly Thr Ser Leu Met Gln
1               5                   10                  15

<210> SEQ ID NO 74
<211> LENGTH: 7
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 74

Gly Ala Ser Asn Val Glu Ser
1               5

<210> SEQ ID NO 75
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Gln Gln Ser Arg Lys Val Pro Trp Thr
1               5

<210> SEQ ID NO 76
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

Asp Ile Val Leu Thr Gln Ser Pro Ala Ser Leu Ala Val Ser Leu Gly
1               5                   10                  15

Gln Ser Val Thr Ile Ser Cys Arg Ala Ser Glu Ser Val Glu Tyr Tyr
            20                  25                  30

Gly Thr Ser Leu Met Gln Trp Tyr Gln Gln Lys Pro Gly Gln Pro Pro
        35                  40                  45

Lys Leu Leu Ile Tyr Gly Ala Ser Asn Val Glu Ser Gly Val Pro Ala
    50                  55                  60

Arg Phe Ser Gly Ser Gly Ser Gly Thr Asp Phe Ser Leu Asn Ile His
65                  70                  75                  80

Pro Val Glu Glu Asp Asp Ile Ala Met Tyr Phe Cys Gln Gln Ser Arg
                85                  90                  95

Lys Val Pro Trp Thr Phe Gly Gly Gly Thr Lys Leu Glu Ile Lys Arg
            100                 105                 110

<210> SEQ ID NO 77
<211> LENGTH: 37
<212> TYPE: PRT
<213> ORGANISM: Homo sapiens

<400> SEQUENCE: 77

Gly Leu Ala Val Ser Thr Ile Ser Ser Phe Phe Pro Pro Gly Tyr Gln
1               5                   10                  15

Val Ser Phe Cys Leu Val Met Val Leu Leu Phe Ala Val Asp Thr Gly
            20                  25                  30

Leu Tyr Phe Ser Val
        35

<210> SEQ ID NO 78
<211> LENGTH: 17
<212> TYPE: PRT
<213> ORGANISM: Homo sapiens
```

-continued

<400> SEQUENCE: 78

Gly Leu Ala Val Ser Thr Ile Ser Ser Phe Phe Pro Pro Gly Tyr Gln
1               5                   10                  15
Val

<210> SEQ ID NO 79
<211> LENGTH: 20
<212> TYPE: PRT
<213> ORGANISM: Homo sapiens

<400> SEQUENCE: 79

Ser Phe Cys Leu Val Met Val Leu Leu Phe Ala Val Asp Thr Gly Leu
1               5                   10                  15
Tyr Phe Ser Val
            20

<210> SEQ ID NO 80
<211> LENGTH: 25
<212> TYPE: PRT
<213> ORGANISM: Homo sapiens

<400> SEQUENCE: 80

Lys Thr Asn Ile Arg Ser Ser Thr Arg Asp Trp Lys Asp His Lys Phe
1               5                   10                  15
Lys Trp Arg Lys Asp Pro Gln Asp Lys
            20                  25

<210> SEQ ID NO 81
<211> LENGTH: 28
<212> TYPE: PRT
<213> ORGANISM: Homo sapiens

<400> SEQUENCE: 81

Ile His Gln Asp Tyr Thr Thr Gln Asn Leu Ile Arg Met Ala Val Ala
1               5                   10                  15
Gly Leu Val Leu Val Ala Leu Leu Ala Ile Leu Val
            20                  25

<210> SEQ ID NO 82
<211> LENGTH: 9
<212> TYPE: PRT
<213> ORGANISM: Homo sapiens

<400> SEQUENCE: 82

Ile His Gln Asp Tyr Thr Thr Gln Asn
1               5

<210> SEQ ID NO 83
<211> LENGTH: 19
<212> TYPE: PRT
<213> ORGANISM: Homo sapiens

<400> SEQUENCE: 83

Leu Ile Arg Met Ala Val Ala Gly Leu Val Leu Val Ala Leu Leu Ala
1               5                   10                  15
Ile Leu Val

<210> SEQ ID NO 84
<211> LENGTH: 41
<212> TYPE: PRT
<213> ORGANISM: Homo sapiens

```
<400> SEQUENCE: 84

Glu Asn Trp His Ser His Thr Ala Leu Asn Lys Glu Ala Ser Ala Asp
1               5                   10                  15

Val Ala Glu Pro Ser Trp Ser Gln Gln Met Cys Gln Pro Gly Leu Thr
            20                  25                  30

Phe Ala Arg Thr Pro Ser Val Cys Lys
        35                  40

<210> SEQ ID NO 85
<211> LENGTH: 13
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 85
wwwuauuuau uuw                                                          13

<210> SEQ ID NO 86
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Ser Ile Asn Phe Glu Cys Lys Glu Leu
1               5

<210> SEQ ID NO 87
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Ser Ile Ile Asn Phe Glu Lys Leu
1               5
```